US012624086B2

(12) United States Patent
Durrant et al.

(10) Patent No.: US 12,624,086 B2
(45) Date of Patent: May 12, 2026

(54) MATERIALS AND METHODS FOR TREATING CANCER

(71) Applicant: MAYO FOUNDATION FOR MEDICAL EDUCATION AND RESEARCH, Rochester, MN (US)

(72) Inventors: Cameron Durrant, Oxford, FL (US); Dale Chappell, Dolores, CO (US); Saad J. Kenderian, Rochester, MN (US); Rosalie M. Sterner, Claremont, MN (US); Michelle J. Cox, Rochester, MN (US); Reona Sakemura, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 971 days.

(21) Appl. No.: 17/290,185

(22) PCT Filed: Oct. 31, 2019

(86) PCT No.: PCT/US2019/059275
§ 371 (c)(1),
(2) Date: Apr. 29, 2021

(87) PCT Pub. No.: WO2020/092850
PCT Pub. Date: May 7, 2020

(65) Prior Publication Data
US 2022/0040229 A1     Feb. 10, 2022

Related U.S. Application Data

(60) Provisional application No. 62/753,485, filed on Oct. 31, 2018.

(51) Int. Cl.

| | |
|---|---|
| *G01N 31/00* | (2006.01) |
| *A61K 31/7105* | (2006.01) |
| *A61K 38/17* | (2006.01) |
| *A61K 38/46* | (2006.01) |
| *A61K 39/395* | (2006.01) |
| *A61K 40/11* | (2025.01) |
| *A61K 40/31* | (2025.01) |
| *A61K 40/42* | (2025.01) |
| *A61P 35/00* | (2006.01) |
| *C07K 14/705* | (2006.01) |
| *G01N 33/53* | (2006.01) |
| *A61K 48/00* | (2006.01) |

(52) U.S. Cl.
CPC .... *C07K 14/70596* (2013.01); *A61K 31/7105* (2013.01); *A61K 38/1774* (2013.01); *A61K 38/465* (2013.01); *A61K 39/3955* (2013.01); *A61K 40/11* (2025.01); *A61K 40/31* (2025.01); *A61K 40/4211* (2025.01); *A61P 35/00* (2018.01); *C07K 14/70578* (2013.01); *A61K*
*48/00* (2013.01); *A61K 2239/38* (2023.05); *A61K 2239/48* (2023.05)

(58) Field of Classification Search
None
See application file for complete search history.

(56) References Cited

U.S. PATENT DOCUMENTS

| | | | |
|---|---|---|---|
| 3,687,808 | A | 8/1972 | Merigan, Jr. et al. |
| 4,034,074 | A | 7/1977 | Miles |
| 4,036,945 | A | 7/1977 | Haber |
| 4,098,876 | A | 7/1978 | Piasio et al. |
| 4,233,402 | A | 11/1980 | Maggio et al. |
| 4,257,774 | A | 3/1981 | Richardson et al. |
| 4,272,398 | A | 6/1981 | Jaffe |
| 4,331,647 | A | 5/1982 | Goldenberg |
| 4,376,110 | A | 3/1983 | David et al. |
| 4,469,863 | A | 9/1984 | Ts'o et al. |
| 4,650,764 | A | 3/1987 | Temin et al. |
| 4,769,330 | A | 9/1988 | Paoletti et al. |
| 4,816,567 | A | 3/1989 | Cabilly et al. |
| 4,861,627 | A | 8/1989 | Mathiowitz et al. |
| 4,861,719 | A | 8/1989 | Miller |
| 4,925,673 | A | 5/1990 | Steiner et al. |
| 4,935,496 | A | 6/1990 | Kudo et al. |
| 4,946,778 | A | 8/1990 | Ladner et al. |
| 4,980,289 | A | 12/1990 | Temin et al. |
| 4,987,071 | A | 1/1991 | Cech et al. |
| 5,013,556 | A | 5/1991 | Woodle et al. |
| 5,124,263 | A | 6/1992 | Temin et al. |
| 5,155,020 | A | 10/1992 | Paoletti |
| 5,155,027 | A | 10/1992 | Sledziewski et al. |
| 5,175,099 | A | 12/1992 | Wills |
| 5,204,243 | A | 4/1993 | Paoletti |
| 5,214,136 | A | 5/1993 | Lin et al. |
| 5,218,105 | A | 6/1993 | Cook et al. |

(Continued)

FOREIGN PATENT DOCUMENTS

| | | |
|---|---|---|
| CN | 101165070 A | 4/2008 |
| CN | 103492406 A | 1/2014 |

(Continued)

OTHER PUBLICATIONS

Santomasso et al. "Clinical and Biological Correlates of Neurotoxicity Associated with CAR T-cell Therapy in Patients with B-cell Acute Lymphoblastic Leukemia," Cancer Discovery, Aug. 1, 2018 (Aug. 1, 2018), vol. 8, No. 8, pp. 958-971. (Year: 2018).*

(Continued)

*Primary Examiner* — Lisa V Cook
(74) *Attorney, Agent, or Firm* — Fish & Richardson P.C.

(57) ABSTRACT

This document provides methods and materials involved in treating cancer. For example, chimeric antigen receptor T cells having reduced levels of GM-CSF are provided. Also provided as methods for making and using chimeric antigen receptor T cells having reduced levels of GM-CSF.

11 Claims, 25 Drawing Sheets
Specification includes a Sequence Listing.

(56)                  References Cited

U.S. PATENT DOCUMENTS

| | | | |
|---|---|---|---|
| 5,225,336 A | 7/1993 | Paoletti | |
| 5,225,538 A | 7/1993 | Capon et al. | |
| 5,235,033 A | 8/1993 | Summerton et al. | |
| 5,240,846 A | 8/1993 | Collins et al. | |
| 5,254,678 A | 10/1993 | Haseloff et al. | |
| 5,278,056 A | 1/1994 | Bank et al. | |
| 5,284,656 A | 2/1994 | Platz et al. | |
| 5,296,347 A | 3/1994 | LaMotte, III | |
| 5,391,682 A | 2/1995 | Ogawa et al. | |
| 5,451,569 A | 9/1995 | Wong et al. | |
| 5,502,167 A | 3/1996 | Waldmann et al. | |
| 5,521,288 A | 5/1996 | Linsley et al. | |
| 5,530,101 A | 6/1996 | Queen et al. | |
| 5,558,864 A | 9/1996 | Bendig et al. | |
| 5,565,332 A | 10/1996 | Hoogenboom et al. | |
| 5,567,584 A | 10/1996 | Sledziewski et al. | |
| 5,585,089 A | 12/1996 | Queen et al. | |
| 5,596,086 A | 1/1997 | Matteucci et al. | |
| 5,639,641 A | 6/1997 | Pedersen et al. | |
| 5,674,704 A | 10/1997 | Goodwin et al. | |
| 5,675,848 A | 10/1997 | Kappel | |
| 5,693,493 A | 12/1997 | Robinson et al. | |
| 5,693,761 A | 12/1997 | Queen et al. | |
| 5,693,762 A | 12/1997 | Queen et al. | |
| 5,698,417 A | 12/1997 | Robinson et al. | |
| 5,705,154 A | 1/1998 | Dalie et al. | |
| 5,714,147 A | 2/1998 | Capon et al. | |
| 5,733,743 A | 3/1998 | Johnson et al. | |
| 5,750,078 A | 5/1998 | Shitara et al. | |
| 5,750,375 A | 5/1998 | Sledziewski et al. | |
| 5,750,666 A | 5/1998 | Caruthers et al. | |
| 5,770,403 A | 6/1998 | Dalie et al. | |
| 5,843,725 A | 12/1998 | Sledziewski et al. | |
| 5,861,310 A | 1/1999 | Freeman et al. | |
| 5,874,240 A | 2/1999 | Ni et al. | |
| 5,928,893 A | 7/1999 | Kang et al. | |
| 5,942,607 A | 8/1999 | Freeman et al. | |
| 6,018,026 A | 1/2000 | Sledziewski et al. | |
| 6,210,669 B1 | 4/2001 | Aruffo et al. | |
| 6,291,212 B1 | 9/2001 | Sledziewski et al. | |
| 6,291,646 B1 | 9/2001 | Sledziewski et al. | |
| 6,297,008 B1 | 10/2001 | Okamoto et al. | |
| 6,300,099 B1 | 10/2001 | Sledziewski et al. | |
| 6,303,121 B1 | 10/2001 | Kwon | |
| 6,323,323 B1 | 11/2001 | Sledziewski et al. | |
| 6,355,779 B1 | 3/2002 | Goodwin et al. | |
| 6,423,885 B1 | 7/2002 | Waterhouse et al. | |
| 6,458,934 B1 | 10/2002 | Hong et al. | |
| 6,630,575 B2 | 10/2003 | Coyle et al. | |
| 6,635,750 B1 | 10/2003 | Coyle et al. | |
| 6,740,493 B1 | 5/2004 | Long et al. | |
| 6,743,619 B1 | 6/2004 | Tang et al. | |
| 6,803,192 B1 | 10/2004 | Chen | |
| 6,891,030 B2 | 5/2005 | Chen | |
| 6,919,193 B2 | 7/2005 | Tang et al. | |
| 6,943,150 B1 | 9/2005 | Altieri | |
| 6,965,018 B2 | 11/2005 | Mikesell et al. | |
| 7,029,674 B2 | 4/2006 | Carreno et al. | |
| 7,030,219 B2 | 4/2006 | Pardoll et al. | |
| 7,122,351 B2 | 10/2006 | Moore et al. | |
| 7,279,567 B2 | 10/2007 | Mikesell et al. | |
| 7,358,354 B2 | 4/2008 | Mikesell et al. | |
| 7,368,531 B2 | 5/2008 | Rosen et al. | |
| 7,381,794 B2 | 6/2008 | Moore et al. | |
| 7,414,122 B2 | 8/2008 | Fox et al. | |
| 7,432,059 B2 | 10/2008 | Freeman et al. | |
| 7,432,062 B2 | 10/2008 | Coyle et al. | |
| 7,432,351 B1 | 10/2008 | Chen | |
| 7,449,300 B2 | 11/2008 | Chen et al. | |
| 7,560,540 B2 | 7/2009 | Pardoll et al. | |
| 7,563,869 B2 | 7/2009 | Honjo et al. | |
| 7,582,439 B2 | 9/2009 | Cory et al. | |
| 7,595,048 B2 | 9/2009 | Honjo et al. | |
| 7,651,686 B2 | 1/2010 | Chen et al. | |
| 7,709,214 B2 | 5/2010 | Freeman et al. | |
| 7,723,479 B2 | 5/2010 | Mikesell et al. | |
| 7,794,710 B2 | 9/2010 | Chen et al. | |
| 7,892,540 B2 | 2/2011 | Chen et al. | |
| 8,008,449 B2 | 8/2011 | Korman et al. | |
| 8,039,589 B1 | 10/2011 | Chen | |
| 8,053,414 B2 | 11/2011 | Pardoll et al. | |
| 8,053,558 B2 | 11/2011 | Pardoll et al. | |
| 8,163,550 B2 | 4/2012 | Chen et al. | |
| 8,168,183 B2 | 5/2012 | Bebbington et al. | |
| 8,268,635 B2 | 9/2012 | Ferrante et al. | |
| 8,273,864 B2 | 9/2012 | Chen | |
| 8,383,405 B2 | 2/2013 | Orme | |
| 8,460,927 B2 | 6/2013 | Chen | |
| 8,518,409 B2 | 8/2013 | Orme | |
| 8,772,026 B2 | 7/2014 | Chen et al. | |
| 8,901,120 B2 | 12/2014 | Bearss et al. | |
| 8,981,063 B2 | 3/2015 | Chen | |
| 9,017,674 B2 | 4/2015 | Bebbington et al. | |
| 9,302,005 B2 | 4/2016 | Dong et al. | |
| 9,534,058 B2 | 1/2017 | Stull et al. | |
| 9,598,491 B2 | 3/2017 | Ahmed et al. | |
| 9,730,988 B2 | 8/2017 | Ince et al. | |
| 10,221,245 B2 | 3/2019 | Brogdon et al. | |
| 10,870,703 B2 * | 12/2020 | Durrant | C07K 16/2893 |
| 11,246,890 B2 | 2/2022 | Lin et al. | |
| 11,419,898 B2 | 8/2022 | Lu et al. | |
| 11,673,962 B2 * | 6/2023 | Durrant | A61K 39/4611 |
| | | | 424/145.1 |
| 2002/0076409 A1 | 6/2002 | March et al. | |
| 2002/0091246 A1 | 7/2002 | Pardoll et al. | |
| 2002/0095024 A1 | 7/2002 | Mikesell et al. | |
| 2002/0106730 A1 | 8/2002 | Coyle et al. | |
| 2002/0107363 A1 | 8/2002 | Fox et al. | |
| 2002/0110836 A1 | 8/2002 | Freeman et al. | |
| 2002/0119121 A1 | 8/2002 | Vitiello et al. | |
| 2002/0160395 A1 | 10/2002 | Altieri et al. | |
| 2002/0160973 A1 | 10/2002 | Pero et al. | |
| 2002/0164600 A1 | 11/2002 | Freeman et al. | |
| 2002/0168719 A1 | 11/2002 | Kwon | |
| 2002/0177551 A1 | 11/2002 | Terman | |
| 2003/0039653 A1 | 2/2003 | Chen et al. | |
| 2003/0142359 A1 | 7/2003 | Bean et al. | |
| 2003/0171551 A1 | 9/2003 | Rosenblatt et al. | |
| 2003/0208058 A1 | 11/2003 | Fiscella et al. | |
| 2003/0223989 A1 | 12/2003 | Pluenneke | |
| 2003/0232323 A1 | 12/2003 | Freeman et al. | |
| 2004/0010134 A1 | 1/2004 | Rosen et al. | |
| 2004/0109847 A1 | 6/2004 | Chen et al. | |
| 2004/0180047 A1 | 9/2004 | Chen | |
| 2004/0247563 A1 | 12/2004 | Lynch et al. | |
| 2005/0013811 A1 | 1/2005 | Chen et al. | |
| 2005/0228170 A1 | 10/2005 | Fox et al. | |
| 2005/0260716 A1 | 11/2005 | Moore et al. | |
| 2006/0034826 A1 | 2/2006 | Carreno et al. | |
| 2006/0068386 A1 | 3/2006 | Slesarev et al. | |
| 2006/0084794 A1 | 4/2006 | Rosen et al. | |
| 2006/0110383 A1 | 5/2006 | Honjo et al. | |
| 2006/0159685 A1 | 7/2006 | Mikesell et al. | |
| 2006/0223088 A1 | 10/2006 | Rosen et al. | |
| 2006/0276422 A1 | 12/2006 | Usman et al. | |
| 2007/0037206 A1 | 2/2007 | Rosen et al. | |
| 2007/0041963 A1 | 2/2007 | Rosen et al. | |
| 2007/0065427 A1 | 3/2007 | Freeman et al. | |
| 2007/0092504 A1 | 4/2007 | Carreno et al. | |
| 2007/0099833 A1 | 5/2007 | Rosen et al. | |
| 2007/0122378 A1 | 5/2007 | Freeman et al. | |
| 2007/0224663 A1 | 9/2007 | Rosen et al. | |
| 2007/0231344 A1 | 10/2007 | Leadbetter et al. | |
| 2008/0025979 A1 | 1/2008 | Honjo et al. | |
| 2008/0118511 A1 | 5/2008 | Freeman et al. | |
| 2008/0226662 A1 | 9/2008 | Pardoll et al. | |
| 2008/0241175 A1 | 10/2008 | Pardoll et al. | |
| 2009/0042292 A1 | 2/2009 | Chen | |
| 2009/0068193 A1 | 3/2009 | Chen et al. | |
| 2009/0075338 A1 | 3/2009 | Moore et al. | |
| 2009/0176317 A1 | 7/2009 | Kwon et al. | |
| 2009/0215084 A1 | 8/2009 | Kwon et al. | |
| 2009/0269783 A1 | 10/2009 | Coyle et al. | |
| 2009/0304711 A1 | 12/2009 | Pardoll et al. | |

(56) References Cited

U.S. PATENT DOCUMENTS

| | | |
|---|---|---|
| 2010/0015642 A1 | 1/2010 | Kwon et al. |
| 2010/0055116 A1* | 3/2010 | Liou .................. A61K 31/515 |
| | | 548/366.1 |
| 2010/0080816 A1 | 4/2010 | Hadeiba et al. |
| 2010/0092470 A1 | 4/2010 | Bhatt et al. |
| 2010/0285039 A1 | 11/2010 | Chen |
| 2011/0010409 A1 | 1/2011 | DeLaquil et al. |
| 2011/0020325 A1 | 1/2011 | Kwon et al. |
| 2012/0065374 A1 | 3/2012 | Pardoll et al. |
| 2012/0065385 A1 | 3/2012 | Pardoll et al. |
| 2012/0225043 A1 | 9/2012 | Chen et al. |
| 2013/0058936 A1 | 3/2013 | Bruenker et al. |
| 2013/0123566 A1 | 5/2013 | Lupold et al. |
| 2013/0251736 A1 | 9/2013 | Kwon et al. |
| 2013/0273656 A1 | 10/2013 | Hendrickson |
| 2014/0031260 A1 | 1/2014 | O'Donnell et al. |
| 2014/0127814 A1 | 5/2014 | Chandrasegaran et al. |
| 2014/0234298 A1 | 8/2014 | Steidl |
| 2014/0242080 A1 | 8/2014 | Roche |
| 2014/0271674 A1 | 9/2014 | Dong |
| 2014/0322275 A1 | 10/2014 | Brogdon et al. |
| 2014/0329248 A1 | 11/2014 | Kwon et al. |
| 2014/0335541 A1 | 11/2014 | Kwon et al. |
| 2015/0024500 A1 | 1/2015 | Yu et al. |
| 2015/0111232 A1 | 4/2015 | Kwon et al. |
| 2015/0203580 A1 | 7/2015 | Papadopoulos et al. |
| 2015/0246121 A1 | 9/2015 | Bebbington et al. |
| 2015/0273033 A1 | 10/2015 | Bosch et al. |
| 2015/0283178 A1 | 10/2015 | June et al. |
| 2015/0337048 A1 | 11/2015 | Stull et al. |
| 2016/0045581 A1 | 2/2016 | Ince et al. |
| 2016/0051651 A1 | 2/2016 | Brogdon et al. |
| 2016/0068601 A1 | 3/2016 | Brogdon et al. |
| 2016/0153996 A1 | 6/2016 | Kwon et al. |
| 2016/0154000 A1 | 6/2016 | Kwon |
| 2016/0176967 A1 | 6/2016 | Dong et al. |
| 2016/0186208 A1 | 6/2016 | Jaenisch et al. |
| 2016/0206656 A1 | 7/2016 | Gilbert |
| 2016/0237407 A1 | 8/2016 | Wagner et al. |
| 2016/0251437 A1 | 9/2016 | Dong et al. |
| 2016/0333089 A1 | 11/2016 | Sass et al. |
| 2017/0044500 A1 | 2/2017 | Cooper et al. |
| 2017/0089918 A1 | 3/2017 | Dong |
| 2017/0121416 A1 | 5/2017 | Stull et al. |
| 2017/0173030 A1 | 6/2017 | Dong |
| 2017/0274095 A1 | 9/2017 | Meyer et al. |
| 2017/0275375 A1 | 9/2017 | Rossi et al. |
| 2017/0327590 A1 | 11/2017 | Lowy et al. |
| 2017/0363634 A1 | 12/2017 | Kwon et al. |
| 2018/0105573 A1 | 4/2018 | Pule et al. |
| 2018/0139940 A1 | 5/2018 | Macdonald et al. |
| 2018/0154183 A1 | 6/2018 | Sahadevan |
| 2018/0252727 A1 | 9/2018 | Garfall et al. |
| 2018/0258149 A1 | 9/2018 | Motz et al. |
| 2018/0273932 A1 | 9/2018 | Bothmer et al. |
| 2019/0038671 A1 | 2/2019 | Fan et al. |
| 2019/0107537 A1 | 4/2019 | Chaudhary |
| 2019/0112380 A1 | 4/2019 | Chaudhary |
| 2019/0136230 A1 | 5/2019 | Sather et al. |
| 2019/0194343 A1 | 6/2019 | Durrant et al. |
| 2019/0262399 A1 | 8/2019 | Wang et al. |
| 2019/0284271 A1 | 9/2019 | Durrant |
| 2019/0292539 A1 | 9/2019 | Fulga et al. |
| 2019/0298774 A1 | 10/2019 | Lin et al. |
| 2019/0315869 A1 | 10/2019 | Dong |
| 2019/0361033 A1 | 11/2019 | Dong |
| 2020/0054673 A1 | 2/2020 | Ports et al. |
| 2020/0061077 A1 | 2/2020 | Dong |
| 2020/0147117 A1 | 5/2020 | Ben Yakar et al. |
| 2020/0190196 A1 | 6/2020 | Dong |
| 2020/0270355 A1 | 8/2020 | Faustman |
| 2020/0271656 A1 | 8/2020 | Cumba-Garcia et al. |
| 2020/0338112 A1 | 10/2020 | Lou et al. |
| 2021/0003556 A1 | 1/2021 | Dong |
| 2021/0145830 A1 | 5/2021 | Kenderian et al. |
| 2021/0145881 A1 | 5/2021 | Kenderian et al. |
| 2021/0214723 A1 | 7/2021 | Kenderian et al. |
| 2021/0238253 A1 | 8/2021 | Li et al. |
| 2021/0284714 A1 | 9/2021 | Durrant et al. |
| 2021/0355190 A1 | 11/2021 | Kenderian et al. |
| 2021/0401886 A1 | 12/2021 | Kenderian et al. |
| 2022/0041686 A1 | 2/2022 | Mackall et al. |
| 2022/0401488 A1 | 12/2022 | Kenderian et al. |
| 2023/0045174 A1 | 2/2023 | Rezvani et al. |
| 2024/0158467 A1 | 5/2024 | Durrant et al. |
| 2024/0384266 A1 | 11/2024 | Kenderian et al. |
| 2025/0313608 A1 | 10/2025 | Kenderian et al. |

FOREIGN PATENT DOCUMENTS

| | | |
|---|---|---|
| CN | 103641917 A | 3/2014 |
| CN | 105814074 A | 7/2016 |
| CN | 105874061 A | 8/2016 |
| CN | 105949323 A | 9/2016 |
| CN | 106459918 A | 2/2017 |
| CN | 107208069 A | 9/2017 |
| CN | 107271675 A | 10/2017 |
| CN | 107406517 A | 11/2017 |
| CN | 107746831 A | 3/2018 |
| CN | 107849112 A | 3/2018 |
| CN | 109608549 A | 4/2019 |
| CN | 109734813 A | 5/2019 |
| CN | 110747211 A | 2/2020 |
| CN | 2019 8 0072681.3 | 3/2024 |
| CN | 113194715 B | 3/2024 |
| EP | 1074617 A2 | 2/2001 |
| EP | 1537878 A1 | 6/2005 |
| EP | 2968415 A2 | 1/2016 |
| EP | 2997141 A1 | 3/2016 |
| EP | 3130350 A1 | 2/2017 |
| EP | 3964265 A1 | 3/2022 |
| JP | 2010-538676 A | 12/2010 |
| JP | 2015-134742 A | 7/2015 |
| JP | 2015-522081 A | 8/2015 |
| JP | 2016-538861 A | 12/2016 |
| JP | 7411578 | 1/2024 |
| WO | WO 1990/007861 A1 | 7/1990 |
| WO | WO 1991/010741 A1 | 7/1991 |
| WO | WO 1991/011465 A1 | 8/1991 |
| WO | WO 1991/017271 A1 | 11/1991 |
| WO | WO 1992/000092 A1 | 1/1992 |
| WO | WO 1992/001047 A1 | 1/1992 |
| WO | WO 1992/020791 A1 | 11/1992 |
| WO | WO 1993/001222 A1 | 1/1993 |
| WO | WO 1995/005464 A1 | 2/1995 |
| WO | WO 1995/007707 A1 | 3/1995 |
| WO | WO 1996/029348 A1 | 9/1996 |
| WO | WO 1997/017613 A1 | 5/1997 |
| WO | WO 1997/017614 A1 | 5/1997 |
| WO | WO 1997/024447 A1 | 7/1997 |
| WO | WO 1998/016249 A1 | 4/1998 |
| WO | WO 1998/023635 A1 | 6/1998 |
| WO | WO 1998/033914 A1 | 8/1998 |
| WO | WO 1998/036096 A1 | 8/1998 |
| WO | WO 1999/036093 A1 | 7/1999 |
| WO | WO 1999/064597 A1 | 12/1999 |
| WO | WO 2000/026342 A1 | 5/2000 |
| WO | WO 2000/029445 A1 | 5/2000 |
| WO | WO 2000/029582 A2 | 5/2000 |
| WO | WO 2000/041508 A2 | 7/2000 |
| WO | WO 2000/055375 A1 | 9/2000 |
| WO | WO 2000/061612 A2 | 10/2000 |
| WO | WO 2001/034629 A1 | 5/2001 |
| WO | WO 2001/062905 A2 | 8/2001 |
| WO | WO 2001/070979 A2 | 9/2001 |
| WO | WO 2001/083750 A2 | 11/2001 |
| WO | WO 2001/094413 A2 | 12/2001 |
| WO | WO 2002/000692 A2 | 1/2002 |
| WO | WO 2002/000730 A2 | 1/2002 |
| WO | WO 2002/002587 A1 | 1/2002 |
| WO | WO 2002/002891 A1 | 1/2002 |
| WO | WO 2002/008279 A2 | 1/2002 |
| WO | WO 2002/024891 A2 | 3/2002 |
| WO | WO 2002/046449 A2 | 6/2002 |

(56) References Cited

FOREIGN PATENT DOCUMENTS

| WO | WO 2002/057453 A2 | 7/2002 |
| WO | WO 2002/078731 A1 | 10/2002 |
| WO | WO 2002/079474 A2 | 10/2002 |
| WO | WO 2002/081731 A2 | 10/2002 |
| WO | WO 2002/086083 A2 | 10/2002 |
| WO | WO 2003/006632 A2 | 1/2003 |
| WO | WO 2003/008583 A2 | 1/2003 |
| WO | WO 2003/049755 A1 | 6/2003 |
| WO | WO 2004/085418 A2 | 10/2004 |
| WO | WO 2006/042237 A2 | 4/2006 |
| WO | WO 2006/050172 A2 | 5/2006 |
| WO | WO 2006/133396 A2 | 12/2006 |
| WO | WO 2008/037080 A1 | 4/2008 |
| WO | WO 2008/083174 A2 | 7/2008 |
| WO | WO 2009/023566 A2 | 2/2009 |
| WO | WO 2009/029342 A2 | 3/2009 |
| WO | WO-2009/038760 | 3/2009 |
| WO | WO 2009/114110 A1 | 9/2009 |
| WO | WO 2010/027423 A2 | 3/2010 |
| WO | WO 2010/027827 A2 | 3/2010 |
| WO | WO 2010/027828 A2 | 3/2010 |
| WO | WO 2010/098788 A2 | 9/2010 |
| WO | WO 2011/066342 A2 | 6/2011 |
| WO | WO 2011/066389 A1 | 6/2011 |
| WO | WO 2011/072246 A2 | 6/2011 |
| WO | WO-2012/079000 | 6/2012 |
| WO | WO 2013/003112 A9 | 1/2013 |
| WO | WO 2013/019906 A1 | 2/2013 |
| WO | WO 2013/090552 A1 | 6/2013 |
| WO | WO 2013/132044 A1 | 9/2013 |
| WO | WO 2014011984 A1 | 1/2014 |
| WO | WO 2014/110045 A2 | 7/2014 |
| WO | WO 2014/144666 A2 | 9/2014 |
| WO | WO 2014/163684 A1 | 10/2014 |
| WO | WO 2014/184143 A1 | 11/2014 |
| WO | WO 2015/049280 A1 | 4/2015 |
| WO | WO 2015/050663 A1 | 4/2015 |
| WO | WO 2015/061668 A1 | 4/2015 |
| WO | WO2015/066262 | 5/2015 |
| WO | WO-2015066262 A1 * | 5/2015 ........... C12N 5/0636 |
| WO | WO 2015/142314 A1 | 9/2015 |
| WO | WO 2015/157252 A1 | 10/2015 |
| WO | WO 2015/179654 A1 | 11/2015 |
| WO | WO 2016/014148 A1 | 1/2016 |
| WO | WO 2016/014576 A1 | 1/2016 |
| WO | WO 2016/018920 A1 | 2/2016 |
| WO | WO 2016/120219 A1 | 8/2016 |
| WO | WO 2016/164731 A2 | 10/2016 |
| WO | WO 2016/201394 A1 | 12/2016 |
| WO | WO 2017/023803 A1 | 2/2017 |
| WO | WO 2017/059796 A1 | 4/2017 |
| WO | WO 2017/066561 A2 | 4/2017 |
| WO | WO 2017/075389 A1 | 5/2017 |
| WO | WO 2017/091546 A1 | 6/2017 |
| WO | WO-2017/096331 | 6/2017 |
| WO | WO 2017/100587 A1 | 6/2017 |
| WO | WO-2017/141243 | 8/2017 |
| WO | WO 2017/143094 A1 | 8/2017 |
| WO | WO 2017/172981 A2 | 10/2017 |
| WO | WO 2017/173360 A2 | 10/2017 |
| WO | WO 2017/177179 A1 | 10/2017 |
| WO | WO 2017/220704 A1 | 12/2017 |
| WO | WO 2017/222593 A1 | 12/2017 |
| WO | WO 2018/005712 A1 | 1/2018 |
| WO | WO 2018/013918 A2 | 1/2018 |
| WO | WO 2018/045069 A1 | 3/2018 |
| WO | WO 2018/067991 A1 | 4/2018 |
| WO | WO 2018/073391 A1 | 4/2018 |
| WO | WO-2018/145206 | 8/2018 |
| WO | WO 2018/195339 A1 | 10/2018 |
| WO | WO 2018/237325 A1 | 12/2018 |
| WO | WO 2019/036724 A2 | 2/2019 |
| WO | WO 2019/108756 A1 | 6/2019 |
| WO | WO 2019/133793 A1 | 7/2019 |
| WO | WO 2019/178334 A1 | 9/2019 |
| WO | WO 2019/195142 A1 | 10/2019 |
| WO | WO 2019/217423 A1 | 11/2019 |
| WO | WO 2019232370 A1 | 12/2019 |
| WO | WO 2020/018620 A1 | 1/2020 |
| WO | WO 2020/055932 A2 | 3/2020 |
| WO | WO 2020/092455 A2 | 5/2020 |
| WO | WO 2020/092850 A1 | 5/2020 |
| WO | WO 2020/146239 A1 | 7/2020 |
| WO | WO 2020/247521 A1 | 12/2020 |
| WO | WO 2021/092577 A1 | 5/2021 |
| WO | WO 2022/236049 A1 | 11/2022 |
| WO | WO 2022/236142 A2 | 11/2022 |
| WO | WO 2022/266396 A1 | 12/2022 |
| WO | WO 2024/059641 A2 | 3/2024 |
| WO | WO 2024/097276 A1 | 5/2024 |
| WO | WO 2024/097852 A1 | 5/2024 |

OTHER PUBLICATIONS

Santomasso et al. (Cancer Discovery, Aug. 1, 2018, vol. 8, No. 8, pp. 958-971) (Year: 2018).*

Quan Bingjie et al., "Safety and Progress of Genetically Modified T Cells for Cancer Adoptive Immunotherapy", Chinese Journal of Cancer Biotherapy, vol. 24, No. 4, pp. 436-441, Apr. 2017.

Office Action and Search Report dated Jan. 19, 2023 with English translation in respect of Chinese Application No. 2019800726813.

European Patent Office Communication under Rule 71(3) EPC dated Feb. 21, 2023 in respect of European Application No. EP19812602.1.

Joung et al., "TALENs: a widely applicable technology for targeted genome editing", Nat Rev Mol Cell Biol 2013, 14(1): pp. 49-55.

Sachdeva et al., "Granulocyte-macrophage colony-stimulating factor inactivation in CAR T-Cells prevents monocyte-dependent release of key cytokine release syndrome mediators", Journal of Biological Chemistry 2019, vol. 294, No. 14, pp. 5430-5437.

Santomasso et al., "Clinical and Biologic Correlates of Neurotoxicity Associated with Car T Cell Therapy in Patients with B-cell Acute Lymphoblastic Leukemia (B-All)", Cancer Discov. 2018, 8(8): pp. 958-971.

Sterner et al., "GM-CSF inhibition reduces cytokine release syndrome and neuroinflammation but enhances CAR-T cell function in xenografts", Blood 2018, vol. 133, Iss. 7, pp. 697-709.

Taraseviciute et al., "Chimeric Antigen Receptor T Cell-Mediated Neurotoxicity in Nonhuman Primates", Cancer Discovery 2018, vol. 8, No. 6,, pp. 750-763.

International Search Report dated Feb. 21, 2020 from corresponding International Patent Application No. PCT/US2019/059275.

EPO Communication pursuant to Rule 70(2) and 70a(2) dated Apr. 26, 2022 in respect of EP Application No. EP19812602.1.

EPO Communication pursuant to Rule 70(2) and 70a(2) dated Apr. 26, 2022 in respect of EP Application No. EP19880756.2.

Office Action (2nd OA) and Search Report dated Jun. 6, 2022 with English translation in respect of Russian Patent Application No. 2020142342.

Wada, H et al.; "T cell functions in granulocyte/macrophage colony-stimulating factor deficient mice"; Proc. Natl. Acad. Sci. USA, 1997, vol. 94, pp. 12557-12561.

Office Action dated May 27, 2023 and English translation in respect of Japanese Patent Application No. 2020-566666.

Office Action dated Aug. 10, 2023 and English translation in respect of Chinese Patent Application No. 201980046671.2.

Office Action dated Sep. 26, 2023 and English translation in respect of Chinese Patent Application No. 201980072681.3.

Office Action dated Sep. 26, 2023 and English translation in respect of Japanese Application No. 2021-548569.

Office Action dated Oct. 9, 2023 in respect of EP Patent Application No. 19 880 756.2.

Office Action dated Oct. 17, 2023 and English translation in respect of Brazilian Application No. BR112020024501-8.

Notice of Allowance dated Dec. 5, 2023 and English translation in respect of Japanese Patent Application No. 2020-566666.

Notice of Allowance dated Dec. 14, 2023 and English translation in respect of Chinese Patent Application No. 201980072681.3.

(56)                    References Cited

OTHER PUBLICATIONS

International Preliminary Report on Patentability dated Oct. 5, 2023 in respect of International Patent Application No. PCT/US2022/020459.

Cox et al., "Improved Anti-Tumor Response of Chimeric Antigen Receptor T Cell (CART) Therapy after GM-CSF Inhibition is Mechanistically Supported by a Novel Direct Interaction of GM-CSF with Activated Carts", *Blood* 2019, vol. 134, No. Suppl. 1, 3868.

Sterner et al., GM-CSF Blockade during Chimeric Antigen Receptor T Cell Therapy Reduces Cytokine Release syndrome and Neurotoxicity and May Enhance Their Effector Functions, *Blood* 2018, vol. 132, No. Suppl. 1: 961.

Sterner et al., "Using CRISPR/Cas9 to Knock Out GM-CSF in CART-T Cells", *Journal of Visualized Experiments* 2019, vol. 149, E59629.

Sterner et al., "GM-CSF inhibition reduces cytokine release syndrome and neuroinflammation but enhances CAR-T cell function in xenografts", Blood 2019, vol. 133, No. 7, pp. 697-709.

International Search Report dated Oct. 22, 2019 in respect of PCT Int'l Application No. PCT/US2019/034900.

International Preliminary Report on Patentability dated Dec. 10, 2020 in respect of PCT Int'l Application No. PCT/US19/034900.

International Preliminary Report on Patentability dated Apr. 27, 2021 from corresponding International Patent Application No. PCT/US2019/059275.

Office Action dated Mar. 10, 2022 with English translation in respect of Chinese Patent Application No. 2019800726813.

European Search Report dated Apr. 7, 2022 from corresponding EP Application No. 19 81 2602.1.

European Search Report dated Apr. 8, 2022 from corresponding EP Application No. 19 88 0756.2.

International Search Report and Written Opinion dated Jun. 27, 2022 in respect of Application No. PCT/US2022/020459.

Notice of Allowance/Acceptance dated Nov. 15, 2022 with English translation in respect of Russian Application No. 2020142342.

International Preliminary Report on Patentability dated May 14, 2021 in respect of International Patent Application No. PCT/US2019/059275.

Office Action dated Jan. 10, 2022 in respect of Russian Patent Application No. 2020142342.

Academic Press Dictionary of Science and Technology (definition for the term "polyclonal"; Oxford: Elsevier Science & Technology (1996); retrieved Oct. 22, 2008, from http://www.credoreference.com/entry/3144515/.

Acsadi et al., "Direct gene transfer and expression into rat heart in vivo," New Biol., 3(1):71-81, Jan. 1991.

Adachi et al., "Aberrant transcription caused by the insertion of an early transposable element in an intron of the Fas antigen gene of lpr mice," Proc Natl Acad Sci USA., 90(5):1756-1760, Mar. 1, 1993.

Adachi et al., "Enhanced and accelerated lymphoproliferation in Fas-null mice," Proc Natl Acad Sci USA., 93(5):2131-2136, Mar. 5, 1996.

Adada et al., "Favorable Modulation of Chimeric Antigen Receptor T Cells Safety and Efficacy by the Non-Covalent BTK Inhibitor Vecabrutinib," Abstract, Presented at Proceedings of the American Society of Hematology Annual Meeting & Exposition, Dec. 11-14, 2021, Atlanta, GA, USA, Blood, Nov. 2021, 138(Supplement 1):906.

Adusumilli et al., "Regional delivery of mesothelin-targeted CAR T cell therapy generates potent and long-lasting CD4-dependent tumor immunity," Sci. Transl. Med., Nov. 5, 2014, 6(261):261ra151.

Afonina et al., "Cytotoxic and non-cytotoxic roles of the CTL/NK protease granzyme B," Immunol Rev., 235(1):105-116, May 2010.

Agace et al., "T-lymphocyte-epithelial-cell interactions: integrin αE(CD103)β7, LEEP-CAM and chemokines," Curr. Opin. Cell Biology, Oct. 1, 2000, 12(5):563-568.

Agarwal et al., "In vivo generated human CAR T cells eradicate tumor cells," Oncoimmunology, Oct. 10, 2019, 8(12):E1671761, 7 pages.

Agata et al., "Expression of the PD-1 antigen on the surface of stimulated mouse T and B lymphocytes, " Int Immunol., 8(5):765-772, May 1996.

Ahmadzadeh et al., "Tumor antigen-specific CD8 T cells infiltrating the tumor express high levels of PD-1 and are functionally impaired, " Blood, 114(8):1537-1544, May 7, 2009.

Ahonen et al., "Combined TLR and CD40 triggering induces potent CD8+ T cell expansion with variable dependence on type I Ifn," J Exp Med., 199(6):775-784, Mar. 8, 2004.

Akalu et al., "TAM receptor tyrosine kinases as emerging targets of innate immune checkpoint blockade for cancer therapy," Immunol. Rev., Mar. 2017, 276(1):165-177.

Akira et al., "Toll-like receptor signalling," Nat. Rev. Immunol., Jul. 2004, 4(7):499-511.

Alderson et al., "Molecular and biological characterization of human 4-1BB and its ligand," Eur J Immunol., 24(9):2219-2227, Sep. 1994.

Aldovini et al., "Humoral and cell-mediated immune responses to live recombinant BCG- HIV vaccines," Nature, 351(6326):479-482, Jun. 6, 1991.

Ali et al., "Tumor-Derived Extracellular Vesicles Impair CD171-Specific CD4+ Car T Cell Efficacy," Front. Immunol., Mar. 2020, 11:531.

Alizadeh et al., "Chemotherapeutic targeting of cancer-induced immunosuppressive cells," Cancer Res., 74(10):2663-2668, May 15, 2014.

Allie et al., "Programmed death 1 regulates development of central memory CD8 T cells after acute viral infection," J Immunol., 186(11):6280-6286, Apr. 27, 2011.

Altin et al., "The role of CD45 and CD45-associated molecules in T cell activation," Immunol. Cell Biology, 75(5):430-445, Oct. 1997.

Altschul et al., "Gapped BLAST and PSI-BLAST: a new generation of protein database search programs," Nucleic Acids Research, Sep. 1, 1997, 25(17):3389-3402.

Ambrosini et al., "A novel anti-apoptosis gene, survivin, expressed in cancer and lymphoma," Nat Med., 3(8):917-921, Aug. 1997.

An et al., "Anti-Multiple Myeloma Activity of Nanobody-Based Anti-CD38 Chimeric Antigen Receptor T Cells," Mol. Pharmaceutics, Sep. 5, 2018, 15(10):4577-4588.

Anders et al., "HTSeq-a Python framework to work with high-throughput sequencing data," Bioinformatics, 31(2):166-169, Jan. 15, 2015.

Anderson, "Human gene therapy," Science, 256(5058):808-813, May 8, 1992.

Andorsky et al., "Programmed death ligand 1 is expressed by non-hodgkin lymphomas and inhibits the activity of tumor-associated T cells," Clin Cancer Res., 17(13):4232-4244, May 3, 2011.

Anikeeva et al., "Distinct role of lymphocyte function-associated antigen-1 in mediating effective cytolytic activity by cytotoxic T lymphocytes," Proc Natl Acad Sci USA., 102(18):6437-6442, Apr. 25, 2005.

Ansari et al., "The programmed death-1 (PD-1) pathway regulates autoimmune diabetes in nonobese diabetic (NOD) mice," J Exp Med., 198(1):63-69, Jul. 7, 2003.

Anukam et al., "Augmentation of antimicrobial metronidazole therapy of bacterial vaginosis with oral probiotic Lactobacillus rhamnosus GR-1 and Lactobacillus reuteri RC-14: randomized, double-blind, placebo controlled trial," Microbes Infect., 8(6):1450-1454, Mar. 29, 2006.

Ao et al., "Anti-αFR CAR-engineered NK-92 Cells Display Potent Cytotoxicity Against aFR-positive Ovarian Cancer," J. Immunother., Oct. 2019, 42(8):284-296.

Atsaves et al., "AP-1 Transcription Factors as Regulators of Immune Responses in Cancer," Cancers, Jul. 2019, 11(7):1037.

Attwood et al., "Genomics. The Babel of bioinformatics," Science, 290(5491):471-473, Oct. 20, 2000.

Axelrod et al., "AXL Is a Putative Tumor Suppressor and Dormancy Regulator in Prostate Cancer," Mol. Cancer Res., Feb. 2019, 17(2):356-369.

Azuma et al., "B7-H1 is a ubiquitous antiapoptotic receptor on cancer cells," Blood., 111(7):3635-3643, Jan. 25, 2008.

(56)        References Cited

OTHER PUBLICATIONS

Baek et al., "In vitro migration capacity of human adipose tissue-derived mesenchymal stem cells reflects their expression of receptors for chemokines and growth factors," Exp. Mol. Medicine, Oct. 2011, 43(10):596-603.

Baitsch et al., "Exhaustion of tumor-specific CD8+ T cells in metastases from melanoma patients," J Clin Invest., 121(6):2350-2360, May 9, 2011.

Bajorath et al., "Molecular modeling of CD28 and three-dimensional analysis of residue conservation in the CD28/CD152 family," J Mol Graph Model., 15(2):135-139, 108-111, Apr. 1997.

Baldrick, "Pharmaceutical excipient development: the need for preclinical guidance," Regul Toxicol Pharmacol., 32(2):210-218, Oct. 2000.

Balkhi et al., "YY1 Upregulates Checkpoint Receptors and Downregulates Type I Cytokines in Exhausted, Chronically Stimulated Human T Cells," iScience, Apr. 2018, 2:105-122.

Banáth et al., "Residual gammaH2AX foci as an indication of lethal DNA lesions," BMC Cancer., 10:4, Jan. 5, 2010.

Barbarino et al., "Functional role of Bruton's tyrosine kinase inhibitor therapy in the tumor microenvironment of B-cell malignancies," Oncol Res Treat, Oct. 2019, 42(suppl 4):220-221, 5 pages (Abstract Only).

Barber et al., "Restoring function in exhausted CD8 T cells during chronic viral infection," Nature, 439(7077):682-687, Dec. 28, 2005.

Barlic et al., "IL-15 and IL-2 oppositely regulate expression of the chemokine receptor CX3CR1," Blood, 102(10):3494-3503, Nov. 15, 2003.

BD PharmingenTM Technical Data Sheet, "Purified Rat Anti-Mouse Ly-6G (Gr-1) Monoclonal Antibody for Immunohistochemistry (IHC)" 1 page, 2003.

Belov et al., "Extensive surface protein profiles of extracellular vesicles from cancer cells may provide diagnostic signatures from blood samples," J. Extracell. Vesicles, Apr. 15, 2016, 5:25355, 12 pages.

Bender et al., "Receptor-Targeted Nipah Virus Glycoproteins Improve Cell-Type Selective Gene Delivery and Reveal a Preference for Membrane-Proximal Cell Attachment," PLOS Pathogens, Jun. 9, 2016, 12(6):E1005641, 28 pages.

Benita et al., "Characterization of drug-loaded poly(d,l-lactide) microspheres," J Pharm Sci., 73(12):1721-1724, Dec. 1984.

Benlalam et al., "Comprehensive analysis of the frequency of recognition of melanoma-associated antigen (MAA) by CD8 melanoma infiltrating lymphocytes (TIL) implications for immunotherapy," Eur J Immunol., 31(7):2007-2015, Jul. 31, 2001.

Bennardo et al., "Alternative-NHEJ is a mechanistically distinct pathway of mammalian chromosome break repair," PLoS Genet., 4(6):e1000110, Jun. 27, 2008.

Berman et al., "The Protein Data Bank," Nucleic Acids Res., 28(1):235-242, Jan. 1, 2000.

Berrien-Elliott et al., "Durable adoptive immunotherapy for leukemia produced by manipulation of multiple regulatory pathways of CD8+ T-cell tolerance," Cancer Res., 73(2):605-616, Jan. 15, 2013.

Berthon et al., "In acute myeloid leukemia, B7-H1 (PD-L1) protection of blasts from cytotoxic T cells is induced by TLR ligands and interferon-gamma and can be reversed using MEK inhibitors," Cancer Immunol Immunother., 59(12):1839-1849, Sep. 4, 2010.

Betts et al., "Sensitive and viable identification of antigen-specific CD8+ T cells by a flow cytometric assay for degranulation," J Immunol Methods, 281(1-2):65-78, Oct. 1, 2003.

Beyersdorf et al., "CD28 co-stimulation in T-cell homeostasis: a recent perspective," Immunotargets Therapy, May 2015, 4:111-122.

Bezu et al., "Combinatorial strategies for the induction of immunogenic cell death," Front Immunol., 6:187, Apr. 24, 2015, 11 pages.

Bibikova et al., "Enhancing gene targeting with designed zinc finger nucleases," Science, May 2, 2003, 300(5620):764.

Bielamowicz et al., "Trivalent Car T cells overcome interpatient antigenic variability in glioblastoma," Neuro Oncol., Mar. 2018, 20(4):506-518.

Bird et al., "Single-chain antigen-binding proteins," Science, 242(4877):423-426, Oct. 21, 1988.

Bitinaite et al., "FokI dimerization is required for DNA cleavage," Proc. Natl. Acad. Sci. USA, Sep. 1, 1998, 95(18):10570-10575.

Black et al., "Activation of the PD-1/PD-L1 immune checkpoint confers tumor cell chemoresistance associated with increased metastasis," Oncotarget, 7(9):10557-10567, Mar. 2016.

Blank et al., "Blockade of PD-L1 (B7-H1) augments human tumor-specific T cell responses in vitro," Int J Cancer, 119(2):317-327, Jul. 15, 2006.

Blank et al., "Interaction of PD-L1 on tumor cells with PD-1 on tumor-specific T cells as a mechanism of immune evasion: implications for tumor immunotherapy," Cancer Immunol Immunother., 54(4):307-314, Dec. 15, 2004.

Blank et al., "PD-L1/B7H-1 inhibits the effector phase of tumor rejection by T cell receptor (TCR) transgenic CD8+ T cells," Cancer Res., 64(3):1140-1145, Feb. 1, 2004.

Blat et al., "Suppression of Murine Colitis and its Associated Cancer by Carcinoembryonic Antigen-Specific Regulatory T Cells," Mol. Therapy, May 2014, 22(5):1018-1028.

Blazar et al., "Infusion of anti-B7.1 (CD80) and anti-B7.2 (CD86) monoclonal antibodies inhibits murine graft-versus-host disease lethality in part via direct effects on CD4+ and CD8+ T cells," J Immunol., 157(8):3250-3259, Oct. 15, 1996.

Block, "Medicated Applications," Remington's Pharmaceutical Sciences, 18th edition, Mack Publishing Company, Easton, PA, Chpt 87, pp. 1596-1614, 1990.

Boardman et al., "Expression of a Chimeric Antigen Receptor Specific for Donor HLA Class I Enhances the Potency of Human Regulatory T Cells in Preventing Human Skin Transplant Rejection," Am. J. Transplantation, Feb. 2017, 17(4):931-943.

Bodine, "mTOR signaling and the molecular adaptation to resistance exercise," Med Sci Sports Exerc., 38(11):1950-1957, Nov. 2006.

Boggio et al., "Interleukin 12-mediated prevention of spontaneous mammary adenocarcinomas in two lines of Her-2/neu transgenic mice," J Exp Med., 188(3):589-596, Aug. 3, 1998.

Boise et al., "CD28 costimulation can promote T cell survival by enhancing the expression of Bcl-XL," Immunity, 3(1):87-98, Jul. 1995.

Boletta et al., "High efficient non-viral gene delivery to the rat kidney by novel polycationic vectors," J Am Soc Nephrol., 7(9):1728, abstr A2409, Sep. 1, 1996.

Bolger et al., "Trimmomatic: a flexible trimmer for Illumina sequence data," Bioinformatics, 30(15):2114-2120, Aug. 1, 2014.

Bona et al., "Immune response: Idiotype anti-idiotype network," CRC Crit Rev Immunol., 33-81, Mar. 1981.

Bonfoco et al., "Inducible nonlymphoid expression of Fas ligand is responsible for superantigen-induced peripheral deletion of T cells," Immunity, 9(5):711-720, Nov. 1998.

Bonifaz et al., "Efficient targeting of protein antigen to the dendritic cell receptor DEC-205 in the steady state leads to antigen presentation on major histocompatibility complex class I products and peripheral CD8+ T cell tolerance," J Exp Med., 196(12):1627-1638, Dec. 16, 2002.

Bonifaz et al., "In vivo targeting of antigens to maturing dendritic cells via the DEC-205 receptor improves T cell vaccination, " J Exp Med., 199(6):815-824, Mar. 15, 2004.

Bonni et al., "Cell survival promoted by the Ras-MAPK signaling pathway by transcription- dependent and -independent mechanisms," Science, 286(5443):1358-1362, Nov. 12, 1999.

Boon et al., "Human T cell responses against melanoma," Annu Rev Immunol., 24:175-208, 2006.

Boroughs et al., "Chimeric antigen receptor costimulation domains modulate human regulatory T cell function," JCI Insight, Mar. 2019, 5(8):e126194, 19 pages.

Borson et al., "Brain-infiltrating cytolytic T lymphocytes specific for Theiler's virus recognize H2Db molecules complexed with a viral VP2 peptide lacking a consensus anchor residue," J Virol., 71(7):5244-5250, Jul. 1997.

Bottcher et al., "Functional classification of memory CD8(+) T cells by CX3CR1 expression," Nat Commun., 6:8306, Sep. 25, 2015.

(56)          References Cited

OTHER PUBLICATIONS

Bouillet et al., "CD95, BIM and T cell homeostasis," Nat Rev Immunol., 9(7):514-519, Jul. 2009.
Bowie et al., "Deciphering the message in protein sequences: tolerance to amino acid substitutions," Science, 247(4948):1306-1310, Mar. 16, 1990.
Boyiadzis et al., "The emerging roles of tumor-derived exosomes in hematological malignancies," Leukemia, Mar. 21, 2017, 31(6):1259-1268.
Boysen et al., "Dynamics of microvesicle generation in B-cell chronic lymphocytic leukemia: implication in disease progression," Leukemia, 31(2):350-360, Aug. 2, 2016.
Brahmer et al., "Safety and activity of anti-PD-L1 antibody in patients with advanced cancer," N Engl J Med., 366(26):2455-2465, Jun. 2, 2012.
Brand et al., "Collagen-induced arthritis," Nat. Protoc., 2(5):1269-1275, May 17, 2007.
Braquet et al., "Effect of endothelin-1 on blood pressure and bronchopulmonary system of the guinea pig," J Cardiovasc Pharmacol., 13(Suppl 5):S143-146, discussion S150, 1989.
Brentjens et al., "Safety and persistence of adoptively transferred autologous CD19-targeted T cells in patients with relapsed or chemotherapy refractory B-cell leukemias," Blood, Nov. 2011, 118(18):4817-4828.
Brinkman et al., "Easy quantitative assessment of genome editing by sequence trace decomposition," Nucleic Acids Res., Dec. 2014, 42(22):e168.
Brinkmann et al., "FTY720: altered lymphocyte traffic results in allograft protection," Transplantation., 72(5):764-769, Sep. 15, 2001.
Britton et al., "Leprosy," Lancet, 363(9416):1209-1219, Apr. 10, 2004.
Brooks, "Translational genomics: the challenge of developing cancer biomarkers," Genome Res., 22(2):183-187, Feb. 2012.
Brown et al., "A mass spectrometry-based assay for improved quantitative measurements of efflux pump inhibition," PLoS One, 10(5):e0124814, May 11, 2015, 12 pages.
Brown et al., "Blockade of programmed death-1 ligands on dendritic cells enhances T cell activation and cytokine production.," J Immunol., 170(3):1257-1266, Feb. 1, 2003.
Brown et al., "CAR T cell therapy: inroads to response and resistance," Nat. Rev. Immunology, 19(2):73-74, Jan. 10, 2019.
Brozovic et al., "Activation of mitogen-activated protein kinases by cisplatin and their role in cisplatin-resistance," Cancer Lett., 251(1):1-16, Nov. 27, 2006.
Bu et al., "Learning from PD-1 Resistance: New Combination Strategies, " Trends Mol Med., 22(6):448-451, Jun. 2016.
Bubenik, "Genetically engineered dendritic cell-based cancer vaccines (Review)," Int J Oncol., 18(3):475-478, Mar. 2001.
Buchholz et al., "Surface-Engineered Viral Vectors for Selective and Cell Type-Specific Gene Delivery," Trends in Biotechnology, Dec. 2015, 33(12):777-790.
Burmer et al., "Frequency and spectrum of c-Ki-ras mutations in human sporadic colon carcinoma, carcinomas arising in ulcerative colitis, and pancreatic adenocarcinoma," Environ Health Perspect., 93:27-31, Jun. 1991.
Businesswire.com [online], "Incyte Reports Third Quarter 2011 Financial Results and Provides Update on Key Clinical Programs," Oct. 27, 2011, retrieved on Mar. 24, 2021, retrieved from URL<https://www.businesswire.com/news/home/20111027005220/en/Incyte-Reports-Third-Quarter-2011-Financial-Results-and-Provides-Update-on-Key-Clinical-Programs>, 4 pages.
Buskens et al., "Adenocarcinomas of the gastro-esophageal junction: A comparative study of the gastric cardia and the esophagus with respect to cyclooxygenase-2 expression," Digestive Disease Week Abstracts and Itinerary Planner, abstract No. 850, 2003.
Butte et al., "Interaction of human PD-L1 and B7-1," Mol Immunol., 45(13):3567-3572, Jun. 27, 2008.
Butte et al., "PD-L1 interacts specifically with B7-1 to inhibit T cell proliferation," Immunity., 27:111-122, 2007.

Cairns et al., "Immortalization of multipotent growth-factor dependent hemopoietic progenitors from mice transgenic for GATA-1 driven SV40 tsA58 gene," EMBO J., 13(19):4577-4586, Oct. 3, 1994.
Caivano et al., "Extracellular Vesicles in Hematological Malignancies: From Biology to Therapy," Int. J. Mol. Sciences, Jun. 2, 2017, 18(6):1183, 23 pages.
Cannons et al., "4-1BB ligand induces cell division, sustains survival, and enhances effector function of CD4 and CD8 T cells with similar efficacy," J Immunol., 167(3):1313-1324, Aug. 1, 2001.
Cao et al., "B7-H1 overexpression regulates epithelial-mesenchymal transition and accelerates carcinogenesis in skin," Cancer Res., 71(4):1235-1243, Dec. 15, 2010.
Carey et al., "IL-4 protects the B-cell lymphoma cell line CH31 from anti-IgM-induced growth arrest and apoptosis: contribution of the PI-3 kinase/AKT pathway," Cell Res., Nov. 2007, 17(11):942-955.
Carreno et al., "The B7 family of ligands and its receptors: new pathways for costimulation and inhibition of immune responses," Annu Rev Immunol., 20:29-53, Oct. 4, 2001.
Carter et al., "PD-1:PD-L inhibitory pathway affects both CD4(+) and CD8(+) T cells and is overcome by IL-2," Eur J Immunol., 32(3):634-643, Mar. 2002.
Carter et al., "Humanization of an anti-p185HER2 antibody for human cancer therapy," Proc Natl Acad Sci USA., 89(10):4285-4289, May 15, 1992.
Caruso et al., "Tuning Sensitivity of CAR to EGFR Density Limits Recognition of Normal Tissue While Maintaining Potent Antitumor Activity," Cancer Res., Aug. 2015, 75(17):3505-3518.
CAS No. 1433820-83-7, "GNE-431 ," MOLBASE, retrieved on May 8, 2025, retrieved from URL<https://www.molbase.com/moldata/33940169.html#>, 2 pages.
CAS No. 1434048-34-6, "Fenebrutinib," MOLBASE, retrieved on May 8, 2025, retrieved from URL<https://www.molbase.com/moldata/33927924.html#>, 2 pages.
CAS No. 1510829-06-7, "Vecabrutinib," MOLBASE, retrieved on May 8, 2025, retrieved from URL<https://www.molbase.com/moldata/33928126.html#>, 2 pages.
CAS No. 2031152-08-4, "XMU-MP-3," Sigma Aldrich, retrieved on May 8, 2025, retrieved from URL<https://www.sigmaaldrich.com/US/en/product/aablocksinc/aabh9a2242df?context=bbe>, 3 pages.
CAS No. 2095393-15-8, "ARQ-531," MOLBASE, retrieved on May 8, 2025, retrieved from URL<https://www.molbase.com/moldata/33928988.html>, 2 pages.
CAS No. 2101700-15-4, "Pirtobrutinib," Sigma Aldrich, retrieved on May 8, 2025, retrieved from URL<https://www.sigmaaldrich.com/US/en/product/ambeedinc/ambh97f0446b?context=bbe>, 3 pages.
Catalano et al., "Inhibiting extracellular vesicles formation and release: a review of EV inhibitors," J. Extracell. Vesicles, 9(1):1703244, Dec. 19, 2019, 22 pages.
Chakrabarti et al., "Vaccinia virus expression vector: coexpression of beta-galactosidase provides visual screening of recombinant virus plaques," Mol Cell Biol., 5(12):3403-3409, Dec. 1985.
Chambers et al., "Co-stimulation in T cell responses," Curr Opin Immunol., 9(3):396-404, Jun. 1997.
Champiat et al., "Hyperprogressive Disease Is a New Pattern of Progression in Cancer Patients Treated by Anti-PD-1/PD-L1," Clin Cancer Res., 23(8):1920-1928, Apr. 15, 2017.
Chan et al., "Arthritis and Tenosynovitis Associated With the Anti-PDI Antibody Pembrolizumab in Metastatic Melanoma," J. Immunother., 38(1):37-39, Jan. 2015.
Chan et al., "Autophosphorylation of the DNA-dependent protein kinase catalytic subunit is required for rejoining of DNA double-strand breaks," Genes Dev., 16(18):2333-2338, Sep. 15, 2002.
Chapoval et al., "B7-H3: A costimulatory molecule for T cell activation and IFN-y production," Nat Immunol., 2(3):269-274, Mar. 2001.
Charman, "Lipids, lipophilic drugs, and oral drug delivery-some emerging concepts," J. Pharm. Sci., 89(8):967-978, Aug. 2000.
Charvet et al., "Vav1 promotes T cell cycle progression by linking TCR/CD28 costimulation to FOXO1 and p27kipl expression," J. Immunology, Oct. 2006, 177(8):5024-5031.

(56) References Cited

OTHER PUBLICATIONS

Chaurand et al., "Peptide and Protein Identification by Matrix-Assisted Laser Desorption Ionization (MALDI) and MALDI-Post-Source Decay Time-of-Flight Mass Spectrometry," J Am Soc Mass Spectrom., 10(2):91-103, Feb. 1999.

Chen et al., "Anti-PD-1/PD-L1 therapy of human cancer: past, present, and future," J. Clin. Investigation, 125(9):3384-3391, Sep. 2015.

Chen et al., "CD44-deficient mice exhibit enhanced hepatitis after concanavalin A injection: evidence for involvement of CD44 in activation-induced cell death," J Immunol., 166(10):5889-5897, May 1, 2001.

Chen et al., "Costimulation of antitumor immunity by the B7 counterreceptor of the T lymphocyte molecules CD28 and CTLA-4," Cell, 71(7):1093-1102, Dec. 24, 1992.

Chen et al., "Development of a sandwich ELISA for evaluating soluble PD-L1 (CD274) in human sera of different ages as well as supematants of PD-L1+ cell lines," Cytokine, 56(2):231-238, Nov. 2011.

Chen et al., "Molecular Pathways: Next-Generation Immunotherapy—Inhibiting Programmed Death-Ligand 1 and Programmed Death-1," Clin. Cancer Research, 18(24):6580-6587, Oct. 19, 2012.

Chen et al., "PD-L1 Expression Promotes Epithelial to Mesenchymal Transition in Human Esophageal Cancer," Cell Physiol. Biochemistry, 42(6):2267-2280, Aug. 17, 2017.

Chen et al., "Tumor immunogenicity determines the effect of co-stimulation by B7 on T-cell mediated tumor immunity," J Exp Med., 179(2):523-532, Feb. 1, 1994.

Chen et al., "Upregulation of PD-L1 by EGFR Activation Mediates the Immune Escape in EGFR-Driven NSCLC: Implication for Optional Immune Targeted Therapy for NSCLC Patients with EGFR Mutation," J. Thorac. Oncology, 10(6):910-923, Jun. 2015.

Chen, "Co-inhibitory molecules of the B7-CD28 family in the control of T-cell immunity," Nat Rev Immunol., 4(5):336-347, May 2004.

Cheng et al., "The influence of fibroblast growth factor 2 on the senescence of human adipose-derived mesenchymal stem cells during long-term culture," Stem Cells Transl. Medicine, Dec. 2019, 9(4):518-530.

Cheville et al., "Comparisons of outcome and prognostic features among histologic subtypes of renal cell carcinoma," Am J Surg Pathol., 27(5):612-624, May 2003.

Chi et al., "Significantly increased anti-tumor activity of carcinoembryonic antigen-specific chimeric antigen receptor T cells in combination with recombinant human IL-12," Cancer Medicine, Jun. 25, 2019, 8(10):4753-4765.

Cho et al., "Targeted genome engineering in human cells with the Cas9 RNA-guided endonuclease," Nat. Biotechnology, 31(3):230-232, Jan. 29, 2013.

Choi et al., "Genomic Organization and expression Analysis of B7-H4, an Immune Inhibitory Molecule of the B7 Family," J Immunol., 171(9):4650-4654, Nov. 1, 2003.

Chowdhury et al., "Programmed death-ligand 1 overexpression is a prognostic marker for aggressive papillary thyroid cancer and its variants," Oncotarget, 7(22):32318-32328, May 31, 2016.

Chu et al., "CS1-specific chimeric antigen receptor (CAR)-engineered natural killer cells enhance in vitro and in vivo antitumor activity against human multiple myeloma," Leukemia, Apr. 2014, 28(4):917-927.

Chung et al., "Seeding Open Innovation Drug Discovery and Translational Collaborations to Leverage Government Funding: A Case Study of Strategic Partnership between Sanford-Burnham and Mayo Clinic," Collaborative Innovation in Drug Discovery: Strategies for Public and Private Partnerships, 27:451-486, Apr. 2014.

ClinicalTrials.gov [online], "A Clinical Research of CAR T Cells Targeting EpCAM Positive Cancer (CARTEPC)," NCT03013712, Jan. 2017, last updated Jan. 2017, retrieved from URL<https://www.clinicaltrials.gov/study/NCT03013712>, 9 pages.

ClinicalTrials.gov [online], "First-in-human Study of Oral TP-0903 (a Novel Inhibitor of AXL Kinase) in Patients With Advanced Solid Tumors," NCT02729298, last updated Jan. 25, 2021, retrieved on Apr. 23, 2021, retrieved from URL<https://www.clinicaltrials.gov/ct2/show/NCT02729298>, 24 pages.

ClinicalTrials.gov [online], "Phase 1/2 Study of TP-0903 (an Inhibitor of AXL Kinase) in Patients With Previously Treated CLL," NCT03572634, last updated Feb. 2, 2021, retrieved on Apr. 23, 2021, retrieved from URL<https://clinicaltrials.gov/ct2/show/NCT03572634>, 34 pages.

ClinicalTrials.gov [online], "Safety, PK, PD, and Antitumor Activity of Vecabrutinib (SNS-062) in B Lymphoid Cancers," NCT03037645, last updated Oct. 19, 2020, retrieved on Jan. 5, 2022, retrieved from URL<https://clinicaltrials.gov/ct2/show/NCT03037645>, 21 pages.

Cocuzza et al., "[Importance and evaluation of red cell indices obtained with semi-automatic cell counters during the screening of heterozygote beta-thalassemia]," Minerva Med, 74(18):1017-1020, Apr. 28, 1983 (with Machine English Abstract).

Cogoni et al., "Gene silencing in Neurospora crassa requires a protein homologous to RNA-dependent RNA polymerase," Nature, 399(6732):166-169, May 13, 1999.

Cogoni et al., "Transgene silencing of the al-1 gene in vegetative cells of Neurospora is mediated by a cytoplasmic effector and does not depend on DNA-DNA interactions or DNA methylation," EMBO J., 15(12):3153-3163, Jun. 17, 1996.

Cohen et al., "B cell maturation antigen-specific CAR T cells are clinically active in multiple myeloma," J. Clin. Investigation, Mar. 21, 2019, 129(6):2210-2221.

Cohen et al., "Lpr and gld: Single Gene Models of Systemic Autoimmunity and Lymphoproliferative Disease," Annu Rev Immunol., 9:243-269, 1991.

Colado et al., "Effect of the BTK inhibitor ibrutinib on macrophage- and gammadelta T cell-mediated response against *Mycobacterium tuberculosism*" Blood Cancer Journal, Nov. 5, 2018, 8(11):100, 6 pages.

Cole et al., "The EBV-hybridoma technique and its application to human lung cancer," Monoclonal Antibodies and Cancer Therapy, 27:77-96, Jan./Feb. 1985.

Collins et al., "The B7 family of immune-regulatory ligands," Genome Biol., 6(6):223, May 31, 2005, 7 pages.

Collis et al., "The life and death of DNA-PK," Oncogene., 24(6):949-961, Feb. 3, 2005.

Conacci-Sorrell et al., "Autoregulation of E-cadherin expression by cadherin-cadherin interactions: the roles of beta-catenin signaling, Slug, and MAPK," J Cell Biol., 163(4):847-857, Nov. 17, 2003.

Cone et al., "High-efficiency gene transfer into mammalian cells: generation of helper-free recombinant retrovirus with broad mammalian host range," Proc Natl Acad Sci USA., 81(20):6349-6353, Oct. 1984.

Cong et al., "Multiplex genome engineering using CRISPR/Cas systems," Science, 339(6121):819-823, Jan. 3, 2013.

Connolly, "Analytical molecular surface calculation," J Appl Crystallogr., 16(5):548-558, Oct. 1, 1983.

Cooley et al., "Trans-presentation of IL-15 modulates STAT5 activation and Bcl-6 expression in THl cells," Sci Rep, 5:15722, Oct. 26, 2015, 9 pages.

Corcoran et al., "Docetaxel-Resistance in Prostate Cancer: Evaluating Associated Phenotypic Changes and Potential for Resistance Transfer via Exosomes," PLoS One, Dec. 10, 2012, 7(12):e50999, 12 pages.

Corpet, "Multiple sequence alignment with hierarchical clustering," Nucleic Acids Res., 16(22):10881-10890, Nov. 25, 1988.

Cote et al., "Generation of human monoclonal antibodies reactive with cellular antigens," Proc Natl Acad Sci USA., 80(7):2026-2030, Apr. 1983.

Coumans et al., "Methodological Guidelines to Study Extracellular Vesicles," Circ. Research, 120(10):1632-1648, May 12, 2017.

Cox et al., "GM-CSF disruption in CART cells modulates T cell activation and enhances CART cell anti-tumor activity," Leukemia, 36:1635-1645, Apr. 19, 2022.

Cox et al., "Leukemic extracellular vesicles induce chimeric antigen receptor T cell dysfunction in chronic lymphocytic leukemia," Mol. Therapy, Jan. 2021, 29(4):1529-1540.

(56) References Cited

OTHER PUBLICATIONS

Coyle et al., "The expanding B7 superfamily: increasing complexity in costimulatory signals regulating T cell function," Nat Immunol., 2(3):203-209, Mar. 2001.

Crispe et al., "The liver as a site of T-cell apoptosis: graveyard, or killing field?" Immunol Rev., 174:47-62, Apr. 2000.

Crispe, "Hepatic T cells and liver tolerance," Nat Rev Immunol., 3(1):51-62, Jan. 2003.

Cristiano et al., "Molecular conjugates: a targeted gene delivery vector for molecular medicine," J Mol Med (Berl)., 73(10):479-486, Oct. 1995.

Crotti et al., "Spotlight on mavrilimumab for the treatment of rheumatoid arthritis: evidence to date," Drug Des. Devel. Ther., Jan. 2017, 11:211-223.

Cruz-Guilloty et al., "Runx3 and T-box proteins cooperate to establish the transcriptional program of effector CTLs," J. Exp. Med., 206(1):51-59, Jan. 16, 2009.

Crystal, "Gene therapy strategies for pulmonary disease" Am J Med., 92(suppl 6A):44S-52S, Jun. 22, 1992.

Curiel et al., "Blockade of B7-H1 improves myeloid dendritic cell-mediated antitumor immunity," Nat Med., 9(5):562-567, Apr. 21, 2003.

Dahlhamer et al., "Prevalence of Inflammatory Bowel Disease Among Adults Aged 18 Years—United States, 2015," MMWR Morb. Mortal. Wkly Report, Oct. 28, 2016, 65(42):1166-1169.

Daly et al., "Clinical Trials Integrating Immunotherapy and Radiation for Non-Small-Cell Lung Cancer," J. Thorac. Oncology, 10(12):1685-1693, Dec. 1, 2015.

Daniele et al., "A role for Rab7 in the movement of secretory granules in cytotoxic T lymphocytes," Traffic, 12(7):902-911, Jul. 2011.

Dao et al., "Involvement of CD1 in peripheral deletion of T lymphocytes is independent of NK T cells," J Immunol., 166(5):3090-3097, Mar. 1, 2001.

Database EM-MUS [Online] EMBL, Accession No. AF142780.1 (version 1), Jun. 1, 1999, 2 pages.

Datta et al., "Akt phosphorylation of BAD couples survival signals to the cell-intrinsic death machinery," Cell., 91(2):231-241, Oct. 17, 1997.

Daud et al., "Tumor immune profiling predicts response to anti-PD-1 therapy in human melanoma," J. Clin. Invest., 126(9):3447-3452, Sep. 1, 2016.

Davidson et al., "Phenotypic, functional, and molecular genetic comparisons of the abnormal lymphoid cells of C3H-lpr/lpr and C3H-gld/gld mice," J Immunol., 136(11):4075-4084, Jun. 1, 1986.

Davidson et al., "Small Molecules, Inhibitors of DNA-PK, Targeting DNA Repair, and Beyond," Front Pharmacol., 4(5):1-7, Jan. 31, 2013.

Davila et al., "Efficacy and toxicity management of 19-28z CAR T cell therapy in B cell acute lymphoblastic leukemia," Sci. Transl. Med., Feb. 2014, 6(224):224ra225.

Davis et al., "Proline 326 in the C terminus of murine CX3CRI prevents G-protein and phosphatidylinositol 3-kinase-dependent stimulation of Akt and extracellular signal-regulated kinase in Chinese hamster ovary cells," J. Pharmacol. Exp. Ther., 316(1):356-363, Jan. 2006.

De StGroth et al., "Production of monoclonal antibodies: strategy and tactics," J Immunol Methods., 35(1-2):1-21, 1980.

Debs et al., "Lung-specific delivery of cytokines induces sustained pulmonary and systemic immunomodulation in rats," J Immunol., 140(10):3482-3488, May 15, 1988.

Del Peso et al., "Interleukin-3-induced phosphorylation of BAD through the protein kinase Akt," Science, 278(5338):687-689, Oct. 24, 1997.

Dezutter-Dambuyan et al., "A novel regulation of PD-1 ligands on mesenchymal stromal cells through MMP-mediated proteolytic cleavage," OncoImmunology, 5(3):e1091146, Mar. 2016, 24 pages.

Dheda et al., "Lung remodeling in tuberculosis," J Infect Dis., 192(7):1201-1209, Aug. 29, 2005.

Dicarlo et al., "Genome engineering in Saccharomyces cerevisiae using CRISPR-Cas systems," Nucleic Acids Research, 41(7):4226-4343, Mar. 4, 2013.

Diehl et al., "In vivo triggering through 4-1BB enables Th-independent priming of CTL in the presence of an intact CD28 costimulatory pathway," J Immunol., 168(8):3755-3762, Apr. 15, 2002.

Dietz et al., "A novel source of viable peripheral blood mononuclear cells from leukoreduction system chambers," Transfusion, Dec. 2006, 46(12):2083-2089.

Dimopoulos et al., "Elotuzumab plus Pomalidomide and Dexamethasone for Multiple Myeloma," N. Engl. J. Medicine, Nov. 8, 2018, 379(19):1811-1822.

Ding et al., "[Human adipose-derived mesenchymal stem cells and inflammatory bowel disease]," Anhui Medical and Pharmaceutical Journal, Apr. 2010, 14(4):378-380 (with English Abstract).

Ding et al., "Release of reactive nitrogen intermediates and reactive oxygen intermediates from mouse peritoneal macrophages. Comparison of activating cytokines and evidence for independent production," J Immunol., 141(7):2407-2412, Oct. 1, 1988.

Dini, "Recognizing death: liver phagocytosis of apoptotic cells," Eur J Histochem., 44(3):217-227, 2000.

Dmitrieva et al., "Bone marrow- and subcutaneous adipose tissue-derived mesenchymal stem cells: differences and similarities," Cell Cycle, Jan. 2012, 11(2):377-383.

Dobin et al., "STAR: ultrafast universal RNA-seq aligner," Bioinformatics, 29(1):15-21, Jan. 2013.

Doering et al., "Network analysis reveals centrally connected genes and pathways involved in CD8+ T cell exhaustion versus memory," Immunity, 37(6):1130-1144, Nov. 15, 2012.

Doan et al., "E-cadherin expression in intestinal epithelium," J. Clin. Pathol., 1995, 48(2):143-146.

Dominici et al., "Minimal criteria for defining multipotent mesenchymal stromal cells. The International Society for Cellular Therapy position statement," Cytotherapy, Feb. 2006, 8(4):315-317.

Dong et al., "A novel method for identifying downstream signals in tumor-reactive T cells following PD-1 engagement and monitoring endogenous tumor immunity and immunotherapy," Journal of Clinical Oncology, 32(15):Abstract3049-3049, 2014.

Dong et al., "B7-H1 determines accumulation and deletion of intrahepatic CD8(+) T lymphocytes," Immunity., 20(3):327-336, Mar. 2004.

Dong et al., "B7-H1 pathway and its role in the evasion of tumor immunity," J Mol Med (Berl)., 81(5):281-287, Apr. 30, 2003.

Dong et al., "B7-H1, a third member of the B7 family, co-stimulates T-cell proliferation and interleukin-10 secretion," Nat Med., 5(12):1365-1369, Dec. 1999.

Dong et al., "Immune regulation by novel costimulatory molecules," Immunol Res., 28(1):39-48, 2003.

Dong et al., "Immunoregulatory role of B7-H1 in chronicity of inflammatory responses," Cell Mol Immunol., 3(3):179-187, Jun. 2006.

Dong et al., "Tumor-associated B7-H1 promotes T-cell apoptosis: A potential mechanism of immune evasion," Nat. Med., 8(8):793-800, Jun. 2002.

Dorronsoro et al., "Human mesenchymal stromal cells modulate T-cell responses through TNF-α-mediated activation of NF-κB," Eur. J. Immunology, Dec. 2013, 44(2):480-488.

Dorronsoro et al., "Intracellular role of IL-6 in mesenchymal stromal cell immunosuppression and proliferation," Sci. Reports, Dec. 2020, 10(1):21853, 12 pages.

Dragoi et al., "DNA-PKcs, but not TLR9, is required for activation of Akt by CpG-DNA," EMBO J., 24(4):779-789, Jan. 27, 2005.

Dronca et al., "BCL-2-interacting mediator of cell death (Bim) is a novel biomarker for response to anti-PD-1 therapy in patients with advanced melanoma," Immunotherapy., 8(12)1351-1353, Dec. 1, 2016.

Dronca et al., "Bim and soluble PD-L1 (sPD-L1) as predictive biomarkers of response to anti-PD-1 therapy in patients with melanoma and lung carcinoma," J Clin Oncol., 35(15suppl):11534, May 30, 2017.

Dronca et al., "Soluble PD-L1 (sPD-L1) is associated with decreased survival in metastatic melanoma ," Abstract, Presented at Proceed-

(56)            References Cited

OTHER PUBLICATIONS ings of Society for Melanoma Research 2015 Congress, San Francisco, CA, Nov. 18-21, 2015, 2 pages.

Dronca et al., "T cell Bim levels reflect responses to anti-PD-1 cancer therapy," JCI Insight, 1(6):e86014, May 5, 2016, 14 pages.

Dubovsky et al., "Ibrutinib treatment ameliorates murine chronic graft-versus-host disease," J. Clin. Invest., Nov. 2014, 124(11):4867-4876.

Dudler et al., "Gene transfer of programmed death Ligand-l.lg prolongs cardiac allograft survival," Transplantation, 82(12):1733-1737, Dec. 27, 2006.

Dunussi-Joannopoulos et al., "Gene therapy with B7.1 and GM-CSF vaccines in a murine AML model," J Pediatr Hematol Oncol., 19(6):536-540, Nov./Dec. 1997.

Durai et al., "Zinc finger nucleases: custom-designed molecular scissors for genome engineering of plant and mammalian cells," Nucleic Acids Research, Oct. 26, 2005, 33(18):5978-5990.

Duraiswamy et al., "Phenotype, function, and gene expression profiles of programmed death-1(hi) CD8 T cells in healthy human adults," J Immunol., 186(7):4200-4212, Apr. 1, 2011.

Duraiswamy et al., "Replenish the source within Rescuing tumor-infiltrating lymphocytes by double checkpoint blockade," Oncol., 2(10):e25912, Oct. 2013, 3 pages.

Ehl et al., "Different susceptibility of cytotoxic T cells to CD95 (Fas/Apo-1) ligand-mediated cell death after activation in vitro versus in vivo," J Immunol., 156(7):2357-2360, Apr. 1, 1996.

Elliott et al., "Mitoxantrone in combination with an inhibitor of DNA-dependent protein kinase: a potential therapy for high risk B-cell chronic lymphocytic leukaemia," Br J Haematol., 152(1):61-71, Nov. 18, 2010.

EMBL-EBI Accession No. AF 142780.2 "Mus musculus butyrophilin-like protein (Btdc) mRNA, complete cds," created Jun. 1, 1999, 2 pages.

EMBL-EBI Accession No. Q9WUL5, "Programmed cell death 1 ligand 2," Nov. 1, 1999, 5 pages.

Engh et al., "Accurate bond and angle parameters for X-ray protein structure refinement," Acta Cryst., A47(4):392-400, Jul. 1, 1991.

English et al., "IFN-γ and TNF-α differentially regulate immunomodulation by murine mesenchymal stem cells," Immunol. Letters, Apr. 2007, 110(2):91-100.

Ennis et al., "Effect of Novel Limited Spectrum MMP Inhibitor XL784 in Abdominal Aortic Aneurysms," J. Cardiovasc. Pharmacol. Ther., 17(4):417-426, Dec. 2012.

Escudier et al., "Treatment Beyond Progression in Patients with Advanced Renal Cell Carcinoma Treated with Nivolumab in CheckMate 025," Eur Urol., 72(3):368-376, Apr. 12, 2017.

Estrada-Capetillo et al., "CD28 is expressed by macrophages with anti-inflammatory potential and limits their T-cell activating capacity," Eur. J. Immunology, Nov. 2020, 51(4):824-834.

Fajgenbaum et al., "Cytokine Storm," N. Engl. J. Med., Dec. 2020, 383(23):2255-2273.

Falkner et al., "pUV I: a new vaccinia virus insertion and expression vector," Nucleic Acids Res., 15(17):7192, Sep. 11, 1987.

Fan et al., "HNS, a nuclear-cytoplasmic shuttling sequence in HuR," Proc. Natl. Acad. Sci. USA, 95(26):15293-15298, Dec. 1998.

Fan et al., "Mesenchymal stem cells alleviate experimental autoimmune cholangitis through immunosuppression and cytoprotective function mediated by galectin-9," Stem Cell Res. Therapy, Sep. 2018, 9(1):237, 12 pages.

Farley et al., "p38 mitogen-activated protein kinase mediates the Fas-induced mitochondrial death pathway in CD8+ T cells," Mol Cell Biol., 26(6):2118-2129, Mar. 2006.

Favre et al., "DOK4 and DOK5: new dok-related genes expressed in human T cells," Genes Immunity, Jan. 16, 2003, 4(1):40-45.

Fechteler et al., "Prediction of protein three-dimensional structures in insertion and deletion regions: a procedure for searching data bases of representative protein fragments using geometric scoring criteria," J Mol Biol., 253(1):114-131, Oct. 13, 1995.

Feng et al., "Identification of a PKB/Akt hydrophobic motif Ser-473 kinase as DNA-dependent protein kinase," J Biol Chem., 279(39):41189-41196, Jul. 15, 2004.

Ferrari et al., "Flow cytometric analysis of circulating dendritic cell subsets and intracellular cytokine production in advanced breast cancer patients," Oncol Rep., 14(1):113-120, Jul. 2005.

Figlin et al., "Treatment of metastatic renal cell carcinoma with nephrectomy, interleukin-2 and cytokine-primed or CD8(+) selected tumor infiltrating lymphocytes from primary tumor," J Urol., 158(3 Pt 1):740-745, Sep. 1997.

Finck et al., "Treatment of Murine Lupus with CTLA4lg," Science, 265(5176):1225-1227, Aug. 26, 1994.

Fire et al., "Potent and specific genetic interference by double-stranded RNA in Caenorhabditis elegans," Nature, 391(6669):806-811, Feb. 19, 1998.

Fitzgerald et al., "Cytokine release syndrome after chimeric antigen receptor T cell therapy for acute lymphoblastic leukemia," Crit. Care Med., Feb. 2017, 45(2):e124-e131.

Flaherty et al., "Phase III trial of carboplatin and paclitaxel with or without sorafenib in metastatic melanoma," J Clin Oncol., 31(3):373-379, Jan. 20, 2013.

Fleming et al., Selective expression of Ly-6G on myeloid lineage cells in mouse bone marrow. RB6-8C5 mAb to granulocyte-differentiation antigen (Gr-1) detects members of the Ly-6 family, J Immunol., 151(5):2399-2408, Sep. 1, 1993.

Foell et al., "CD137 costimulatory T cell receptor engagement reverses acute disease in lupus-prone NZB x NZW F1 mice," J Clin Invest., 111(10):1505-1518, May 2003.

Foell et al., "CD137-Mediated T Cell Co-Stimulation Terminates Existing Autoimmune Disease in SLE-Prone NZB/NZW F1 Mice," Ann N Y Acad Sci., 987:230-235, Apr. 2003.

Forsberg et al., "HER2 CAR-T Cells Eradicate Uveal Melanoma and T-cell Therapy-Resistant Human Melanoma in IL2 Transgenic NOD/SCID IL2 Receptor Knockout Mice," Cancer Research, Mar. 2019, 79(5):899-904.

Forsman et al., "Size Matters: Identification of Larger Size CD19 Positive Extracellular Vesicles in Chronic Lymphocytic Leukemia That Inhibit Chimeric Antigen Receptor T Cell Functions," Blood, Nov. 29, 2018, 132(S1):1865.

Fortugno et al., "Survivin exists in immunochemically distinct subcellular pools and is involved in spindle microtubule function," J Cell Sci., 115(Pt 3):575-585, Feb. 1, 2002.

Fraietta et al., "Author Correction: Determinants of response and resistance to CD19 chimeric antigen receptor (CAR) T cell therapy of chronic lymphocytic leukemia," Nat. Medicine, 27(3):561, Feb. 5, 2021.

Fraietta et al., "Determinants of response and resistance to CD19 chimeric antigen receptor (CAR) T cell therapy of chronic lymphocytic leukemia," Nat. Medicine, 24(5):563-571, Apr. 30, 2018.

Fraietta et al., "Disruption of TET2 promotes the therapeutic efficacy of CD19-targeted T cells," Nature, 558(7709):307-312, May 30, 2018.

Fraietta et al., "Ibrutinib enhances chimeric antigen receptor T-cell engraftment and efficacy in leukemia," Blood, Mar. 2016, 127(9):1117-1127.

Franciszkiewicz et al., "Role of chemokines and chemokine receptors in shaping the effector phase of the anti tumor immune response," Cancer Res., 72(24):6325-6332, Dec. 15, 2012.

Frank et al., "An outcome prediction model for patients with clear cell renal cell carcinoma treated with radical nephrectomy based on tumor stage, size, grade and necrosis: the SSIGN score," J Urol., 168(6):2395-2400, Dec. 2002.

Frank et al., "Surface-Engineered Lentiviral Vectors for Selective Gene Transfer into Subtypes of Lymphocytes," Mol. Ther. Methods Clin. Development, Mar. 2019, 12:19-31.

Freeman et al., "B7, a new member of the Ig superfamily with unique expression on activated and neoplastic B cells," J Immunol., 143(8):2714-2722, Oct. 15, 1989.

Freeman et al., "Cloning of B7-2: a CTLA-4 counter-receptor that co stimulates human T cell proliferation," Science, 262(5135):909-911, Nov. 5, 1993.

(56)     References Cited

OTHER PUBLICATIONS

Freeman et al., "Engagement of the PD-1 Immunolnhibitory receptor by a novel B7 family member leads to negative regulation of lymphocyte activation," J Exp Med., 192(7):1027-1034, Oct. 2, 2000.

Freeman et al., "Structure, expression, and T cell proliferation costimulatory activity of the murine homologue of the human B lymphocyte activation antigen B7," J Exp Med., 174(3):625-631, Sep. 1, 1991.

Frey et al., "Refractory cytokine release syndrome in recipients of chimeric antigen receptor (CAR) T cells," Blood, Dec. 2014, 124(21):2296.

Friedlander et al., "miRDeep2 accurately identifies known and hundreds of novel microRNA genes in seven animal clades," Nucleic Acids Research, 40(1):37-52, Jan. 1, 2012.

Friedman et al., "Clinical Benefit of INCB7839, a Potent and Selective Inhibitor of ADAM10 and ADAM17, in Combination with Trastuzumab in Metastatic HER2 Positive Breast Cancer Patients," Cancer Res., 69(24 Suppl):Abstract5056, Dec. 2009.

Friedmann et al., "Interaction of the epidermal growth factor receptor and the DNA-dependent protein kinase pathway following gefitinib treatment," Mol Cancer Ther., 5(2):209-218, Feb. 2006.

Frigola et al., "Identification of a soluble form of B7-H 1 that retains immunosuppressive activity and is associated with aggressive renal cell carcinoma," Clin Cancer Res., 17(7):1915-1923, Apr. 2011.

Frigola et al., "Soluble B7-H1: Differences in production between dendritic cells and T cells," Immunol Lett., 142(1-2):78-82, Feb. 29, 2012.

Fry et al., "CD22-targeted Car T cells induce remission in B-ALL that is naive or resistant to CD19-targeted CAR immunotherapy," Nat. Medicine, Nov. 20, 2017, 24(1):20-28.

Fuerst et al., "Transfer of the inducible lac repressor/operator system from *Escherichia coli* to a vaccinia expression vector," Proc Natl Acad Sci USA., 86(8):2549-2553, Apr. 1989.

Fujimori et al., "The Axl receptor tyrosine kinase is a discriminator of macrophage function in the inflamed lung," Mucosal Immunol., Sep. 2015, 8(5):1021-1030.

Fyfe et al., "Results of treatment of 255 patients with metastatic renal cell carcinoma who received high-dose recombinant interleukin-2 therapy," J Clin Oncol., 13(3):688-696, Mar. 1995.

Gai et al., "Extracellular vesicles in onco-nephrology," Exp. Mol. Medicine, 51:1-8, Mar. 15, 2019.

Gao et al., "CYSLTRI promotes adenoid hypertrophy by activating ERK1/2," Exp. Ther. Medicine, Aug. 2018, 16(2):966-970.

Gao et al., "Mesenchymal stem cells and immunomodulation: current status and future prospects," Cell Death Disease, Jan. 2016, 7:e2062, 11 pages.

Gardner et al., "CD19CAR T Cell Products of Defined CD4:CD8 Composition and Transgene Expression Show Prolonged Persistence and Durable MRD-Negative Remission in Pediatric and Young Adult B-Cell ALL," Blood, Dec. 2016, 128(22):219.

Garon et al., "Pembrolizumab for the Treatment of Non-Small-Cell Lung Cancer," N Engl J Med., 372(21):2018-2028, May 21, 2015.

Gaud et al., "Regulatory mechanisms in T cell receptor signalling," Nat. Rev. Immunol., Aug. 2018, 18(8):485-497.

Gauthier et al., "Efficacy and Toxicity of CD19-Specific Chimeric Antigen Receptor T Cells Alone or in Combination with Ibrutinib for Relapsed and/or Refractory CLL," Biol. Blood Marrow Transplant., Mar. 2019, 25(3 Suppl.):S9-S10.

Geller et al., "Combination therapy with IL-15 superagonist (ALT-803) and PD-1 blockade enhances human NK cell immunotherapy against ovarian cancer," Gynecologic Oncology, 145(S1):19, Jun. 1, 2017.

GenBank Accession No. AAC51660 "apoptosis inhibitor survivin [*Homo sapiens*]," Sep. 2, 2004, 2 pages.

GenBank Accession No. AAF25807 (GI No. 6708119), "B7-H1 [*Homo sapiens*]," Jan. 18, 2000, 2 pages.

GenBank Accession No. AAH32229.1, "AXL receptor tyrosine kinase [*Homo sapiens*]," dated Jul. 15, 2006, 3 pages.

GenBank Accession No. AAH74740.1, GI No. 49902307, "Programmed cell death 1 [*Homo sapiens*]," Jul. 15, 2006, 2 pages.

GenBank Accession No. AAP37283, "immune costimulatory protein B7-H4 [*Homo sapiens*]," Jun. 1, 2003, 1 page.

GenBank Accession No. AAX29153.1, GI No. 60652917, "integrin alpha L, partial [synthetic construct]," Mar. 29, 2005, 2 pages.

GenBank Accession No. AB032738.1, "*Homo sapiens* gene for chemokine receptor CXCR3, partial cds," dated Jul. 26, 2016, 2 pages.

GenBank Accession No. AC003959.1, "*Homo sapiens* 5, PI clone 1029A7 (*Homo sapiens*H15), complete sequence," dated Jul. 24, 2016, 23 pages.

GenBank Accession No. AC011377.6, "*Homo sapiens* 5 clone CTB-120L21, complete sequence," dated Aug. 15, 2001, 13 pages.

GenBank Accession No. AF177937 (GI No. 6708118), "*Homo sapiens* B7-H1 mRNA, complete cds," Jan. 18, 2000, 1 page.

GenBank Accession No. AF363458.1, "*Homo sapiens* programmed cell death 1 (PDCD1) gene, exons 1 through 5 and complete cds," dated Mar. 18, 2003, 4 pages.

GenBank Accession No. AK001872.1,"*Homo sapiens* cDNA FLJ11010 fis, clone PLACE1003145," Feb. 22, 2000, 2 pages.

GenBank Accession No. AL136985.11, "Human DNA sequence from clone RP11-63G10 on chromosome 1p32.1-32.3, complete sequence," dated Jan. 24, 2013, 33 pages.

GenBank Accession No. AL162253, "Human DNA sequence from clone RP11-574F11 on chromosome 9 contains the gene for B7-H1 protein (PD-LI), the gene for programmed death ligand 2 (PDL2) (PDCD1L2) and a novel gene, complete sequence" Feb. 24, 2008, 35 pages.

GenBank Accession No. AY280972,"*Homo sapiens* immune costimulatory protein B7-H4 mRNA, complete cds," Jun. 1, 2003, 1 page.

GenBank Accession No. BC008777.2, GI No. 33870544, "*Homo sapiens* integrin, alpha L (antigen CD11A (p180), lymphocyte function-associated antigen 1; alpha polypeptide), mRNA (cDNA clone MGC:1714 IMAGE:3142951), complete cds," Jul. 28, 2005, 4 pages.

GenBank Accession No. BC074740.2, GI No. 50960296, "*Homo sapiens* programmed cell death 1, mRNA (cDNA clone MGC:103817 IMAGE:30915198), complete cds," Jul. 15, 2006, 3 pages.

GenBank Accession No. CH471059.2, "*Homo sapiens* 211000035844098 genomic scaffold, whole genome shotgun sequence," dated Mar. 23, 2015, 7 pages.

GenBank Accession No. CH471062.2, "*Homo sapiens* 211000035832302 genomic scaffold, whole genome shotgun sequence," dated Mar. 23, 2015, 6 pages.

GenBank Accession No. CQ834184.1, "Sequence 55 from Patent WO2004058805," dated Jul. 29, 2004, 2 pages.

GenBank Accession No. DQ789232.1, "*Homo sapiens* interferon regulatory factor-1 (IRF1) gene, promoter region and complete cds," dated Jul. 11, 2007, 3 pages.

GenBank Accession No. EAW57023.1, "AXL receptor tyrosine kinase, isoform CRA_b [*Homo sapiens*]," dated Mar. 23, 2015, 2 pages.

GenBank Accession No. EF064716.1, "*Homo sapiens* programmed cell death 1 (PDCD1) gene, complete cds," dated Nov. 13, 2006, 7 pages.

GenBank Accession No. M76125.1, "Human tyrosine kinase receptor (axl) mRNA, complete cds," dated Jan. 14, 1995, 2 pages.

GenBank Accession No. NM_000418.3, "*Homo sapiens* interleukin 4 receptor (IL4R), transcript variant 1, mRNA," dated Oct. 3, 2017, 6 pages.

GenBank Accession No. NM_000572.2, "*Homo sapiens* interleukin 10 (IL10), mRNA," dated Oct. 6, 2016, 3 pages.

GenBank Accession No. NM_000589.3, "*Homo sapiens* interleukin 4 (IL4), transcript variant 1, mRNA," dated Oct. 3, 2017, 4 pages.

GenBank Accession No. NM_000594.3, "*Homo sapiens* tumor necrosis factor (TNF), mRNA," dated Oct. 6, 2016, 4 pages.

GenBank Accession No. NM_000758.3, "*Homo sapiens* colony stimulating factor 2 (CSF2), mRNA," dated Jan. 16, 2016, 3 pages.

GenBank Accession No. NM_000759.3, "*Homo sapiens* colony stimulating factor 3 (CSF3), transcript variant 1, mRNA," dated Oct. 6, 2016, 4 pages.

(56)        References Cited

OTHER PUBLICATIONS

GenBank Accession No. NM_001008540.2, "*Homo sapiens* C-X-C motif chemokine receptor 4 (CXCR4), transcript variant 1, mRNA," dated Apr. 8, 2017, 4 pages.
GenBank Accession No. NM_001134851.3, "*Homo sapiens* transcription factor 7 (TCF7), transcript variant 3, mRNA," dated Oct. 3, 2017, 4 pages.
GenBank Accession No. NM_001142797.1, "*Homo sapiens* C-X-C motif chemokine receptor 3 (CXCR3), transcript variant 2, mRNA," dated Oct. 6, 2016, 4 pages.
GenBank Accession No. NM_001145368.1, "*Homo sapiens* protein tyrosine phosphatase, non-receptor type 3 (PTPN3), transcript variant 2, mRNA," dated Oct. 2, 2017, 5 pages.
GenBank Accession No. NM_001145369.1, "*Homo sapiens* protein tyrosine phosphatase, non-receptor type 3 (PTPN3), transcript variant 3, mRNA," dated Oct. 2, 2017, 5 pages.
GenBank Accession No. NM_001165412.1, "*Homo sapiens* nuclear factor kappa B subunit 1 (NFKB1), transcript variant 2, mRNA," dated May 18, 2016, 7 pages.
GenBank Accession No. NM_001257406.1, "*Homo sapiens* interleukin 4 receptor (IL4R), transcript variant 3, mRNA," dated Oct. 2, 2017, 6 pages.
GenBank Accession No. NM_001257407.1, "*Homo sapiens* interleukin 4 receptor (IL4R), transcript variant 4, mRNA," dated Oct. 3, 2017, 4 pages.
GenBank Accession No. NM_001257997.1, "*Homo sapiens* interleukin 4 receptor (IL4R), transcript variant 5, mRNA," dated Oct. 3, 2017, 4 pages.
GenBank Accession No. NM_001278599.1, "*Homo sapiens* AXL receptor tyrosine kinase (AXL), transcript variant 3, mRNA," dated Oct. 3, 2017, 4 pages.
GenBank Accession No. NM_001319226.1, "*Homo sapiens* nuclear factor kappa B subunit 1 (NFKB1), transcript variant 3, mRNA," dated May 18, 2016, 7 pages.
GenBank Accession No. NM_001330163.1, "*Homo sapiens* galectin 9 (LGALS9), transcript variant 4, mRNA," dated Sep. 11, 2016, 3 pages.
GenBank Accession No. NM_001348056.1, "*Homo sapiens* C-X-C motif chemokine receptor 4 (CXCR4), transcript variant 3, mRNA," dated Apr. 8, 2017, 4 pages.
GenBank Accession No. NM_001348059.1, "*Homo sapiens* C-X-C motif chemokine receptor 4 (CXCR4), transcript variant 4, mRNA," dated Apr. 8, 2017, 4 pages.
GenBank Accession No. NM_001354924.1, "*Homo sapiens* interferon regulatory factor 1 (IRF1), transcript variant 2, mRNA," dated Aug. 29, 2017, 4 pages.
GenBank Accession No. NM_001354925.1, "*Homo sapiens* interferon regulatory factor 1 (IRF1), transcript variant 3, mRNA," dated Aug. 29, 2017, 4 pages.
GenBank Accession No. NM_001354990.1, "*Homo sapiens* interleukin 4 (IL4), transcript variant 3, mRNA," dated Oct. 4, 2017, 3 pages.
GenBank Accession No. NM_001361665.1, "*Homo sapiens* fibroblast growth factor 2 (FGF2), mRNA," dated Mar. 28, 2018, 5 pages.
GenBank Accession No. NM_001382624.1, "*Homo sapiens* interleukin 10 (IL10), transcript variant 2, mRNA," dated May 18, 2020, 3 pages.
GenBank Accession No. NM_001382625.1, "*Homo sapiens* nuclear factor kappa B subunit 1 (NFKB1), transcript variant 4, mRNA," dated May 18, 2020, 8 pages.
GenBank Accession No. NM_001411087.1, "*Homo sapiens* RELB proto-oncogene, NF-kB subunit (RELB), transcript variant 2, mRNA," dated Aug. 22, 2022, 5 pages.
GenBank Accession No. NM_001504.1, "*Homo sapiens* C-X-C motif chemokine receptor 3 (CXCR3), transcript variant 1, mRNA," dated Oct. 6, 2016, 5 pages.
GenBank Accession No. NM_001699.5, "*Homo sapiens* AXL receptor tyrosine kinase (AXL), transcript variant 2, mRNA," dated Oct. 6, 2016, 5 pages.

GenBank Accession No. NM_002006.4, "*Homo sapiens* fibroblast growth factor 2 (FGF2), mRNA," dated Oct. 6, 2016, 6 pages.
GenBank Accession No. NM_002198.2, "*Homo sapiens* interferon regulatory factor 1 (IRF1), mRNA," dated Aug. 12, 2016, 4 pages.
GenBank Accession No. NM_002228.3, "*Homo sapiens* Jun proto-oncogene, AP-1 transcription factor subunit (JUN), mRNA," dated Jan. 4, 2017, 6 pages.
GenBank Accession No. NM_002308.3, "*Homo sapiens* galectin 9 (LGALS9), transcript variant 2, mRNA," dated Sep. 10, 2016, 4 pages.
GenBank Accession No. NM_002829.3, "*Homo sapiens* protein tyrosine phosphatase, non-receptor type 3 (PTPN3), transcript variant 1, mRNA," dated Oct. 2, 2017, 6 pages.
GenBank Accession No. NM_002986.2, "*Homo sapiens* C-C motif chemokine ligand 11 (CCL11), mRNA," dated Mar. 3, 2016, 4 pages.
GenBank Accession No. NM_003202.4, "*Homo sapiens* transcription factor 7 (TCF7), transcript variant 1, mRNA," dated Oct. 4, 2017, 4 pages.
GenBank Accession No. NM_005018.2, "*Homo sapiens* programmed cell death 1 (PDCD1), mRNA," dated Sep. 15, 2016, 4 pages.
GenBank Accession No. NM_005191.3 (GI No. 113722122), "*Homo sapiens* CD80 molecule (CD80), mRNA," Jun. 15, 2013, 5 pages.
GenBank Accession No. NM_006509.3, "*Homo sapiens* RELB proto-oncogene, NF-kB subunit (RELB), mRNA," dated May 1, 2016, 4 pages.
GenBank Accession No. NM_009587.2, "*Homo sapiens* galectin 9 (LGALS9), transcript variant 1, mRNA," dated Sep. 10, 2016, 4 pages.
GenBank Accession No. NM_021913.4, "*Homo sapiens* AXL receptor tyrosine kinase (AXL), transcript variant 1, mRNA," dated Oct. 3, 2017, 5 pages.
GenBank Accession No. NM_032782.4, "*Homo sapiens* hepatitis A virus cellular receptor 2 (HAVCR2), mRNA," dated Sep. 1, 2016, 4 pages.
GenBank Accession No. NM_172219.2, "*Homo sapiens* colony stimulating factor 3 (CSF3), transcript variant 2, mRNA," dated Oct. 6, 2016, 4 pages.
GenBank Accession No. NM 172348.2, "*Homo sapiens* interleukin 4 (IL4), transcript variant 2, mRNA," dated Oct. 3, 2017, 4 pages.
GenBank Accession No. NM_213648.4, "*Homo sapiens* transcription factor 7 (TCF7), transcript variant 5, mRNA," dated Oct. 3, 2017, 4 pages.
GenBank Accession No. NP_000052.1, "tyrosine-protein kinase BTK isoform 1 [*Homo sapiens*]," dated Nov. 1, 2020, 4 pages.
GenBank Accession No. NP_005182.1 (GI No. 4885123), "T-lymphocyte activation antigen CD80 precursor [*Homo sapiens*]," Jun. 15, 2013, 3 pages.
GenBank Accession No. U75285 "*Homo sapiens* apoptosis inhibitor survivin gene, complete cds," Sep. 2, 2004, 5 pages.
GenPept Accession No. Q9NZQ7.1, "Programmed cell death 1 ligand 1," Nov. 30, 2016, 5 pages.
Gérard et al., "Dok-4 is a novel negative regulator of T cell activation," J. Immunology, Jun. 2009, 182(12):7681-7689.
Gerdes et al. "Cell cycle analysis of a cell proliferation-associated human nuclear antigen defined by the monoclonal antibody Ki-67," J Immunol., 133(4):1710-1715, Oct. 1984.
Gerlach et al., "The Chemokine Receptor CX3CR1 Defines Three Antigen-Experienced CD8 T Cell Subsets with Distinct Roles in Immune Surveillance and Homeostasis," Immunity, 45(6):1270-1284, Dec. 20, 2016.
Gerstmayer et al., "Costimulation of T cell proliferation by a chimeric B7-2 antibody fusion protein specifically targeted to cells expressing the erbB2 proto-oncogene," J Immunol., 158(10):4584-4590, May 15, 1997.
Gerstmayer et al., "Costimulation of T-cell proliferation by a chimeric B7 antibody fusion protein," Cancer Immunol Immunother., 45(3-4):156-158, Nov./Dec. 1997.
Gevaert et al., "Protein identification based on matrix assisted laser desorption/ionization-post source decay-mass spectrometry," Electrophoresis, 22(9):1645-1651, May 2001.

(56) References Cited

OTHER PUBLICATIONS

Ghebeh et al., "Doxorubicin downregulates cell surface B7-H1 expression and upregulates its nuclear expression in breast cancer cells: role of B7-H1 as an anti-apoptotic molecule," Breast Cancer Res., 12(4):R48, Jul. 13, 2010.

Ghebeh et al., "The B7-H1 (PD-L1) T lymphocyte-inhibitory molecule is expressed in breast cancer patients with infiltrating ductal carcinoma: correlation with important high risk prognostic factors," Neoplasia, 8(3):190-198, Mar. 2006.

Ghiringhelli et al., "Metronomic cyclophosphamide regimen selectively depletes CD4+CD25+ regulatory T cells and restores T and NK effector functions in end stage cancer patients," Cancer Immunol Immunother., 56(5):641-648, May 2007.

Giavridis et al., "Car T cell-induced cytokine release syndrome is mediated by macrophages and abated by IL-1 blockade," Nat. Med., Jun. 2018, 24(6):731-738.

Gibbons et al., "B7-H1 limits the entry of effector CD8(+) T cells to the memory pool by upregulating Bim," Oncoimmunology, 1(7):1061-1073, Oct. 1, 2012.

Gibbons Johnson et al., "Functional Expression of Programmed Death-Ligand 1 (B7-H1) by Immune Cells and Tumor Cells," Front Immunol, 8:961, Aug. 10, 2017, 9 pages.

Gilbert et al., "RNA Immunoprecipitation for Determining RNA-Protein Associations In Vivo," Curr. Protoc. Mol. Biology, Chapter 27, Unit 27.4, Aug. 2006, 11 pages.

Gill et al., "Preclinical targeting of human acute myeloid leukemia and myeloablation using chimeric antigen receptor-modified T cells," Blood, Apr. 10, 2014, 123(15):2343-2354.

Gillings et al., "Apoptosis and autophagy: BIM as a mediator of tumour cell death in response to oncogene-targeted therapeutics," FEBS J., 276(21):6050-6062, Sep. 29, 2009.

Gimmi et al., "B-cell surface antigen B7 provides a costimulatory signal that induces T cells to proliferate and secrete interleukin 2," Proc Natl Acad Sci USA., 88(9):3671-3675, May 1, 1991.

Gofshteyn et al., "Neurotoxicity after CTL019 in a pediatric and young adult cohort," Ann. Neurol., Oct. 2018, 84(4):537-546.

Golinelli et al., "Targeting GD2-positive glioblastoma by chimeric antigen receptor empowered mesenchymal progenitors," Cancer Gene Ther., Aug. 2020, 27(7-8):558-570.

Golovina et al., "CD28 costimulation is essential for human T regulatory expansion and function," J. Immunology, Aug. 2008, 181(4):2855-2868.

Gomes et al., "Analytical Considerations in Nanoscale Flow Cytometry of Extracellular Vesicles to Achieve Data Linearity," Thromb. Haemost., Sep. 2018, 118(9):1612-1624.

Gomes-Silva et al., "Tonic 4-1BB Costimulation in Chimeric Antigen Receptors Impedes T Cell Survival and Is Vector-Dependent," Cell Reports, 21(1):17-26, Oct. 3, 2017.

Goodwin et al., "Molecular cloning and expression of the type 1 and type 2 murine receptors for tumor necrosis factor," Mol Cell Biol., 11(6):3020-3026, Jun. 1991.

Goodwin et al., "Molecular cloning of a ligand for the inducible T cell gene 4-1BB: a member of an emerging family of cytokines with homology to tumor necrosis factor," Eur J Immunol., 23(10):2631-2641, Oct. 1993.

Gottesman et al., "Multidrug resistance in cancer: role of ATP-dependent transporters," Nat Rev Cancer, 2(1):48-58, Jan. 2002.

Grayson et al., "Cutting edge: increased expression of Bcl-2 in antigen-specific memory CD8+ T cells," J Immunol., 164(8):3950-3954, Apr. 15, 2000.

Green et al., "Activation-induced cell death in T cells," Immunol Rev., 193:70-81, Jun. 2003.

Green et al., "Antigen-specific human monoclonal antibodies from mice engineered with human Ig heavy and light chain YACs," Nat Genet., 7(1):13-21, May 1994.

Greenwald et al., "The B7 family revisited," Annu Rev Immunol., 23:515-548, 2005.

Griffiths-Jones et al., "miRBase: microRNA sequences, targets and gene nomenclature," Nucleic Acids Res., Jan. 2006, 34(Database issue):D140-D144.

Griffiths-Jones et al., "miRBase: tools for microRNA genomics," Nucleic Acids Res., Jan. 2008, 36(Database issue):D154-D158.

Griffiths-Jones, "The microRNA Registry," Nucleic Acids Res., Jan. 2004, 32(Database issue):D109-D111.

Grivennikov et al. "Immunity, inflammation, and cancer," Cell., 140(6):883-899, Mar. 19, 2010.

Gros et al., "PD-1 identifies the patient-specific CD8(+) tumor-reactive repertoire infiltrating human tumors," J Clin Invest., 124(5):2246-2259, May 2014.

Gros et al., "Prospective identification of neoantigen-specific lymphocytes in the peripheral blood of melanoma patients," Nat Med., 22(4):433-438, Apr. 2016.

Grupp et al., "Chimeric antigen receptor-modified T cells for acute lymphoid leukemia," N. Engl. J. Med., Apr. 18, 2013, 368(16):1509-1518.

Grupp et al., "T cells engineered with a chimeric antigen receptor (CAR) targeting CD19 (CTL019) produce significant in vivo proliferation, complete responses and long-term persistence without GVHD in children and adults with relapsed, refractory ALL" Blood, Nov. 15, 2013, 122(21):67, 3 pages.

Gu et al., "R gene expression induced by a type-III effector triggers disease resistance in rice," Nature, 435(7045):1122-1125, Jun. 23, 2005.

Guatelli et al., "Isothermal, in vitro amplification of nucleic acids by a multi enzyme reaction modeled after retroviral replication," Proc Natl Acad Sci USA., 87(5):1874-1878, Mar. 1990.

Guess et al., "Safety Profile of Good Manufacturing Practice Manufactured Interferon gamma-Primed Mesenchymal Stem/Stromal Cells for Clinical Trials," Stem Cells Transl. Medicine, Sep. 2017, 6(10):1868-1879.

Guinn et al., "4-1BBL cooperates with B7-1 and B7-2 in converting a B cell lymphoma cell line into a long-lasting antitumor vaccine," J Immunol., 162(8):5003-5010, Apr. 15, 1999.

Gunn et al., "Correct end use during end joining of multiple chromosomal double strand breaks is influenced by repair protein RAD50, DNA-dependent protein kinase DNA-PKcs, and transcription context," J Biol Chem., 286(49):42470-42482, Oct. 24, 2011.

Guo et al., "A novel fusion protein of IP1 O-scFv retains antibody specificity and chemokine function," Biochem Biophys Res Commun., 320(2):506-513, Jul. 23, 2004.

Guo et al., "Axl Inhibition Induces The Antitumor Immune Response Which Can Be Further Potentiated by PD-1 Blockade in The Mouse Cancer Models," Oncotarget, Sep. 21, 2017, 8(52):89761-8977.

Guo et al., "Directed evolution of an enhanced and highly efficient FokI cleavage domain for zinc finger nucleases," J Mol. Biology, Jul. 2, 2010, 400(1):96-107.

Guo et al., "Interleukin-1β induces CXCR3-mediated chemotaxis to promote umbilical cord mesenchymal stem cell transendothelial migration," Stem Cell Res. Therapy, Oct. 2018, 9(1):281, 15 pages.

Guo et al., "NF-KappaB Pathway Is Involved in Bone Marrow Stromal Cell-Produced Pain Relief," Front. Integr. Neuroscience, Oct. 2018, 12:49, 10 pages.

Gust et al., "Endothelial activation and blood-brain barrier disruption in neurotoxicity after adoptive immunotherapy with CD19 Car-T cells," Cancer Discov., Dec. 2017, 7(12):1404-1419.

Gyorgy et al., "Membrane vesicles, current state-of-the-art: emerging role of extracellular vesicles," Cell. Mol. Life Sciences, May 11, 2011, 68(16):2667-2688.

Haas et al., "Phase I Study of Lentiviral-Transduced Chimeric Antigen Receptor-Modified T Cells Recognizing Mesothelin in Advanced Solid Cancers," Mol. Therapy, Nov. 6, 2019, 27(11):1919-1929.

Hacein-Bey et al., "A serious adverse event after successful gene therapy for X-linked severe combined immunodeficiency," N. Engl. J. Medicine, Jan. 2003, 348(3):255-266.

Haendeler et al., "Nitric Oxide and Apoptosis," Vitam Horm., 57:49-77, 1999.

Hamanishi et al., "PD-1/PD-L1 blockade in cancer treatment: perspectives and issues," Int. J. Clin. Oncology, 21(3):462-473, Jun. 2016.

Hamid et al., "Safety and Tumor Responses with Lambrolizumab (Anti-PD-1) in Melanoma," N Engl J Med., 369(2):134-144, Jul. 11, 2013.

(56) References Cited

OTHER PUBLICATIONS

Hansen et al., "Monoclonal antibodies identifying a novel T-cell antigen and la antigens of human lymphocytes," Immunogenetics, 10(1-4):247-260, Feb. 1, 1980.

Hardenberg et al., "A Yin and Yang in Epithelial Immunology: The Roles of the αE(CD103)β7 Integrin in T Cells," J. Invest. Dermatology, Jan. 2018, 138(1):23-31.

Haring et al., "Interfering With Inflammation: Heterogeneous Effects of Interferons in Graft-Versus-Host Disease of the Gastrointestinal Tract and Inflammatory Bowel Disease," Front. Immunology, Jun. 2021, 12:705342, 16 pages.

Harlow et al., "Antibodies: A Laboratory Manual," Cold Spring Harbor Laboratory Press, Cold Spring Harbor, NY, pp. 553, 555-582, 584-589, 591-612, 1988.

Harrell et al., "Mesenchymal Stem Cell-Derived Exosomes and Other Extracellular Vesicles as New Remedies in the Therapy of Inflammatory Diseases," Cells, Dec. 2019, 8(12):1605, 22 pages.

Harrington et al., "Differentiating between memory and effector CD8 T cells by altered expression of cell surface O-glycans," J Exp Med., 191(7):1241-1246, Apr. 3, 2000.

Hatzoglou et al., "Hepatic gene transfer in animals using retroviruses containing the promoter from the gene for phosphoenolpyruvate carboxykinase" J Biol Chem., 265(28):17285-17293, Oct. 5, 1990.

Haugland et al., "Unit 16.5 antibody conjugates for cell biology," Current Protocols in Cell Biology, 6:16.5:16.5-16.5.22, May 1, 2001.

Hawiger et al., "Dendritic cells induce peripheral T cell unresponsiveness under steady state conditions in vivo," J Exp Med., 194(6): 769-779, Sep. 17, 2001.

Hayakawa et al., "Inhibition of BAD phosphorylation either at serine 112 via extracellular signal-regulated protein kinase cascade or at serine 136 via Akt cascade sensitizes human ovarian cancer cells to cisplatin," Cancer Res., 60(21):5988-5994, Nov. 1, 2000.

He et al., "Development of PD-1/PD-L1 Pathway in Tumor Immune Microenvironment and Treatment for Non-Small Cell Lung Cancer," Sci. Reports, 5:13110, Aug. 17, 2015, 9 pages.

He et al., "Identification of a novel splice variant of human PD-L1 mRNA encoding an isoform-lacking Igv-like domain," Acta. Pharmacol. Sin., 26(4):462-468, Apr. 2005.

Hefazi et al., "Regulatory T Cell Therapy of Graft-versus-Host Disease: Advances and Challenges," Int. J. Mol. Sciences, Sep. 2021, 22(18):9676, 27 pages.

Heinz et al., "Simple Combinations of Lineage-Determining Transcription Factors Prime cis-Regulatory Elements Required for Macrophage and B Cell Identities," Mol. Cell, 38(4):576-589, May 28, 2010.

Hellstrom et al., "T cell immunity to tumor antigens," Crit Rev Immunol., 18(1-2):1-6, 1998.

Henry et al., "Cloning, structural analysis, and mapping of the B30 and B7 multigenic families to the major histocompatibility complex (MHC) and other chromosomal regions," Immunogenetics, 46(5):383-395, 1997.

Henry et al., "Structure and evolution of the extended B7 family," Immunol Today, 20(6):285-288, Jun. 1999.

Hentikoff, "Amino acid substitution matrices from protein blocks," Proc Natl Acad Sci USA., 89(22):10915-10919, Nov. 15, 1992.

Her et al., "Increased expression of soluble inducible costimulator ligand (ICOSL) in patients with systemic lupus erythematosus," Lupus, 18(6):501-507, May 2009.

Hercus et al., "Specific human granulocyte-macrophage colony-stimulating factor antagonists," Proc. Natl. Acad. Sci USA, Jun. 1994, 91:5838-5842.

Herold et al., "Impact of conditional deletion of the pro-apoptotic BCL-2 family member BIM in mice," Cell Death Dis., 5(10):e1446, Oct. 9, 2014, 7 pages.

Hestdal et al., "Characterization and regulation of RB6-8C5 antigen expression on murine bone marrow cells," J Immunol., 147(1):22-28, Jul. 1, 1991.

Hidalgo et al., "The transcriptome of human cytotoxic T cells: similarities and disparities among allostimulated CD4(+) CTL, CD8( +) CTL and NK cells," Am J Transplant., 8(3):627-636, Mar. 2008.

Hildeman et al., "Activated T cell death in vivo mediated by proapoptotic bcl-2 family member bim," Immunity, 16(6):759-767, Jun. 2002.

Hirano et al., "Blockade of B7-H1 and PD-1 by monoclonal antibodies potentiates cancer therapeutic immunity," Cancer Res., 65(3):1089-1096, Feb. 1, 2005.

Hiroishi et al., "Interferon-alpha gene therapy in combination with CDSO transduction reduces tumorigenicity and growth of established tumor in poorly immunogenic tumor models," Gene Ther., 6(12):1988-1994, Dec. 1999.

Hochman et al., "An active antibody fragment (Fv) composed of the variable portions of heavy and light chains," Biochemistry, 12(6):1130-1135, Mar. 13, 1973.

Hock et al., "Retrovirus-mediated transfer and expression of drug resistance genes in human haematopoietic progenitor cells," Nature, 320:275-277, 1986.

Hodi et al., "Evaluation of Immune-Related Response Criteria and RECIST v1.1 in Patients With Advanced Melanoma Treated With Pembrolizumab," J Clin Oncol., 34(13):1510-1517, May 1, 2016.

Hoeijmakers, "Genome maintenance mechanisms for preventing cancer," Nature, 411(6835):366-374, May 17, 2011.

Hoffman, "T Cells in the Pathogenesis of Systemic Lupus Erythematosus," Front Biosci., 6:D1369-D1378, Oct. 1, 2001.

Hoffmann et al., "Only the CD45RA+ subpopulation of CD4+ CD25high T cells gives rise to homogeneous regulatory T-cell lines upon in vitro expansion," Blood, Dec. 15, 2006, 108(13):4260-4267.

Hoiseth et al., "Aromatic-dependent *Salmonella typhimurium* are non-virulent and effective as live vaccines," Nature, 291(5812):238-239, May 21, 1981.

Holland et al., "R428, a selective small molecule inhibitor of Axl kinase, blocks tumor spread and prolongs survival in models of metastatic breast cancer," Cancer Res., Feb. 2010, 70(4): 1544-1554.

Hollinger et al., "'Diabodies': small bivalent and bispecific antibody fragments," Proc Natl Acad Sci USA., 90(14):6444-6448, Jul. 15, 1993.

Holt et al., "Domain antibodies: proteins for therapy," Trends Biotechnol., 21(11):484-490, Nov. 2003.

Hoos et al., "CCR 20th Anniversary Commentary: Immune-Related Response Criteria—Capturing Clinical Activity in Immuno-Oncology," Clin Cancer Res., 21(22):4989-4991, Nov. 2015.

Hori et al., "B7-H1-induced apoptosis as a mechanism of immune privilege of corneal allografts," J Immunol., 177(9):5928-5935, Nov. 1, 2006.

Hou et al., "Correlation between infiltration of FOXP3+ regulatory T cells and expression of B7- H1 in the tumor tissues of gastric cancer," Exp. Mot. Pathol., 96(3):284-291, Jun. 2014.

Houseley et al., "The many pathways of RNA degradation," Cell, 136(4):763-776, Feb. 20, 2009.

Howe et al., "Insertional mutagenesis combined with acquired somatic mutations causes leukemogenesis following gene therapy of SCID-X1 patients," J. Clin. Investigation, Sep. 2008, 118(9):3143-3150.

Hua et al., "B7-H1 expression is associated with expansion of regulatory T cells in colorectal carcinoma," World J. Gastroenterol., 18(9):971-978, Mar. 2012.

Huai et al., "Inducible gene expression with the Tet-on system in CD4+ T cells and thymocytes of mice," Genesis, 45(7):427-431, Jul. 2007.

Huang et al., "CDK2-Dependent Phosphorylation of FOXO1 as an Apoptotic Response to DNA Damage," Science, 314(5797):294-297, Oct. 13, 2006.

Huang et al., "Fragile Histidine Triad (FHIT) Suppresses Proliferation and Promotes Apoptosis in Cholangiocarcinoma Cells by Blocking PI3K-Akt Pathway," Sci. World J., Mar. 16, 2014, 2014:179698, 8 pages.

Huang et al., "T-cell invigoration to tumour burden ratio associated with anti-PD-1 response," Nature, 545(7652):60-65, Apr. 10, 2017.

(56)　　　　References Cited

OTHER PUBLICATIONS

Huang et al., "The liver eliminates T cells undergoing antigen-triggered apoptosis in vivo," Immunity, 1(9):741-749, Dec. 31, 1994.

Huang, "Structural chemistry and therapeutic intervention of protein-protein interactions in immune response, human immunodeficiency virus entry, and apoptosis," Pharmacol Ther., 86(3):201-215, Jun. 2000.

Hubbard et al., "Anti-neutrophil-elastase defenses of the lower respiratory tract in alpha 1-antitrypsin deficiency directly augmented with an aerosol of alpha I-antitrypsin," Ann Intern Med., 111(3):206-212, Aug. 1, 1989.

Hui et al., "T cell costimulatory receptor CD28 is a primary target for PD-1-mediated inhibition," Science, 355(6332):1428-1433, Mar. 9, 2017.

Hunter, "Diabetes in pregnancy," Effective Care in Pregnancy and Childbirth, Chalmers et al. (eds.), Oxford University Press, 1:578-593, 1989.

Huse et al., "Generation of a large combinatorial library of the immunoglobulin repertoire in phage lambda," Science, 246(4935):1275-1281, Dec. 8, 1989.

Huston et al., "Protein engineering of antibody binding sites: recovery of specific activity in an anti-digoxin single-chain Fv analogue produced in *Escherichia coli,*" Proc Natl Acad Sci USA., 85(16):5879-5883, Aug. 1988.

Hutloff et al., "ICOS is an inducible T-cell co-stimulator structurally and functionally related to CD28," Nature, 397(6716):263-266, Jan. 21, 1999.

Hwang et al., "Efficient genome editing in zebrafish using a CRISPR-Cas system," Nat. Biotechnology, 31(3):227-229, Jan. 29, 2013.

Hyrup et al., "Peptide nucleic acids (PNA): synthesis, properties and potential applications," Bioorg Med Chem., 4(1):5-23, Jan. 31, 1996.

Ice et al., "AB0143: Immunomodulation followed by quantitative transcriptional profiling to characterize the functional role of the sjÖgren's-associated ncrna ac092580.4," Ann Rheum Dis., 76(S2):1096, Jun. 15, 2017.

Ichikawa et al., "Role of B7-H1 and B7-H4 molecules in down-regulating effector phase of T-cell immunity: novel cancer escaping mechanisms," Front Biosci., 10:2856-2860, Sep. 1, 2005.

Ikemizu et al., "Structure and dimerization of a soluble form of B7-1," Immunity, 12(1):51-60, Jan. 2000.

Ikonomidis, "Delivery of a viral antigen to the class I processing and presentation pathway by Listeria monocytogenes," J Exp Med., 180(6):2209-2218, Dec. 1, 1994.

Imai et al., "Identification and molecular characterization of fractalkine receptor CX3CR1, which mediates both leukocyte migration and adhesion," Cell, 91(4):521-530, Nov. 14, 1997.

Infante et al., "A multicenter phase Ib study of the safety, pharmacokinetics, biological activity and clinical efficacy of INCB7839, a potent and selective inhibitor of ADAM10 and ADAM17," Breast Cancer Res. Treat., 106(1):S269, 6064, Dec. 2007.

Inman et al. "PD-L1 (B7-H1) expression by urothelial carcinoma of the bladder and BCG-induced granulomata: associations with localized stage progression," Cancer, 109(8):1499-1505, Apr. 15, 2007.

Inman et al., "Questionable relevance of gamma delta T lymphocytes in renal cell carcinoma," J Immunol., 180(5):3578-3584, Mar. 1, 2008.

Ishida et al., "Differential expression of PD-LI and PD-L2, ligands for an inhibitory receptor PD-1, in the cells of lymphohematopoietic tissues," Immunol Lett., 84(1):57-62, Oct. 21, 2002.

Ishida et al., "Induced expression of PD-1, a novel member of the immunoglobulin gene superfamily, upon programmed cell death," EMBO J., 11(11):3887-3895, Nov. 1992.

Iwai et al., "Involvement of PD-L1 on tumor cells in the escape from host immune system and tumor immunotherapy by PD-L1 blockade," Proc Natl Acad Sci USA., 99(19):12293-12297, Sep. 6, 2002.

Iwai et al., "PD-1 inhibits antiviral immunity at the effector phase in the liver," J Exp Med., 198(1):39-50, Jul. 7, 2003.

Iyer et al., "No unexpected CRISPR-Cas9 off-target activity revealed by trio sequencing of gene-edited mice," PLoS Genet., Jul. 2018, 14(7):e1007503.

Jacinto et al., "SIN1/MIP1 maintains rictor-mTOR complex integrity and regulates Akt phosphorylation and substrate specificity," Cell, 127(1):125-137, Sep. 7, 2006.

Jacobs et al., "Regulatory T cells in melanoma: the final hurdle towards effective immunotherapy?," Lancet Oncol., 13(1):e32-42, Jan. 2012.

Jacobsohn et al., "Acute graft versus host disease," Orphanet. J. Rare Diseases, Sep. 4, 2007, 2:35, 9 pages.

Jacobson et al., "Unique site of IgG2a and rheumatoid factor production in MRL/lpr mice," Immunol Rev., 156:103-110, Apr. 1997.

Jacquelot et al., "Predictors of responses to immune checkpoint blockade in advanced melanoma," Nat. Commun., 8(1):592, Sep. 19, 2017.

Jamaly et al., "Impact of preanalytical conditions on plasma concentration and size distribution of extracellular vesicles using Nanoparticle Tracking Analysis," Sci. Rep., Nov. 2018, 8(1):17216.

Janeway et al. "Immunobiology: the Immune System in Health and Disease," Elsevier Science., 4:36, 1999.

Janssen et al., "CD4+ T-cell help controls CD8+ T-cell memory via TRAIL-mediated activation-induced cell death," Nature, Mar. 2005, 434(7029):88-93.

Jayaraman, "Flow cytometric determination of mitochondrial membrane potential changes during apoptosis of T lymphocytic and pancreatic beta cell lines: comparison of tetramethylrhodamineethylester (TMRE), chloromethyl-X-rosamine (H2-CMX-Ros) and MitoTracker Red 580 (MTR580)," J Immunol Methods., 306(1-2):68-79, Sep. 29, 2005.

Jeannin et al., "Soluble CD86 is a costimulatory molecule for human T lymphocytes," Immunity, 13(3):303-312, Sep. 2000.

Jemal et al., "Cancer Statistics, 2005," CA Cancer J Clin, 55(1):10-30, Jan./Feb. 2005.

Jerne, "Towards a network theory of the immune system," Ann Immunol (Paris)., 125C(1-2):373-389, Jan. 1974.

Jiang et al., "Genome-wide association study for biomarker identification of Rapamycin and Everolimus using a lymphoblastoid cell line system," Front Genet., 4:166, Aug. 30, 2013.

Jiang et al., "RNA-guided editing of bacterial genomes using CRISPR-Cas systems," Nat. Biotechnology, 31(3):233-239, Jan. 29, 2013.

Jiang et al., "Selective Targeting of Glioblastoma with EGFRvIII/EGFR Bitargeted Chimeric Antigen Receptor T Cell," Cancer Immunol. Res., Nov. 2018, 6(11):1314-1326.

Jinek et al., "A programmable dual-RNA-guided DNA endonuclease in adaptive bacterial immunity," Science, 337(6096):816-821, Jun. 28, 2012.

Johnsen et al., "What is the blood concentration of extracellular vesicles? Implications for the use of extracellular vesicles as blood-borne biomarkers of cancer," Biochim. Biophys. Acta. Rev. Cancer, 1871(1):109-116, Jan. 2019.

Johnson et al., "CD8 T cell-initiated blood-brain barrier disruption is independent of neutrophil support," J. Immunol., Aug. 2012, 189(4):1937-1945.

Johnson et al., "Combinatorial therapy with an IL-15 superagonist (ALT-803) and anti-PD-L1 mAb augment T cell mediated anti-tumor immunity in mice," J. Immunother. Cancer, 2(Suppl. 3):P234, Nov. 6, 2014.

Johnson et al., "Fulminant Myocarditis with Combination Immune Checkpoint Blockade," N. Engl. J. Med., 375(18):1749-1755, Nov. 2016.

Johnston et al., "Biolistic transformation of animal tissue," In Vitro Cell Dev Biol Anim., 27P:11-14, 1991.

Jones et al., "Replacing the complementarity-determining regions in a human antibody with those from a mouse," Nature, 321(6069):522-525, May 29-Jun. 4, 1986.

June et al., "Car T cell immunotherapy for human cancer," Science, Mar. 2018, 359(6382):1361-1365.

June et al., "Chimeric Antigen Receptor Therapy," N. Engl. J. Med., Jul. 2018, 379(1):64-73.

(56) References Cited

OTHER PUBLICATIONS

Jutz et al., "Assessment of costimulation and coinhibition in a triple parameter T cell reporter line: Simultaneous measurement of NF-kappaB, NFAT and AP-1," J. Immunol. Methods, Jan. 2016, 430:10-20.

Juvet et al., "Phosphodiesterase 3b Inhibition Expands Stable Regulatory T Cells for Cell Therapy in Transplantation," J. Heart Lung Transplantation, Apr. 2015, 34(4):S147.

Kabat et al., "Sequences of Proteins of Immunological Interest, Fifth Edition," U.S. Department of Health and Human Services, NIH Publication No. 91-3242, Table of Contents, 20 pages, 1991.

Kaech et al., "Transcriptional control of effector and memory CD8+ T cell differentiation," Nat Rev Immunol., 12(11): 749-761, Nov. 2012.

Kalafatovic et al., "Cell-Penetrating Peptides: Design Strategies beyond Primary Structure and Amphipathicity," Molecules, 22(11):1929, Nov. 8, 2017, 38 pages.

Kaleko et al., "Persistent gene expression after retroviral gene transfer into liver cells in vivo," Hum Gene Ther., 2(1):27-32, 1991.

Kalimuthu et al., "In Vivo Tracking of Chemokine Receptor CXCR4-Engineered Mesenchymal Stem Cell Migration by Optical Molecular Imaging," Stem Cells International, Jun. 2017, 2017:8085637, 10 pages.

Kaliyaperumal et al., "Antigen-specific therapy of murine lupus nephritis using nucleosomal peptides: tolerance spreading impairs pathogenic function of autoimmune T and B cells," J Immunol., 162(10):5775-5783, May 15, 1999.

Kalled et al., "Anti-CD40 ligand antibody treatment of SNF1 mice with established nephritis: preservation of kidney function," J Immunol., 160(5):2158-2165, Mar. 1, 1998.

Kalos et al., "T cells with chimeric antigen receptors have potent antitumor effects and can establish memory in patients with advanced leukemia," Sci. Transl. Med., Aug. 2011, 3(95):95ra73.

Kaltschmidt et al., "The Transcription Factor NF-kappaB in Stem Cells and Development," Cells, Aug. 2021, 10(8):2042, 17 pages.

Kamphorst et al., "Proliferation of PD-1+ CD8 T cells in peripheral blood after PD-1-targeted therapy in lung cancer patients," Proc Natl Acad Sci USA., 114(19):4993-4998, May 9, 2017.

Kamphorst et al., "Rescue of exhausted CD8 T cells by PD-1-targeted therapies is CD28-dependent," Science, 355(6332):1423-1427, Mar. 31, 2017.

Kanai et al., "Blockade of B7-H1 suppresses the development of chronic intestinal inflammation," J Immunol., 171(8):4156-4163, Oct. 15, 2003.

Kanai et al., "Interferon-gamma enhances the therapeutic effect of mesenchymal stem cells on experimental renal fibrosis," Sci. Reports, Jan. 2021, 11(1):850, 14 pages.

Kaneko et al., "Augmentation of Val4 NKT cell-mediated cytotoxicity by interleukin 4 in an autocrine mechanism resulting in the development of concanavalin A-induced hepatitis," J Exp Med., 191(1):105-114, Jan. 3, 2000.

Kang et al., "Current clinical trials testing the combination of immunotherapy with radiotherapy," J. Immunother. Cancer, 4:51, Sep. 20, 2016, 20 pages.

Kang et al., "Identification of Potent CD19 scFv for CAR T Cells through scFv Screening with NK/T-Cell Line," Int. J. Mol. Sci., Dec. 2020, 21(23):9163.

Kantarjian et al., "Inotuzumab Ozogamicin versus Standard Therapy for Acute Lymphoblastic Leukemia," N. Engl. J. Med., Aug. 2016, 375(8): 740-753.

Karakhanova et al., "ERK/p38 MAP-kinases and PI3K are involved in the differential regulation of B7-H1 expression in DC subsets," Eur J Immunol., 40(1):254-266, Jan. 2010.

Kataoka et al., "Flow cytometric analysis of phosphorylated histone H2AX following exposure to ionizing radiation in human microvascular endothelial cells," J Radiat Res., 47(3-4):245-257, Sep. 2006.

Katou et al., "Differing phenotypes between intraepithelial and stromal lymphocytes in early-stage tongue cancer," Cancer Res., 67(23):11195-11201, Dec. 1, 2007.

Katz et al., "Phase I Hepatic Immunotherapy for Metastases Study of Intra-Arterial Chimeric Antigen Receptor-Modified T-cell Therapy for CEA+ Liver Metastases," Clin. Cancer Res., Jul. 2015, 21(14):3149-3159.

Kaufman et al., "A phase I trial of intra lesional RV-B7.1 vaccine in the treatment of malignant melanoma," Hum Gene Ther., 11(7):1065-1082, May 1, 2000.

Kawabe et al., "Programmed cell death and extrathymic reduction of VB8+ CD4+ T cells in mice tolerant to Staphylococcus aureus enterotoxin B," Nature, 349(6306):245-248, Jan. 17, 1991.

Kawalekar et al., "Distinct Signaling of Coreceptors Regulates Specific Metabolism Pathways and Impacts Memory Development in Car T Cells," Immunity, 44(2):380-390, Feb. 16, 2016.

Kay et al., "A bacterial effector acts as a plant transcription factor and induces a cell size regulator," Science, 318(5850):648-651, Oct. 26, 2007.

Kee et al., "Antitumor immune activity by chemokine CX3CL1 in an orthotopic implantation of lung cancer model in vivo," Mol Clin Oncol., 1(1):35-40, Jan. 2013.

Keir et al., "PD-1 and its ligands in tolerance and immunity," Annu Rev Immunol., 26:677-704, 2008.

Kelley et al., "Cytokines in the Pathogenesis of Systemic Lupus Erythematosus," Semin Nephrol., 19(1):57-66, Jan. 1999.

Kellner et al., "The Fc-engineered CD19 antibody MOR208 (XmAb5574) induces natural killer cell-mediated lysis of acute lymphoblastic leukemia cells from pediatric and adult patients," Leukemia, Jan. 1, 2013, 27(7):1595-1598.

Kemp et al., "Lck Mediates Th2 Differentiation through Effects on T-bet and GATA-3," J. Immunology, Apr. 15, 2010, 184(8):4178-4184.

Kenderian et al., "CD33-specific chimeric antigen receptor T cells exhibit potent preclinical activity against human acute myeloid leukemia," Leukemia, Feb. 27, 2015, 29(8):1637-1647.

Kenderian et al., "Chimeric antigen receptor T-cell therapy to target hematologic malignancies," Cancer Research, 74(22):6383-6389, Nov. 4, 2014.

Kenderian et al., "Identification of PD1 and TIM3 as Checkpoints That Limit Chimeric Antigen Receptor T Cell Efficacy in Leukemia," Blood, Dec. 3, 2015, 126(23):852.

Kenderian et al., "Leukemia Stem Cells Are Characterized by CLEC12A Expression and Chemotherapy Refractoriness That Can be Overcome by Targeting with Chimeric Antigen Receptor T Cells," Blood, Dec. 2, 2016, 128(22):766.

Kenderian et al., "Ruxolitinib Prevents Cytokine Release Syndrome after CART Cell Therapy without Impairing the Anti-Tumor Effect in a Xenograft Model," Blood, Dec. 2, 2016, 128(22):652.

Kennerdell et al., "Use of dsRNA-mediated genetic interference to demonstrate that frizzled and frizzled 2 act in the wingless pathway," Cell, 95(7):1017-1026, Dec. 23, 1998.

Kharbanda et al., "Translocation of SAPK/JNK to mitochondria and interaction with Bcl-x(L) in response to DNA damage," J Biol Chem., 275(1):322-327, Jan. 7, 2000.

Kiessling et al., "High-throughput mutation profiling of CTCL samples reveals KRAS and NRAS mutations sensitizing tumors toward inhibition of the RAS/RAF/MEK signaling cascade," Blood, 117(8):2433-2440, Jan. 5, 2011.

Kim et al., "Enhanced Immunosuppressive Properties of Human Mesenchymal Stem Cells Primed by Interferon-gamma," EBioMedicine, Jan. 2018, 28:261-273.

Kim et al., "Fas Ligand-Positive Membranous Vesicles Isolated from Sera of Patients with Oral Cancer Induce Apoptosis of Activated T Lymphocytes," Clin. Cancer Res., Feb. 2005, 11(3):1010-1020.

Kim et al., "Features of responding T cells in cancer and chronic infection," Curr Opin Immunol., 22(2):223-230, Mar. 6, 2010.

Kim et al., "Galectin-9 is Involved in Immunosuppression Mediated by Human Bone Marrow-derived Clonal Mesenchymal Stem Cells," Immune Network, Oct. 2015, 15(5):241-251.

Kim et al., "Hybrid restriction enzymes: zinc finger fusions to Fok I cleavage domain," Proc. Natl. Acad Sci. USA, 93(3): 1156-1160, Feb. 6, 1996.

Kim et al., "MicroRNAs miR-125a and miR-125b constitutively activate the NF-KB pathway by targeting the tumor necrosis factor

(56)　　　　　References Cited

OTHER PUBLICATIONS alpha-induced protein 3 (TNFAIP3, A20)," Proc. Natl. Acad. Sci. USA, May 15, 2012, 109(20):7865-7870.

Kim et al., "Therapeutic potential of 4-1BB (CD137) as a regulator for effector CD8(+) T cells," J Hematother Stem Cell Res., 10(4):441-449, Aug. 2001.

Kim et al., "TNFR2-deficient memory CD8 T cells provide superior protection against tumor cell growth," J. Immunology, Nov. 15, 2009, 183(10):6051-6057.

Kim et al., "TopHat2: accurate alignment of transcriptomes in the presence of insertions, deletions and gene fusions," Genome Biology, 14:R36, Apr. 25, 2013, 13 pages.

Klebanoff et al., "Memory T cell-driven differentiation of naive cells impairs adoptive immunotherapy," J. Clin. Invest., Jan. 2016, 126(1):318-334.

Klimka et al., "Human anti-CD30 recombinant antibodies by guided phage antibody selection using cell panning," Brit. J. Can., 83(2):252-260, Jul. 2000.

Kochenderfer et al., "B-cell depletion and remissions of malignancy along with cytokine-associated toxicity in a clinical trial of anti-CD19 chimeric-antigen-receptor-transduced T cells," Blood, Mar. 2012, 119(12):2709-2720.

Köhler et al., "Continuous cultures of fused cells secreting antibody of predefined specificity," Nature, 256(5517):495-497, Aug. 7, 1975.

Kohn et al. "Gene therapy for genetic diseases," Cancer Invest., 7(2):179-192, 1989.

Koneru et al., "IL-12 secreting tumor-targeted chimeric antigen receptor T cells eradicate ovarian tumors in vivo," Oncoimmunology, Jan. 23, 2015, 4(3):e994446.

Kong et al., "Suppression of human glioma xenografts with second-generation IL13R-specific chimeric antigen receptor-modified T cells," Clin. Cancer Res., Nov. 2012, 18(21):5949-5960.

Konieczny et al., "The combination of IgM subunits and proteolytic IgG fragment by controlled formation of interchain disulphides," Haematologia (Budap)., 14(1):95-99, 1981.

Korkola et al., "Gene expression-based classification of nonseminomatous male germ cell tumors," Oncogene, 24(32):5101-5107, Jul. 28, 2005.

Kosari et al., "Clear cell renal cell carcinoma: gene expression analyses identify a potential signature for tumor aggressiveness," Clin Cancer Res., 11(14):5128-5139, Jul. 15, 2005.

Kozbor et al. "The production of monoclonal antibodies from human lymphocytes," Immunology Today, 4(3):72-79, Mar. 1, 1983.

Kozomara et al., "miRBase: annotating high confidence microRNAs using deep sequencing data," Nucleic Acids Res., Jan. 2014, 42(Database issue):D68-D73.

Kozomara et al., "miRBase: from microRNA sequences to function," Nucleic Acids Res., Jan. 2019, 47(D1):D155-D162.

Kozomara et al., "miRBase: integrating microRNA annotation and deepsequencing data," Nucleic Acids Res., Jan. 2011, 39(Database issue):D152-D157.

Krämer et al., "Causal analysis approaches in Ingenuity Pathway Analysis," Bioinformatics, Dec. 2013, 30(4):523-530.

Kreitman et al., "Moxetumomab pasudotox in relapsed/refractory hairy cell leukemia," Leukemia, Aug. 2018, 32(8):1768-1777.

Krempski et al., "Tumor-infiltrating programmed death receptor-1+ dendritic cells mediate immune suppression in ovarian cancer," J Immunol., 186(12):6905-6913, May 6, 2011.

Krieg et al., "High-dimensional single-cell analysis predicts response to anti-PD-1 immunotherapy," Nat Med., 24:144-153, Jan. 8, 2018.

Kruege et al., "The role of CD95 in the regulation of peripheral T-cell apoptosis," Immunol Rev., 193:58-69, Jun. 2003.

Krummel et al., "CTLA-4 engagement inhibits IL-2 accumulation and cell cycle progression upon activation of resting T cells," J Exp Med., 183(6):2533-2540, Jun. 1, 1996.

Kuiper et al., "B7.1 and Cytokines: Synergy in cancer gene therapy," Adv Exp Med Biol., 465:381-390, 2000.

Kulakovskiy et al., "HOCOMOCO: a comprehensive collection of human transcription factor binding sites models," Nucl. Acids Research, 41(Database issue):D195-D202, Jan. 2013.

Kurtulus et al., "Bcl-2 allows effector and memory CD8+ T cells to tolerate higher expression of Bim," J Immunol., 186(10):5729-5737, May 15, 2011.

Kusmartsev et al., "Gr-1+ myeloid cells derived from tumor-bearing mice inhibit primary T cell activation induced through CD3/CD28 costimulation," J Immunol., 165(2):779-785, Jul. 15, 2000.

Kwon et al., "4-1BB: Still in the Midst of Darkness," Mol Cells., 10(2):119-126, Apr. 30, 2000.

Labaer, "So, you want to look for biomarkers (introduction to the special biomarkers issue)," J Proteome Res., 4(4):1053-1059, Jul./Aug. 2005.

Lafleur et al., "PTPN2 regulates the generation of exhausted CD8+ T cell subpopulations and restrains tumor immunity," Nat. Immunol., Oct. 2019, 20(10):1335-1347.

Lai et al., "Fibroblast growth factor 2 (Fgf2) inhibits differentiation of mesenchymal stem cells by inducing Twist2 and Spry4, blocking extracellular regulated kinase activation, and altering Fgf receptor expression levels," Stem Cells, Jul. 2011, 29(7):1102-1111.

Lamb et al., "Gut-Selective Integrin-Targeted Therapies for Inflammatory Bowel Disease," J. Crohns Colitis, Aug. 2018, 12(S2):S653-S668.

Langer et al., "Carboplatin and pemetrexed with or without pembrolizumab for advanced, non-squamous non-small-cell lung cancer: a randomised, phase 2 cohort of the open-label KEYNOTE-021 study," Lancet Oncol., 17(11):1497-1508, Nov. 2016.

Larkin et al., "Combined Nivolumab and Ipilimumab or Monotherapy in Untreated Melanoma," N Engl J Med., 373(1):23-34, Jul. 2, 2015.

Larrubia et al., "Bim-mediated apoptosis and PD-1/PD-L1 pathway impair reactivity of PD1(+)/CD127(-) HCV-specific CD8(+) cells targeting the virus in chronic hepatitis C virus infection," Cell Immunol., 269(2):104-114, Mar. 17, 2011.

Latchman et al., "PD-L2 is a second ligand for PD-1 and inhibits T cell activation," Nat Immunol., 2(3):261-268, Mar. 2001.

Lau et al., "Exacerbation of myasthenia gravis in a patient with melanoma treated with pembrolizumab," Muscle Nerve, 54(1):157-161, Jun. 2016.

Laurenzana et al., "Extracellular Vesicles: A New Prospective in Crosstalk between Microenvironment and Stem Cells in Hematological Malignancies," Stem Cells International, May 27, 2018, 2018:9863194, 11 pages.

Lawler et al., "Immune Escape Mediated by Exosomal PD-L1 in Cancer," Adv. Biosyst., Dec. 2020, 4(12):e2000017.

Lawson et al., "Treatment of murine lupus with cDNA encoding IFN-gammaR/Fc," J Clin Invest., 106(2):207-215, Jul. 2000.

Lazarevic et al., "T-bet in disease," Nat Immunol., 12(7):597-606, Jun. 20, 2011.

Lee et al., "Survivin expression and its clinical significance in pancreatic cancer," BMC Cancer, 5:127, Oct. 4, 2005.

Lee et al., "Current concepts in the diagnosis and management of cytokine release syndrome," Blood, Jul. 2014, 124(2):188-195.

Lee et al., "Increased vaccine-specific T cell frequency after peptide-based vaccination correlates with increased susceptibility to in vitro stimulation but does not lead to tumor regression," J Immunol., 163(11):6292-6300, Dec. 1, 1999.

Lee et al., "Preclinical Optimization of a CD20-specific Chimeric Antigen Receptor Vector and Culture Conditions," J. Immunother., Jan. 2018, 41(1):19-31.

Lee et al., "T cells expressing CD19 chimeric antigen receptors for acute lymphoblastic leukaemia in children and young adults: a phase 1 dose-escalation trial," Lancet, Feb. 2015, 385(9967):517-528.

Leggett et al., "Sequencing quality assessment tools to enable data-driven informatics for high throughput genomics," Front. Genetics, 4:288, Dec. 2013, 5 pages.

Leibovich et al., "Prediction of progression after radical nephrectomy for patients with clear cell renal cell carcinoma: a stratification tool for prospective clinical trials," Cancer, 97(7):1663-1671, Apr. 1, 2003.

Lemke et al., "Immunobiology of the TAM receptors," Nat. Rev. Immunol., May 2008, 8(5):327-336.

(56)         References Cited

OTHER PUBLICATIONS

Lenardo et al., "Mature T lymphocyte apoptosis—immune regulation in a dynamic and unpredictable antigenic environment," Annu Rev Immunol., 17:221-253, 1999.

Lenschow et al., "CD28/B7 system of T cell costimulation," Annu Rev Immunol., 14:233-258, 1996.

Leuci et al., "CD44v6 as innovative sarcoma target for CAR-redirected CIK cells," Oncoimmunology, Feb. 2018, 7(5):e1423167.

Levitt, "Accurate modeling of protein conformation by automatic segment matching," J Mol Biol., 226(2):507-533, Jul. 20, 1992.

Lewinski et al., "Retroviral DNA integration: viral and cellular determinants of target-site selection," PLOS Pathog., 2(6):e60, Jun. 23, 2006.

Lewis et al., "Conserved seed pairing, often flanked by adenosines, indicates that thousands of human genes are microRNA targets," Cell, Jan. 2005, 120(1):15-20.

Lewis et al., "Surrogate tumor antigen vaccination induces tumor-specific immunity and the rejection of spontaneous metastases," Cancer Res., 65(7):2938-2946, Apr. 1, 2005.

Lewis, "PCR's Competitors Are Alive and Well and Moving Rapidly Towards Commercialization," Genetic Engineering News, vol. 12, 3 pages, 1992.

Ley et al., "Regulatory phosphorylation of Bim: sorting out the ERK from the JNK," Cell Death Differ., 12(8):1008-1014, Aug. 2005.

Li et al., "Anti-programmed death-1 synergizes with granulocyte macrophage colony-stimulating factor—secreting tumor cell immunotherapy providing therapeutic benefit to mice with established tumors," Clin Cancer Res., 15(5):1623-1634, Feb. 10, 2009.

Li et al., "Fast and accurate long-read alignment with Burrows-Wheeler transform," Bioinformatics, Mar. 2010, 26(5):589-595.

Li et al., "Gemcitabine and arabinosylcytosin pharmacogenomics: genome-wide association and drug response biomarkers," PLoS One., 4(11):e7765, Nov. 9, 2009.

Li et al., "The emerging roles and therapeutic potential of exosomes in epithelial ovarian cancer," Mol. Cancer, May 15, 2017, 16(1):92.

Liang et al., "Autoantibody responses and pathology regulated by B7-1 and B7-2 costimulation in MRL/lpr lupus," J Immunol., 165(6):3436-3443, Sep. 15, 2000.

Liao et al., "featureCounts: an efficient general purpose program for assigning sequence reads to genomic features," Bioinformatics, 30(7):923-930, Apr. 2014.

Lim et al., "The Principles of Engineering Immune Cells to Treat Cancer," Cell, Feb. 2017, 168(4): 724-740.

Lin et al., "Efficient lentiviral transduction of human mesenchymal stem cells that preserves proliferation and differentiation capabilities," Stem Cells Transl. Medicine, Nov. 2012, 1(12):886-897.

Lin et al., "Preconditioning of murine mesenchymal stem cells synergistically enhanced immunomodulation and osteogenesis," Stem Cell Res. Therapy, Dec. 2017, 8:277, 9 pages.

Lin et al., "The PD-1/PD-L1 complex resembles the antigen-binding Fv domains of antibodies and T cell receptors," Proc Natl Acad Sci USA., 105(8):3011-3016, Feb. 26, 2008.

Linsley et al., "Binding of the B cell activation antigen B7 to CD28 costimulates T cell proliferation and interleukin 2 mRNA accumulation" J Exp Med., 173(3):721-730, Mar. 1, 1991.

Linsley et al., "Extending the B7 (CD80) gene family," Protein Sci., 3(8):1341-1343, Aug. 1994.

Linsley et al., "T-cell antigen CD28 mediates adhesion with B cells by interacting with activation antigen 87188-1," Proc Natl Acad Sci USA., 87(13):5031-5035, Jul. 1990.

Lio et al., "CD28 facilitates the generation of Foxp3(-) cytokine responsive regulatory T cell precursors," J. Immunology, Apr. 2010, 184(11):6007-6013.

Liotta et al., "Toll-like receptors 3 and 4 are expressed by human bone marrow-derived mesenchymal stem cells and can inhibit their T-cell modulatory activity by impairing Notch signaling," Stem Cells, Oct. 2007, 26(1):279-289.

Liu et al., "B7DC/PDL2 promotes tumor immunity by a PD-1-independent mechanism," J Exp Med., 197(12): 1721-1730, Jun. 16, 2003.

Liu et al., "B7-H3 silencing increases paclitaxel sensitivity by abrogating Jak2/Stat3 phosphorylation," Mol Cancer Ther., 10(6):960-971, Apr. 25, 2011.

Liu et al., "CRISPR-Cas9-mediated multiplex gene editing in CAR-T cells," Cell Research, Jan. 2017, 27(1):154-157.

Liu et al., CTL-vs Treg lymphocyte-attracting chemokines, CCL4 and CCL20, are strong reciprocal predictive markers for survival of patients with oesophageal squamous cell carcinoma. Br J Cancer, 113(5):747-755, Sep. 1, 2015.

Liu et al., "Endogenous tumor-reactive CD8+ T cells are differentiated effector cells expressing high levels of CD11a and PD-1 but are unable to control tumor growth," Oncoimmunology., 2(6):e23972, Jun. 6, 2013.

Liu et al., "Fas-mediated apoptosis causes elimination of virus-specific cytotoxic T cells in the virus-infected liver," J Immunol., 166(5):3035-3041, Mar. 1, 2001.

Liu et al., "Immunosuppressive Property of MSCs Mediated by Cell Surface Receptors," Front. Immunology, Jul. 2020, 11:1076, 15 pages.

Liu et al., "Interferon gamma plays a critical role in induced cell death of effector T cell: a possible third mechanism of self-tolerance," J Exp Med., 172(6):1735-1739, Dec. 1, 1990.

Liu et al., "Plasma cells from multiple myeloma patients express B7-H1 (PD-L1) and increase expression after stimulation with IFN-{gamma} and TLR ligands via a MyD88-, TRAF6-, and MEK-dependent pathway," Blood, 110(1):296-304, Mar. 15, 2007.

Liu et al., "RAxML and FastTree: Comparing Two Methods for Large-Scale Maximum Likelihood Phylogeny Estimation," PLoS One, Nov. 21, 2011, 6(11): e27731, 11 pages.

Liu et al., "Targeting Alpha-Fetoprotein (AFP)-MHC Complex with CAR T-Cell Therapy for Liver Cancer," Clin. Cancer Res., Jan. 2017, 23(2):478-488.

Liu, "Differential Expression of Cell Surface Molecules in Prostate Cancer Cells," Cancer Research, Jul. 1, 2000, 60:3429-3434.

Locke et al., "Long-term safety and activity of axicabtagene ciloleucel in refractory large B-cell lymphoma (ZUMA-1): a single-arm, multicentre, phase 1-2 trial," Lancet Oncol., Jan. 2019, 20(1):31-42.

Locke et al., "Preliminary results of prophylactic tocilizumab after axicabtageneciloleucel (axi-cel; KTE-C19) treatment for patients with refractory, aggressive non-Hodgkin lymphoma (NHL)," Blood, Dec. 2017, 130(Suppl 1):1547.

Lonberg et al., "Antigen-specific human antibodies from mice comprising four distinct genetic modifications," Nature, 368(6474):856-859, Apr. 28, 1994.

Long et al., "4-1BB costimulation ameliorates T cell exhaustion induced by tonic signaling of chimeric antigen receptors," Nat. Med., Jun. 2015, 21(6):581-590.

Losman et al., "Baboon anti-idiotype antibodies mimic a carcinoembryonic antigen epitope," Int J Cancer., 46(2):310-314, Aug. 15, 1990.

Love et al., "Moderated estimation of fold change and dispersion for RNA-seq data with DESeq2," Genome Biology, 15:550, Dec. 5, 2014, 21 pages.

Lu et al., "EGF-IL-18 fusion protein as a potential anti-tumor reagent by induction of immune response and apoptosis in cancer cells," Cancer Lett., 260(1-2):187-197, 2008.

Luciano et al., "Phosphorylation of Bim-EL by Erk1/2 on serine 69 promotes its degradation via the proteasome pathway and regulates its proapoptotic function," Oncogene., 22(43):6785-6793, Oct. 2, 2003.

Ludwinski et al., "Critical roles of Bim in T cell activation and T cell-mediated autoimmune inflammation in mice," J Clin Invest., 119(6):1706-1713, Jun. 2009.

Luettig et al., "Naive and memory T lymphocytes migrate in comparable mumbers through normal rat liver: activated T cells accumulate in the periportal field," J Immunol., 163(8):4300-4307, Oct. 15, 1999.

Luke et al., "Targeted agents and immunotherapies: optimizing outcomes in melanoma," Nat Rev Clin Oncol., 14(8):463-482, Aug. 2017.

Lunsford et al., "Targeting LFA-1 and cd154 suppresses the in vivo activation and development of cytolytic (cd4-Independent) CD8+ T cells," J Immunol., 175(12):7855-7866, Dec. 15, 2005.

(56)     References Cited

OTHER PUBLICATIONS

Luo et al., "Bim inhibits autophagy by recruiting Beclin 1 to microtubules," Mol Cell, 47(3):359-370, Aug. 10, 2012.

Luz-Crawford et al., "Mesenchymal stem cells generate a CD4+ CD25+Foxp3+ regulatory T cell population during the differentiation process of Th1 and Th17 cells," Stem Cell Res. Therapy, Jun. 2013, 4(3):65, 12 pages.

Lynn et al., "c-Jun overexpression in Car T cells induces exhaustion resistance," Nature, Dec. 2019, 576(7786):293-300.

Ma et al., "The DNA-dependent protein kinase catalytic subunit phosphorylation sites in human Artemis," J Biol Chem., 280(40):33839-33846, Aug. 10, 2005.

Ma et al., "The Role of PD-1 Ligand in Immune Evasion by Breast Cancer," Dana-Farber Cancer Institute Annual Summary Report 1—May 2002-Apr. 30, 2005, pp. 5-6, 9, 11, report date: May 2005.

Maacha et al., "Extracellular vesicles-mediated intercellular communication: roles in the tumor microenvironment and anti-cancer drug resistance," Mol. Cancer, Mar. 2019, 18(1):55.

MacDonald et al., "Alloantigen-specific regulatory T cells generated with a chimeric antigen receptor," J. Clin. Investigation, Mar. 21, 2016, 126(4):1413-1424.

Machanick et al., "MEME-ChIP: motif analysis of large DNA datasets," Bioinformatics, 27(12):1696-1697, Jun. 15, 2011.

Mah et al., "gammaH2AX: a sensitive molecular marker of DNA damage and repair," Leukemia, 24(4):679-686, Feb. 4, 2010.

Mahotka et al., "Distinct in vivo expression patterns of survivin splice variants in renal cell carcinomas," Int J Cancer, 100(1):30-36, Jul. 1, 2002.

Majzner et al., "Clinical lessons learned from the first leg of the CAR T cell journey," Nat. Med., Sep. 2019, 25(9):1341-1355.

Makarova et al., "Evolution and classification of the CRISPR-Cas systems," Nat. Rev. Microbiology, 9(6):467-477, May 9, 2011.

Makita et al., "Clinical development of anti-CD19 chimeric antigen receptor T-cell therapy for B-cell non-Hodgkin lymphoma," Cancer Sci., Jun. 2017, 108(6):1109-1118.

Mali et al., "RNA-guided human genome engineering via Cas9," Science, 339(6121):823-826, Feb. 15, 2013.

Man et al., "Transcription Factor IRF4 Promotes CD8+ T Cell Exhaustion and Limits the Development of Memory-like T Cells during Chronic Infection," Immunity, Dec. 2017, 47(6):1129-1141. e5.

Mandell et al., "Zinc Finger Tools: custom DNA-binding domains for transcription factors and nucleases," Nucleic Acids Research, Jul. 1, 2006, 34(suppl_2):W516-W523.

Mann et al., "Construction of a retrovirus packaging mutant and its use to produce helper-free defective retrovirus" Cell, 33(1):153-159, May 1983.

Manriquez Roman et al., "Assessment of Chimeric Antigen Receptor T Cell-Associated Toxicities Using an Acute Lymphoblastic Leukemia Patient-derived Xenograft Mouse Model," J. Vis. Exp., Feb. 2023, 192:e64535.

Mantovani et al., "Macrophage polarization: tumor-associated macrophages as a paradigm for polarized M2 mononuclear phagocytes," Trends Immunol., Nov. 2002, 23(11):549-555.

Martin et al. "Combination gene therapy with CD86 and the MHC Class II transactivator in the control of lung tumor growth," J Immunol., 162(11):6663-6670, Jun. 1, 1999.

Martin et al., "National Institutes of Health Consensus Development Project on Criteria for Clinical Trials in Chronic Graft-versus-Host Disease: VI. The 2014 Clinical Trial Design Working Group Report," Biol. Blood Marrow Transplantation, Aug. 2015, 21(8):1343-1359.

Martin, "Cutadapt removes adapter sequences from high-throughput sequencing reads," EMBnet.journal, May 2011, 17(1):10-12.

Martinez et al., "Alternative activation of macrophages: an immunologic functional perspective," Annu. Rev. Immunol., 2009, 27:451-483.

Martinez et al., "CAR T Cells for Solid Tumors: New Strategies for Finding, Infiltrating, and Surviving in the Tumor Microenvironment," Front. Immunol., Feb. 2019, 10:128.

Matejcek et al., "Pharmaco-EEG and Psychometric study of the effect of single doses of temazepam and nitrazepam," Neuropsychobiology, 1983, 9(1):52-65.

Mathiowitz et al., "Morphology of poly anhydride microsphere delivery systems," Scanning Microsc., 4(2):329-340, Jun. 1990.

Mathiowitz et al., "Polyanhydride microspheres as drug carriers. I. Hot-melt microencapsulation," J. Controlled Release, 5(1):13-22, Jun. 1, 1987.

Mathiowitz et al., "Polyanhydride microspheres. IV. Morphology and characterization of systems made by spray drying," J. Appl. Polymer Sci., 45(1):125-134, May 5, 1992.

Mathiowitz, Novel microcapsules for delivery systems, Reactive Polymers, 6(2):275-283, Oct. 31, 1987.

Mathiowitz, "Polyanhydride microspheres as drug carriers, II. Microencapsulation by solvent removal," J. Appl. Polymer Sci., 35(3):755-774, Feb. 20, 1988.

Matsumoto et al., "CIS, a cytokine inducible SH2 protein, is a target of the JAK-STAT5 pathway and modulates STAT5 activation," Blood, 89(9):3148-3154, May 1, 1997.

Maude et al., "Chimeric Antigen Receptor T Cells for Sustained Remissions in Leukemia," N. Engl. J. Med., Oct. 2014, 371(16):1507-1517.

Maude et al., "Tisagenlecleucel in Children and Young Adults with B-Cell Lymphoblastic Leukemia," N. Engl. J. Medicine, 378(5):439-448, Feb. 1, 2018.

Mayo.edu [online] "Center for Clinical and Translational Science (CCaTS): Study Design," Available on or before Oct. 12, 2012, via Internet Archive: Wayback Machine URL<https://web.archive.org/web/20121012161818/http://www.mayo.edu/ctsa/education/professional-development/online-courses/study-design>, retrieved on Mar. 23, 2021, retrieved from URL<https://web.archive.org/web/20170816080726/http://www.mayo.edu/ctsa/education/professional-development/online-courses/study-design>, 2 pages.

McCubrey et al., "Roles of the Raf/MEK/ERK pathway in cell growth, malignant transformation and drug resistance," Biochim Biophys Acta., 1773(8):1263-1284, Oct. 7, 2006.

McDermott et al., "PD-1 as a potential target in cancer therapy," Cancer Med., 2(5):662-673. Jul. 21, 2013.

McGregor et al., "Results of a Multicenter Phase II Study of Atezolizumab and Bevacizumab for Patients With Metastatic Renal Cell Carcinoma With Variant Histology and/or Sarcomatoid Features," J. Clin. Oncol., Jan. 2020, 38(1):63-70.

McKenna et al., "The Genome Analysis Toolkit: a MapReduce framework for analyzing next-generation DNA sequencing data," Genome Res., Sep. 2010, 20(9):1297-1303.

McLachlin et al., "Retroviral-mediated gene transfer," Prog Nucleic Acid Res Mol Biol., 38:91-135, 1990.

Mehal et al., "Antigen presentation by liver cells controls intrahepatic T cell trapping, whereas bone marrow-derived cells preferentially promote intrahepatic T cell apoptosis," J Immunol., 167(2):667-673, Jul. 15, 2001.

Mehal et al., "TCR ligation on CD8+ T cells creates double-negative cells in vivo," J Immunol., 161(4):1686-1693, Aug. 15, 1998.

Mejstrikova et al., "CD19-negative relapse of pediatric B-cell precursor acute lymphoblastic leukemia following blinatumomab treatment," Blood Cancer Journal, Dec. 20, 2017, 7(12):659, 5 pages.

Melero et al., "Amplification of tumor immunity by gene transfer of the co-stimulatory 4-1BB ligand: synergy with the CD28 co-stimulatory pathway," Eur J Immunol., 28(3):1116-1121, Mar. 1998.

Melero et al., "Monoclonal antibodies against the 4-1BB T-cell activation molecule eradicate established tumors," Nat Med., 3(6):682-685, Jun. 1997.

Melero et al., "NK1.1 cells express 4-1BB (CDw137) costimulatory molecule and are required for tumor immunity elicited by anti-4-1BB monoclonal antibodies," Cell Immunol., 190(2):167-172, Dec. 15, 1998.

Melief et al., "Multipotent stromal cells induce human regulatory T cells through a novel pathway involving skewing of monocytes toward anti-inflammatory macrophages," Stem Cells, Sep. 2013, 31(9):1980-1991.

(56) References Cited

OTHER PUBLICATIONS

Melief et al., "Strategies for immunotherapy of cancer," Advances in Immunology, 75:235-282, Jan. 1, 2000.

Mellado et al., "A potential immune escape mechanism by melanoma cells through the activation of chemokine-induced T cell death," Curr Biol., 11(9):691-696, May 1, 2001.

Mendez-Fernandez et al., "Clearance of Theiler's virus infection depends on the ability to generate a CD8+ T cell response against a single immunodominant viral peptide," Eur J Immunol., 33(9):2501-2510, Sep. 2003.

Merrill, "Emergence of targeted immune therapies for systemic lupus," Expert Opin Emerg Drugs, 10(1):53-65, Feb. 2005.

Merritt et al., "Activation of p38 mitogen-activated protein kinase in vivo selectively induces apoptosis of CD8(+) but not CD4(+) T cells," Mol Cell Biol., 20(3):936-946, Feb. 2000.

Metzler et al., "Solution structure of human CTLA-4 and delineation of a CD80/CD86 binding site conserved in CD28," Nat Struct Biol., 4(7):527-531, Jul. 1997.

Meyts et al., "Deficiency of Adenosine Deaminase 2 (DADA2): Updates on the Phenotype, Genetics, Pathogenesis, and Treatment," J. Clin. Immunology, Jun. 27, 2018, 38(5):569-578.

Mezzadra et al., "Identification of CMTM6 and CMTM4 as PD-L1 Protein Regulators," Nature, 549(7670):106-110, Sep. 7, 2017.

Miller et al., "Gene transfer by retrovirus vectors occurs only in cells that are actively replicating at the time of infection," Mol Cell Biol., 10(8):4239-4242, Aug. 1990.

Miller et al., "Generation of helper-free amphotropic retroviruses that transduce a dominant-acting, methotrexate-resistant dihydrofolate reductase gene," Mol Cell Biol., 5(3):431-437, Mar. 1985.

Miller et al., "Molecular Pathways: Receptor Ectodomain Shedding in Treatment, Resistance, and Monitoring of Cancer," Clin. Cancer Research, 23(3):623-629, Feb. 1, 2017.

Miller et al., "Redesign of retrovirus packaging cell lines to avoid recombination leading to helper virus production," Mol Cell Biol., 6(8):2895-2902, Aug. 1986.

Miller, "Human gene therapy comes of age," Nature, 357(6378):455-460, Jun. 11, 1992.

Mills, "IL-17 and IL-17-producing cells in protection versus pathology," Nat. Rev. Immunol., Jan. 2023, 23(1):38-54.

Milone et al., "Chimeric receptors containing CD137 signal transduction domains mediate enhanced survival of T cells and increased antileukemic efficacy in vivo," Mol. Ther., Aug. 2009, 17(8):1453-1464.

Minderman et al., "DiOC2(3) is not a substrate for multidrug resistance protein (MRP)-mediated drug efflux," Cytometry, 25(1):14-20, Sep. 1, 1996.

Minter et al., "Protein engineering and preclinical development of a GM-CSF receptor antibody for the treatment of rheumatoid arthritis," Br. J. Pharmacol., Jan. 2013, 168(1):200-211.

Misquitta et al., "Targeted disruption of gene function in *Drosophila* by RNA interference (RNA-i): A role for nautilus in embryonic somatic muscle formation," Proc Natl Acad Sci USA., 96(4):1451-1456, Feb. 16, 1999.

Mizuhara et al., "T cell activation-associated hepatic injury: mediation by tumor necrosis factors and protection by interleukin 6," J Exp Med., 179(5):1529-1537, May 1, 1994.

Mohammadi et al., "Exosomes and cancer: From oncogenic roles to therapeutic applications," IUBMB Life, Apr. 2020, 72(4):724-748.

Mohan et al., "Interaction between CD40 and its ligand gp39 in the development of murine lupus nephritis," J Immunol., 154(3):1470-1480, Feb. 1, 1995.

Molfino et al., "Phase 2, randomised placebo-controlled trial to evaluate the efficacy and safety of an anti-GM-CSF antibody (KB003) in patients with inadequately controlled asthma," BMJ Open, Jan. 2016, 6(1):e007709.

Molinero et al., "High TCR stimuli prevent induced regulatory T cell differentiation in a NF-kappaB-dependent manner," J. Immunology, Mar. 2011, 186(8):4609-4617.

Montesano et al., "Genetic alterations in esophageal cancer and their relevance to etiology and pathogenesis: a review," Int J Cancer., 69(3):225-235, Jun. 21, 1996.

Monticelli et al., "IL-33 promotes an innate immune pathway of intestinal tissue protection dependent on amphiregulin-EGFR interactions," Proc. Natl. Acad. Sci. USA, Aug. 2015, 112(34):10762-10767.

Morrison et al., "Chimeric human antibody molecules: mouse antigen-binding domains with human constant region domains," Proc Natl Acad Sci USA., 81(21):6851-6855, Nov. 1984.

Morse et al., "Abnormalities induced by the mutant gene lpr: expansion of a unique lymphocyte subset," J Immunol., 129(6):2612-2615, Dec. 1982.

Moscou et al., "A simple cipher governs DNA recognition by TAL effectors," Science, Dec. 2009, 326(5959):1501.

Moskowitz et al., "PD-1 Blockade with the Monoclonal Antibody Pembrolizumab (MK-3475) in Patients with Classical Hodgkin Lymphoma after Brentuximab Vedotin Failure: Preliminary Results from a Phase 1b Study (KEYNOTE-013)," Blood, 124(21):290, Dec. 6, 2014.

Moss, "Poxvirus expression vectors," Curr Top Microbiol Immunol., 158:25-38, 1992.

Moss, "Poxvirus vectors: cytoplasmic expression of transferred genes," Curr Opin Genet Dev., 3(1):86-90, Feb. 1993.

Moss, "Use of vaccinia virus as an infectious molecular cloning and expression vector," Gene Amplif Anal., 3:201-213, 1983.

Moss, "Vaccinia virus vectors," Biotechnology, 20:345-362, 1992.

Moss, "Vaccinia virus: a tool for research and vaccine development," Science, 252(5013):1662-1667, Jun. 21, 1991.

Motzer et al., "Nivolumab versus Everolimus in Advanced Renal-Cell Carcinoma," N Engl J Med., 373(19):1803-1813, Nov. 5, 2015.

Motzer et al., "Renal Cell Carcinoma," N Engl J Med., 335(12):865-75, Sep. 19, 1996.

Mukherjee et al., "DNA-PK phosphorylates histone H2AX during apoptotic DNA fragmentation in mammalian cells," DNA Repair (Amst)., 5(5):575-590, Mar. 29, 2006.

Muller et al., "Tumor-derived exosomes regulate expression of immune function-related genes in human T cell subsets," Sci. Rep., Feb. 2016, 6:20254.

Mumprecht et al., "Programmed death 1 signaling on chronic myeloid leukemia-specific T cells results in T-cell exhaustion and disease progression," Blood, 114(8):1528-1536, May 6, 2009.

Murata et al., "Off-the-shelf bone marrow-derived mesenchymal stem cell treatment for acute graft-versus-host disease: real-world evidence," Bone Marrow Transplantation, May 2021, 56(10):2355-2366.

Murooka et al., "CCL5-CCR5-mediated apoptosis in T cells: Requirement for glycosaminoglycan binding and CCL5 aggregation," J Biol Chem., 281(35):25184-25194, Sep. 1, 2006.

Muyldermans, "Single domain camel antibodies: current status," J Biotechnol., 74(4):277-302, Jun. 2001.

Myers et al., "AXL Inhibitors in Cancer: A Medicinal Chemistry Perspective," J. Med. Chemistry, Nov. 10, 2015, 59(8):3593-3608.

Myers et al., "Targeting Tyro3, Axl and MerTK (TAM receptors): implications for macrophages in the tumor microenvironment," Mol. Cancer, May 2019, 18(1):94.

Nabel et al., "Recombinant gene expression in vivo within endothelial cells of the arterial wall," Science, 244(4910):1342-1344, Jun. 16, 1989.

Naji et al., "Biological functions of mesenchymal stem cells and clinical implications," Cell. Mol. Life Sciences, May 2019, 76(17):3323-3348.

National Cancer Institute, "Fact Sheet: Tumor Markers," cancer.gov [online] Dec. 7, 2011 [retrieved on Apr. 3, 2014]. Retrieved from the Internet: <URL: http://www.cancer.gov/cancertopics/factsheet/detection/tumor-markers/print>, 8 pages.

National Comprehensive Cancer Network, "NCCN Clinical Practice Guidelines in Oncology (NCCN Guidelines): Melanoma—Version 3.2016," Jul. 7, 2016, 154 pages.

Nava-Parada et al., "Peptide vaccine given with a Toll-like receptor agonist is effective for the treatment and prevention of spontaneous breast tumors," Cancer Res., 67(3):1326-1334, Feb. 1, 2007.

(56) References Cited

OTHER PUBLICATIONS

Nechiporuk et al., "The mouse SCA2 gene: cDNA sequence, alternative splicing and protein expression," Hum Mol Genet., 7(8):1301-1309, Aug. 1998.

Needleman et al., "A general method applicable to the Search for similarities in the amino acid sequence of two proteins," J Mol Biol., 48(3):443-453, Mar. 1970.

Neelapu et al., "Axicabtagene Ciloleucel CAR T-Cell Therapy in Refractory Large B-Cell Lymphoma," N. Engl. J. Med., Dec. 2017, 377(26):2531-2544.

Neelapu et al., "Chimeric antigen receptor T-cell therapy—assessment and management of toxicities," Nat. Rev. Clin. Oncol., Jan. 2018, 15(1):47-62.

Neer, "Vasopressin-responsive, Soluble Adenylate Cyclase from the Rat Renal Medulla," J. Biol. Chemistry, 248(10):3742-3744, May 25, 1973.

Nellan et al., "Durable regression of Medulloblastoma after regional and intravenous delivery of anti-HER2 chimeric antigen receptor T cells," J. Immunother. Cancer, Apr. 2018, 6(1):30.

Nelson et al., "Tumor progression despite efficient tumor antigen cross-presentation and effective "arming" of tumor antigen-specific CTL," J Immunol., 166(9):5557-5566, May 1, 2001.

Nevala et al., "Evidence of systemic Th2-driven chronic inflammation in patients with metastatic melanoma," Clin Cancer Res., 15(6):1931-1939, Mar. 15, 2009.

Neves et al., "Surgical treatment of renal cancer with vena cava extension," Br J Urol., 59(5):390-395, May 1987.

Newmark et al., "Preparation and properties of adducts of streptokinase and streptokinase-plasmin complex with poly ethylene glycol and pluronic polyol F38," J Appl Biochem., 4:185-189, 1982.

Newton et al., "Clinical benefit of INCB7839, a potent and selective ADAM inhibitor, in combination with trastuzumab in patients with metastatic HER2+ breast cancer.," J. Clin. Oncol., 28(15 Suppl):3025, May 2010.

Neyns et al., "Dose-dense temozolomide regimens: antitumor activity, toxicity, and immunomodulatory effects," Cancer, 116(12):2868-2877, Jun. 15, 2010.

Ngiow et al., "A Threshold Level of Intratumor CD8+ T-cell PD1 Expression Dictates Therapeutic Response to Anti-PD1," Cancer Res., 75(18):3800-3811, Sep. 15, 2015.

Nicolau et al., "In vivo expression of rat insulin after intravenous administration of the liposome-entrapped gene for rat insulin I," Proc Natl Acad Sci USA., 80(4):1068-1072, Feb. 1983.

Nielsen et al., "Melanoma vaccines: the paradox of T cell activation without clinical response," Cancer Chemother Pharmacol., 46 Suppl:S62-S66, 2000.

Nielsen et al., "Peptide nucleic acid (PNA). A DNA mimic with a peptide backbone," Bioconjug Chem., 5(1):3-7, Jan./Feb. 1994.

Nielsen et al., "Sequence-selective recognition of DNA by strand displacement with a thymine-substituted polyamide," Science, 254(5037):1497-1500, Dec. 6, 1991.

Nishimura et al., "Autoimmune dilated cardiomyopathy in PD-1 receptor-deficient mice," Science, 291(5502):319-322, Jan. 12, 2001.

Nishimura et al., "Development of lupus-like autoimmune diseases by disruption of the PD-1 gene encoding an ITIM motif-carrying immunoreceptor," Immunity, 11(2):141-151, Aug. 1999.

Nishimura et al., "Dual functions of fractalkine/CX3C ligand 1 in trafficking of perforin+/granzyme B+ cytotoxic effector lymphocytes that are defined by CX3CR1 expression," J Immunol., 168(12):6173-6180, Jun. 15, 2002.

Nishimura et al., "Immunological studies on PD-1-deficient mice: implication of PD-1 as a negative regulator for B cell responses," Int Immunol., 10(10):1563-1572, Oct. 1998.

Nishino et al., "Monitoring immune-checkpoint blockade: response evaluation and biomarker development," Nat. Reviews, 14(11):655-668, Nov. 2017.

Nisonhoff et al., "Separation of univalent fragments from the bivalent rabbit antibody molecule by reduction of disulfide bonds," Arch Biochem Biophys., 89:230-244, Aug. 1960.

Niu et al., "TLR-4/microRNA-125a/NF-κB signaling modulates the immune response to *Mycobacterium tuberculosis* infection," Cell Cycle, Sep. 6, 2018, 17(15):1931-1945.

Norelli et al., "Monocyte-derived IL-1 and IL-6 are differentially required for cytokine-release syndrome and neurotoxicity due to Car T cells," Nat. Med., Jun. 2018, 24(6):739-748.

Noronha et al., "Priming approaches to improve the efficacy of mesenchymal stromal cell-based therapies," Stem Cell Res. Therapy, May 2019, 10:131, 21 pages.

Noyan et al., "Prevention of Allograft Rejection by Use of Regulatory T Cells With an MHC-Specific Chimeric Antigen Receptor," Am. J. Transplantation, Feb. 2017, 17(4):917-930.

Oh et al., "Ribonucleoprotein Transfection for CRISPR/Cas9-Mediated Gene Knockout in Primary T Cells," Curr. Protoc. Immunol., Feb. 2019, 124(1):e69.

Ohaegbulam et al., "Human cancer immunotherapy with antibodies to the PD-1 and PD-L1 pathway," Trends. Mol. Medicine, 21(1):24-33, Jan. 2015.

Ohigashi et al., "Clinical significance of programmed death-1 ligand-1 and programmed death-1 ligand-2 expression in human esophageal cancer," Clin Cancer Res., 11(8):2947-2953, Apr. 15, 2005.

Ohnishi et al., "Prolonged survival of mice with human gastric cancer treated with an anti-c-ErbB-2 monoclonal antibody," Br. J. Cancer, May 1995, 71(5):969-973.

Okazaki et al., "PD-1 and PD-1 ligands: from discovery to clinical application," Int Immunol., 19(7):813-824, Jul. 2, 2007.

Okazaki et al., "PD-1 immunoreceptor inhibits B cell receptor-mediated signaling by recruiting src homology 2-domain-containing tyrosine phosphatase 2 to phosphotyrosine," Proc Natl Acad Sci USA., 98(24):13866-13871, Nov. 20, 2001.

Oksvold et al., "Expression of B-Cell Surface Antigens in Subpopulations of Exosomes Released From B-Cell Lymphoma Cells," Clin. Therapeutics, Jun. 18, 2014, 36(6):847-862.e1.

Okura et al., "ONO-7475, a Novel AXL Inhibitor, Suppresses the Adaptive Resistance to Initial EGFR-TKI Treatment in EGFR-Mutated Non-Small Cell Lung Cancer," Clin. Cancer Res., May 2020, 26(9):2244-2256.

Opferman al., "Linear differentiation of cytotoxic effectors into memory T lymphocytes," Science, 283(5408):1745-1748, Mar. 12, 1999.

Orabona et al., "CD28 induces immunostimulatory signals in dendritic cells via CD80 and CD86," Nat. Immunology, Oct. 2004, 5(11):1134-1142.

O'Reilly et al., "MEK/ERK-mediated phosphorylation of Bim is required to ensure survival of T and B lymphocytes during mitogenic stimulation," J Immunol., 183(1):261-269, Jul. 1, 2009.

Orlandi et al., "Cloning immunoglobulin variable domains for expression by the polymerase chain reaction," Proc Natl Acad Sci USA., 86(10):3833-3837, May 1989.

Orme et al., "ADAM10 and ADAM17 cleave PD-L1 to mediate PD-(L)1 inhibitor resistance," Oncoimmunology, Apr. 2020, 9(1):1744980.

Orme et al., "Disparate outcomes of patients with Multiple Myeloma based on geographic distance from NCI-Designated National Cancer Centers: A Seer based analysis," Blood, 130(S1):4689, Dec. 7, 2017.

Orme et al., "Heightened cleavage of Axl receptor tyrosine kinase by ADAM metalloproteases may contribute to disease pathogenesis in SLE," Clin. Immunol., 169:58-68, Aug. 2016.

Orme et al., "Leukocyte betacatenin expression is disturbed in systemic lupus erythematosus," PLoS One, 11(8):e0161682, 14 pages.

Orme et al., "Macrophage subpopulations in systemic lupus erythematosus.," Discov. Med., 13(69):151-158, Feb. 2012.

Orme et al., "Macrophages and neutrophils in SLE—An online molecular catalog," Autoimmun. Rev., 11(5):365-372, Mar. 2012.

Ormhoj et al., "Chimeric Antigen Receptor T Cells Targeting CD79b Show Efficacy in Lymphoma with or without Cotargeting CD19," Clin. Cancer Res., Dec. 2019, 25(23):7046-7057.

Ostrov et al., "Structure of murine CTLA-4 and its role in modulating T cell responsiveness," Science, 290(5492):816-819, Oct. 27, 2000.

(56)        References Cited

OTHER PUBLICATIONS

Otano et al., "Human CD8 T cells are susceptible to TNF-mediated activation-induced cell death," Theranostics, Mar. 15, 2020, 10(10):4481-4489.

Ott et al., "Pembrolizumab in Patients With Extensive-Stage Small-Cell Lung Cancer: Results From the Phase Ib KEYNOTE-028 Study," J. Clin. Oncol., 35(34):3823-3829, Aug. 16, 2017.

Ouyang et al., "Novel Foxol-dependent transcriptional programs control T(reg) cell function," Nature, Nov. 2012, 491(7425):554-559, 8 pages.

Ozkaynak et al., "Programmed death-1 targeting can promote allograft survival," J Immunol., 169(11):6546-6553, Dec. 1, 2002.

Padron et al., "GM-CSF-dependent pSTAT5 sensitivity is a feature with therapeutic potential in chronic myelomonocytic leukemia," Blood, Jun. 2013, 121(25):5068-5077.

Palmer et al., "Cish actively silences TCR signaling in CD8+ T cells to maintain tumor tolerance," J Exp Med., 212(12):2095-2113, Nov. 2, 2015.

Panes et al., "Long-term Efficacy and Safety of Stem Cell Therapy (Cx601) for Complex Perianal Fistulas in Patients With Crohn's Disease," Gastroenterology, Apr. 2018, 154(5):1334-1342.e4.

Pangault et al., "Follicular lymphoma cell niche: identification of a preeminent IL-4-dependent T(FH)-B cell axis," Leukemia, Dec. 2010, 24(12):2080-2089.

Panta et al., "ATM and the catalytic subunit of DNA-dependent protein kinase activate NF-kappaB through a common MEK/extracellular signal-regulated kinase/p90(rsk) signaling pathway in response to distinct forms of DNA damage," Mol Cell Biol., 24(5):1823-1835, Mar. 2004.

Pantuck et al., "The changing natural history of renal cell carcinoma," J Urol., 166(5):1611-1623, Nov. 2001.

Paolino et al., "The E3 ligase Cbl-b and TAM receptors regulate cancer metastasis via natural killer cells," Nature, Mar. 2014, 507(7493):508-512.

Pardoll, "Spinning molecular immunology into successful immunotherapy," Nat Rev Immunol., 2(4):227-238, Apr. 2002.

Pardoll., "The Blockade of Immune Checkpoints in Cancer Immunotherapy," Nat Review., 12:252-264, Apr. 2012.

Parihar et al., "NK Cells Expressing a Chimeric Activating Receptor Eliminate MDSCs and Rescue Impaired CAR-T Cell Activity against Solid Tumors," Cancer Immunol. Res., Mar. 2019, 7(3):363-375.

Parikh, "Chronic lymphocytic leukemia treatment algorithm 2018," Blood Cancer J., Oct. 3, 2018, 8:93, 10 pages.

Park et al., "Adipose-derived stem cells ameliorate colitis by suppression of inflammasome formation and regulation of M1-macrophage population through prostaglandin E2," Biochem. Biophys. Res. Commun., Apr. 2018, 498(4):988-995.

Park et al., "B7-H1/CD80 interaction is required for the induction and maintenance of peripheral T-cell tolerance," Blood., 116(8):1291-1298, May 14, 2010.

Park et al., "CD70 as a target for chimeric antigen receptor T cells in head and neck squamous cell carcinoma," Oral Oncol., Mar. 2018, 78:145-150.

Park et al., "Cytokine release syndrome grade as a predictive marker for infections in patients with relapsed or refractory B-cell acute lymphoblastic leukemia treated with chimeric antigen receptor T cells," Clin. Infect. Dis., Aug. 2018, 67(4):533-540.

Park et al., "Increased Response Rates to Salvage Chemotherapy Administered after Pd-1/PD-L1 Inhibitors in Patients with Non-Small Cell Lung Cancer," J Thorac Oncol., 13(1):106-111, Jan. 2018.

Park et al., "Long-Term Follow-up of CD19 Car Therapy in Acute Lymphoblastic Leukemia," N. Engl. J. Med., Jan. 2018, 378(5):449-459.

Park et al., "PD-1 Restrains Radiotherapy-Induced Abscopal Effect," Cancer Immunol Res., 3(6):610-619, Jun. 2015.

Parker et al., "Potential utility of uroplakin III, thrombomodulin, high molecular weight cytokeratin, and cytokeratin 20 in noninvasive, invasive, and metastatic urothelial (transitional cell) carcinomas," Am J Surg Pathol., 27(1):1-10, Jan. 2003.

Parmentier et al., "Human TH2 cells respond to cysteinyl leukotrienes through selective expression of cysteinyl leukotriene receptor 1," J. Allergy Clin. Immunology, Apr. 2012, 129(4):1136-1142.

Parry et al., "CTLA-4 and PD-1 receptors inhibit T-cell activation by distinct mechanisms," Mol Cell Biol., 25(21):9543-9553, Nov. 2005.

Parsa et al., "Loss of tumor suppressor PTEN function increases B7-H1 expression and immunoresistance in glioma," Nat Med., 13(1):84-88, Dec. 10, 2006.

Paterson et al., "The PD-L1:B7-1 pathway restrains diabetogenic effector T cells in vivo," J Immunol., 187(3):1097-1105, Aug. 1, 2011.

Patrone et al., "Nuclear Run-On Assay Using Biotin Labeling, Magnetic Bead Capture and Analysis by Fluorescence-Based RT-PCR," BioTechniques, 29(5):1012-1017, Nov. 2000.

Patsoukis et al., "Revisiting the PD-1 pathway," Sci. Advances, Sep. 2020, 6(38):eabd2712, 14 pages.

Patsoukis et al., "Selective effects of PD-1 on Akt and Ras pathways regulate molecular components of the cell cycle and inhibit T cell proliferation," Sci Signal., 5(230):ra46, Jun. 26, 2012.

Pavelko et al., "The epitope integration site for vaccine antigens determines virus control while maintaining efficacy in an engineered cancer vaccine," Mol Ther., 21(5):1087-1095, Apr. 9, 2013.

Peach et al., "Both extracellular immunoglobulin-like domains of CD80 contain residues critical for binding T cell surface receptors CTLA-4 and CD28," J Biol Chem., 270(36):21181-21187, Sep. 8, 1995.

Pece et al., "Signaling from E-cadherins to the MAPK pathway by the recruitment and activation of epidermal growth factor receptors upon cell-cell contact formation," J Biol Chem., 275(52):41227-41233, Dec. 29, 2000.

Pedraza-Alva et al., "Activation of p38 MAP kinase by DNA double-strand breaks in V(D)J recombination induces a G2/M cell cycle checkpoint," EMBO J., 25(4):763-773, Feb. 2, 2006.

Peghini et al., [Immunophaenotyping in the diagnosis of lymphoma]. Praxis (Bern 1994)., 93(41):1687-1692, Oct. 6, 2004, Article in German, English abstract included.

Pei et al., "FKBP51 affects cancer cell response to chemotherapy by negatively regulating Akt," Cancer Cell., 16(3):259-266, Sep. 8, 2009.

Pemmaraju et al., "Tagraxofusp in Blastic Plasmacytoid Dendritic-Cell Neoplasm," N. Engl. J. Med., Apr. 2019, 380(17):1628-1637.

Peng et al., "PD-1 blockade enhances T-cell migration to tumors by elevating IFN-gamma inducible chemokines," Cancer Res, 72(20):5209-5218, Oct. 15, 2012.

Penix et al., "Two essential regulatory elements in the human interferon gamma promoter confer activation specific expression in T cells," J Exp Med., 178(5):1483-1496, Nov. 1, 1993.

Perriman et al., "Effective ribozyme delivery in plant cells," Proc Natl Acad Sci USA., 92(13):6175-6179, Jun. 20, 1995.

Petroff et al., "B7 family molecules: novel immunomodulators at the maternal-fetal interface," Placenta, 23 Suppl A:S95-101, Apr. 2002.

Pfeiffer et al., "In vivo generation of human CD19-CAR T cells results in B-cell depletion and signs of cytokine release syndrome," EMBO Mol. Medicine, Sep. 17, 2018, 10(11):E9158, 11 pages.

Phinney et al., "MSCs: science and trials," Nat. Medicine, Jul. 2013, 19(7):812.

Piccini, "Vaccinia: virus, vector, vaccine," Adv Virus Res., 34:43-64, 1988.

Ping et al., "Activation of NF-KB driven inflammatory programs in mesenchymal elements attenuates hematopoiesis in low-risk myelodysplastic syndromes," Leukemia, Oct. 2018, 33(2):536-541.

Pinto et al., "A network map of IL-33 signaling pathway," J. Cell Commun. Signal., Sep. 2018, 12(3):615-624.

Pitt et al., "Resistance Mechanisms to Immune-Checkpoint Blockade in Cancer: Tumor-Intrinsic and -Extrinsic Factors," Immunity, 44(6):1255-1269, Jun. 21, 2016.

Pittenger et al., "Multilineage potential of adult human mesenchymal stem cells," Science, Apr. 1999, 284(5411):143-147.

(56)                References Cited

OTHER PUBLICATIONS

Pluckthun et al., "Expression of functional antibody Fv and Fab fragments in Escherichia coli," Methods Enzymol., 178:497-515, 1989.

Plückthun, "Antibodies from *Escherichia coli*." The Pharmacology of Monoclonal Antibodies. Handbook of Experimental Pharmacology, Springer Berlin Heidelberg, pp. 269-315, 1994.

Poirier, "Protective immunity evoked by oral administration of attenuated aroA *Salmonella typhimurium* expressing cloned streptococcal M protein," J Exp Med., 168(1):25-32, Jul. 1, 1988.

Pollard, "Tumour-educated macrophages promote tumour progression and metastasis," Nat. Rev. Cancer, Jan. 2004, 4(1):71-78.

Pollok et al., "4-1BB T-cell antigen binds to mature B cells and macrophages, and costimulates anti-mu-primed splenic B cells," Eur J Immunol., 24(2):367-374, Feb. 1994.

Pollok et al., "Inducible T Cell Antigen 4-1BB," J Immunol., 150(3):771-781, Feb. 1, 1993.

Ponder et al., "Tertiary templates for proteins. Use of packing criteria in the enumeration of allowed sequences for different structural classes," J Mol Biol., 193(4):775-791, Feb. 20, 1987.

Ponten et al., "The Human Protein Atlas - a tool for pathology," J Pathol, Sep. 2008, 216(4):387-393.

Porter et al., "Chimeric antigen receptor T cells persist and induce sustained remissions in relapsed refractory chronic lymphocytic leukemia," Sci. Transl. Med., Sep. 2, 2015, 7(303):303ra139.

Porter et al., "Chimeric antigen receptor-modified T cells in chronic lymphoid leukemia," N. Engl. J. Med., Aug. 2011, 365(8):725-733.

Porter, "The hydrolysis of rabbit y-globulin and antibodies with crystalline papain," Biochem J., 73:119-126, Sep. 1959.

Porteus et al., "Gene targeting using zinc finger nucleases," Nat. Biotechnology, Aug. 2005, 23(8):967-973.

Posey et al., "Distinguishing Truncated and Normal MUC1 Glycoform Targeting from Tn-MUC1-Specific Car T Cells: Specificity Is the Key to Safety," Immunity, Nov. 2016, 45(5):947-948.

Postow et al., "Immune Checkpoint Blockade in Cancer Therapy," J. Clin. Oncology, 33(17):1974-1982, Jun. 10, 2015.

Potenza et al., "Molecular mechanisms governing microRNA-125a expression in human hepatocellular carcinoma cells," Sci. Reports, Sep. 6, 2017, 7:10712, 9 pages.

Powell et al., "Compendium of excipients for parenteral formulations," PDA J Pharm Sci Technol., 52(5):238-311, Sep./Oct. 1998.

Powles et al., "MPDL3280A (anti-PD-L1) treatment leads to clinical activity in metastatic bladder cancer," Nature, 515(7528):558-562, Nov. 27, 2014.

Prabhu et al., "Gamma interferon regulates contraction of the influenza virus-specific CD8 T cell response and limits the size of the memory population," J Virol., 87(23):12510-12522, Dec. 2013.

Prasad et al., "B7S1, a novel B7 family member that negatively regulates T cell activation," Immunity, 18(6):863-873, Jun. 2003.

Prasanna et al., "Pro-Inflammatory Cytokines, IFNc and TNFa, Influence Immune Properties of Human Bone Marrow and Wharton Jelly Mesenchymal Stem Cells Differentially," PLoS One, Feb. 2010, 5(2):e9016, 16 pages.

Presta, "Antibody engineering," Curr Opin Biotechnol., 2(4):593-596, 1992.

Presta, "Antibody engineering," Curr Opin Biotechnol., 3(4):394-398, Aug. 1992.

Prévost-Blondel et al., "Tumor-infiltrating lymphocytes exhibiting high ex vivo cytolytic activity fail to prevent murine melanoma tumor growth in vivo," J Immunol., 161(5):2187-2194, Sep. 1, 1998.

Priceman et al., "Regional Delivery of Chimeric Antigen Receptor-Engineered T Cells Effectively Targets HER2+ Breast Cancer Metastasis to the Brain," Clin. Cancer Res., Jan. 2018, 24(1):95-105.

Prlic et al., "Exploring regulatory mechanisms of CD8+ T cell contraction," Proc Natl Acad Sci USA., 105(43):16689-16694, Oct. 28, 2008.

PRNewswire.com [online], "Global $4.92 Billion Programmed Death-1 (PD-1) & Programmed Death Ligand-1 (PD-L1) Inhibitors Pipeline Analysis 2017-2025—Research and Markets," Mar. 13, 2017, retrieved on Mar. 25, 2021, retrieved from URL<https://www.prnewswire.com/news-releases/global-492-billion-programmed-death-1-pd-1--programmed-death-ligand-1-pd-11-inhibitors-pipeline-analysis-2017-2025---research-and-markets-300422553.html>, 3 pages.

Probst-Cousin et al., "Annexin-1 is No. useful surrogate marker of multiple sclerosis—an immunocytochemical study of the cerebrospinal fluid," Clin. Neuropathol., 30(1):18-24, Jan. 2011.

Pu et al., "Mechanisms and functions of lysosome positioning," J Cell Sci., 129(23):4329-4339, Dec. 2016.

Puissant et al., "Immunomodulatory effect of human adipose tissue-derived adult stem cells: comparison with bone marrow mesenchymal stem cells," Br. J. Haematology, Apr. 2005, 129(1):118-129.

Pulko et al., "B7-h1 expressed by activated CD8 T cells is essential for their survival," J Immunol., 187(11):5606-5614, Oct. 24, 2011.

Pulko et al., "TLR3-stimulated dendritic cells up-regulate B7-H1 expression and influence the magnitude of CD8 T cell responses to tumor vaccination," J Immunol., 183(6):3634-3641, Aug. 26, 2009.

Putri et al., "Analysing high-throughput sequencing data in Python with HTSeq 2.0," Bioinformatics, May 2022, 38(10):2943-2945.

Qi et al., "Evidence that Ser87 of BimEL is phosphorylated by Akt and regulates BimEL apoptotic function," J Biol Chem., 281(2):813-823, Nov. 10, 2005.

Quinnell et al., "A Small-Molecule Inhibitor to the Cytokine Interleukin-4," ACS Chem. Biol., Oct. 2020, 15(10):2649-2654.

Radhakrishnan et al., "Dendritic cells activated by cross-linking B7-DC (PD-L2) block inflammatory airway disease," J Allergy Clin Immunol., 116(3):668-674, Sep. 2005.

Rai et al., "Tracking the total CD8 T cell response to infection reveals substantial discordance in magnitude and kinetics between inbred and outbred hosts," J Immunol., 183(12):7672-7681, Dec. 15, 2009.

Raje et al., "Anti-BCMA CAR T-Cell Therapy bb2121 in Relapsed or Refractory Multiple Myeloma," N. Engl. J. Med., May 2019, 380(18):1726-1737.

Rajewsky et al., "Genetics, expression, and function of idiotypes," Annu Rev Immunol., 1:569-607, 1983.

Rak et al., "IL-33-Dependent Group 2 Innate Lymphoid Cells Promote Cutaneous Wound Healing," J. Invest. Dermatol., Feb. 2016, 136(2):487-496.

Rathmell et al., "The central effectors of cell death in the immune system," Annu. Rev. Immunol., 17:781-828, 1999.

Razi-Wolf, "Expression and function of the murine B7 antigen, the major costimulatory molecule expressed by peritoneal exudate cells," Proc Natl Acad Sci USA., 89(9):4210-4214, May 1, 1992.

Refaeli et al., "Interferon gamma is required for activation-induced death of T lymphocytes," J Exp Med., 196(7):999-1005, Oct. 7, 2002.

Ren et al., "A versatile system for rapid multiplex genome-edited CAR T cell generation," Oncotarget, Mar. 2017, 8(10):17002-17011.

Ren et al., "Analysis of the Effects of the Bruton's tyrosine kinase (Btk) Inhibitor Ibrutinib on Monocyte Fcgamma Receptor (FcgammaR) Function," J. Biol. Chemistry, Feb. 5, 2016, 291(6):3043-3052.

Renauld et al., "Expression cloning of the murine and human interleukin 9 receptor cDNAs," Proc Natl Acad Sci USA., 89(12):5690-5694, Jun. 15, 1992.

Reyon et al., "FLASH assembly of TALENs for high-throughput genome editing," Nat. Biotechnol., May 2012, 30(5):460-465.

Ribas et al., "Association of Pembrolizumab With Tumor Response and Survival Among Patients With Advanced Melanoma," JAMA, 315(15):1600-1609, Apr. 19, 2016.

Ribas et al., "Pembrolizumab versus investigator-choice chemotherapy for ipilimumab- refractory melanoma (KEYNOTE-002): a randomised, controlled, phase 2 trial," Lancet Oncol., 16(8):908-918, Aug. 2015.

Riches et al., "T cells from CLL patients exhibit features of T-cell exhaustion but retain capacity for cytokine production," Blood, Feb. 28, 2013, 121(9):1612-1621.

Riechmann et al., "Reshaping human antibodies for therapy," Nature, 332(6162):323-327, Mar. 24, 1988.

(56) References Cited

OTHER PUBLICATIONS

Rincon et al., "Signal transduction by MAP kinases in T lymphocytes," Oncogene, Apr. 30, 2001, 20(19):2490-2497.

Rincon et al., "JNK and p38 MAP kinases in CD4+ and CD8+ T cells," Immunol Rev., 192:131-142, Apr. 2003.

Rios-Doria et al., "A Monoclonal Antibody to ADAM17 Inhibits Tumor Grovrth by Inhibiting EGFR and Non-EGFR-Mediated Pathways," Mol. Cancer Ther., 14(7):1637-1649, Jul. 2015.

Rios-Doria et al., "Doxil synergizes with cancer immunotherapies to enhance antitumor responses in syngeneic mouse models," Neoplasia, 17(8):661-670, Aug. 2015.

Ritz et al., "Bioassay analysis using R," J Stat Softw., 12(5):1-22, Jan. 19, 2005.

Rivoltini et al., "Immunity to cancer: attack and escape in T lymphocyte-tumor cell interaction," Immunol Rev., 188:97-113, Oct. 2002.

Rizvi et al., "Nivolumab in Combination With Platinum-Based Doublet Chemotherapy for First-Line Treatment of Advanced Non-Small-Cell Lung Cancer," J Clin Oncol., 34(25):2969-2979, Sep. 1, 2016.

Robbins et al., "Regulation of immune responses by extracellular vesicles," Nat. Rev. Immunol., Mar. 2014, 14(3):195-208.

Robert et al., "Anti-programmed-death-receptor-1 treatment with pembrolizumab in ipilimumab-refractory advanced melanoma: a randomised dose-comparison cohort of a phase 1 trial," Lancet, 384(9948): 1109-1117, Sep. 20, 2014.

Robert et al., "Nivolumab in previously untreated melanoma without BRAF mutation," N Engl J Med., 372(4):320-330, Jan. 22, 2015.

Robert et al., "Pembrolizumab versus Ipilimumab in Advanced Melanoma," N Engl J Med., 372(26):2521-2532, Jun. 25, 2015.

Robison-Cox, "Multiple estimation of concentrations in immunoassay using logistic models," J Immunol Methods, 186(1): 79-88, Oct. 12, 1995.

Roman et al., "TNFR2 As a Target to Improve CD19-Directed CART Cell Fitness and Antitumor Activity in Large B Cell Lymphoma," Blood, Nov. 2021, 138(Supplement 1):901.

Romano et al., "Quelling: transient inactivation of gene expression in Neurospora crassa by transformation with homologous sequences," Mol Microbiol., 6(22):3343-3353, Nov. 1992.

Romer et al., "Plant pathogen recognition mediated by promoter activation of the pepper Bs3 resistance gene," Science, 318(5850):645-648, Oct. 26, 2007.

Romero et al., "Ex vivo staining of metastatic lymph nodes by class I major histocompatibility complex tetramers reveals high numbers of antigen-experienced tumor- specific cytolytic T lymphocytes," J Exp Med., 188(9):1641-1650, Nov. 2, 1998.

Romero et al., "Four functionally distinct populations of human effector-memory CD8+ T lymphocytes," J Immunol., 178(7):4112-4119, Apr. 1, 2007.

Roos et al., "DNA damage and the balance between survival and death in cancer biology," Nat. Rev. Cancer, 16(1):20-33, Jan. 2016.

Rosenberg, "Progress in human tumor immunology and immunotherapy," Nature, 411(6835):380-384, May 17, 2001.

Rosenfeld et al., "Adenovirus-mediated transfer of a recombinant alpha 1-antitrypsin gene to the lung epithelium in vivo," Science, 252(5004):431-434, Apr. 19, 1991.

Rothlin et al., "TAM receptor signaling and autoimmune disease," Curr. Opin. Immunol., Dec. 2010, 22(6):740-746.

Rothlin et al., "TAM receptors are pleiotropic inhibitors of the innate immune response," Cell, Dec. 2007, 131(6): 1124-1136.

Rousseaux et al., "Optimal conditions for the preparation of proteolytic fragments from monoclonal IgG of different rat IgG subclasses," Methods Enzymol., 121:663-669, 1986.

Rowe et al., "PDL-1 blockade impedes T cell expansion and protective immunity primed by attenuated Listeria monocytogenes," J Immunol., 180(11):7553-7557, Jun. 1, 2008.

Ruella et al., "Catch me if you can: Leukemia Escape after CD19-Directed T Cell Immunotherapies," Comput. Struct. Biotechnol. Journal, Sep. 28, 2016, 14:357-362.

Ruella et al., "Combination of Anti-CD123 and Anti-CD19 Chimeric Antigen Receptor T Cells for the Treatment and Prevention of Antigen-Loss Relapses Occurring after CD19- Targeted Immunotherapies," Blood, Dec. 2015, 126(23):2523.

Ruella et al., "Kinase inhibitor ibrutinib to prevent cytokine-release syndrome after anti-CD19 chimeric antigen receptor T cells for B-cell neoplasms," Leukemia, Jan. 2017, 31(1):246-248.

Ruella et al., "Overcoming the Immunosuppressive Tumor Microenvironment of Hodgkin Lymphoma Using Chimeric Antigen Receptor T Cells," Cancer Discov., Oct. 2017, 7(10):1154-1167.

Ruppert et al., "The major isoforms of Bim contribute to distinct biological activities that govern the processes of autophagy and apoptosis in interleukin-7 dependent lymphocytes," Biochim Biophys Acta., 1823(10):1877-1893, Oct. 2012.

Rutishauser et al., "TCF-1 regulates HIV-specific CD8+ T cell expansion capacity," JCI insight, Feb. 2021 6(3):e136648.

Sadoff, "Oral salmonella typhimurium vaccine expressing circumsporozoite protein protects against malaria," Science, 240(4850):336-338, Apr. 15, 1988.

Saito et al., "Metformin suppresses the growth of leukemia cells partly through downregulation of AXL receptor tyrosine kinase," Leukemia Research, May 15, 2020, 94:106383, 6 pages.

Sakemura et al., "A Tet-On Inducible System for Controlling CD19-Chimeric Antigen Receptor Expression upon Drug Administration," Cancer Immunol. Res., Aug. 2016, 4(8):658-668.

Sakemura et al., "AXL Inhibition Improves the Antitumor Activity of Chimeric Antigen Receptor T Cells," Cancer Immunol. Res., Sep. 2023, 11(9):1222-1236.

Sakemura et al., "Axl-RTK Inhibition Modulates T Cell Functions and Synergizes with Chimeric Antigen Receptor T Cell Therapy in B Cell Malignancies," Biol. Blood Marrow Transplantation, Mar. 2019, 25(3S):S165.

Sakemura et al., "Development of a Clinically Relevant Reporter for Chimeric Antigen Receptor T-cell Expansion, Trafficking, and Toxicity," Cancer Immunol. Research, Jul. 2021, 9(9):1035-1046.

Sakemura et al., "Dynamic Imaging of Chimeric Antigen Receptor T Cells with [18F]Tetrafluoroborate Positron Emission Tomography/Computed Tomography," J. Vis. Exp., Feb. 2022, 180:e62334.

Sakemura et al., "Resistance to CART cell therapy: lessons learned from the treatment of hematological malignancies," Leuk. Lymphoma, Mar. 2021, 62(9):2052-2063.

Sakemura et al., "Targeting Cancer Associated Fibroblasts in the Bone Marrow Prevents Resistance to Chimeric Antigen Receptor T Cell Therapy in Multiple Myeloma," Blood, 134(Supplement_ 1):865, Nov. 13, 2019, 7 pages.

Sakemura et al., "Targeting Cancer-Associated Fibroblasts in the Bone Marrow Prevents Resistance to CART-Cell Therapy in Multiple Myeloma," Blood, Jun. 2022, 139(26):3708-3721.

Salama et al., "Critical role of the programmed death-1 (PD-1) pathway in regulation of experimental autoimmune encephalomyelitis," J Exp Med., 198(1):71-78, Jul. 7, 2003.

Salib et al., "Utilization of sodium alginate in drug microencapsulation," Pharm Ind., 40(11a):1230-1234, 1978.

Salih et al., "4-1 BB ligand -- just another costimulating molecule?" Int J Clin Pharmacol Ther., 40(8):348-353, Aug. 2002.

Salih et al., "The role of leukemia-derived B7-H1 (PD-L1) in tumor-T-call interactions in humans," Exp Hematol., 34(7):888-894, Jul. 2006.

Sallusto et al., "Two subsets of memory T lymphocytes with distinct homing potentials and effector functions," Nature, 401(6754):708-712, Oct. 14, 1999.

Salomon et al., "Complexities of CD28/B7: CTLA-4 costimulatory pathways in autoimmunity and transplantation," Annu Rev Immunol., 19:225-252, 2001.

Sampson et al., "Greater chemotherapy-induced lymphopenia enhances tumor-specific immune responses that eliminate EGFRvIII-expressing tumor cells in patients with glioblastoma," Neuro Oncol., 13(3):324-333, Dec. 10, 2010.

Samulski, "Targeted integration of adenoassociated virus (AAV) into human chromosome 19," Embo J., 10(12):3941-3950, Dec. 1991.

Sandhu, "Protein engineering of antibodies," Crit Rev Biotechnol., 12(5-6):437-462, 1992.

(56)         References Cited

OTHER PUBLICATIONS

Sandstrom et al., "A novel CD44v6 targeting antibody fragment with improved tumor-to-blood ratio," Int. J. Oncol., May 2012, 40(5):1525-1532.
Sanjana et al., "Improved vectors and genome-wide libraries for CRISPR screening," Nat. Methods, Aug. 2014, 11(8):783-784.
Sanni et al., "Evolution of aminoacyl-tRNA synthetase quaternary structure and activity: Saccharomyces cerevisiae mitochondrial phenylalanyl-tRNA synthetase," Proc Natl Acad Sci USA., 88(19):8387-8391, Oct. 1, 1991.
Santagata et al., "G-protein signaling through tubby proteins," Science, Jun. 2001, 292(5524):2041-2050.
Sarbassov et al., "Phosphorylation and regulation of Akt/PKB by the rictor-mTOR complex," Science, 307(5712):1098-1101, Feb. 18, 2005.
Sarkar et al., "Engineered cell homing," Blood, Oct. 2011, 118(25):e184-e191.
Satelli et al., "Potential role of nuclear PD-L1 expression in cell-surface vimentin positive circulating tumor cells as a prognostic marker in cancer patients," Sci Rep., 6:28910, Jul. 1, 2016, 7 pages.
Sawhney et al., "Bioerodible hydrogels based on photopolymerized poly(ethylene glycol)-co-poly(.alpha.-hydroxy acid) diacrylate macromers," Macromolecules, 26(4):581-587, Jul. 1993.
Schafer, "Induction of a cellular immune response to a foreign antigen by a recombinant Listeria monocytogenes vaccine," J Immunol., 149(1):53-59, Jul. 1, 1992.
Schinkel et al., "Mammalian drug efflux transporters of the ATP binding cassette (ABC) family: an overview," Adv Drug Deliv Rev., 55(1):3-29, Jan. 21, 2003.
Schmid et al., "Expression of AMPA receptor subunit flip/flop splice variants in the rat auditory brainstem and inferior colliculus," J Comp Neurol., 430(2):160-171, Feb. 5, 2001.
Schmidt et al., "Extreme CD8 T cell requirements for anti-malarial liver-stage immunity following immunization with radiation attenuated sporozoites," PLoS Pathog., 6(7):e1000998, Jul. 15, 2010.
Schmits et al., "LFA-1-deficient mice show normal CTL responses to virus but fail to reject immunogenic tumor," J Exp Med., 183(4):1415-1426, Apr. 1, 1996.
Schmitz et al., "Controlling NF-κB activation in T cells by costimulatory receptors," Cell Death Differentiation, Jan. 2006, 13:834-842.
Schmitz et al., "IL-33, an interleukin-1-like cytokine that signals via the IL-1 receptor-related protein ST2 and induces T helper type 2-associated cytokines," Immunity, Nov. 2005, 23(5):479-490.
Scholler et al., "Decade-long safety and function of retroviral-modified chimeric antigen receptor T cells," Sci. Transl. Medicine, May 2012, 4(132):1-7, 43 pages.
Schornack et al., "Gene-for-gene-mediated recognition of nuclear-targeted AvrBs3-like bacterial effector proteins," J. Plant Physiology, 163(3):256-272, Feb. 2006.
Schoumacher et al., "Key Roles of AXL and MER Receptor Tyrosine Kinases in Resistance to Multiple Anticancer Therapies," Curr. Oncol. Rep. Curr. Science, Mar. 2017, 19(3):19, 14 pages.
Schurich et al., "The third signal cytokine IL-12 rescues the anti-viral function of exhausted HBV-specific CD8 T cells," PLoS Pathog., 9(3):e1003208, Mar. 14, 2013.
Schuster et al., "Chimeric Antigen Receptor T Cells in Refractory B-Cell Lymphomas," N. Engl. J. Med., Dec. 2017, 377(26):2545-2554.
Schwartz et al., "Costimulation of T lymphocytes: the role of CD28, CTLA-4, and B7/BBI in interluekin-2 production and immunotherapy," Cell, 71(7):1065-1068, Dec. 24, 1992.
Schwartz et al., "Structural basis for co-stimulation by the human CTLA-4/B7-2 complex," Nature, 410(6828):604-608, Mar. 29, 2001.
Schwartz et al., "Structural mechanisms of costimulation," Nat Immunol., 3(5):427-434, May 2002.
ScienceDaily.com [online], "Mayo Clinic Discovers Potential Marker For Aggressive Kidney Cancer," Dec. 9, 2004, retrieved on May 15, 2025, retrieved from URL<https://www.sciencedaily.com/releases/2004/11/041130200858.htm>, Dec. 9, 2004, 4 pages.

Sedletska et al., "Cisplatin is a DNA-damaging antitumour compound triggering multifactorial biochemical responses in cancer cells: importance of apoptotic pathways," Curr Med Chem Anti-cancer Agents., 5(3):251-265, May 2005.
Seitz et al., "Macrophages and dendritic cells use different Axl/Mertk/Tyro3 receptors in clearance of apoptotic cells," J. Immunol., May 2007, 178(9):5635-5642.
Seiwert et al., "Antitumor activity and safety of pembrolizumab in patients (pts) with advanced squamous cell carcinoma of the head and neck (SCCHN): Preliminary results from KEYNOTE-012 expansion cohort," J. Clin. Oncol., 33(18 Suppl):LBA6008, Jun. 20, 2015.
Seki et al., "Optimized RNP transfection for highly efficient CRISPR/Cas9-mediated gene knockout in primary T cells," J. Exp. Med., Feb. 2018, 215(3):985-997.
Seki et al., "Tumor-specific CTL kill murine renal cancer cells using both perforin and Fas ligand-mediated lysis in vitro, but cause tumor regression in vivo in the absence of perforin," J Immunol., 168(7):3484-3492, Apr. 1, 2002.
Selenko-Gebauer et al., "B7-H1 (programmed death-1 ligand) on dendritic cells is involved in the induction and maintenance of T cell anergy," J Immunol., 170(7):3637-3644, Apr. 1, 2003.
Sensi et al., "Human Cutaneous Melanomas Lacking MITF and Melanocyte Differentiation Antigens Express a Functional Axl Receptor Kinase," J. Invest. Dermatol., Dec. 2011, 131(12):2448-2457.
Seo et al., "Blockade of endogenous B7-H1 suppresses antibacterial protection after primary Listeria monocytogenes infection," Immunology, 123(1):90-99, Oct. 25, 2007.
Seymour et al., "iRECIST: guidelines for response criteria for use in trials testing immunotherapeutics," Lancet Oncol., 18(3):e143-e152, Mar. 2017.
Shaknovich et al., "The promyelocytic leukemia zinc finger protein affects myeloid cell growth, differentiation, and apoptosis," Mol Cell Biol., 18(9):5533-5545, Sep. 1998.
Shalabi et al., "Systematic evaluation of neurotoxicity in children and young adults undergoing CD22 chimeric antigen receptor T-cell therapy," J. Immunother., Sep. 2018, 41(7):350-358.
Shalem et al., "Genome-scale CRISPR-Cas9 knockout screening in human cells," Science, Jan. 2014, 343(6166):84-87.
Shao et al., "Deficiency of the DNA repair enzyme ATM in rheumatoid arthritis," J Exp Med., 206(6): 1435-1449, May 18, 2009.
Shao et al., "DNA-dependent protein kinase catalytic subunit mediates T-cell loss in rheumatoid arthritis," EMBO Mol Med., 2(10):415-427, Oct. 2010.
Shao et al., "ERK2 phosphorylation of serine 77 regulates Bmf pro-apoptotic activity," Cell Death Dis., 3(1):e253, Jan. 19, 2012, 10 pages.
Sharma et al., "Immune checkpoint targeting in cancer therapy: toward combination strategies with curative potential," Cell, 161(2):205-214, Apr. 9, 2015.
Sharma et al., "The future of immune checkpoint therapy," Science, 348(6230):56-61, Apr. 3, 2015.
Sharon et al., "Preparation of Fv fragment from the mouse myeloma XRPC-25 immunoglobulin possessing anti-dinitrophenyl activity," Biochemistry, 15(7):1591-1594, Apr. 6, 1976.
Sheather, "Density Estimation," Statistical Sci., 19(4):588-597, 2004.
Shenoy et al., "Exosomes Associated with Human Ovarian Tumors Harbor a Reversible Checkpoint of T-cell Responses," Cancer Immunol. Res., Jan. 2018, 6(2):236-247.
Shenoy et al., "IL-15 regulates Bcl-2 family members Bim and Mcl-1 through JAK/STAT and PI3K/AKT pathways in T cells," Eur J Immunology, 44(8):2500-2507, Aug. 2014.
Shi et al., "Granulocyte-macrophage colony-stimulating factor (GMCSF) and T-cell responses: what we do and don't know," Cell Res., 2006, 16(2):126-133.
Shi et al., "Immunoregulatory mechanisms of mesenchymal stem and stromal cells in inflammatory diseases," Nat. Rev. Nephrology, Aug. 2018, 14(8):493-507.

(56)         References Cited

OTHER PUBLICATIONS

Shibata et al., "Axl Receptor Blockade Ameliorates Pulmonary Pathology Resulting from Primary Viral Infection and Viral Exacerbation of Asthma," J. Immunol., Apr. 2014, 192(8):3569-3581.

Shin et al., "Cooperative B7-1/2 (CD80/CD86) and B7-DC costimulation of CD4+ T cells independent of the PD-1 receptor," J Exp Med., 198(1):31-38, Jul. 7, 2003.

Sica et al., "B7-H4, a molecule of the B7 family, negatively regulates T cell immunity," Immunity, 18(6):849-861, Jun. 2003.

Sica et al., "Biochemical and immunological characteristics of 4-1BB (CD137) receptor and ligand and potential applications in cancer therapy," Arch Immunol Ther Exp (Warsz)., 47(5):275-279, 1999.

Siddiqi et al., "Rapid Undetectable MRD (uMRD) Responses in Patients with Relapsed/Refractory (R/R) Chronic Lymphocytic Leukemia/Small Lymphocytic Lymphoma (CLL/SLL) Treated with Lisocabtagene Maraleucel (liso-cel), a CD19-Directed CAR T Cell Product: Updated Results from Transcend CLL 004, a Phase 1/2 Study Including Patients with High-Risk Disease Previously Treated with Ibrutinib," Blood, Nov. 2019, 134(Suppl. 1):503.

Siddiqui et al., "Enhanced recruitment of genetically modified CX3CR1-positive human T cells into Fractalkine/CX3CL1 expressing tumors: importance of the chemokine gradient," J. Immunotherapy, 4:21, Apr. 19, 2016, 12 pages.

Siddiqui et al., "Tumor-infiltrating Foxp3-CD4+CD25+ T cells predict poor survival in renal cell carcinoma," Clin Cancer Res., 13(7):2075-2081, Apr. 1, 2007.

Siegler et al., "Efficient Gene Editing of CART Cells with CRISPR-Cas12a for Enhanced Antitumor Efficacy," Blood, Nov. 2020, 136(Supplement 1):6-7.

Simon et al., "B7-h4 is a novel membrane-bound protein and a candidate serum and tissue biomarker for ovarian cancer," Cancer Res., 66(3):1570-1575, Feb. 1, 2006.

Singer et al., "Optimal humanization of 1B4, an Anti-CD18 murine monoclonal antibody, is achieved by correct choice of human v-region framework sequences," J Immunol., 150(7):2844-2857, Apr. 1, 1993.

Singh et al., "Monocyte lineage-derived IL-6 does not affect chimeric antigen receptor T-cell function," Cytotherapy, Jul. 2017, 19(7):867-880.

Sinha et al., "Targeted Axl Inhibition Primes Chronic Lymphocytic Leukemia B Cells to Apoptosis and Shows Synergistic/Additive Effects in Combination with BTK Inhibitors," Clin. Cancer Res., Apr. 2015, 21(9):2115-2126.

Sirpilla et al., "Chimeric Antigen Receptor Engineering of Mesenchymal Stromal Cells (CAR-MSC) Enhance Immunosuppression and Outcomes in Graft Versus Host Disease (GvHD) Preclinical Models," Blood, Nov. 2022, 140(S1):1579-1580.

Skerra et al., "Assembly of a functional immunoglobulin Fv fragment in *Escherichia coli*," Science, 240(4855):1038-1041, May 20, 1988.

Skolnick et al., "From genes to protein structure and function: novel applications of computational approaches in the genomic era," Trends Biotechnol., 18(1):34-39, Jan. 2000.

Smallwood et al., "Extracellular vesicles released by CD40/IL-4-stimulated CLL cells confer altered functional properties to CD4+ T cells," Blood, Jul. 2016, 128(4):542-552.

Smith et al., "BCMA-Targeted CAR T-cell Therapy plus Radiotherapy for the Treatment of Refractory Myeloma Reveals Potential Synergy," Cancer Immunol. Res., Jul. 2019, 7(7):1047-1053.

Smith et al., Differential outcome of IL-2/anti-IL-2 complex therapy on effector and memory CD8+ T cells following vaccination with an adenoviral vector encoding EBV epitopes, J Immunol., 186(10):5784-5790, Apr. 11, 2011.

Smith et al., "GPRC5D is a target for the immunotherapy of multiple myeloma with rationally designed CAR T cells," Sci. Transl. Med., Mar. 2019, 11(485):eaau7746.

Smith et al., "miR-29ab1 deficiency identifies a negative feedback loop controlling Th1 bias that is dysregulated in multiple sclerosis," J. Immunology, Aug. 15, 2012, 189(4):1567-1576.

Smith et al., "Pulmonary deposition and clearance of aerosolized alpha-1-proteinase inhibitor administered to dogs and to sheep," J Clin Invest., 84(4):1145-1154, Oct. 1989.

Sneller et al., "A novel lymphoproliferative/autoimmune syndrome resembling murine lpr/gld disease," J Clin Invest., 90(2):334-341, Aug. 1992.

Socie et al., "Acute graft-versus-host disease: from the bench to the bedside, " Blood, Nov. 12, 2009, 114(20):4327-4336.

Solier et al., "Death receptor-induced activation of the Chk2- and histone H2AX-associated DNA damage response pathways," Mol Cell Biol., 29(1):68-82, Oct. 27, 2008.

Song et al., "Effective adoptive immunotherapy of triple-negative breast cancer by folate receptor-alpha redirected Car T cells is influenced by surface antigen expression level," J. Hematol. Oncol., Jul. 2016, 9(1):56.

Sorge et al., "Amphotropic retrovirus vector system for human cell gene transfer," Mol Cell Biol., 4(9):1730-1737, Sep. 1984.

Soriano, "Targeted and nontargeted liposomes for in vivo transfer to rat liver cells of a plasmid containing the preproinsulin I gene," Proc Natl Acad Sci USA., 80(23):7128-7131, Dec. 1983.

Sotillo et al., "Convergence of Acquired Mutations and Alternative Splicing of CD19 Enables Resistance to CART-19 Immunotherapy," Cancer Discov., Dec. 2015, 5(12):1282-1295.

Soubeyrand et al., "Artemis phosphorylated by DNA-dependent protein kinase associates preferentially with discrete regions of chromatin," J Mol Biol., 358(5):1200-1211, Mar. 20, 2006.

Stammers et al., "Btl-Ii: A polymorphic locus with homology to the butyrolphilin gene family, located at the border of the major histocompatibility complex class II and class III regions in human and mouse," Immunogenetics, 51(4-5):373-382, Apr. 2000.

Stamper et al., "Crystal structure of the B7-1/CTLA-4 complex that inhibits human immune responses," Nature, 410(6828):608-611, Mar. 29, 2001.

Steiner et al., "MicroRNA-29 regulates T-box transcription factors and interferon-γ production in helper T cells," Immunity, Aug. 26, 2011, 35(2):169-181.

Stemmer et al., "CCTop: An Intuitive, Flexible and Reliable CRISPR/Cas9 Target Prediction Tool," PLoS One, Apr. 2015, 10(4):e0124633.

Sterner et al., "Myeloid cell and cytokine interactions with chimeric antigen receptor-T-cell therapy: implication for future therapies," Curr. Opin. Hematol., Jan. 2020, 27(1):41-48.

Stewart et al., "Abstract 1153: IL-4 depletion leads to the improvement of CART cell therapy," Cancer Res., Apr. 2023, 83(7_Supplement): 1153.

Stewart et al., "The Identification of IL-4 as a Regulator of Chimeric Antigen Receptor T Cell Exhaustion," bioRxiv, Sep. 30, 2023, 30 pages.

Stoklasek et al., "Combined IL-15/IL-15Ralpha immunotherapy maximizes IL-15 activity in vivo," J Immunol., 177(9):6072-6080, Nov. 1, 2006.

Strasser, "The role of BH3-only proteins in the immune system," Nat Rev Immunol., 5:189-200, Feb. 18, 2005.

Strauss et al., "Targeted deletion of PD-1 in myeloid cells induces antitumor immunity," Sci. Immunology, Jan. 2020, 5(43):1-14.

Strome et al., "B7-H1 blockade augments adoptive T-cell immunotherapy for squamous cell carcinoma," Cancer Res., 63(19):6501-6505, Oct. 1, 2003.

Strome et al., "Enhanced therapeutic potential of adoptive immunotherapy by in vitro CD28/4-1BB costimulation of tumor-reactive T cells against a poorly immunogenic, major histocompatibility complex class I-negative A9P melanoma," J Immunother., 23(4):430-437, Jul./Aug. 2000.

Stroncek et al., "Myeloid cells in peripheral blood mononuclear cell concentrates inhibit the expansion of chimeric antigen receptor T cells," Cytotherapy, 18(7):893-901, Jul. 2016.

Subudhi et al., "Local expression of B7-H1 promotes organ-specific autoimmunity and transplant rejection," J Clin Invest., 113(5):694-700, Mar. 2004.

Suda et al., "Why do defects in the Fas-Fas ligand system cause autoimmunity?" J Allergy Clin Immunol., 100(6 Pt 2):S97-S101, Dec. 1997.

Sugio et al., "Two type III effector genes of *Xanthomonas oryzae* pv. oryzae control the induction of the host genes OsTFIIAy1 and

(56) References Cited

OTHER PUBLICATIONS

OsTFX1 during bacterial blight of rice," Proc. Natl. Acad. Sci. USA, 104(25):10720-10725, Jun. 19, 2007.

Summerton et al., "Morpholino antisense oligomers: design, preparation, and properties," Antisense Nucleic Acid Drug Dev., 7(3):187-195, Jun. 1997.

Sun et al., "CAP-miRSeq: a comprehensive analysis pipeline for microRNA sequencing data," BMC Genomics, 15:423, Jun. 3, 2014, 10 pages.

Sun et al., "950.9: Signaling of 4-1BB Leads to Amelioration of Experimental Autoimmune Encephalomyelitis," Faseb J., vol. 5:A1210, 2010.

Sun et al., "Administration of agonistic anti-4-1BB monoclonal antibody leads to the amelioration of experimental autoimmune encephalomyelitis," J Immunol., 168(3):1457-1465, Feb. 1, 2002.

Sun et al., "Costimulatory molecule-targeted antibody therapy of a spontaneous autoimmune disease," Nat Med., 8(12): 1405-1413, Nov. 11, 2002.

Sun et al., "Safety and efficacy of targeting CD138 with a chimeric antigen receptor for the treatment of multiple myeloma," Oncotarget, Mar. 22, 2019, 10(24):2369-2383.

Sutter et al., "Nonreplicating vaccinia vector efficiently expresses recombinant genes," Proc Natl Acad Sci USA., 89(22):10847-10851, Nov. 15, 1992.

Suzuki et al., "T cell-specific loss of Pten leads to defects in central and peripheral tolerance," Immunity, 14(5):523-534, May 2001.

Suzuki et al., "The dual functions of fas ligand in the regulation of peripheral CD8+ and CD4+ T cells," Proc Natl Acad Sci USA., 97(4):1707-1712, Feb. 15, 2000.

Swallow et al., "B7h, a novel costimulatory homolog of B7.1 and B7.2, is induced by TNFalpha," Immunity, 11(4):423-432, Oct. 1999.

Szajnik et al., "Tumor-derived microvesicles induce, expand and up-regulate biological activities of human regulatory T cells (Treg)," PLoS One, 5(7):e11469, Jul. 22, 2010, 13 pages.

Takahashi et al., "Cutting edge: 4-1BB is a bona fide CD8 T cell survival signal," J Immunol., 162(9):5037-5040, May 1, 1999.

Takahashi et al., "Serum levels of soluble programmed cell death ligand 1 as a prognostic factor on the first-line treatment of metastatic or recurrent gastric cancer," J. Cancer Res. Clin. Oncol., 142(8):1727-1738, Aug. 2016.

Takeda et al., "Critical contribution of liver natural killer T cells to a murine model of hepatitis," Proc Natl Acad Sci USA., 97(10):5498-5503, May 9, 2000.

Takesono et al., "Beyond calcium: new signaling pathways for Tec family kinases," J. Cell Sci., Aug. 2002, 115(Pt 15):3039-3048.

Tamura et al., "B7-H1 costimulation preferentially enhances CD28-indepenent T-helper cell function, " Blood, 97(6):1809-1816, Mar. 15, 2001.

Tamura et al., "Marrow stromal cells induce B7-H1 expression on myeloma cells, generating aggressive characteristics in multiple myeloma," Leukemia, 27(2):464-472, 2013.

Tang et al., "In Vitro-expanded Antigen-specific Regulatory T Cells Suppress Autoimmune Diabetes," J. Exp. Medicine, Jun. 7, 2004, 199(11):1455-1465.

Taylor et al., "Glycogen Synthase Kinase 3 Inactivation Drives T-bet-Mediated Downregulation of Co-receptor PD-1 to Enhance CD8(+) Cytolytic T Cell Responses," Immunity, 44(2):274-286, Feb. 16, 2016.

Taylor et al., "Human immunoglobulin transgenes undergo rearrangement, somatic mutation and class switching in mice that lack endogenous IgM," Int Immunol., 6(4):579-591, Apr. 1994.

Taylor et al., "Tumour-derived exosomes and their role in cancer-associated Tcell signalling defects," Br. J. Cancer, 92(2):305-311, Jan. 18, 2005.

Tazi-Ahnini et al., "Cloning, localization, and structure of new members of the butyrophilin gene family in the juxtatelomenc region of the major histocompatibility complex," Immunogenetics, 47(1):55-63, 1997.

Teachey et al., "Identification of predictive biomarkers for cytokine release syndrome after chimeric antigen receptor T-cell therapy for acute lymphoblastic leukemia," Cancer Discov., Jun. 2016, 6(6):664-679.

Teh et al., "TNF receptor 2-deficient CD8 T cells are resistant to Fas/Fas ligand-induced cell death," J. Immunology, Nov. 1, 2000, 165(9):4814-4821.

Temin, "Safety considerations in somatic gene therapy of human disease with retrovirus vectors," Hum Gene Ther., 1(2):111-123, Summer 1990.

Templeton et al., "Improved DNA: liposome complexes for increased systemic delivery and gene expression," Nat Biotechnol., 15(7):647-652, Jul. 1997.

Teshima et al., "Acute Graft-versus-Host Disease: Novel Biological Insights," Biol. Blood Marrow Transplantation, Oct. 2015, 22(1):11-16.

Thaker et al., "TCR and CD28 activate the transcription factor NF-kappaB in T-cells via distinct adaptor signaling complexes," Immunol. Letters, Oct. 2014, 163(1):113-119.

Tham et al., "Melanoma-initiating cells exploit M2 macrophage TGFbeta and arginase pathway for survival and proliferation," Oncotarget, 5(23):12027-12042, Dec. 15, 2014.

The 1000 Genomes Project Consortium, "A global reference for human genetic variation," Nature, Sep. 2015, 526(7571): 68-74.

Theofilopoulos et al., "Etiopathogenesis of Murine SLE," Immunol Rev., 55:179-216, 1981.

Theofilopoulos et al., "Tumour necrosis factor and other cytokines in murine lupus," Ann Rheum Dis., 58(suppl 1):149-55, Nov. 1, 1999.

Thery et al., "Minimal information for studies of extracellular vesicles 2018 (MISEV2018): a position statement of the International Society for Extracellular Vesicles and update of the MISEV2014 guidelines," J. Extracell. Vesicles, 7(1):1535750, Nov. 23, 2018, 47 pages.

Thiele et al., "miR-9 enhances IL-2 production in activated human CD4(+) T cells by repressing Blimp-1," Eur. J. Immunology, Aug. 2012, 42(8):2100-2108.

Thistlethwaite et al., "The clinical efficacy of first-generation carcinoembryonic antigen (CEACAM5)-specific Car T cells is limited by poor persistence and transient pre- conditioning-dependent respiratory toxicity," Cancer Immunol. Immunother., Jun. 28, 2017, 66(11):1425-1436.

Thompson et al., "cis-acting sequences required for inducible interleukin-2 enhancer function bind a novel Ets-related protein, Elf-1," Mol Cell Biol., 12(3):1043-1053, Mar. 1992.

Thompson et al., "Costimulatory B7-H1 in renal cell carcinoma patients: Indicator of tumor aggressiveness and potential therapeutic target," Proc Natl Acad Sci USA., 101(49):17174-17179, Nov. 29, 2004.

Thompson et al., "Costimulatory molecule B7-H1 in primary and metastatic clear cell renal cell carcinoma," Cancer, 104(10):2084-2091, Nov. 15, 2005.

Thompson et al., "PD-1 is expressed by tumor-infiltrating immune cells and is associated with poor outcome for patients with renal cell carcinoma," Clin Cancer Res., 13(6):1757-1761, Mar. 15, 2007.

Thompson et al., "Tumor B7-H1 is associated with poor prognosis in renal cell carcinoma patients with long-term follow-up," Cancer Res., 66(7):3381-3385, Apr. 1, 2006.

Thompson et al., "Tumor masses support naive T cell infiltration, activation, and differentiation into effectors," J Exp Med., 207(8):1791-1804, Jul. 26, 2010.

Tian et al., "The relationship between the down-regulation of DNA-PKcs or Ku70 and the chemosensitization in human cervical carcinoma cell line HeLa," Oncol Rep., 18(4):927-932, Oct. 2007.

Tickner et al., "Functions and therapeutic roles of exosomes in cancer," Front. Oncology, 4:127, May 27, 2014, 8 pages.

Tiedt et al., "RNA-Seq Identifies Circulating miR-125a-5p, miR-125b-5p, and miR-143-3p as Potential Biomarkers for Acute Ischemic Stroke," Circ. Res., 121(8):970-980, Sep. 29, 2017.

Tiegs et al., "A T cell-dependent experimental liver injury in mice inducible by concanavalin A," J Clin Invest., 90(1):196-203, Jul. 1992.

(56) References Cited

OTHER PUBLICATIONS

Titomirov, "In vivo electroporation and stable transformation of skin cells of newborn mice by plasmid DNA," Biochim Biophys Acta., 1088(1):131-134, Jan. 17, 1991.

Tocknnan et al., "Considerations in bringing a cancer biomarker to clinical application," Cancer Res., 52(9 Suppl.):2711s-2718s, May 1992.

Todd et al., "Transcription of the interleukin 4 gene is regulated by multiple promoter elements," J Exp Med., 177(6):1663-1674, Jun. 1, 1993.

Tokunaga et al., "CXCL9, CXCL10, CXCL11/CXCR3 axis for immune activation—A target for novel cancer therapy," Cancer Treat. Rev., Feb. 2018, 63:40-47.

Topalian et al., "Safety, Activity, and Immune Correlates of Anti-PD-1 Antibody in Cancer," N Engl J Med, 366(26):2443-2454, Jun. 28, 2012.

Townsend et al., "Tumor rejection after direct costimulation of CD8+ T cells by B7-transfected melanoma cells," Science, 259(5093):368-370, Jan. 15, 1993.

Trabattoni et al. "B7-H1 is up-regulated in HIV infection and is a novel surrogate marker of disease progression" Blood, 101(7):2514-2520, Dec. 5, 2002.

Tringler et al., "B7-h4 is highly expressed in ductal and lobular breast cancer," Clin Cancer Res., 11(5):1842-1848, Mar. 1, 2005.

Truneh et al., "Early steps of lymphocyte activation bypassed by synergy between calcium ionophores and phorbol ester," Nature., 313(6000):318-320, Jan. 24, 1985.

Tsai et al., "Long noncoding RNA as modular scaffold of histone modification complexes," Science, 329(5992):689-693, Aug. 6, 2010.

Tseng et al., "B7-DC, a new dendritic cell molecule with potent costimulatory properties for T cells," J Exp Med., 193(7):839-846, Apr. 2, 2001.

Tsuchiya et al., "Differential expression of N-cadherin and E-cadherin in normal human tissues," Arch. Histol. Cytology, Jun. 2006, 69(2):135-145.

Tsukita et al., "Axl kinase drives immune checkpoint and chemokine signalling pathways in lung adenocarcinomas," Mol. Cancer, Feb. 2019, 18(1):24.

Tumeh et al., "PD-1 blockade induces responses by inhibiting adaptive immune resistance," Nature, 515(7528):568-571, Nov. 27, 2014.

Turman et al., "Characterization of a novel gene (NKG7) on human chromosome 19 that is expressed in natural killer cells and T cells, " Hum Immunol., 36(1):34-40, Jan. 1993.

Turtle et al., "A distinct subset of self-renewing human memory CD8+ T cells survives cytotoxic chemotherapy," Immunity, 31(5):834-844, Nov. 20, 2009.

Turtle et al., "CD19 Car-T cells of defined CD4+:CD8+ composition in adult B cell ALL patients," J. Clin. Investigation, 126(6):2123-2138, Jun. 1, 2016.

Turtle et al., "Durable Molecular Remissions in Chronic Lymphocytic Leukemia Treated With CD19-Specific Chimeric Antigen Receptor-Modified T Cells After Failure of Ibrutinib," J. Clin. Oncology, 35(26):3010-3020, Sep. 10, 2017.

Uccelli et al., "Mesenchymal stem cells in health and disease," Nat. Rev. Immunology, Sep. 2008, 8(9):726-736.

Ueda et al., "Sequence-specific DNA damage induced by reduced mitomycin C and 7-N-(p-hydroxyphenyl)mitomycin C.," Nucleic Acids Res., 12(17):6673-6683, Sep. 11, 1984.

Ueha et al., "Robust Antitumor Effects of Combined Anti-CD4-Depleting Antibody and Anti-PD-1/PD-L1 Immune Checkpoint Antibody Treatment in Mice," Cancer Immunol Res., 3(6):631-640, Jun. 2015.

Ullman-Culleré et al., "Body condition scoring: a rapid and accurate method for assessing health status in mice," Lab. Anim. Sci., Jun. 1999, 49(3):319-323.

Umansky et al., "Myeloid-derived suppressor cells in malignant melanoma," J Dtsch Dermatol Ges., 12(11):1021-1027, Nov. 2014.

Van der Meer et al., "TAM receptors, Gas6, and protein S: roles in inflammation and hemostasis," Blood, Apr. 2014, 123(16):2460-2469.

Verhoeyen et al., "Reshaping human antibodies: grafting an antilysozyme activity," Science, 239(4847):1534-1536, Mar. 25, 1988.

Vesely et al., "Natural innate and adaptive immunity to cancer," Annu Rev Immunol., 29:235-271, 2011.

Veuger et al., "Radiosensitization and DNA repair inhibition by the combined use of novel inhibitors of DNA-dependent protein kinase and poly(ADP-ribose) polymerase-1," Cancer Res., 63(18):6008-6015, Sep. 15, 2003.

Vinay et al., "Role of 4-1BB in immune responses," Semin Immunol., 10(6):481-489, Dec. 1998.

Vouri et al., "TAM Receptor Tyrosine Kinases in Cancer Drug Resistance," Cancer Res., May 2017, 77(11):2775-2778.

Wagner et al., "Car T Cell Therapy for Solid Tumors: Bright Future or Dark Reality?" Mol. Ther., Nov. 2020, 28(11):2320-2339.

Wahl et al., "Improved radioimaging and tumor localization with monoclonal F(ab')2" J Nucl Med., 24(4):316-25, Apr. 1983.

Wallin et al., "Atezolizumab in combination with bevacizumab enhances antigen-specific T-cell migration in metastatic renal cell carcinoma," Nat Commun., 7:12624, Aug. 30, 2016, 8 pages.

Walter et al., "The peripheral benzodiazepine receptor ligand PK11195 overcomes different resistance mechanisms to sensitize AML cells to gemtuzumab ozogamicin," Blood, 103(11):4276-4284, Jun. 1, 2004.

Walunas et al., "CTLA-4 ligation blocks CD28-dependent T cell activation," J Exp Med., 183(6):2541-2550, Jun. 1, 1996.

Wang et al., "Costimulation of T cells by B7-H2, a B7-like molecule that binds ICOS," Blood, 96(8):2808-2813, Oct. 15, 2000.

Wang et al., "Doxorubicin induces apoptosis in normal and tumor cells via distinctly different mechanisms. intermediacy of H(2)O(2)- and p53-dependent pathways," J Biol Chem., 279(24):25535-25543, Mar. 30, 2004.

Wang et al., "Lenalidomide Enhances the Function of CS1 Chimeric Antigen Receptor- Redirected T Cells Against Multiple Myeloma," Clin. Cancer Research, Jan. 1, 2018, 24(1):106-119.

Wang et al., "Ligand binding sites of inducible costimulator and high avidity mutants with improved function," J Exp Med., 195(8):1033-1041, Apr. 15, 2002.

Wang et al., "Molecular modeling and functional mapping of B7-H1 and B7-DC uncouple costimulatory function from PD-1 interaction," J Exp Med., 197(9):1083-1091, Apr. 28, 2003.

Wang et al., "Multiple Functions of the RNA-Binding Protein HuR in Cancer Progression, Treatment Responses and Prognosis," Int J Mol Sci., 14(5):10015-10041, May 10, 2013.

Wang et al., "NF-KB-YY1-miR-29 Regulatory Circuitry in Skeletal Myogenesis and Rhabdomyosarcoma," Cancer Cell, Nov. 4, 2008, 14(5):369-381.

Wang et al., "RVboost: RNA-seq variants prioritization using a boosting method," Bioinformatics, 30(23):3414-3416, Dec. 1, 2014.

Wang et al., "Serum levels of soluble programmed death ligand 1 predict treatment response and progression free survival in multiple myeloma," Oncotarget, 6(38):41228-36, Dec. 2015.

Wang et al., "Targeting Fibroblast Activation Protein in Tumor Stroma with Chimeric Antigen Receptor T Cells Can Inhibit Tumor Growth and Augment Host Immunity without Severe Toxicity," Cancer Immunol. Res., Feb. 2014, 2(2):154-166.

Wang, "Lyophilization and development of solid protein pharmaceuticals," Int J Pharm., 203(1-2):1-60, Aug. 10, 2000.

Wang, "pH-sensitive immunoliposomes mediate target-cell-specific delivery and controlled expression of a foreign gene in mouse," Proc Natl Acad Sci USA., 84(22):7851-7855, Nov. 1987.

Ward et al., "Binding activities of a repertoire of single immunoglobulin variable domains secreted from Escherichia coli," Nature, 341(6242):544-546, Oct. 12, 1989.

Waterborg et al., "The level of synovial AXL expression determines the outcome of inflammatory arthritis, possibly depending on the upstream role of TGF-β1," Rheumatology, Mar. 2019, 58(3):536-546.

Waugh et al., "Targeting Transcriptional Regulators of CD8+ T Cell Dysfunction to Boost Anti-Tumor Immunity," Vaccines, Sep. 2015, 3(3):771-802.

(56) References Cited

OTHER PUBLICATIONS

Webster et al., "Targeting molecular and cellular inhibitory mechanisms for improvement of antitumor memory responses reactivated by tumor cell vaccine," J Immunol., 179(5):2860-2869, Sep. 1, 2007.

Weide et al., "Myeloid-derived suppressor cells predict survival of patients with advanced melanoma: comparison with regulatory T cells and NY-ESO-1- or melan-A-specific T cells," Clin Cancer Res., 20(6):1601-1609, Mar. 15, 2014.

Weiss, "Hot Prospect for New Gene Amplifier: Ligase chain reaction, a combination DNA amplifier and genetic screen could do for DNA diagnostics what PCR has done for basic molecular biology," Science, 254(5036):1292-1293, Nov. 29, 1991.

Weitzel et al., "microRNA 184 regulates expression of NFAT1 in umbilical cord blood CD4+T cells," Blood, Jun. 25, 2009, 113(26):6648-6657.

Wherry et al., "Lineage relationship and protective immunity of memory CD8 T cell subsets," Nat Immunol., 4(3):225-234, Feb. 3, 2003.

Whilding et al., "CAR T-cell immunotherapy: The path from the by-road to the freeway?," Mol. Oncology, Oct. 23, 2015, 9(10):1994-2018.

White et al., "Fractalkine has anti-apoptotic and proliferative effects on human vascular smooth muscle cells via epidermal growth factor receptor signalling," Cardiovasc Res., 85(4):825-835, Mar. 1, 2010.

Wick et al., "The hepatic immune system," Crit Rev Immunol., 22(1):47-103, 2002.

Wieckowski et al., "Tumor-derived microvesicles promote regulatory T cell expansion and induce apoptosis in tumor-reactive activated CD8+ T lymphocytes," J. Immunol., Sep. 15, 2009, 183(6):3720-3730.

Wilcox et al., "Provision of antigen and CD137 signaling breaks immunological ignorance, promoting regression of poorly immunogenic tumors," J Clin Invest., 109(5):651-659, Mar. 2002.

Williams et al., "Introduction of foreign genes into tissues of living mice by DNA-coated microprojectiles," Proc Natl Acad Sci USA., 88(7):2726-2730, Apr. 1, 1991.

Williams et al., "Nitric oxide synthase plays a signaling role in TCR-triggered apoptotic death," J Immunol., 161(12):6526-6531, Dec. 15, 1998.

Williams et al., "T cell immune reconstitution following lymphodepletion," Semin Immunol., 19(5):318-330, Oct. 2007.

Williams et al., "The immunoglobulin superfamily—domains for cell surface recognition," Annu Rev Immunol., 6:381-405, 1988.

Willmore et al., "A novel DNA-dependent protein kinase inhibitor, NU7026, potentiates the cytotoxicity of topoisomerase II poisons used in the treatment of leukemia," Blood, 103(12):4659-4665, Mar. 9, 2004.

Winter et al., "Making antibodies by phage display technology," Annu Rev Immunol., 12:433-455, 1994.

Winter et al., "Man-made antibodies," Nature, 349(6307):293-299, Jan. 24, 1991.

Wintterle et al., "Expression of the B7-related molecule B7-H1 by glioma cells: a potential mechanism of immune paralysis," Cancer Res., 63(21):7462-7467, Nov. 1, 2003.

Wofsy et al., "The proliferating cells in autoimmune MRL/lpr mice lack L3T4, an antigen on "helper" T cells that is involved in the response to class II major histocompatibility antigens," J Immunol., 132(6):2686-2689, Jun. 1984.

Wofsy, "Treatment of murine lupus with anti-CD4 monoclonal antibodies," Immunol Ser., 59:221-236, 1993.

Wojciechowski et al., "Bim/Bcl-2 balance is critical for maintaining naive and memory T cell homeostasis," J Exp Med., 204(7):1665-1675, Jul. 9, 2007.

Wolff, "Direct gene transfer into mouse muscle in vivo," Science, 247(4949 Pt 1):1465-1468, Mar. 23, 1990.

Wolke et al., "Assigning the phenotype of a natural regulatory T-cell to the human T-cell line, KARPAS-299," Int J Mol Med., 17(2):275-278, Feb. 2006.

Wong et al., "Human GM-CSF: molecular cloning of the complementary DNA and purification of the natural and recombinant proteins," Science, 228(4701):810-815, May 17, 1985.

Wu et al., "Emerging roles and therapeutic value of exosomes in cancer metastasis," Mol. Cancer, 18(1):53, Mar. 30, 2019, 11 pages.

Wu et al., "MicroRNA Roles in the Nuclear Factor Kappa B Signaling Pathway in Cancer," Front. Immunology, Mar. 19, 2018, 9:546, 9 pages.

Wu et al., "Targeting B7-H1 (PD-L1) Sensitizes Cancer Cells to Chemotherapy," Heliyon, 4(12):e01039, Dec. 18, 2018, 24 pages.

Wu et al., "The double-edged sword of activation-induced cytidine deaminase," J Immunol., 174(2):934-941, Jan. 15, 2005.

Wu, "Receptor-mediated gene delivery and expression in vivo," J Biol Chem., 263(29):14621-14624, Oct. 15, 1988.

Wu, "Targeting genes: delivery and persistent expression of a foreign gene driven by mammalian regulatory elements in vivo," J Biol Chem., 264(29):16985-16987, Ocober. 15, 1989.

Xiaoxia et al., "[Function of diamine oxidase and E-cadherin in Intestinal Injury of Nronatal Rats]," J. Med. Res., Nov. 2012, 41(11):169-172 (with English Abstract).

Xie et al., "M2 macrophages secrete CXCL13 to promote renal cell carcinoma migration, invasion, and EMT," Cancer Cell Int., Dec. 2021, 21(1):677.

Xu et al., "A potential new pathway for PD-L1 costimulation of the CD8-T cell response to Listeria monocytogenes infection," PLoS One, 8(2):e56539, Feb. 11, 2013, 8 pages.

Xu et al., "Autophagy is essential for effector CD8(+) T cell survival and memory formation," Nat Immunol., 15(12):1152-1161, Dec. 2014.

Xu et al., "Exploratory trial of a biepitopic CAR T-targeting B cell maturation antigen in relapsed/refractory multiple myeloma," Proc. Natl. Acad. Sci. USA, May 7, 2019, 116(19):9543-9551.

Xu et al., "The inducible expression of the tumor suppressor gene PTEN promotes apoptosis and decreases cell size by inhibiting the PI3K/Akt pathway in Jurkat T cells," Cell Growth Differ., 13(7):285-296, Jul. 2002.

Yalniz et al., "Safety and Efficacy of Infliximab Therapy in the Setting of Steroid-Refractory Acute Graft-versus-Host Disease," Biol. Blood Marrow Transplantation, Sep. 2017, 23(9):1478-1484.

Yamamoto et al., "B7-H1 expression is regulated by MEK/ERK signaling pathway in anaplastic large cell lymphoma and Hodgkin lymphoma," Cancer Sci., 100(11):2093-2100, Aug. 1, 2009.

Yamauchi et al., "23.02: Defining CD8+ T-cell Subsets that are Rescued by PD-1/PD-L1 Blockade in the Tumor Microenvironment," Abstract, presented at Proceedings of the 13th Annual Academic Surgical Congress, Jacksonville, FL, Jan. 30-Feb. 1, 2018, 4 pages.

Yamazaki et al., "Effective expansion of alloantigen-specific Foxp3+ CD25+ CD4+ regulatory T cells by dendritic cells during the mixed leukocyte reaction," Proc. Natl. Acad. Sci. USA, Feb. 21, 2006, 103(8):2758-2763.

Yamazaki et al., "Expression of programmed death 1 ligands by murine T cells and Apc," J Immunol., 169(10):5538-5545, Nov. 15, 2002.

Yan et al., "CX3CR1 identifies PD-1 therapy-responsive CD8+ T cells that withstand chemotherapy during cancer chemoimmunotherapy," JCI Insight, 3(8):e97828, Apr. 19, 2018, 13 pages.

Yan et al., "Effect of paclitaxel and carboplatin on tumor-reactive T cells and the efficacy of PD-1 blockade," J. Clin. Oncology, 35(7S):65, Mar. 1, 2017.

Yan et al., "The Mayo Clinic experience in patients with metastatic melanoma who have failed previous pembrolizumab treatment," J Clin Oncol., 34(15 Suppl):e21014, May 20, 2016.

Yañez et al., "Improved efficacy of mesenchymal stromal cells stably expressing CXCR4 and IL-10 in a xenogeneic graft versus host disease mouse model," Front Immunol., Feb. 2023, 14:1-15.

Yang et al., "In vitro priming of tumor-reactive cytolytic T lymphocytes by combining IL-10 with B7-CD28 costimulation," J Immunol., 155(8):3897-3903, Oct. 15, 1995.

Yang et al., "In vivo and in vitro gene transfer to mammalian somatic cells by particle bombardment," Proc Natl Acad Sci USA., 87(24):9568-9572, Dec. 1990.

(56)  References Cited

OTHER PUBLICATIONS

Yang et al., "Os8N3 is a host disease-susceptibility gene for bacterial blight of rice," Proc. Natl. Acad. Sci. USA, 103(27):10503-10508, Jul. 5, 2006.

Yang et al., "T cells expressing NKG2D chimeric antigen receptors efficiently eliminate glioblastoma and cancer stem cells," J. Immunother. Cancer, Jul. 2019, 7(1):171.

Yang, "Gene transfer into mammalian somatic cells in vivo," Crit Rev Biotechnol., 12(4):335-356, 1992.

Yao et al., "Interferon regulatory factor 4 sustains CD8(+) T cell expansion and effector differentiation," Immunity, 39(5):833-845, Nov. 14, 2013.

Ye et al., "An anti-Axl monoclonal antibody attenuates xenograft tumor growth and enhances the effect of multiple anticancer therapies," Oncogene, Sep. 2010, 9(38):5254-5264.

Yi et al., "CRISPR-edited CART with GM-CSF knockout and auto secretion of IL6 and IL1 blockers in patients with hematologic malignancy," Cell Discov., Apr. 2021, 7(1):27.

Yin et al., "Checkpoint Blockade Reverses Anergy in IL-13Ralpha2 Humanized scFv-Based Car T Cells to Treat Murine and Canine Gliomas," Mol. Ther. Oncolytics, 11:20-38, Aug. 28, 2018.

Yin et al., "CpG-induced antitumor immunity requires IL-12 in expansion of effector cells and down-regulation of PD-1," Oncotarget, 7(43):70223-70231, Oct. 25, 2016.

Yokosuka et al., "Programmed cell death 1 forms negative costimulatory microclusters that directly inhibit T cell receptor signaling by recruiting phosphatase SHP2," J Exp Med., 209(6): 1201-1217, Jun. 4, 2012.

Yoon et al., "FVIII-specific human chimeric antigen receptor T-regulatory cells suppress T- and B-cell responses to FVIII," Blood, Jan. 12, 2017, 129(2):238-245.

Yoshida et al., "All-trans retinoic acid enhances cytotoxic effect of T cells with an anti-CD38 chimeric antigen receptor in acute myeloid leukemia," Clin. Transl. Immunol., Dec. 9, 2016, 5(12):e116.

Yoshinaga et al., "T-cell co-stimulation through B7RP-1 and ICOS," Nature, 402(6763):827-832, Dec. 16, 1999.

Yotsumoto et al., "Endosomal translocation of CpG-oligodeoxynucleotides inhibits DNA-PKcs-dependent IL-10 production in macrophages," J Immunol., 180(2):809-816, Jan. 15, 2008.

Youngnak et al., "Differential binding properties of B7-H1 and B7-DC to programmed death-1," Biochem Biophys Res Commun., 307(3):672-677, Aug. 1, 2003.

Yu et al., "Bim is required for T-cell allogeneic responses and graft-versus-host disease in vivo," Am J Blood Res., 2(1):77-85, Jan. 15, 2012.

Yuan et al., "Focus on histone variant H2AX: to be or not to b," FEBS Lett., 584(17):3717-3724, May 21, 2010.

Zahuczky et al., "Differentiation and glucocorticoid regulated apopto-phagocytic gene expression patterns in human macrophages. Role of Mertk in enhanced phagocytosis," PLoS One, Jun. 2011, 6(6):e21349.

Zain et al., "Structure-function relationships of covalent and non-covalent BTK inhibitors," Front. Immunol., Jul. 2021, 12:694853.

Zang et al., "B7x: a widely expressed b7 family member that inhibits T cell activation," Proc Natl Acad Sci USA., 100(18):10388-10392, Aug. 14, 2003.

Zang et al., "The B7 family and cancer therapy: costimulation and coinhibition," Clin Cancer Res., 13(18 Pt 1):5271-5279, Sep. 15, 2007.

Zavialov et al., "Human adenosine deaminase 2 induces differentiation of monocytes into macrophages and stimulates proliferation of T helper cells and macrophages," J. Leukoc. Biology, Aug. 2010, 88(2):279-290.

Zeiser et al., "Acute Graft-versus-Host Disease - Biologic Process, Prevention, and Therapy," N. Engl. J. Medicine, Nov. 30, 2017, 377(22):2167-2179.

Zelenin et al., "Genetic transformation of mouse cultured cells with the help of high-velocity mechanical DNA injection," FEBS Lett., 244(1):65-67, Feb. 13, 1989.

Zelenin et al., "High-velocity mechanical DNA transfer of the chloramphenicolacetyl transferase gene into rodent liver, kidney and mammary gland cells in organ explants and in vivo," FEBS Lett., 280(1):94-96, Mar. 11, 1991.

Zeng et al., "miR-9 enhances the transactivation of nuclear factor of activated T cells by targeting KPNB1 and DYRKIB," Am. J. Physiol. Cell Physiology, May 1, 2015, 308(9):C720-C728.

Zhang et al., "25-Hydroxyvitamin D3-enhanced PTPN2 positively regulates periodontal inflammation through the JAK/STAT pathway in human oral keratinocytes and a mouse model of type 2 diabetes mellitus," J. Periodontal Res., Jun. 2018, 53(3):467-477.

Zhang et al., "A high M1/M2 ratio of tumor-associated macrophages is associated with extended survival in ovarian cancer patients," J Ovarian Res., 7:19, Feb. 8, 2014.

Zhang et al., "An Anti-CD103 Immunotoxin Promotes Long-Term Survival of Pancreatic Islet Allografts," Am. J. Transplantation, Aug. 20, 2009, 9(9):2012-2023.

Zhang et al., "Biallelic targeting of expressed genes in mouse embryonic stem cells using the Cas9 system," Methods, Sep. 2014, 69(2):171-178.

Zhang et al., "Chimeric Antigen Receptor (CAR) Treg: A Promising Approach to Inducing Immunological Tolerance," Front. Immunol., Oct. 2018, 9:2359, 8 pages.

Zhang et al., "Exosomes and cancer: a newly described pathway of immune suppression," Clin. Cancer Research, 17(5):959-964, Mar. 1, 2011.

Zhang et al., "Expressions of E-cadherin, p120ctn, β-catenin and NF-ĸB in ulcerative colitis," Journal of Huazhong University of Science and Technology [Medical Sciences], Jun. 2015, 35:368-373.

Zhang et al., "Mesenchymal Stem Cells to Treat Crohn's Disease with Fistula," Hum. Gene Ther., Jul. 2017, 28(7):534-540.

Zhang et al., "PD-1/PD-L1 interactions inhibit antitumor immune responses in a murine acute myeloid leukemia model," Blood, 114(8):1545-1552, May 5, 2009.

Zhang et al., "Theiler's virus-infected L-selectin-deficient mice have decreased infiltration of CD8(+) T lymphocytes in central nervous system but clear the virus," J Neuroimmunol., 116(2):178-187, Jun. 1, 2001.

Zhang et al., "Treatment of CD20-directed Chimeric Antigen Receptor-modified T cells in patients with relapsed or refractory B-cell non-Hodgkin lymphoma: an early phase IIa trial report," Signal Transduct. Target. Ther., Mar. 11, 2016, 1:16002.

Zhao et al., "A phase 1, open-label study of LCAR-B38M, a chimeric antigen receptor T cell therapy directed against B cell maturation antigen, in patients with relapsed or refractory multiple myeloma," J. Hematol. Oncol., Dec. 20, 2018, 11(1):141.

Zhao et al., "Galectin-9 Mediates the Therapeutic Effect of Mesenchymal Stem Cells on Experimental Endotoxemia," Front. Cell Dev. Biology, Feb. 2022, 10:700702, 17 pages.

Zhao et al., "Growth Arrest-Specific 6 Enhances the Suppressive Function of CD4+CD25+ Regulatory T Cells Mainly through Axl Receptor," Mediators Inflamm., Feb. 2017, 2017:6848430.

Zhao et al., "In vivo-activated CD103+CD4+ regulatory T cells ameliorate ongoing chronic graft-versus-host disease," Blood, Sep. 1, 2008, 112(5):2129-2138.

Zheng et al., "MiR-125b regulates proliferation and apoptosis of nasopharyngeal carcinoma by targeting A20/NF-ĸB signaling pathway," Cell Death Disease, Jun. 1, 2017, 8(6):e2855, 13 pages.

Zhou et al., "Exclusive Transduction of Human CD4+ T Cells upon Systemic Delivery of CD4-Targeted Lentiviral Vectors," J. Immunology, Jul. 31, 2015, 195(5):2493-2501.

Zhou et al., "Inducible-costimulator-mediated suppression of human immunodeficiency virus type 1 replication in CD4+ T lymphocytes," Virology, 325(2):252-263, Aug. 1, 2004.

Zhou et al., "Polyploid giant cancer cells and cancer progression," Front. Cell Dev. Biol., Oct. 2022, 10:1017588.

Zhou et al., "Single-cell deletion analyses show control of pro-T cell developmental speed and pathways by Tcf7, Spi1, Gata3, Bcl11a, Erg, and Bcl11b," Sci. Immunol., May 2022, 7(71):eabm 1920.

Zhu et al., "AXL receptor tyrosine kinase as a promising anti-cancer approach: functions, molecular mechanisms and clinical applications," Mol. Cancer, Nov. 2019, 18(1):153.

(56)  References Cited

OTHER PUBLICATIONS

Zitvogel et al., "Immunological aspects of cancer chemotherapy," Nat Rev Immunol., 8(1):59-73, Jan. 2008.

Zou et al., "Inhibitory B7-family molecules in the tumour microenvironment," Nat Rev Immunol., 8(6):467-477, Jun. 2008.

Zula et al., "The role of cell type-specific responses in IFN-β therapy of multiple sclerosis," Proc Natl Acad Sci USA., 108(49):19689-19694, Nov. 21, 2011.

Zumla et al. "Granulomatous infections: etiology and classification," Clin Infect Dis., 23(1):146-158, Jul. 1996.

Zwiebel et al., "Drug delivery by genetically engineered cell implants," Ann NY Acad Sci., 618:394-404, 1991.

* cited by examiner

```
ATGGCCTTACCAGTGACCGCCTTGCTCCTGCCGCTGGCCTTGCTGCTCCACGCCGCC
AGGCCGGACATCCAGATGACACAGACTACATCCTCCCTGTCTGCCTCTCTGGGAGAC
AGAGTCACCATCAGTTGCAGGGCAAGTCAGGACATTAGTAAATATTTAAATTGGTAT
CAGCAGAAACCAGATGGAACTGTTAAACTCCTGATCTACCATACATCAAGATTACAC
TCAGGAGTCCCATCAAGGTTCAGTGGCAGTGGGTCTGGAACAGATTATTCTCTCACC
ATTAGCAACCTGGAGCAAGAAGATATTGCCACTTACTTTTGCCAACAGGGTAATACG
CTTCCGTACACGTTCGGAGGGGGGACCAAGCTGGAGATCACAGGTGGCGGTGGCTCG
GGCGGTGGTGGGTCGGGTGGCGGCGGATCTGAGGTGAAACTGCAGGAGTCAGGACCT
GGCCTGGTGGCGCCCTCACAGAGCCTGTCCGTCACATGCACTGTCTCAGGGGTCTCA
TTACCCGACTATGGTGTAAGCTGGATTCGCCAGCCTCCACGAAAGGGTCTGGAGTGG
CTGGGAGTAATATGGGGTAGTGAAACCACATACTATAATTCAGCTCTCAAATCCAGA
CTGACCATCATCAAGGACAACTCCAAGAGCCAAGTTTTCTTAAAAATGAACAGTCTG
CAAACTGATGACACAGCCATTTACTACTGTGCCAAACATTATTACTACGGTGGTAGC
TATGCTATGGACTACTGGGGCCAAGGAACCTCAGTCACCGTCTCCTCAACCACGACG
CCAGCGCCGCGACCACCAACACCGGCGCCCACCATCGCGTCGCAGCCCCTGTCCCTG
CGCCCAGAGGCGTGCCGGCCAGCGGCGGGGGGCGCAGTGCACACGAGGGGGCTGGAC
TTCGCCTGTGATATCTACATCTGGGCGCCCTTGGCCGGGACTTGTGGGGTCCTTCTC
CTGTCACTGGTTATCACCCTTTACTGCAAACGGGGCAGAAAGAAACTCCTGTATATA
TTCAAACAACCATTTATGAGACCAGTACAAACTACTCAAGAGGAAGATGGCTGTAGC
TGCCGATTTCCAGAAGAAGAAGAAGGAGGATGTGAACTGAGAGTGAAGTTCAGCAGG
AGCGCAGACGCCCCCGCGTACAAGCAGGGCCAGAACCAGCTCTATAACGAGCTCAAT
CTAGGACGAAGAGAGGAGTACGATGTTTTGGACAAGAGACGTGGCCGGGACCCTGAG
ATGGGGGGAAAGCCGAGAAGGAAGAACCCTCAGGAAGGCCTGTACAATGAACTGCAG
AAAGATAAGATGGCGGAGGCCTACAGTGAGATTGGGATGAAAGGCGAGCGCCGGAGG
GGCAAGGGGCACGATGGCCTTTACCAGGGTCTCAGTACAGCCACCAAGGACACCTAC
GACGCCCTTCACATGCAGGCCCTGCCCCCTCGC
```

FIG. 5

Human Cytokines

Mouse Cytokines

| gRNA/Primer | Sequence |
|---|---|
| CSF2 Primer For | TGACTACAGAGAGGCACAGA |
| CSF2 Primer Rev | TCACCTCTGACCTCATTAACC |
| | |
| CSF2 CRISPR gRNA 1 | GACCTGCCTACAGACCCGCC |

In Clinical Trials, CNS Infiltration of Myeloid Cells Correlates with Severe NT[§]

| Cell Populations in CSF* | NT Grade 0-2 (n=15) Median cells/mL (Q1, Q3)** | NT Grade ≥ 3 (N=10) Median cells/mL (Q1, Q3) | NT Grade ≥ 3/Grade 0-2 Ratio |
|---|---|---|---|
| CD45+ (leukocytes) | 166 (18, 1504) | 570 (170, 1700) | 3.4 |
| CD14+ (myeloid cells) | 18 (11, 436) | 306 (125, 1063) | 17*** |
| CAR+ T cells | | | |
| CD3+ | 35 (6, 324) | 79 (47, 81) | 2.3 |
| CD4+ | 26 (3, 213) | 52 (34, 65) | 2 |
| CD8+ | 17 (1, 85) | 15 (10, 34) | 0.9 |
| CD4/CD8 T cell ratio | 2 (1, 5) | 3 (2, 5) | 1.6 |
| CAR+ CD4/CAR CD8 T cell ratio | 9 (8, 53) | 17 (11, 22) | 2 |

***17x increase of CD14+ myeloid cells in CSF in patients with Grade 3+ NT vs. Grades 0-2

*CSF = cerebrospinal fluid; **Q = quartile
§ Locke et al., ASH 2017, Abstract 1547

Fig. 17A

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: guideRNA targeting location in a GM-CSF nucleic -continued acid

<400> SEQUENCE: 1
gacctgccta cagacccgcc                                                    20

<210> SEQ ID NO 2
<211> LENGTH: 1458
<212> TYPE: DNA
<213> ORGANISM: Artificial Sequence
<220> FEATURE:
<223> OTHER INFORMATION: nucleic acid encoding a chimeric antigen
      receptor targeting CD19 (CAR19)

<400> SEQUENCE: 2
atggccttac cagtgaccgc cttgctcctg ccgctggcct tgctgctcca cgccgccagg      60
ccggacatcc agatgacaca gactacatcc tccctgtctg cctctctggg agacagagtc     120
accatcagtt gcagggcaag tcaggacatt agtaaatatt taaattggta tcagcagaaa     180
ccagatggaa ctgttaaact cctgatctac catacatcaa gattacactc aggagtccca     240
tcaaggttca gtggcagtgg gtctggaaca gattattctc tcaccattag caacctggag     300
caagaagata ttgccactta cttttgccaa caggtaaata cgcttccgta cacgttcgga     360
ggggggacca agctggagat cacaggtggc ggtggctcgg gcggtggtgg gtcgggtggc     420
ggcggatctg aggtgaaact gcaggagtca ggacctggcc tggtggcgcc ctcacagagc     480
ctgtccgtca catgcactgt ctcaggggtc tcattacccg actatggtgt aagctggatt     540
cgccagcctc cacgaaaggg tctggagtgg ctgggagtaa tatggggtag tgaaaccaca     600
tactataatt cagctctcaa atccagactg accatcatca aggacaactc caagagccaa     660
gttttcttaa aaatgaacag tctgcaaact gatgacacag ccatttacta ctgtgccaaa     720
cattattact acggtggtag ctatgctatg gactactggg gccaaggaac ctcagtcacc     780
gtctcctcaa ccacgacgcc agcgccgcga ccaccaacac cggcgcccac catcgcgtcg     840
cagcccctgt ccctgcgccc agaggcgtgc cggccagcgg cggggggcgc agtgcacacg     900
agggggctgg acttcgcctg tgatatctac atctgggcgc ccttggccgg acttgtgggg     960
gtccttctcc tgtcactggt tatcaccctt tactgcaaac ggggcagaaa gaaactcctg    1020
tatatattca aacaaccatt tatgagacca gtacaaacta ctcaagagga agatggctgt    1080
agctgccgat ttccagaaga agaagaagga ggatgtgaac tgagagtgaa gttcagcagg    1140
agcgcagacg ccccccgcgta caagcagggc cagaaccagc tctataacga gctcaatcta    1200
ggacgaagag aggagtacga tgtttttggac aagagacgtg gccgggaccc tgagatgggg    1260
ggaaagccga gaaggaagaa ccctcaggaa ggcctgtaca atgaactgca gaaagataag    1320
atggcggagg cctacagtga gattgggatg aaaggcgagc gccggagggg caaggggcac    1380
gatggccttt accagggtct cagtacagcc accaaggaca cctacgacgc ccttcacatg    1440
caggccctgc cccctcgc                                                  1458

<210> SEQ ID NO 3
<211> LENGTH: 20
<212> TYPE: DNA
<213> ORGANISM: Artificial Sequence
<220> FEATURE:
<223> OTHER INFORMATION: guideRNA targeting location in a GM-CSF nucleic
      acid

<400> SEQUENCE: 3
tcaggagacg ccgggcctcc                                                    20

```
<210> SEQ ID NO 4
<211> LENGTH: 20
<212> TYPE: DNA
<213> ORGANISM: Artificial Sequence
<220> FEATURE:
<223> OTHER INFORMATION: guideRNA targeting location in a GM-CSF nucleic
      acid

<400> SEQUENCE: 4
cagcagcagt gtctctactc                                                     20

<210> SEQ ID NO 5
<211> LENGTH: 20
<212> TYPE: DNA
<213> ORGANISM: Artificial Sequence
<220> FEATURE:
<223> OTHER INFORMATION: guideRNA targeting location in a GM-CSF nucleic
      acid

<400> SEQUENCE: 5
ctcagaaatg tttgacctcc                                                     20

<210> SEQ ID NO 6
<211> LENGTH: 20
<212> TYPE: DNA
<213> ORGANISM: Artificial Sequence
<220> FEATURE:
<223> OTHER INFORMATION: guideRNA targeting location in a GM-CSF nucleic
      acid

<400> SEQUENCE: 6
ggccggtctc actcctggac                                                     20

<210> SEQ ID NO 7
<211> LENGTH: 23
<212> TYPE: DNA
<213> ORGANISM: Artificial Sequence
<220> FEATURE:
<223> OTHER INFORMATION: guideRNA targeting location in a CSF2 gene
      nucleic acid

<400> SEQUENCE: 7
gacctgccta cagacccgcc tgg                                                 23

<210> SEQ ID NO 8
<211> LENGTH: 19
<212> TYPE: DNA
<213> ORGANISM: Artificial Sequence
<220> FEATURE:
<223> OTHER INFORMATION: CSF2 nucleic acid having a deletion caused by a
      CRISPR/Cas system

<400> SEQUENCE: 8
gacctgccta cagaccgcc                                                      19

<210> SEQ ID NO 9
<211> LENGTH: 21
<212> TYPE: DNA
<213> ORGANISM: Artificial Sequence
<220> FEATURE:
<223> OTHER INFORMATION: CSF2 nucleic acid having an insertion caused by
      a CRISPR/Cas system

<400> SEQUENCE: 9
gacctgccta cagaccccgc c                                                   21
```

-continued

<210> SEQ ID NO 10
<211> LENGTH: 20
<212> TYPE: DNA
<213> ORGANISM: Artificial Sequence
<220> FEATURE:
<223> OTHER INFORMATION: guideRNA targeting location in a GM-CSF nucleic
      acid

<400> SEQUENCE: 10
gcagtgctgc ttgtagtggc                                                   20

<210> SEQ ID NO 11
<211> LENGTH: 26
<212> TYPE: DNA
<213> ORGANISM: Artificial Sequence
<220> FEATURE:
<223> OTHER INFORMATION: guideRNA targeting location in a CSF2 gene
      nucleic acid including protospacer adjacent motif (PAM)

<400> SEQUENCE: 11
ccgacctgcc tacagacccg cctgga                                            26

<210> SEQ ID NO 12
<211> LENGTH: 20
<212> TYPE: DNA
<213> ORGANISM: Artificial Sequence
<220> FEATURE:
<223> OTHER INFORMATION: synthetic primer

<400> SEQUENCE: 12
tgactacaga gaggcacaga                                                   20

<210> SEQ ID NO 13
<211> LENGTH: 21
<212> TYPE: DNA
<213> ORGANISM: Artificial Sequence
<220> FEATURE:
<223> OTHER INFORMATION: synthetic primer

<400> SEQUENCE: 13
tcacctctga cctcattaac c                                                 21

<210> SEQ ID NO 14
<211> LENGTH: 54
<212> TYPE: DNA
<213> ORGANISM: Homo sapiens
<220> FEATURE:
<221> NAME/KEY: misc_feature
<222> LOCATION: (1)..(54)
<223> OTHER INFORMATION: GM-CSF EXON 1 putative ZNF targeting sequence

<400> SEQUENCE: 14
atgtggctgc agagcctgct gctctcgggc ctcgcccagc cccagcacgc agcc           54

<210> SEQ ID NO 15
<211> LENGTH: 54
<212> TYPE: DNA
<213> ORGANISM: Homo sapiens
<220> FEATURE:
<221> NAME/KEY: misc_feature
<222> LOCATION: (1)..(54)
<223> OTHER INFORMATION: GM-CSF EXON 1 complementary strand of putative
      ZNF targeting sequence

<400> SEQUENCE: 15
tacaccgacg tctcggacga cgagagcccg gagcgggtcg gggtcgtgcg tcgg           54

-continued

```
<210> SEQ ID NO 16
<211> LENGTH: 54
<212> TYPE: DNA
<213> ORGANISM: Homo sapiens
<220> FEATURE:
<221> NAME/KEY: misc_feature
<222> LOCATION: (1)..(54)
<223> OTHER INFORMATION: GM-CSF EXON 2 putative ZNF targeting sequence

<400> SEQUENCE: 16
aatgaaacag tagaagtcat ctcagaaatg gaagtcatct cagaaatgtt tgac            54

<210> SEQ ID NO 17
<211> LENGTH: 54
<212> TYPE: DNA
<213> ORGANISM: Homo sapiens
<220> FEATURE:
<221> NAME/KEY: misc_feature
<222> LOCATION: (1)..(54)
<223> OTHER INFORMATION: GM-CSF EXON 2 complementary strand of putative
      ZNF targeting sequence

<400> SEQUENCE: 17
ttactttgtc atcttcagta gagtctttac cttcagtaga gtctttacaa actg            54

<210> SEQ ID NO 18
<211> LENGTH: 55
<212> TYPE: DNA
<213> ORGANISM: Artificial Sequence
<220> FEATURE:
<223> OTHER INFORMATION: design Exon 3 GM-CSF

<400> SEQUENCE: 18
gagccgacct gcctacagac ccgcctggag gcctacagac ccgcctggag ctgta           55

<210> SEQ ID NO 19
<211> LENGTH: 55
<212> TYPE: DNA
<213> ORGANISM: Artificial Sequence
<220> FEATURE:
<223> OTHER INFORMATION: GM-CSF Exon 3 complementary strand

<400> SEQUENCE: 19
ctcggctgga cggatgtctg ggcggacctc cggatgtctg ggcggacctc gacat           55

<210> SEQ ID NO 20
<211> LENGTH: 55
<212> TYPE: DNA
<213> ORGANISM: Homo sapiens
<220> FEATURE:
<221> NAME/KEY: misc_feature
<222> LOCATION: (1)..(55)
<223> OTHER INFORMATION: Exon 4

<400> SEQUENCE: 20
gaaacttcct gtgcaaccca gattatcacc tgcaacccag attatcacct ttgaa           55

<210> SEQ ID NO 21
<211> LENGTH: 55
<212> TYPE: DNA
<213> ORGANISM: Homo sapiens
<220> FEATURE:
<221> NAME/KEY: misc_feature
<222> LOCATION: (1)..(55)
<223> OTHER INFORMATION: Exon 4 complementary strand

<400> SEQUENCE: 21
```

```
ctttgaagga cacgttgggt ctaatagtgg acgttgggtc taatagtgga aactt          55

<210> SEQ ID NO 22
<211> LENGTH: 51
<212> TYPE: DNA
<213> ORGANISM: Homo sapiens
<220> FEATURE:
<221> NAME/KEY: misc_feature
<222> LOCATION: (1)..(51)
<223> OTHER INFORMATION: GM-CSF Exon 1

<400> SEQUENCE: 22
tggctgcaga gcctgctgct cttgggcact gtggcctgca gcatctctgc a              51

<210> SEQ ID NO 23
<211> LENGTH: 52
<212> TYPE: DNA
<213> ORGANISM: Homo sapiens
<220> FEATURE:
<221> NAME/KEY: misc_feature
<222> LOCATION: (1)..(52)
<223> OTHER INFORMATION: GM-CSF Exon 4

<400> SEQUENCE: 23
ttgggcactg tggcctgcag catctctgca cccgcccgct cgcccagccc ca             52

<210> SEQ ID NO 24
<211> LENGTH: 50
<212> TYPE: DNA
<213> ORGANISM: Homo sapiens
<220> FEATURE:
<221> NAME/KEY: misc_feature
<222> LOCATION: (1)..(50)
<223> OTHER INFORMATION: GM-CSF Exon 4

<400> SEQUENCE: 24
tgtgcaaccc agattatcac ctttgaaagt ttcaaagaga acctgaagga                50

<210> SEQ ID NO 25
<211> LENGTH: 50
<212> TYPE: DNA
<213> ORGANISM: Homo sapiens
<220> FEATURE:
<221> NAME/KEY: misc_feature
<222> LOCATION: (1)..(50)
<223> OTHER INFORMATION: GM-CSF Exon 4

<400> SEQUENCE: 25
tcctgtgcaa cccagattat cacctttgaa agtttcaaag agaacctgaa                50

<210> SEQ ID NO 26
<211> LENGTH: 51
<212> TYPE: DNA
<213> ORGANISM: Homo sapiens
<220> FEATURE:
<221> NAME/KEY: misc_feature
<222> LOCATION: (1)..(51)
<223> OTHER INFORMATION: GM-CSF Exon 4

<400> SEQUENCE: 26
ttatcacctt tgaaagtttc aaagagaacc tgaaggactt tctgcttgtc a              51
```

MATERIALS AND METHODS FOR TREATING CANCER

CROSS-REFERENCE TO RELATED APPLICATIONS

This application is a U.S. national stage application under 37 U.S.C. 371 of PCT International Application PCT/US2019/059275, filed Oct. 31, 2019, which claims benefit of U.S. Provisional Application No. 62/753,485 filed Oct. 31, 2018, the priority dates of which are hereby claimed, and the contents of each of which are hereby incorporated by reference in their entireties.

SEQUENCE LISTING INCORPORATION

The ".txt" Sequence Listing filed with this application by EFS and which is entitled P-588784-US1-SEQ-LISTING-8MAR.2022_ST25.txt, is 12.0 kilobytes in size and which was created on Mar. 8, 2022, is hereby incorporated by reference.

1. TECHNICAL FIELD

This document relates to methods and materials involved in treating cancer. For example, this document provides methods and materials for using chimeric antigen receptor T cells having reduced expression levels of one or more cytokines (e.g., GM-CSF) in an adoptive cell therapy (e.g., a chimeric antigen receptor T cell therapy) to treat a mammal (e.g., a human) having cancer.

2. BACKGROUND INFORMATION

Unprecedented results from pivotal trials evaluating the safety and efficacy of CD19 directed chimeric antigen receptor T cells (CART19) have led to the recent FDA approval of CART19 (Tisagenlecleucel) for relapsed refractory acute lymphoblastic leukemia (ALL) and CART19 (Axi-Cel) for the treatment of diffuse large B cell lymphoma (DLBCL). The application of CART cell therapy is associated with toxicities resulting in cytokine release syndrome (CRS) and neurotoxicity. Additionally, the efficacy of CART cell therapy is limited to only 40% durable remissions in lymphoma and 50-60% durable remissions in acute leukemia.

SUMMARY

This document provides methods and materials for generating T cells (e.g., chimeric antigen receptor (CAR) T cells (CARTs)) having a reduced expression level of one or more cytokine (e.g., GM-CSF) polypeptides. For example, a T cell (e.g., a CART) can be engineered to have reduced GM-CSF polypeptide expression (e.g., for use in adoptive cell therapy). In some cases, a T cell (e.g., a CART) can be engineered to knock out (KO) a nucleic acid encoding one or more cytokine polypeptides (e.g., a GM-CSF polypeptide) to reduce cytokine polypeptide (e.g., GM-CSF polypeptide) expression in that T cell. This document also provides methods and materials for using T cells (e.g., CARTs) having a reduced expression level of one or more cytokines (e.g., GM-CSF polypeptides). For example, T cells (e.g., CARTs) having a reduced level of GM-CSF polypeptides can be administered (e.g., in an adoptive cell therapy) to a mammal having cancer to treat the mammal.

In one aspect, this invention provides a method for enhancing anti-tumor efficacy of immunotherapy in a subject, the method comprising administering to the subject CAR-T cells having a GM-CSF gene inactivation, GM-CSF gene knock-down or gene knockout (GM-CSF$^{k/o}$ CAR-T cells), wherein administration of the CAR-T cells reduces or prevents immunotherapy-related toxicity.

In another aspect, this invention provides a method for reducing a level of a non-GM-CSF cytokine in a subject treated with immunotherapy, the method comprising administering to the subject CAR-T cells having a GM-CSF gene inactivation, GM-CSF gene knock-down or gene knockout (GM-CSF$^{k/o}$ CAR-T cells).

In one aspect, this invention provides a method for GM-CSF gene inactivation, GM-CSF gene knock-down or GM-CSF knockout (KO) in a cell comprising targeted genome editing or GM-CSF gene silencing.

In one aspect, this invention provides a method for making a chimeric antigen receptor T cell having a reduced level of granulocyte-macrophage colony-stimulating factor (GM-CSF) polypeptides, said method comprising: introducing a nucleic acid construct into an ex vivo T cell, wherein said nucleic acid construct comprises: a) a nucleic acid encoding a guide RNA, wherein said guide RNA is complementary to a GM-CSF messenger RNA; b) a nucleic acid encoding a Cas nuclease, and c) a nucleic acid encoding said chimeric antigen receptor.

In another aspect, this invention provides a method for making a chimeric antigen receptor T cell having a reduced level of granulocyte-macrophage colony-stimulating factor (GM-CSF) polypeptides, said method comprising: introducing a complex into an ex vivo T cell, wherein said complex comprises: a) a guide RNA, wherein said guide RNA is complementary to a GM-CSF messenger RNA; and b) a Cas nuclease; and introducing a nucleic acid encoding said chimeric antigen receptor into said ex vivo T cell.

In an aspect, this invention provides a method for making a chimeric antigen receptor T cell having a reduced level of cytokine polypeptides, said method comprising: introducing a nucleic acid construct into an ex vivo T cell, wherein said nucleic acid construct comprises: a) a nucleic acid encoding a guide RNA, wherein said guide RNA is complementary to a cytokine messenger RNA; b) a nucleic acid encoding a Cas nuclease, and c) a nucleic acid encoding said chimeric antigen receptor.

In another aspect, this invention provides a method for making a chimeric antigen receptor T cell having a reduced level of cytokine polypeptides, said method comprising: introducing a complex into an ex vivo T cell, wherein said complex comprises: a) a guide RNA, wherein said guide RNA is complementary to a cytokine messenger RNA; and b) a Cas nuclease; and introducing a nucleic acid encoding said chimeric antigen receptor into said ex vivo T cell.

In a further aspect, this invention provides a method for improving T cell effector functions of a chimeric antigen receptor T cell, said method comprising: introducing a nucleic acid construct into an ex vivo T cell, wherein said nucleic acid construct comprises: a) a nucleic acid encoding a guide RNA, wherein said guide RNA is complementary to a GM-CSF messenger RNA; b) a nucleic acid encoding a Cas nuclease, and c) a nucleic acid encoding said chimeric antigen receptor.

In an aspect, this invention provides a method for improving T cell effector functions of a chimeric antigen receptor T cell, said method comprising: introducing a complex into an ex vivo T cell, wherein said complex comprises: a) a guide RNA, wherein said guide RNA is complementary to a GM-CSF messenger RNA; and b) a Cas nuclease; and introducing a nucleic acid encoding said chimeric antigen receptor into said ex vivo T cell.

As demonstrated herein, GM-CSF KO CARTs produce reduced levels of GM-CSF and continue to function normally in both in vitro and in vivo models. Also as demonstrated herein, GM-CSF KO CARTs can have enhanced CART cell function and antitumor activity. For example, enhanced CART cell proliferation and anti-tumor activity can be observed after GM-CSF depletion. CART19 antigen specific proliferation in the presence of monocytes can be increased in vitro after GM-CSF depletion. In ALL patient derived xenografts, CART19 cells can result in a more durable disease control when combined with lenzilumab, and GM-CSF$^{k/o}$ CART cells can be more effective in controlling leukemia in NALM6 xenografts. In some cases, GM-CSF KO CARTs can be incorporated into adoptive T cell therapies (e.g., CART cell therapies) to treat, for example, mammals having cancer without resulting in CRS and/or neurotoxicity. For example, GM-CSF KO CARTs can be incorporated into adoptive T cell therapies (e.g., CART cell therapies) to enhance the therapeutic window after CART cell therapy. In some cases, a single construct can be used both to introduce a CAR into a cell (e.g., a T cell) and to reduce or knock out expression of one or more cytokine polypeptides in that same cell.

In another aspect, this invention provides a method for treating a mammal having cancer, wherein said method comprises administering chimeric antigen receptor T cells having a reduced level of granulocyte-macrophage colony-stimulating factor (GM-CSF) polypeptides to said mammal.

In still another aspect, this invention provides a method for treating a mammal having cancer, wherein said method comprises administering chimeric antigen receptor T cells having a reduced level of cytokine polypeptides to said mammal.

In general, one aspect of this document features methods for making a CART cell having a reduced level of cytokine polypeptides. The methods can include, or consist essentially of introducing a nucleic acid construct into an ex vivo T cell, wherein the nucleic acid construct includes: a) a nucleic acid encoding a guide RNA (gRNA) complementary to a cytokine messenger RNA (mRNA); b) a nucleic acid encoding a Cas nuclease, and c) a nucleic acid encoding a chimeric antigen receptor. The cytokine polypeptides can include granulocyte-macrophage colony-stimulating factor (GM-CSF) polypeptides, interleukin 6 (IL-6) polypeptides, IL-1 polypeptides, M-CSF polypeptides, and/or MIP-1B polypeptides. The cytokine polypeptides can be GM-CSF polypeptides, and the gRNA can include a nucleic acid sequence set forth in SEQ ID NO: 1. The Cas nuclease can be a Cas9 nuclease. The nucleic acid encoding the CAR can include a nucleic acid sequence set forth in SEQ ID NO: 2. The nucleic acid construct can be a viral vector (e.g., a lentiviral vector). The CAR can target a tumor-associated antigen. (e.g., CD19). The introducing step can include transduction.

In another aspect, this document features methods for making a CAR T cell having a reduced level of cytokine polypeptides. The methods can include, or consist essentially of, introducing a complex into an ex vivo T cell, where the complex includes: a) a gRNA complementary to a cytokine mRNA; and b) a Cas nuclease; and introducing a nucleic acid encoding the CAR into the ex vivo T cell. The cytokine polypeptides can include GM-CSF Polypeptides and/or IL-6 polypeptides. The cytokine polypeptides can be GM-CSF polypeptides, and the gRNA can include a nucleic acid sequence set forth in SEQ ID NO: 1. The Cas nuclease can be a Cas9 nuclease. The nucleic acid encoding the CAR can include a nucleic acid sequence set forth in SEQ ID NO: 2. The complex can be a ribonucleoprotein (RNP). The CAR can target a tumor-associated antigen (e.g., CD19). The introducing steps can include electroporation.

In another aspect, this document features methods for making a CAR T cell having a reduced level of GM-CSF polypeptides. The methods can include, or consist essentially of introducing a nucleic acid construct into an ex vivo T cell, where the nucleic acid construct includes: a) a nucleic acid encoding a gRNA complementary to a GM-CSF mRNA; b) a nucleic acid encoding a Cas nuclease, and c) a nucleic acid encoding the CAR. The gRNA can include a nucleic acid sequence set forth in SEQ ID NO: 1. The Cas nuclease can be a Cas9 nuclease. The nucleic acid encoding the CAR can include a nucleic acid sequence set forth in SEQ ID NO: 2. The nucleic acid construct can be a viral vector (e.g., a lentiviral vector). The CAR can target a tumor-associated antigen (e.g., CD19). The introducing step can include transduction.

In another aspect, this document features methods for making a CAR T cell having a reduced level of GM-CSF polypeptides. The methods can include, or consist essentially of, introducing a complex into an ex vivo T cell, where the complex includes: a) a gRNA complementary to a GM-CSF mRNA; and b) a Cas nuclease; and introducing a nucleic acid encoding the CAR into the ex vivo T cell. The gRNA can include a nucleic acid sequence set forth in SEQ ID NO: 1. The Cas nuclease can be a Cas9 nuclease. The nucleic acid encoding the CAR can include a nucleic acid sequence set forth in SEQ ID NO: 2. The complex can be a RNP. The CAR can target a tumor-associated antigen (e.g., CD19). The introducing steps can include electroporation.

In another aspect, this document features methods for treating a mammal having cancer. The methods can include, or consist essentially of, administering CART cells having a reduced level of cytokine polypeptides to a mammal having cancer. The cytokine polypeptides can include GM-CSF polypeptides and/or IL-6 polypeptides. The cytokine polypeptides can be GM-CSF polypeptides, and the gRNA can include a nucleic acid sequence set forth in SEQ ID NO: 1. The mammal can be a human. The cancer can be a lymphoma (e.g., a DLBCL). The cancer can be a leukemia (e.g., an ALL). The CAR can target a tumor-associated antigen (e.g., CD19).

In another aspect, this document features methods for treating a mammal having cancer. The methods can include, or consist essentially of, administering CAR T cells having a reduced level of GM-CSF polypeptides to a mammal having cancer. The mammal can be a human. The cancer can be a lymphoma (e.g., a DLBCL). The cancer can be a leukemia (e.g., ALL). The CAR can target a tumor-associated antigen (e.g., CD19).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 2A contains a graph showing that CRISPR/Cas9 lentivirus with a guide RNA directed to exon 3 of GM-CSF resulted in a knockout efficiency of 24.1%. At the end of the expansion, CART cells were harvested, and DNA was isolated and sent for sequencing to be compared to control sequences. This yielded in a knockout efficiency of 24.1%. FIG. 2B contains a flow cytometric analysis showing that CAR transduction efficiency after transduction with lentivirus was 73%. Flow cytometric analysis was performed on Day 6 after lentivirus transduction.

FIG. 5 shows an exemplary nucleic acid sequence (SEQ ID NO: 2) encoding a CAR targeting CD19 (CAR19).

FIG. 6A contains a graph showing that lenzilumab neutralizes CAR-T cell produced GM-CSF in vitro compared to isotype control treatment as assayed by multiplex after 3 days of culture with CART19 in media alone or CART19 co-cultured with NALM6, n=2 experiments, 2 replicates per experiment, representative experiment depicted, *p<0.001 between lenzilumab and isotype control treatment, t test, mean±SEM. FIG. 6B contains a graph showing that GM-CSF neutralizing antibody treatment did not inhibit the ability of CAR-T cells to proliferate as assayed by CSFE flow cytometry proliferation assay of live CD3 cells, n=2 experiments, 2 replicates per experiment, representative experiment at 3 day time point depicted, ns p>0.05 between lenzilumab and isotype control treatment, t test, mean±SEM. Alone: CART19 in media alone, MOLM13: CART19+ MOLM13, PMA/ION: CART19+5 ng/mL PMA/0.1 μg/mL ION, NALM6: CART19+NALM6. FIG. 6C contains a graph showing that lenzilumab enhanced the proliferation of CART19 compared to isotype control treated with CART19 when co-cultured with monocytes n=3 biologic replicates at 3 day time point, 2 replicates per biological replicate,  p<0.0001, mean±SEM. FIG. 6D** contains a graph showing that lenzilumab treatment did not inhibit cytotoxicity of CART19 or untransduced T cells (UTD) when cultured with NALM6, n=2 experiments, 2 replicates per experiment, representative experiment at 48 hr time point depicted, ns p>0.05 between lenzilumab and isotype control treatment, t test, mean±SEM.

FIG. 7A contains an experimental schema showing that NSG mice were injected with the CD19+ luciferase+ cell line NALM6 ($1×10^6$ cells per mouse I.V). 4-6 days later, mice were imaged, randomized, and received $1-1.5×10^6$ CAR-T 19 or equivalent number of total cells of control UTD cells the following day with either lenzilumab or control IgG (10 mg/Kg, given IP daily for 10 days, starting on the day of CAR-T injection). Mice were followed with serial bioluminescence imaging to assess disease burden beginning day 7 post CAR-T cell injection and were followed for overall survival. Tail vein bleeding was performed 7-8 days after CAR-T cell injection. FIG. 7B contains a graph showing that lenzilumab neutralizes CAR-T produced serum GM-CSF in vivo compared to isotype control treatment as assayed by GM-CSF singleplex, n=2 experiments, 7-8 mice per group, representative experiment, serum from day 8 post CAR-T cell/UTD injection, *p<0.001 between lenzilumab and isotype control treatment, t test, mean±SEM. FIG. 7C contains a graph showing that lenzilumab treated CAR-T in vivo are equally effective at controlling tumor burden compared to isotype control treated CAR-T in a high tumor burden relapse xenograft model of ALL, day 7 post CAR-T injection, n=2 experiments, 7-8 mice per group, representative experiment depicted, *p<0.001, *p<0.05, ns p>0.05, t test, mean±SEM. FIG. 7D contains an experimental schema showing that NSG mice were injected with the blasts derived from patients with ALL ($1×10^6$ cells per mouse I.V). Mice were bled serially and when the CD19+ cells ≥1/uL, mice were randomized to receive $5×10^6$ CART19 (transduction efficiency is around 50%) or UTD cells with either lenzilumab or control IgG (10 mg/Kg, given IP daily for 10 days, starting on the day of CAR-T injection). Mice were followed with serial tail vein bleeding to assess disease burden beginning day 14 post CAR-T cell injection and were followed for overall survival. FIG. 7E contains a graph showing that lenzilumab treatment with CAR-T therapy results in more sustained control of tumor burden over time in a primary acute lymphoblastic leukemia (ALL) xenograft model compared to isotype control treatment with CAR-T therapy, 6 mice per group, **p<0.01, *p<0.05, ns p>0.05, t test, mean±SEM.

FIG. 10A contains graphs showing that the CRISPR Cas9

GMCSF$^{k/o}$ CAR-T exhibit reduced GMCSF production compared to wild type CART19, but other cytokine production and degranulation are not inhibited by the GM-CSF gene disruption, n=3 experiments, 2 replicates per experiment, *** p<0.001, *p<0.05, ns p>0.05 comparing GM-CSF k/o CAR-T and CAR-T, t test, mean±SEM. FIG. 10B contains a graph showing that GM-CSF k/o CAR-T have reduced serum human GM-CSF in vivo compared to CAR-T treatment as assayed by multiplex, 5-6 mice per group (4-6 at time of bleed, 8 days post CART injection), **p<0.0001, *p<0.001 between GM-CSF k/o CAR-T cells and wild type CAR-T cells, t test, mean±SEM. FIG. 10C contains a graph showing that GM-CSF$^{k/o}$ CART19 in vivo enhances overall survival compared to wild type CART19 in a high tumor burden relapse xenograft model of ALL, 5-6 mice per group, p<0.01, log-rank. FIGS. 10D and 10E contain heat maps showing human (FIG. 10D) and mouse (FIG. 10E) cytokines from multiplex of serum, other than human GM-CSF, show no statistical differences between the GM-CSF k/o CAR-T cells and wild type CAR-T cells, further implicating critical T-cell cytokines aren't adversely depleted by reducing GM-CSF expression, 5-6 mice per group (4-6 at time of bleed), **p<0.0001, t test.

FIG. 12A contains an experimental schema showing that mice received 1-3×10$^6$ primary blasts derived from the peripheral blood of patients with primary ALL. Mice were monitored for engraftment for ~10-13 weeks via tail vein bleeding. When serum CD19+ cells were 2:10 cells/uL the mice received CART19 (2-5×10$^6$ cells) and commenced antibody therapy for a total of 10 days, as indicated. Mice were weighed on a daily basis as a measure of their well-being. Mouse brain MRIs were performed 5-6 days post CART19 injection and tail vein bleeding for cytokine and T cell analysis was performed 4-11 days post CART19 injection, 2 independent experiments. FIG. 12B contains a graph showing that combination of GM-CSF neutralization with CART19 is equally effective as isotype control antibodies combined with CART19 in controlling CD19+ burden of ALL cells, representative experiment, 3 mice per group, 11 days post CART19 injection, *p<0.05 between GM-CSF neutralization+CART19 and isotype control+ CART19, t test, mean±SEM. FIG. 12C contains an image showing that brain MRI with CART19 therapy exhibits T1 enhancement, suggestive of brain blood-brain barrier disruption and possible edema. 3 mice per group, 5-6 days post CART19 injection, representative image. FIG. 12D contains graphs showing that high tumor burden primary ALL xenografts treated with CART19 show human CD3 cell infiltration of the brain compared to untreated PDX controls. 3 mice per group, representative image.

FIG. 13A contains a graph showing that lenzilumab & anti-mouse GM-CSF antibody prevent CRS induced weight loss compared to mice treated with CART19 and isotype control antibodies, 3 mice per group, 2 way anova, mean±SEM. FIG. 13B contains a graph showing that human GM-CSF was neutralized in patient derived xenografts treated with lenzilumab and mouse GM-CSF neutralizing antibody, 3 mice per group, ***p<0.001, *p<0.05, t test, mean±SEM. FIG. 13C contains a heat map showing that human cytokines (serum collected 11 days after CART19 injection) exhibit increase in cytokines typical of CRS after CART19 treatment. GM-CSF neutralization results in significant decrease in several cytokines compared to mice treated with CART19 and isotype control antibodies, including several myeloid associated cytokines, as indicated in the panel, 3 mice per group, serum from day 11 post CART19 injection, *p<0.001, p<0.01, *p<0.05, comparing GM-CSF neutralizing antibody treated and isotype control treated mice that received CAR-T cell therapy, t test. FIG. 13D contains a heat map showing that mouse cytokines (serum collected 11 days after CART19 injection) exhibit increase in mouse cytokines typical of CRS after CART19 treatment. GM-CSF neutralization results in significant decrease in several cytokines compared to treated with CART19 with control antibodies, including several myeloid differentiating cytokines, as indicated in the panel, 3 mice per group, serum from day 11 post CART19 injection, *p<0.05, comparing GM-CSF neutralizing antibody treated and isotype control treated mice that received CAR-T cell therapy, t test.

FIGS. 14A and 14B show that gadolinium enhanced T1-hyperintensity (cubic mm) MRI showed that GM-CSF neutralization helped reduced brain inflammation, blood-brain barrier disruption, and possible edema compared to isotype control (A) representative images, (B) 3 mice per group, **p<0.01, *p<0.05, 1 way ANOVA, mean±SD. FIG. 14C contains a graph showing that human CD3 T cells were present in the brain after treatment with CART19 therapy. GM-CSF neutralization resulted in a trend toward decreased CD3 infiltration in the brain as assayed by flow cytometry in brain hemispheres, 3 mice per group, mean±SEM. FIG. 14D contains a graph showing that CD1 1b+ bright macrophages were decreased in the brains of mice receiving GM-CSF neutralization during CAR-T therapy compared to isotype control during CAR-T therapy as assayed by flow cytometry in brain hemispheres, 3 mice per group, mean±SEM.

FIGS. 17A-17B show respectively, that CD14+ cells are a greater proportion of the CNS cell population in human patients with grade 3 or above neurotoxicity (FIG. 17A) and that anti-hGM-CF antibody, Lenzilumab, caused a reduction in CNS infiltration by CD14+ cells and by CD11b+ cells in the primary ALL mouse model used for the NT experiments (FIG. 17B), as detailed in Example 4.

DETAILED DESCRIPTION

Figure 1:
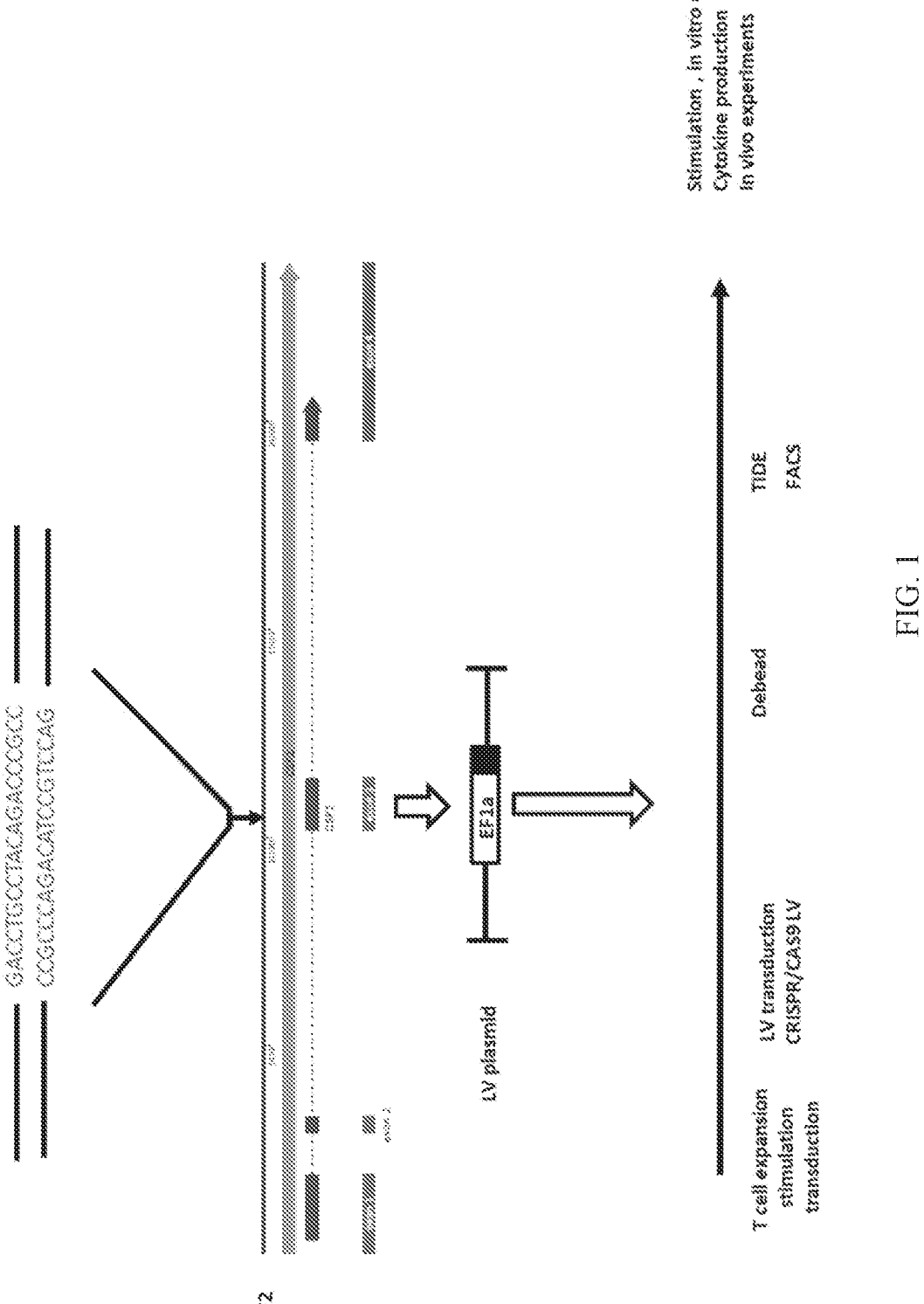
FIG. 1 contains a schematic of an exemplary method of using CRISPR to engineer a GM-CSF knock out (KO) cell. Guide RNA (GACCTGCCTACAGACCCGCC; SEQ ID NO: 1) targeting exon 3 of GM-CSF (also known as colony-stimulating factor 2 (CSF2)) was synthesized and cloned into a lentivirus (LV) plasmid. This LV plasmid was used to transduce 293T cells and lentivirus particles were collected at 24 hours and 48 hours and were concentrated. To generate GM-CSF knocked out CART cells, T cells were stimulated with CD3/CD28 beads on day 0. On day 1, T cells were transduced with CAR19 lentivirus particles, and simultaneously with GMCSF knockout CRISPR/Cas9 lentivirus particles. T cells were expanded for 8 days and then harvested.

This document provides methods and materials for generating T cells (e.g., chimeric antigen receptor (CAR) T cells (CARTs)) having a reduced expression level of one or more cytokine polypeptides (e.g., GM-CSF polypeptides). In some cases, a T cell (e.g., CART) can be engineered to knock out (KO) a nucleic acid encoding a GM-CSF polypeptide to reduce GM-CSF polypeptide expression in that T cell (e.g., as compared to a T cell that is not engineered to KO a nucleic acid encoding a GM-CSF polypeptide). A T cell that is engineered to KO a nucleic acid encoding a GM-CSF polypeptide can also be referred to herein as a GM-CSF KO T cell. In some cases, the methods and materials provided herein can be used to modulate myeloid cells. In some cases, the methods and materials provided herein can be used to deplete myeloid cells. In some cases, the methods and materials provided herein can be used to enhance T cell (e.g., CARTs) efficacy.

T cells (e.g., CARTs) provided herein can be designed to have a reduced expression level of any appropriate cytokine polypeptide or combination of cytokine polypeptides. For example, a T cell (e.g., a CART) provided herein can be designed to have a reduced expression level of a GM-CSF polypeptide, an interleukin 6 (IL-6) polypeptide, a G-CSF, a interferon gamma (IFN-g) polypeptide, an IL-1B polypeptide, an IL-10 polypeptide, a monocyte chemoattractant protein 1 (MCP-1) polypeptide, a monokine induced by gamma (MIG) polypeptide, a macrophage inflammatory protein (MIP) polypeptide (e.g., a MIP-1β polypeptide), a tumor necrosis factor alpha (TNF-a) polypeptide, an IL-2 polypeptide, a perforin polypeptide, or any combination thereof. For example, a T cell can be designed to have a reduced expression level of both GM-CSF and IL-6 polypeptides.

In one aspect, this invention provides a method for enhancing anti-tumor efficacy of immunotherapy in a subject, the method comprising administering to the subject CAR-T cells having a GM-CSF gene inactivation, GM-CSF gene knock-down or gene knockout (GM-CSF$^{k/o}$ CAR-T cells), wherein administration of the CAR-T cells reduces or prevents immunotherapy-related toxicity. In an embodiment of the herein provided method, the method further comprises administering to the subject an anti-hGM-CSF antibody, wherein the anti-hGM-CSF antibody is a recombinant anti-hGM-CSF antibody that binds to and neutralizes human GM-CSF. In a particular embodiment, the method comprises administering to the subject an anti-hGM-CSF antibody. In another embodiment, the immunotherapy-related toxicity CAR-T comprises Cytokine Release Syndrome (CRS), neurotoxicity (NT), neuroinflammation or a combination thereof.

In certain embodiments of the herein provided methods, the administration of (i) the CAR-T cells having a GM-CSF gene inactivation, GM-CSF gene knock-down or gene knockout (GM-CSF$^{k/o}$ CAR-T cells) or (ii) the CAR-T cells and the anti-hGM-CSF antibody decreases or prevents CD14+ myeloid cell trafficking to a central nervous system (CNS) of the subject. In an embodiment, a high level of CD14+ myeloid cells in the central nervous system (CNS) of the subject is indicative of neurotoxicity. A level of CD14+ myeloid cells in the CNS is determined by performing a lumbar puncture, removing a sample of cerebrospinal fluid (CSF), and measuring the CD14+ cells in the CSF, for example by cytometric flow analysis (Flow Cytometry), ELISA, anti-CD14-FITC monoclonal antibody or other suitable measurement techniques.

In an embodiment of the herein provided methods, an objective response rate of the subject administered the anti-hGM-CSF antibody is improved compared to a subject that is not administered the anti-hGM-CSF antibody. In a specific embodiment, the objective response rate is a complete response rate or a partial response rate. In another embodiment, a progression free response and/or survival of the subject is improved compared to a subject that is not administered the anti-hGM-CSF antibody and/or the CAR-T cells having a GM-CSF gene inactivation, GM-CSF gene knock-down or gene knockout (GM-CSF$^{k/o}$ CAR-T cells). In a further embodiment, the survival is overall survival of the subject. In another embodiment, the anti-hGM-CSF antibody is administered to the subject before, during or after administration of the CAR-T cells having a GM-CSF gene inactivation, GM-CSF gene knock-down or GM-CSF$^{k/o}$ CAR-T cells.

In a particular embodiment of the herein provided methods, the immunotherapy comprises administering chimeric antigen receptor-expressing T-cells (CAR T-cells). In an embodiment, wherein the CAR T-cells are CART19 cells. In another embodiment of the herein provided methods, of claim 1, the immunotherapy comprises adoptive cell transfer selected from the group consisting of administering T-cell receptor (TCR) modified T-cells, tumor-infiltrating lymphocytes (TIL), chimeric antigen receptor (CAR)-modified natural killer cells, or dendritic cells, or any combination thereof. In some embodiments, the immunotherapy comprises administration of a monoclonal antibody, a cytokine, a cancer vaccine, a T cell engaging bispecific antibody, or any combination thereof. In a particular embodiment, the subject has a cancer. In certain embodiments, the cancer is lymphoma or a leukemia. In another embodiment, the lymphoma is a diffuse large B cell lymphoma (DLBCL). In still another embodiment, the leukemia is acute lymphoblastic leukemia (ALL).

In another aspect, this invention provides a method for reducing a level of a non-GM-CSF cytokine in a subject treated with immunotherapy, the method comprising administering to the subject CAR-T cells having a GM-CSF gene inactivation, GM-CSF gene knock-down or gene knockout (GM-CSF$^{k/o}$ CAR-T cells). In a specific embodiment of the herein provided method, the method further comprising administering to the subject an anti-hGM-CSF antibody to the subject. In another embodiment, the non-GM-CSF cytokine is IP-10, IL-1a, IL-1b, IL-2, IL-3, IL-4, IL-5, IL-6, IL-1Ra, IL-9, IL-10, VEGF, TNF-a, FGF-2, IFN-γ, IL-12p40, IL-12p70, sCD40L, KC, MDC, MCP-1, MIP-1a, MIP-1b or a combination thereof. In another embodiment of the herein provided methods, the immunotherapy-related toxicity CAR-T comprises CRS, NT, neuroinflammation or a combination thereof.

In one aspect, this invention provides a method for GM-CSF gene inactivation, GM-CSF gene knock-down or GM-CSF knockout (KO) in a cell comprising targeted genome editing or GM-CSF gene silencing. In an embodiment of the herein provided method, the method further comprises an endonuclease as a nucleic acid cutting enzyme. In some embodiments, the endonuclease is a Fok1 restriction enzyme or a flap endonuclease 1 (FEN-1). In certain embodiments, the endonuclease is a Cas9 CRISPR associated protein 9 (Cas9). In a specific embodiment, the GM-CSF gene inactivation by CRISPR/Cas9 targets and edits a GM-CSF gene at Exon 1, Exon 2, Exon 3 or Exon 4. In an embodiment, the GM-CSF gene inactivation comprising CRISPR/Cas9 targets and edits the GM-CSF gene at Exon 3. In another embodiment, the GM-CSF gene inactivation comprising CRISPR/Cas9 targets and edits the GM-CSF gene at Exon 1.

In still another embodiment, the GM-CSF gene inactivation comprises multiple CRISPR/Cas9 enzymes, wherein each Cas9 enzyme targets and edits a different sequence of the GM-CSF gene at Exon 1, Exon 2, Exon 3 or Exon 4. In another embodiment, the GM-CSF gene inactivation comprises bi-allelic CRISPR/Cas9 targeting and knockout/inactivation of the GM-CSF genes.

In a particular embodiment of the herein provided methods, the method further comprises treating primary T cells with valproic acid to enhance bi-allele gene knockout/inactivation. In another embodiment the targeted genome editing comprises Zinc finger (ZnF) proteins. In certain embodiments, the targeted genome editing comprises transcription activator-like effector nucleases (TALENS). In particular embodiments, the targeted genome editing comprises a homing endonuclease, wherein the homing endonuclease is an ARC nuclease (ARCUS) or a meganuclease. In an embodiment of the herein provided methods, the targeted genome editing comprises a flap endonuclease (FEN-1). In a specific embodiment, the cell is a CAR T cell. In a particular embodiment, the CAR T cell is a CD19 CAR-T cell. In another embodiment, the CAR T cell is a BCMA CAR-T cell. In another embodiment, the GM-CSF gene silencing is selected from the group consisting of RNA interference (RNAi), short interfering RNS (siRNA), and DNA-directed RNA interference (ddRNAi).

In one aspect, this invention provides a method for making a chimeric antigen receptor T cell having a reduced level of granulocyte-macrophage colony-stimulating factor (GM-CSF) polypeptides, said method comprising: introducing a nucleic acid construct into an ex vivo T cell, wherein said nucleic acid construct comprises: a) a nucleic acid encoding a guide RNA, wherein said guide RNA is complementary to a GM-CSF messenger RNA; b) a nucleic acid encoding a Cas nuclease, and c) a nucleic acid encoding said chimeric antigen receptor. In an embodiment of said herein provided method, said guide RNA comprises a nucleic acid sequence set forth in SEQ ID NO: 1. In another embodiment, said Cas nuclease is Cas9 nuclease. In a further embodiment, said nucleic acid encoding said chimeric antigen receptor comprises a nucleic acid sequence set forth in SEQ ID NO: 2. In another embodiment, said nucleic acid construct is a viral vector. In a particular embodiment, said viral vector is a lentiviral vector. In a further embodiment, said chimeric antigen receptor targets a tumor-associated antigen. In another embodiment, said tumor-associated antigen is CD19. In a further embodiment, said introducing step comprises transduction.

In another aspect, this invention provides a method for making a chimeric antigen receptor T cell having a reduced level of granulocyte-macrophage colony-stimulating factor (GM-CSF) polypeptides, said method comprising: introducing a complex into an ex vivo T cell, wherein said complex comprises: a) a guide RNA, wherein said guide RNA is complementary to a GM-CSF messenger RNA; and b) a Cas nuclease; and introducing a nucleic acid encoding said chimeric antigen receptor into said ex vivo T cell. In an embodiment of the herein provided method, said guide RNA comprises a nucleic acid sequence set forth in SEQ ID NO: 1. In another embodiment, said Cas nuclease is Cas9 nuclease. In a particular embodiment, said nucleic acid encoding said chimeric antigen receptor comprises a nucleic acid sequence set forth in SEQ ID NO: 2. In another embodiment, said complex is a ribonucleoprotein. In a further embodiment, said chimeric antigen receptor targets a tumor-associated antigen. In a particular embodiment, said tumor-associated antigen is CD19. In another embodiment of the herein provided method, said introducing steps comprise electroporation.

In another aspect, this invention provides a method for treating a mammal having cancer, wherein said method comprises administering chimeric antigen receptor T cells having a reduced level of granulocyte-macrophage colony-stimulating factor (GM-CSF) polypeptides to said mammal. In a particular embodiment, said mammal is a human. In another embodiment, said cancer is a lymphoma. In a further embodiment, said lymphoma is a diffuse large B cell lymphoma. In another embodiment, said cancer is a leukemia. In another embodiment, said leukemia is an acute lymphoblastic leukemia. In an embodiment, said chimeric antigen receptor targets a tumor-associated antigen. In a particular embodiment, said tumor-associated antigen is CD19.

In an aspect, this invention provides a method for making a chimeric antigen receptor T cell having a reduced level of cytokine polypeptides, said method comprising: introducing a nucleic acid construct into an ex vivo T cell, wherein said nucleic acid construct comprises: a) a nucleic acid encoding a guide RNA, wherein said guide RNA is complementary to a cytokine messenger RNA; b) a nucleic acid encoding a Cas nuclease, and c) a nucleic acid encoding said chimeric antigen receptor. In certain embodiments of said herein provided method, said cytokine polypeptides comprise granulocyte-macrophage colony-stimulating factor (GM-CSF) polypeptides and/or interleukin 6 (IL-6) polypeptides. In a particular embodiment, said cytokine polypeptides are GM-CSF polypeptides, and wherein said guide RNA comprises a nucleic acid sequence set forth in SEQ ID NO: 1. In an embodiment, said Cas nuclease is Cas9 nuclease. In another embodiment, said nucleic acid encoding said chimeric antigen receptor comprises a nucleic acid sequence set forth in SEQ ID NO: 2. In a further embodiment, said nucleic acid construct is a viral vector. In a specific embodiment, said viral vector is a lentiviral vector. In another embodiment, said chimeric antigen receptor targets a tumor-associated antigen. In various embodiments, said tumor-associated antigen is CD19. In another embodiment, said introducing step comprises transduction.

In another aspect, this invention provides a method for making a chimeric antigen receptor T cell having a reduced level of cytokine polypeptides, said method comprising: introducing a complex into an ex vivo T cell, wherein said complex comprises: a) a guide RNA, wherein said guide RNA is complementary to a cytokine messenger RNA; and b) a Cas nuclease; and introducing a nucleic acid encoding said chimeric antigen receptor into said ex vivo T cell. In an embodiment of said herein provided method, said cytokine polypeptides comprise granulocyte-macrophage colony-stimulating factor (GM-CSF) polypeptides and/or interleukin 6 (IL-6) polypeptides. In a particular embodiment, said cytokine polypeptides are GM-CSF polypeptides, and wherein said guide RNA comprises a nucleic acid sequence set forth in SEQ ID NO: 1. In another embodiment, said Cas nuclease is Cas9 nuclease. In another embodiment, said nucleic acid encoding said chimeric antigen receptor comprises a nucleic acid sequence set forth in SEQ ID NO: 2. In a further embodiment, said complex is a ribonucleoprotein. In a still further embodiment, said chimeric antigen receptor targets a tumor-associated antigen. In a specific embodiment, said tumor-associated antigen is CD19. In another embodiment, said introducing steps comprises electroporation.

In still another aspect, this invention provides a method for treating a mammal having cancer, wherein said method comprises administering chimeric antigen receptor T cells having a reduced level of cytokine polypeptides to said mammal. In an embodiment of said provided method, said cytokine polypeptides comprise granulocyte-macrophage colony-stimulating factor (GM-CSF) polypeptides and/or interleukin 6 (IL-6) polypeptides. In another embodiment, said cytokine polypeptides are GM-CSF polypeptides, and wherein said guide RNA comprises a nucleic acid sequence set forth in SEQ ID NO: 1. In a further embodiment, said mammal is a human. In another embodiment, said cancer is a lymphoma. In still another embodiment, said lymphoma is a diffuse large B cell lymphoma. In another embodiment, said cancer is a leukemia. In a further embodiment, said leukemia is an acute lymphoblastic leukemia. In an embodiment, said chimeric antigen receptor targets a tumor-associated antigen. In a particular embodiment, said tumor-associated antigen is CD19.

In one aspect, this invention provides a method for improving T cell effector functions of a chimeric antigen receptor T cell, said method comprising: introducing a nucleic acid construct into an ex vivo T cell, wherein said nucleic acid construct comprises: a) a nucleic acid encoding a guide RNA, wherein said guide RNA is complementary to a GM-CSF messenger RNA; b) a nucleic acid encoding a Cas nuclease, and c) a nucleic acid encoding said chimeric antigen receptor.

In another aspect, this invention provides a method for improving T cell effector functions of a chimeric antigen receptor T cell, said method comprising: introducing a complex into an ex vivo T cell, wherein said complex comprises: a) a guide RNA, wherein said guide RNA is complementary to a GM-CSF messenger RNA; and b) a Cas nuclease; and introducing a nucleic acid encoding said chimeric antigen receptor into said ex vivo T cell.

The term "reduced level" as used herein with respect to an expression level of a cytokine (e.g., GM-CSF) refers to any level that is lower than a reference expression level of that cytokine (e.g., GM-CSF). The term "reference level" as used herein with respect to a cytokine (e.g., GM-CSF) refers to the level of that cytokine (e.g., GM-CSF) typically observed in a sample (e.g., a control sample) from one or more mammals (e.g., humans) not engineered to have a reduced expression level of that cytokine (e.g., GM-CSF polypeptides) as described herein. Control samples can include, without limitation, T cells that are wild-type T cells (e.g., T cells that are not GM-SCF KO T cells). In some cases, a reduced expression level of a cytokine polypeptide (e.g., a GM-CSF polypeptide) can be an undetectable level of that cytokine (e.g., GM-CSF). In some cases, a reduced expression level of GM-CSF polypeptides can be an eliminated level of GM-CSF.

In some cases, a T cell having (e.g., engineered to have) a reduced expression level of one or more cytokine polypeptides such as a GM-CSF KO T cell can maintain normal T cell functions such as T cell degranulation and release of cytokines (e.g., as compared to a CART that is not engineered to have a reduced expression level of that cytokine (e.g., GM-CSF polypeptides) as described herein).

In some cases, a T cell having (e.g., engineered to have) a reduced level of GM-CSF polypeptides (e.g., a GM-CSF KO T cell) can have enhanced CART function such as antitumor activity, proliferation, cell killing, cytokine production, exhaustion susceptibility, antigen specific effector functions, persistence, and differentiation (e.g., as compared to a CART that is not engineered to have a reduced level of GM-CSF polypeptides as described herein).

In some cases, a T cell having (e.g., engineered to have) a reduced level of GM-CSF polypeptides (e.g., a GM-CSF KO T cell) can have enhanced T cell expansion (e.g., as compared to a CART that is not engineered to have a reduced level of GM-CSF polypeptides as described herein).

A T cell having (e.g., engineered to have) a reduced expression level of one or more cytokines (e.g., a GM-CSF polypeptide) such as a GM-CSF KO T cell can be any appropriate T cell. A T cell can be a naive T cell. Examples of T cells that can be designed to have a reduced expression level of one or more cytokines as described herein include, without limitation, cytotoxic T cells (e.g., CD4+ CTLs and/or CD8+ CTLs). For example, a T cell that can be engineered to have a reduced level of GM-CSF polypeptides as described herein can be a CART. In some cases, one or more T cells can be obtained from a mammal (e.g., a mammal having cancer). For example, T cells can be obtained from a mammal to be treated with the materials and method described herein.

A T cell having (e.g., engineered to have) a reduced expression level of one or more cytokine polypeptides (e.g., a GM-CSF polypeptide) such as a GM-CSF KO T cell can be generated using any appropriate method. In some cases, a T cell (e.g., CART) can be engineered to KO a nucleic acid encoding a GM-CSF polypeptide to reduce GM-CSF polypeptide expression in that T cell.

In some cases, when a T cell (e.g., CART) is engineered to KO a nucleic acid encoding a cytokine (e.g., a GM-CSF polypeptide) to reduce expression of that cytokine polypeptide in that T cell, any appropriate method can be used to KO a nucleic acid encoding that cytokine. Examples of techniques that can be used to knock out a nucleic acid sequence encoding a cytokine polypeptide (e.g., a GM-CSF polypeptide) include, without limitation, gene editing, homologous recombination, non-homologous end joining, and microhomology end joining. For example, gene editing (e.g., with engineered nucleases) can be used to KO a nucleic acid encoding a GM-CSF polypeptide. Nucleases useful for genome editing include, without limitation, CRISPR-associated (Cas) nucleases, zinc finger nucleases (ZFNs), transcription activator-like effector (TALE) nucleases, and homing endonucleases (HE; also referred to as meganucleases).

In some cases, a clustered regularly interspaced short palindromic repeat (CRISPR)/Cas system can be used (e.g., can be introduced into one or more T cells) to KO a nucleic acid encoding cytokine polypeptide (e.g., a GM-CSF polypeptide) (see, e.g., FIG. 1 and Example 1). A CRISPR/Cas system used to KO a nucleic acid encoding a cytokine polypeptide (e.g., a GM-CSF polypeptide) can include any appropriate guide RNA (gRNA). In some cases, a gRNA can be complementary to a nucleic acid encoding a GM-CSF polypeptide (e.g., a GM-CSF mRNA). Examples of gRNAs that are specific to a nucleic acid encoding a GM-CSF polypeptide include, without limitation, GACCTGCCTA-CAGACCCGCC (SEQ ID NO: 1), GCAGTGCTGCTTGTAGTGGC, TCAGGA- GACGCCGGGCCTCC (SEQ ID NO: 3), CAGCAGCAGTGTCTCTACTC (SEQ ID NO: 4), CTCAGAAATGTTTGACCTCC (SEQ ID NO: 5), and GGCCGGTCTCACTCCTGGAC (SEQ ID NO: 6). In some cases, a gRNA component of a CRISPR/Cas system designed to KO a nucleic acid encoding a GM-CSF polypeptide can include the nucleic acid sequence set forth in SEQ ID NO: 1.

A CRISPR/Cas system used to KO a nucleic acid encoding a cytokine polypeptide (e.g., a GM-CSF polypeptide) can include any appropriate Cas nuclease. Examples of Cas nucleases include, without limitation, Cas1, Cas2, Cas3, Cas9, Cas10, and Cpf1. In some cases, a Cas component of a CRISPR/Cas system designed to KO a nucleic acid encoding a cytokine polypeptide (e.g., a GM-CSF polypeptide) can be a Cas9 nuclease. For example, the Cas9 nuclease of a CRISPR/Cas9 system described herein can be a lentiCRISPRv2 (see, e.g., Shalem et al., 2014 Science 343:84-87; and Sanjana et al., 2014 Nature methods 11: 783-784, each of which is incorporated herein by reference in its entirety).

Components of a CRISPR/Cas system (e.g., a gRNA and a Cas nuclease) used to KO a nucleic acid encoding a cytokine polypeptide (e.g., a GM-CSF polypeptide) can be introduced into one or more T cells (e.g., CARTs) in any appropriate format. In some cases, a component of a CRISPR/Cas system can be introduced into one or more T cells as a nucleic acid encoding a gRNA and/or a nucleic acid encoding a Cas nuclease. For example, a nucleic acid encoding at least one gRNA (e.g., a gRNA sequence specific to a nucleic acid encoding a GM-CSF polypeptide) and a nucleic acid at least one Cas nuclease (e.g., a Cas9 nuclease) can be introduced into one or more T cells. In some cases, a component of a CRISPR/Cas system can be introduced into one or more T cells as a gRNA and/or as a Cas nuclease. For example, at least one gRNA (e.g., a gRNA sequence specific to a nucleic acid encoding a GM-CSF polypeptide) and at least one Cas nuclease (e.g., a Cas9 nuclease) can be introduced into one or more T cells.

In some cases, when components of a CRISPR/Cas system (e.g., a gRNA and a Cas nuclease) are introduced into one or more T cells as nucleic acid encoding the components (e.g., nucleic acid encoding a gRNA and nucleic acid encoding a Cas nuclease), the nucleic acid can be any appropriate form. For example, a nucleic acid can be a construct (e.g., an expression construct). A nucleic acid encoding at least one gRNA and a nucleic acid encoding at least one Cas nuclease can be on separate nucleic acid constructs or on the same nucleic acid construct. In some cases, a nucleic acid encoding at least one gRNA and a nucleic acid encoding at least one Cas nuclease can be on a single nucleic acid construct. A nucleic acid construct can be any appropriate type of nucleic acid construct. Examples of nucleic acid constructs that can be used to express at least one gRNA and/or at least one Cas nuclease include, without limitation, expression plasmids and viral vectors (e.g., lentiviral vectors). In cases where a nucleic acid encoding at least one gRNA and a nucleic acid encoding at least one Cas nuclease are on separate nucleic acid constructs, the nucleic acid constructs can be the same type of construct or different types of constructs. In some cases, a nucleic acid encoding at least one gRNA sequence specific to a nucleic acid encoding a cytokine polypeptide (e.g., a GM-CSF polypeptide) and a nucleic acid encoding at least one Cas nuclease can be on a single lentiviral vector. For example, a lentiviral vector encoding at least one gRNA sequence specific to a nucleic acid encoding a cytokine polypeptide (e.g., GM-CSF polypeptide), encoding at least one gRNA including the sequence set forth in SEQ ID NO: 1, and encoding at least one Cas9 nuclease can be used in ex vivo engineering of T cells to have a reduced expression level of that cytokine (e.g., a GM-CSF polypeptide).

In some cases, components of a CRISPR/Cas system (e.g., a gRNA and a Cas nuclease) can be introduced directly into one or more T cells (e.g., as a gRNA and/or as Cas nuclease). A gRNA and a Cas nuclease can be introduced into the one or more T cells separately or together. In cases where a gRNA and a Cas nuclease are introduced into the one or more T cells together, the gRNA and the Cas nuclease can be in a complex. When a gRNA and a Cas nuclease are in a complex, the gRNA and the Cas nuclease can be covalently or non-covalently attached. In some cases, a complex including a gRNA and a Cas nuclease also can include one or more additional components. Examples of complexes that can include components of a CRISPR/Cas system (e.g., a gRNA and a Cas nuclease) include, without limitation, ribonucleoproteins (RNPs) and effector complexes (e.g., containing a CRISPR RNAs (crRNAs) a Cas nuclease). For example, at least one gRNA and at least one Cas nuclease can be included in a RNP. In some cases, a RNP can include gRNAs and Cas nucleases at a ratio of about 1:1 to about 10:1 (e.g., about 1:1 to about 10:1, about 2:1 to about 10:1, about 3:1 to about 10:1, about 5:1 to about 10:1, about 8:1 to about 10:1, about 1:1 to about 9:1, about 1:1 to about 7:1, about 1:1 to about 5:1, about 1:1 to about 4:1, about 1:1 to about 3:1, about 1:1 to about 2:1, about 2:1 to about 8:1, about 3:1 to about 6:1, about 4:1 to about 5:1, or about 5:1 to about 7:1). For example, a RNP can include gRNAs and Cas nucleases at about a 1:1 ratio. For example, a RNP can include gRNAs and Cas nucleases at about a 2:1 ratio. In some cases, a RNP including at least one gRNA sequence specific to a nucleic acid encoding a GM-CSF polypeptide (e.g., encoding at least one gRNA including the sequence set forth in SEQ ID NO: 1) and at least one Cas9 nuclease can be used in ex vivo engineering of T cells to have a reduced level of GM-CSF polypeptides.

Components of a CRISPR/Cas system (e.g., a gRNA and a Cas nuclease) used to KO a nucleic acid encoding a cytokine polypeptide (e.g., a GM-CSF polypeptide) can be introduced into one or more T cells (e.g., CARTs) using any appropriate method. A method of introducing components of a CRISPR/Cas system into a T cell can be a physical method. A method of introducing components of a CRISPR/Cas system into a T cell can be a chemical method. A method of introducing components of a CRISPR/Cas system into a T cell can be a particle-based method. Examples of methods that can be used to introduce components of a CRISPR/Cas system into one or more T cells include, without limitation, electroporation, transfection (e.g., lipofection), transduction (e.g., viral vector mediated transduction), microinjection, and nucleofection. In some cases, when components of a CRISPR/Cas system are introduced into one or more T cells as nucleic acid encoding the components, the nucleic acid encoding the components can be transduced into the one or more T cells. For example, a lentiviral vector encoding at least one gRNA sequence specific to a nucleic acid encoding a GM-CSF polypeptide (e.g., encoding at least one gRNA including the sequence set forth in SEQ ID NO: 1) and at least one Cas9 nuclease can be transduced into T cells (e.g., ex vivo T cells). In some cases, when components of a CRISPR/Cas system are introduced directly into one or more T cells, the components can be electroporated into the one or more T cells. For example, a RNP including at least one gRNA sequence specific to a nucleic acid encoding a GM-CSF polypeptide (e.g., encoding at least one gRNA including the sequence set forth in SEQ ID NO: 1) and at least one Cas9 nuclease can be electroporated into T cells (e.g., ex vivo T cells). In some cases, components of a CRISPR/Cas system can be introduced ex vivo into one or more T cells. For example, ex vivo engineering of T cells have a reduced level of GM-CSF polypeptides can include transducing isolated T cells with a lentiviral vector encoding components of a CRISPR/Cas system. For example, ex vivo engineering of T cells having reduced levels of GM-CSF polypeptides can include electroporating isolated T cells with a complex including components of a CRISPR/Cas system. In cases where T cells are engineered ex vivo to have a reduced level of GM-CSF polypeptides, the T cells can be obtained from any appropriate source (e.g., a mammal such as the mammal to be treated or a donor mammal, or a cell line).

In some cases, a T cell (e.g., a CART) can be treated with one or more inhibitors of GM-CSF polypeptide expression or GM-CSF polypeptide activity to reduce GM-CSF polypeptide expression in that T cell (e.g., as compared to a T cell that was not treated with one or more inhibitors of GM-CSF polypeptide expression or GM-CSF polypeptide activity). An inhibitor of GM-CSF polypeptide expression or GM-CSF polypeptide activity can be any appropriate inhibitor. Example of inhibitors of GM-CSF polypeptide expression or GM-CSF polypeptide activity include, without limitation, nucleic acid molecules designed to induce RNA interference (e.g., a siRNA molecule or a shRNA molecule), antisense molecules, miRNAs, receptor blockade, and antibodies (e.g., antagonistic antibodies and neutralizing antibodies).

A T cell having (e.g., engineered to have) a reduced expression level of one or more cytokines (e.g., a GM-CSF KO T cell) can express (e.g., can be engineered to express) any appropriate antigen receptor. In some cases, an antigen receptor can be a heterologous antigen receptor. In some cases, an antigen receptor can be a CAR. In some cases, an antigen receptor can be a tumor antigen (e.g., tumor-specific antigen) receptor. For example, a T cell can be engineered to express a tumor-specific antigen receptor that targets a tumor-specific antigen (e.g., a cell surface tumor-specific antigen) expressed by a cancer cell in a mammal having cancer. Examples of antigens that can be recognized by an antigen receptor expressed in a T cell having reduced expression of a cytokine polypeptide (e.g., a GM-CSF polypeptide) as described herein include, without limitation, cluster of differentiation 19 (CD19), mucin 1 (MUC-1), human epidermal growth factor receptor 2 (HER-2), estrogen receptor (ER), epidermal growth factor receptor (EGFR), alphafetoprotein (AFP), carcinoembryonic antigen (CEA), CA-125, epithelial tumor antigen (ETA), melanoma-associated antigen (MAGE), CD33, CD123, CLL-1, E-Cadherin, folate receptor alpha, folate receptor beta, IL13R, EGFRviii, CD22, CD20, kappa light chain, lambda light chain, desmopressin, CD44v, CD45, CD30, CD5, CD7, CD2, CD38, BCMA, CD138, FAP, CS-1, and C-met. For example, a T cell having a reduced level of GM-CSF polypeptides can be designed to express an antigen receptor targeting CD19. An exemplary nucleic acid sequence encoding a CAR targeting CD19 (CAR19) is shown in FIG. 5.

Any appropriate method can be used to express an antigen receptor on a T cell having (e.g., engineered to have) a reduced expression level of one or more cytokine polypeptides (e.g., a GM-CSF KO T cell). For example, a nucleic acid encoding an antigen receptor can be introduced into one or more T cells. In some cases, viral transduction can be used to introduce a nucleic acid encoding an antigen receptor into a non-dividing a cell. A nucleic acid encoding an antigen receptor can be introduced in a T cell using any appropriate method. In some cases, a nucleic acid encoding an antigen receptor can be introduced into a T cell by transduction (e.g., viral transduction using a retroviral vector such as a lentiviral vector) or transfection. In some cases, a nucleic acid encoding an antigen receptor can be introduced ex vivo into one or more T cells. For example, ex vivo engineering of T cells expressing an antigen receptor can include transducing isolated T cells with a lentiviral vector encoding an antigen receptor. In cases where T cells are engineered ex vivo to express an antigen receptor, the T cells can be obtained from any appropriate source (e.g., a mammal such as the mammal to be treated or a donor mammal, or a cell line).

In some cases, when a T cell having (e.g., engineered to have) a reduced expression level of one or more cytokine polypeptides (e.g., a GM-CSF KO T cell) also expresses (e.g., is engineered to express) an antigen receptor, that T cell can be engineered to have a reduced expression level of that cytokine and engineered to express an antigen receptor using any appropriate method. In some cases, a T cell can be engineered to have a reduced expression level of a cytokine polypeptide (e.g., a GM-CSF polypeptide) first and engineered to express an antigen receptor second, or vice versa. In some cases, a T cell can be simultaneously engineered to have a reduced expression level of one or more cytokine polypeptides (e.g., a GM-CSF polypeptide) and to express an antigen receptor. For example, one or more nucleic acids used to reduce expression of a cytokine polypeptide such as a GM-CSF polypeptide (e.g., a lentiviral vector encoding at least one gRNA sequence specific to a nucleic acid encoding that cytokine and at least one Cas9 nuclease or a nucleic acid encoding at least one oligonucleotide that is complementary to that cytokine's mRNA) and one or more nucleic acids encoding an antigen receptor (e.g., a CAR) can be simultaneously introduced into one or more T cells. One or more nucleic acids used to reduce expression of a cytokine polypeptide (e.g., a GM-CSF polypeptide) and one or more nucleic acids encoding an antigen receptor can be introduced into one or more T cells on separate nucleic acid constructs or on a single nucleic acid construct. In some cases, one or more nucleic acids used to reduce expression of a cytokine polypeptide (e.g., a GM-CSF polypeptide) and one or more nucleic acids encoding an antigen receptor can be introduced into one or more T cells on a single nucleic acid construct. In some cases, one or more nucleic acids used to reduce expression of a cytokine polypeptide (e.g., a GM-CSF polypeptide) and one or more nucleic acids encoding an antigen receptor can be introduced ex vivo into one or more T cells. In cases where T cells are engineered ex vivo to have a reduced expression levels of one or more cytokine polypeptides (e.g., a GM-CSF polypeptide) and to express an antigen receptor, the T cells can be obtained from any appropriate source (e.g., a mammal such as the mammal to be treated or a donor mammal, or a cell line).

In some cases, a T cell having (e.g., engineered to have) a reduced expression level of one or more cytokine polypeptides (e.g., a GM-CSF KO T cell) can be stimulated. A T cell can be stimulated at the same time as being engineered to have a reduced level of one or more cytokine polypeptides or independently of being engineered to have a reduced level of one or more cytokine polypeptides. For example, one or more T cells having a reduced level of GM-CSF polypeptides used in an adoptive cell therapy can be stimulated first, and can be engineered to have a reduced expression level of GM-CSF polypeptides second, or vice versa. In some cases, one or more T cells having a reduced expression level of a cytokine polypeptide (e.g., a GM-CSF polypeptide) used in an adoptive cell therapy can be stimulated first, and can be engineered to have a reduced level of that cytokine polypeptide second. A T cell can be stimulated using any appropriate method. For example, a T cell can be stimulated by contacting the T cell with one or more CD polypeptides. Examples of CD polypeptides that can be used to stimulate a T cell include, without limitation, CD3, CD28, inducible T cell co-stimulator (ICOS), CD137, CD2, OX40, and CD27. In some cases, a T cell can be stimulated with CD3 and CD28 prior to introducing components of a CRISPR/Cas system (e.g., a gRNA and/or a Cas nuclease) to the T cell to KO a nucleic acid encoding one or more cytokine polypeptides (e.g., a GM-CSF polypeptide).

This document also provides methods and materials involved in treating cancer. For example, one or more T cells having (e.g., engineered to have) a reduced expression level of a cytokine polypeptide (e.g., a GM-CSF KO T cells) can be administered (e.g., in an adoptive cell therapy such as a CART therapy) to a mammal (e.g., a human) having cancer to treat the mammal. In some cases, methods of treating a mammal having cancer as described herein can reduce the number of cancer cells (e.g., cancer cells expressing a tumor antigen) within a mammal. In some cases, methods of treating a mammal having cancer as described herein can reduce the size of one or more tumors (e.g., tumors expressing a tumor antigen) within a mammal.

In some cases, administering T cells having (e.g., engineered to have) a reduced expression level of a cytokine polypeptide (e.g., a GM-CSF KO T cell) to a mammal does not result in CRS. For example, administering T cells having a reduced level of GM-CSF polypeptides to a mammal does not result in release of cytokines associated with CRS (e.g., CRS critical cytokines). Examples of cytokines associated with CRS include, without limitation, IL-6, G-CSF, IFN-g, IL-1B, IL-10, MCP-1, MIG, MIP, MIP 1b, TNF-a, IL-2, and perforin.

In some cases, administering T cells having (e.g., engineered to have) a reduced expression level of a cytokine polypeptide (e.g., a GM-CSF KO T cell) to a mammal does not result in neurotoxicity. For example, administering T cells having a reduced level of GM-CSF polypeptides to a mammal does not result in differentiation and/or activation of white blood cells, the differentiation and/or activation of which, is associated with neurotoxicity. Examples of white blood cells, the differentiation and/or activation of which, is associated with neurotoxicity include, without limitation, monocytes, macrophages, T-cells, dendritic cells, microglia, astrocytes, and neutrophils.

Any appropriate mammal (e.g., a human) having a cancer can be treated as described herein. Examples of mammals that can be treated as described herein include, without limitation, humans, primates (such as monkeys), dogs, cats, horses, cows, pigs, sheep, mice, and rats. For example, a human having a cancer can be treated with one or more T cells having (e.g., engineered to have) a reduced expression level of a cytokine polypeptide (e.g., a GM-CSF polypeptide) in, for example, an adoptive T cell therapy such as a CART cell therapy using the methods and materials described herein.

When treating a mammal (e.g., a human) having a cancer as described herein, the cancer can be any appropriate cancer. In some cases, a cancer treated as described herein can be a solid tumor. In some cases, a cancer treated as described herein can be a hematological cancer. In some cases, a cancer treated as described herein can be a primary cancer. In some cases, a cancer treated as described herein can be a metastatic cancer. In some cases, a cancer treated as described herein can be a refractory cancer. In some cases, a cancer treated as described herein can be a relapsed cancer. In some cases, a cancer treated as described herein can express a tumor-associated antigen (e.g., an antigenic substance produced by a cancer cell). Examples of cancers that can be treated as described herein include, without limitation, B cell cancers (e.g., diffuse large B cell lymphoma (DLBCL) and B cell leukemias), acute lymphoblastic leukemia (ALL), chronic lymphocytic leukemia (CLL), follicular lymphoma, mantle cell lymphoma, non-Hodgkin lymphoma, Hodgkin lymphoma, acute myeloid leukemia (AML), multiple myeloma, head and neck cancers, sarcomas, breast cancer, gastrointestinal malignancies, bladder cancers, urothelial cancers, kidney cancers, lung cancers, prostate cancers, ovarian cancers, cervical cancers, genital cancers (e.g., male genital cancers and female genital cancers), and bone cancers. For example, one or more T cells having (e.g., engineered to have) a reduced level of GM-CSF polypeptides (e.g., a GM-CSF KO T cells) can be used to treat a mammal having DLBCL. For example, one or more T cells having (e.g., engineered to have) a reduced level of GM-CSF polypeptides (e.g., a GM-CSF KO T cells) can be used to treat a mammal having ALL.

Any appropriate method can be used to identify a mammal having cancer. For example, imaging techniques and biopsy techniques can be used to identify mammals (e.g., humans) having cancer.

Once identified as having a cancer (e.g., DLBCL or ALL), a mammal can be administered one or more T cells having (e.g., engineered to have) a reduced expression level of a cytokine polypeptide (e.g., a GM-CSF KO T cells) described herein.

For example, one or more T cells having (e.g., engineered to have) a reduced expression level of a cytokine polypeptide (e.g., a GM-CSF KO T cells) can be used in an adoptive T cell therapy (e.g., a CART cell therapy) to treat a mammal having a cancer. For example, one or more T cells having a reduced level of GM-CSF polypeptides can be used in an adoptive T cell therapy (e.g., a CART cell therapy) targeting any appropriate antigen within a mammal (e.g., a mammal having cancer). In some cases, an antigen can be a tumor-associated antigen (e.g., an antigenic substance produced by a cancer cell). Examples of tumor-associated antigens that can be targeted by an adoptive T cell therapy provided herein include, without limitation, CD19 (associated with DLBCL, ALL, and CLL), AFP (associated with germ cell tumors and/or hepatocellular carcinoma), CEA (associated with bowel cancer, lung cancer, and/or breast cancer), CA-125 (associated with ovarian cancer), MUC-1 (associated with breast cancer), ETA (associated with breast cancer), MAGE (associated with malignant melanoma), CD33 (associated with AML), CD123 (associated with AML), CLL-1 (associated with AML), E-Cadherin (associated with epithelial tumors), folate receptor alpha (associated with ovarian cancers), folate receptor feta (associated with ovarian cancers and AML), IL13R (associated with brain cancers), EGFRviii (associated with brain cancers), CD22 (associated with B cell cancers), CD20 (associated with B cell cancers), kappa light chain (associated with B cell cancers), lambda light chain (associated with B cell cancers), CD44v (associated with AML), CD45 (associated with hematological cancers), CD30 (associated with Hodgkin lymphomas and T cell lymphomas), CD5 (associated with T cell lymphomas), CD7 (associated with T cell lymphomas), CD2 (associated with T cell lymphomas), CD38 (associated with multiple myelomas and AML), BCMA (associated with multiple myelomas), CD138 (associated with multiple myelomas and AML), FAP (associated with solid tumors), CS-1 (associated with multiple myeloma), and c-Met (associated with breast cancer). For example, one or more T cells having a reduced level of GM-CSF polypeptides can be used in CART cell therapy targeting CD19 (e.g., CART19 cell therapy) to treat cancer as described herein.

In some cases, one or more T cells having (e.g., engineered to have) a reduced expression level of a cytokine polypeptide (e.g., a GM-CSF KO T cells) can be used in an adoptive T cell therapy (e.g., a CART cell therapy) to treat a mammal having a disease or disorder other than cancer. For example, one or more T cells having a reduced level of GM-CSF polypeptides can be used in an adoptive T cell therapy (e.g., a CART cell therapy) targeting any appropriate disease-associated antigen (e.g., an antigenic substance produced by cell affected by a particular disease) within a mammal. Examples of disease-associated antigens that can be targeted by an adoptive T cell therapy provided herein include, without limitation desmopressin (associated with auto immune skin diseases). In another embodiment, the disease-associated antigens that can be targeted by an adoptive T cell therapy provided herein include, but are not limited to the DSG3 antigen, the B cell receptor (BCR) that binds to DSG3 in Pemphigus Vulgaris or the antigen MuSK. In a further embodiment, the disease-associated antigens that can be targeted by an adoptive T cell therapy provided herein include, but are not limited to the BCR for MuSK in MuSK Myasthenia Gravis.

In some cases, one or more T cells having (e.g., engineered to have) a reduced expression level of a cytokine polypeptide (e.g., a GM-CSF KO T cells) used in an adoptive T cell therapy (e.g., a CART cell therapy) can be administered to a mammal having a cancer as a combination therapy with one or more additional agents used to treat a cancer. For example, one or more T cells having a reduced level of GM-CSF polypeptides used in an adoptive cell therapy can be administered to a mammal in combination with one or more anti-cancer treatments (e.g., surgery, radiation therapy, chemotherapy (e.g., alkylating agents such as busulfan), targeted therapies (e.g., GM-CSF inhibiting agents such as lenzilumab), hormonal therapy, angiogenesis inhibitors, immunosuppressants (e.g., interleukin-6 inhibiting agents such as tocilizumab)) and/or one or more CRS treatments (e.g., ruxolitinib and ibrutinib). In cases where one or more T cells having a reduced level of GM-CSF polypeptides used in an adoptive cell therapy are used with additional agents treat a cancer, the one or more additional agents can be administered at the same time or independently. In some cases, one or more T cells having a reduced level of GM-CSF polypeptides used in an adoptive cell therapy can be administered first, and the one or more additional agents administered second, or vice versa.

Lenzilumab (Humanigen, Burlingame, CA), an hGM-CSF neutralizing antibody in accordance with embodiments described herein and as described in U.S. Pat. Nos. 8,168,183 and 9,017,674, each of which is incorporated herein by reference in its entirety, is a novel, first in class Humaneered® monoclonal antibody that neutralizes human GM-CSF.

The invention will be further described in the following examples, which do not limit the scope of the invention described in the claims.

EXAMPLES

Example 1

Generation of Cytokine to Deficient CART Cells to Increase Therapeutic Index of CART Cell Therapy This example describes the development of GM-CSF knocked out (GM-CSF KO) CART19 cells, and shows that the resulting GM-CSF KO CART19 cells function normally and have enhanced expansion.

Experimental Design

CAR19 in B cell leukemia xenografts were used. These plasmids were used for packaging and lentivirus production as described herein. As a mouse model, two models were employed:

1. Xenograft models: NSG mice were subcutaneously engrafted with the CD19 positive, luciferase positive cell line NALM6. Engraftment was confirmed by bioluminescence imaging. Mice were treated with human PBMCs intravenously and intra-tumor injection of lentivirus particles. Generation of CART cells is measured by flow cytometry. Trafficking of CARTs to tumor sites is assessed and anti-tumor response is measured by bioluminescence imaging as a measure of disease burden.

2. Humanized Immune System (HIS) mice from the Jackson Laboratory: These mice were injected with fetal CD34+ cells as neonates and therefore develop human hematopoiesis. We will engraft these mice with the CD19+ cell line NALM6, as previously used. Similarly, we will generate CART19 in vivo through the intratumoral injection of lentivirus particles. Then will measure the activity of CART19 cells in eradication of NALM6 and compare that to ex vivo generated lenti-virally transduced CART19 cells (currently used in the clinic).

Materials and Methods

Generation of CAR Plasmid:

The anti-CD19 clone FMC63 was do novo synthesized into a CAR backbone using 41BB and CD3 zeta and then cloned into a third generation lentivirus backbone.

To generate the control CART19 cells, normal donor T cells were negatively selected using pan T cell kit and expanded ex vivo using anti-CD3/CD28 magnetic beads (Dynabeads™, Invitrogen), added on the first day of culture). T cells were transduced with lentiviral supernatant one day following stimulation at a multiplicity of infection (MOI) of 3. The anti-CD3/CD28 magnetic beads (Dynabeads™) were removed on day 6 and T cells were grown in T cell media (X-vivo 15 media, human serum 5%, penicillin, streptomycin and glutamine) for up to 15 days and then cryopreserved for future experiments. Prior to all experiments, T cells were thawed and rested overnight at 37° C.

Generation of GM-CSF Knock Out CART Cells:

GM-CSF knockout CART cells were generated with a CRISR-Cas9 system, using two methodologies:

1. gRNA was generated and cloned into a lentivirus vector that encodes Cas9 and the gRNA. During T cell expansion, T cells were transduced with this lentivirus on Day 1, on the same day and simultaneously with CAR19 lentivirus particles. Cells were expanded for a period of 8 days and then T cell were harvested, DNA isolated and sequenced to assess the efficiency of knockout. These cells were cryopreserved and used for future in vitro or in vivo experiments. A nucleic acid sequence encoding is shown in FIG. 5.

2. mRNA was generated from the gRNA and used it to knock out GM-CSF. To do so, gRNA was mixed with RNP at 1:1 ratio and then T cells were electroporated on Day 3 post stimulation with CD3/CD28 beads. Cells were expanded for a period of 8 days and then T cell were harvested, DNA isolated and sequenced to assess the efficiency of knockout. These cells were cryopreserved and used for future in vitro or in vivo experiments Cells The NALM6 cell line was obtained from the ATCC and maintained in R10 media (RPMI media, 10% fetal calf serum, penicillin, and streptomycin). NALM6-cells transduced with luciferase-GFP cells under the control of the EF1α promoter were used in some experiments as indicated. De-identified primary human ALL specimens were obtained from the Mayo Clinic Biobank. All samples were obtained after informed, written consent. For all functional studies, cells were thawed at least 12 hours before analysis and rested overnight at 37° C.

Flow Cytometry Analysis

Anti-human antibodies were purchased from BioLegend, eBioscience, or BD Biosciences. Cells were isolated from in vitro culture or from animals, washed once in PBS supplemented with 2% fetal calf serum, and stained at 4° C. after blockade of Fc receptors. For cell number quantitation, absolute counting beads (CountBright™, Invitrogen) were used according to the manufacturer's instructions (Invitrogen). In all analyses, the population of interest was gated based on forward vs. side scatter characteristics followed by singlet gating, and live cells were gated using aqua-fluorescent reactive dye LIVE/DEAD™ Fixable Aqua Stain (Invitrogen). Surface expression of anti-CD19 CAR was detected by staining with an Alexa Fluor 647-conjugated goat anti-mouse F(ab')2 antibody from Jackson Immunoresearch.

T Cell Function Assays:

T Cell Degranulation and Intracellular Cytokine Assays:

Briefly, T cells were incubated with target cells at a 1:5 ratio. After staining for CAR expression; CD107a, CD28, CD49d and monensin were added at the time of incubation. After 4 hours, cells were harvested and stained for CAR expression, CD3 and Live Dead staining (Invitrogen). Cells were fixed and permeabilized (FIX & PERM® Cell Fixation & Cell Permeabilization Kit, Life technologies) and intracellular cytokine staining was then performed.

Proliferation Assays:

T cells were washed and resuspended at $1 \times 10^7$/ml in 100 μl of PBS and labeled with 100 μl of CFSE 2.5 μM (Life Technologies) for 5 minutes at 37° C. The reaction was then quenched with cold R10, and the cells were washed three times. Targets were irradiated at a dose of 100 Gy. T cells were incubated at a 1:1 ratio with irradiated target cells for 120 hours. Cells were then harvested, stained for CD3, CAR and aqua-fluorescent reactive dye LIVE/DEAD™ Fixable Aqua Stain (Invitrogen), and absolute counting beads (CountBright™, Invitrogen) were added prior to flow cytometric analysis.

Cytotoxicity Assays:

NALM6-Luc cells or CFSE (Invitrogen) labelled primary ALL samples were used for cytotoxicity assay. In brief, targets were incubated at the indicated ratios with effector T cells for 4, 16, 24, 48, and/or 72 hours. Killing was calculated either by bioluminescence imaging on a Xenogen IVIS-200 Spectrum camera or by flow cytometry. For the latter, cells were harvested; absolute counting beads (CountBright™, Invitrogen) and 7-aminoactinomycin D (7-AAD)

(Invitrogen) were added prior to analysis. Residual live target cells were CFSE+ 7-AAD-.

Secreted Cytokine Measurement:

Effector and target cells were incubated at a 1:1 ratio in T cell media for 24 or 72 hours as indicated. Supernatant was harvested and analyzed by 30-plex Luminex array according to the manufacturer's protocol (Invitrogen).

Results

Figures 2A, 2B:
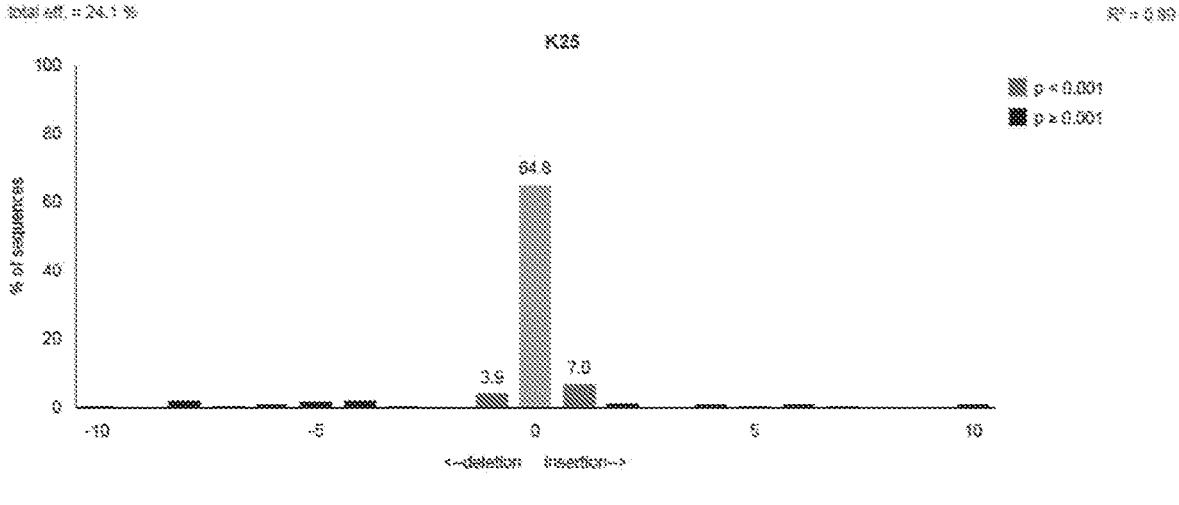
FIGS. 2A-2B show CAR transduction and GM-CSF knockout efficiency.

GM-CSF KO CART cells were generated with a CRISR-Cas9 system. During T cell expansion, T cells were transduced (Day 1) with lentivirus encoding gRNA and Cas9 and lentivirus encoding CARI 9. Cells were expanded for a period of 8 days. After 8 days, T cells were harvested, DNA was isolated, and the isolated DNA was sequenced to assess the efficiency of knockout. See, e.g., FIG. 1. T cells exhibited a knockout efficiency of 24.1% (FIG. 2A), and CAR transduction efficiency was 73% (FIG. 2B).

Figure 3:
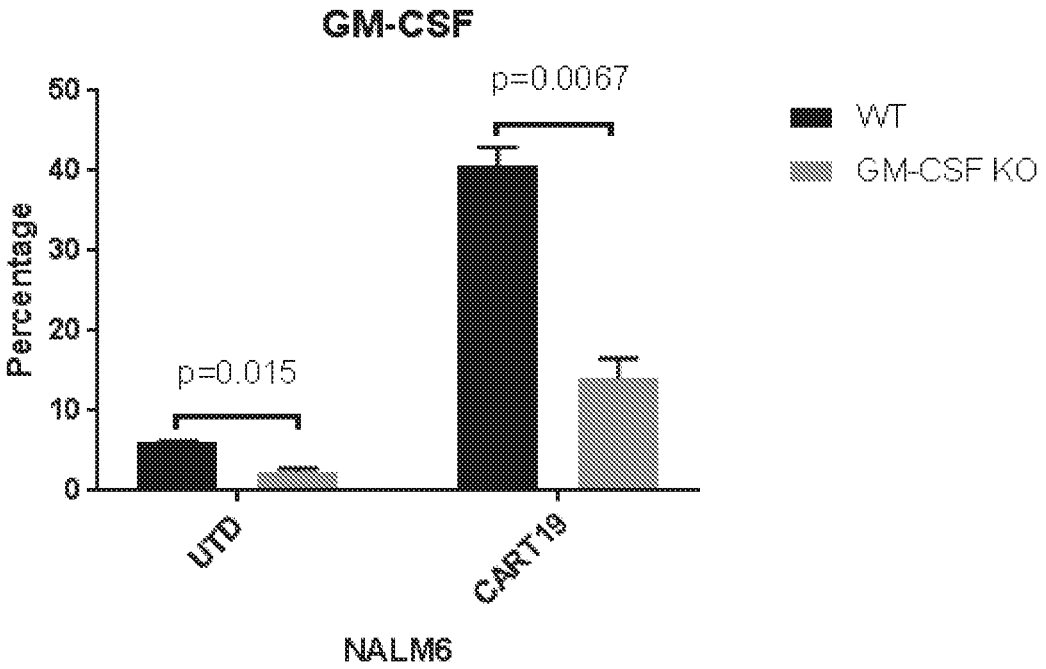
FIG. 3 shows that GM-CSF KO CART19 cells produce less GM-CSF compared to CART cells, and GM-CSF knockout control T cells produce less amount of GM-CSF compared to control untransduced T cells (UTD). CART19, GM-CSF KO CART19, UTD, or GM-CSF KO UTD were co-cultured with the CD19 positive cell line NALM6 at a ratio of 1:5. 4 hours later, the cells were harvested, permeabilized, and fixed; and intra-cellular staining for cytokines was performed.

To evaluate cell effector functions of GM-CSF KO CART cells, CART19, GM-CSF KO CART19, UTD, or GM-CSF KO UTD were co-cultured with the CD19 positive cell line NALM6 at a ratio of 1:5. After 4 hours, the cells were harvested, permeabilized, fixed, and stained for cytokines (FIG. 3).

Figure 4:
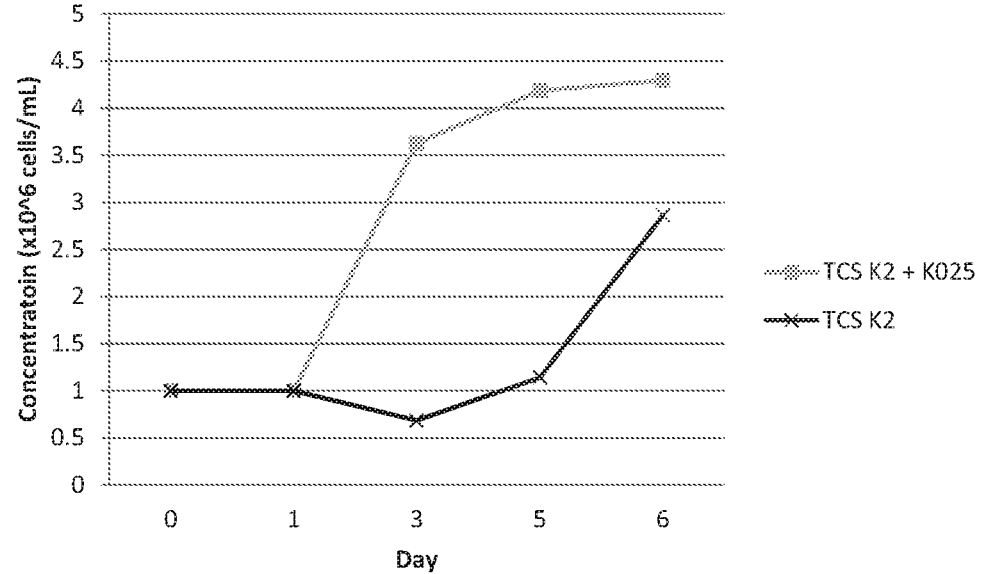
FIG. 4 shows that GM-CSF KO CART19 cells expand more robustly compared to CART19. After T cells were transduced with the virus, their expansion kinetics was followed. GM-CSF KO expand more robustly compared to CART19 alone.

To evaluate proliferation of GM-CSF KO CART cells, expansion kinetics were followed after T cells were transduced. GM-CSF KO CART cells expand more robustly than cells transduced with CART19 alone (FIG. 4).

These results demonstrate that GM-CSF knockout CARTs can enhance CART cell function and antitumor activity. These results also demonstrate that blockade of GMCSF in combination with CART19 does not impact CART cell effector functions.

Example 2

GM-CSF Depletion During CART Therapy Reduces Cytokine Release Syndrome and Neurotoxicity and May Enhance CART Cell Function This example investigates depleting granulocyte macrophage colony-stimulating factor (GM-CSF) and myeloid cells as a potential strategy to manage CART cell associated toxicities. It was found that the GM-CSF blockade with a neutralizing antibody does not inhibit CART function in vitro or in vivo. CART cell proliferation was enhanced in vitro, and CART cells resulted in a more efficient control of leukemia in patient derived xenografts after GM-CSF depletion. Furthermore, in a primary acute lymphoblastic leukemia xenograft model of CRS and NT, GM-CSF blockade resulted in a reduction of myeloid cell and T cell infiltration in the brain, and ameliorated the development of CRS and NT. Finally, GM-CSF knocked out CART cells were generated through CRISPR/cas9 disruption of GM-CSF during CART cell manufacturing. GM-CSF$^{k/o}$ CART cells continued to function normally and had resulted in enhanced anti-tumor activity in vivo. These demonstrate that GM-CSF neutralization can abrogate neurotoxicity and CRS, and also can enhance CART cell functions.

Materials and Methods

Cells Lines and Primary Cells

NALM6 and MOLM13 were purchased from ATCC, Manassas, VA, USA, transduced with a luciferase-ZsGreen lentivirus (addgene) and sorted to 100% purity. Cell lined were cultured in RIO (RPMI, 10% FCS v/v, 1% pen strep v/v). Primary cells were obtained from the Mayo Clinic biobank for patients with acute leukemia under an institutional review board approved protocol. The use of recombinant DNA in the laboratory was approved by the Institutional Biosafety Committee (IBC).

Primary T Cells and CART Cells

Peripheral blood mononuclear cells (PBMC) were isolated from de-identified donor blood apheresis cones using a FICOLL protocol (see, e.g., Dietz et al., 2006 Transfusion 46:2083-2089, which is incorporated herein by reference in its entirety). T cells were separated with negative selection magnetic beads (Stemcell technologies) and monocytes were positively selected using CD14+ magnetic beads (Stemcell technologies). Primary cells were cultured in X-Vivo 15 media with 5% human serum, penicillin, streptomycin and glutamax. CD19 directed CART cells were generated through the lentiviral transduction of normal donor T cells as described below. Second generation CARI 9 constructs were do nova synthesized (IDT) and cloned into a third generation lentivirus under the control of EF-1a promotor. The CD19 directed single chain variable fragment was derived from the clone FMC63. A second generation 41BB co-stimulated (FMC63-41BBz) CAR construct was synthesized and used for these experiments. Lentivirus particles were generated through the transient transfection of plasmid into 293T virus producing cells, in the presence of lipofectamine 3000, VSV-G and packaging plasmids. T cells isolated from normal donors were stimulated using CD3/CD28 stimulating beads (StemCell) at 1:3 ratio and then transduced with lentivirus particles 24 hours after stimulation at a multiplicity of infection of 3.0. Magnetic bead removal was performed on Day 6 and CART cells were harvested and cryopreserved on Day 8 for future experiments. CART cells were thawed and rested in T cell medium 12 hours prior to their use in experiments.

Figures 15A, 15B:
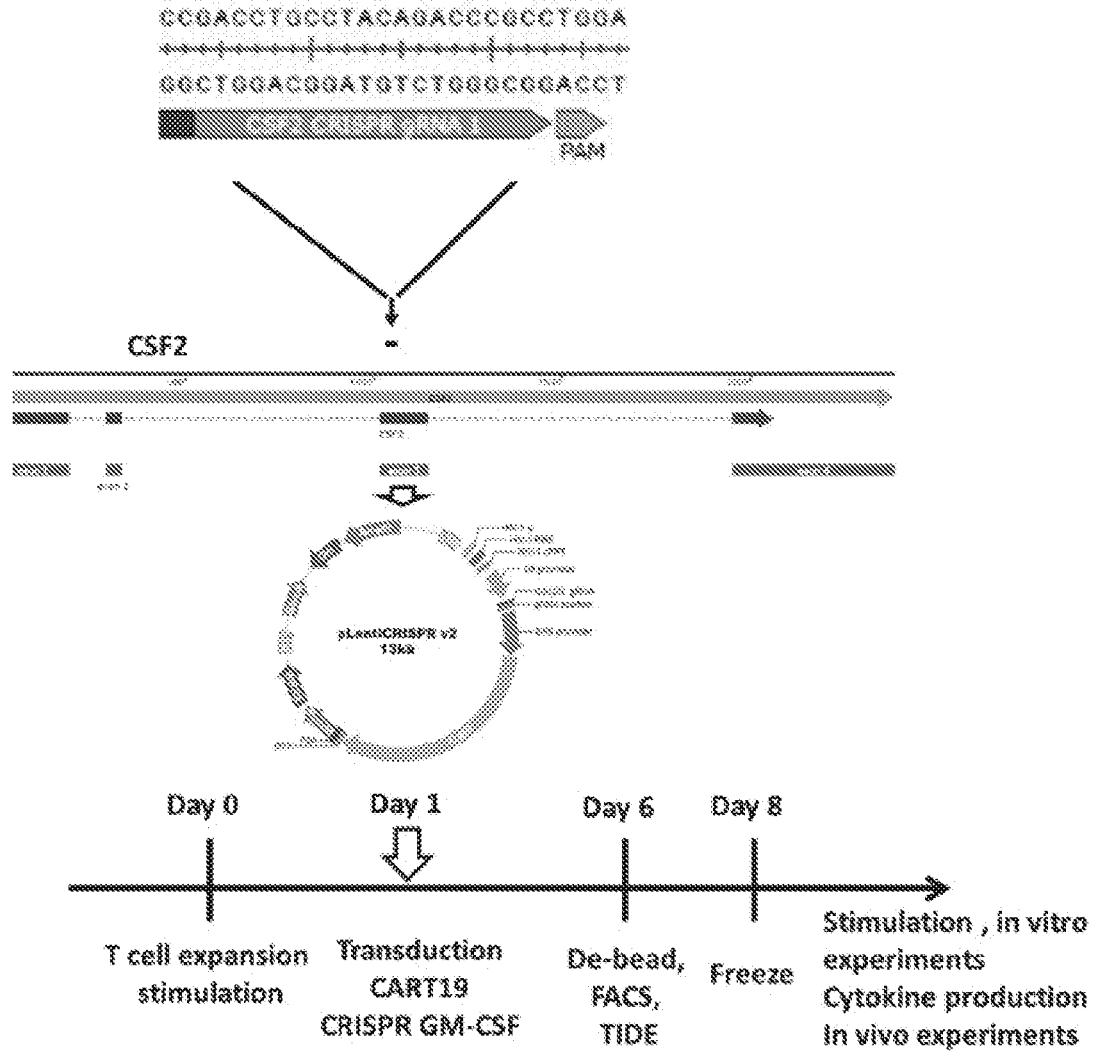
FIGS. 15A-15B shows an exemplary generation of GM-CSFk/o CART19 cells. The experimental schema depicts the schema SEQ ID NO: 11 (FIG. 15A), gRNA sequence SEQ ID NO: 1 (FIG. 15B), and primer sequences SEQ ID NOs: 12-13 (FIG. 15B) for generation of GM-CSFk/o CART19. To generate GM-CSFk/o CART19 cells, gRNA was clones into a Cas9 lentivirus vector under the control of a U6 promotor and used for lentivirus production. T cells derived from normal donors were stimulated with CD3/CD28 beads and dual transduced with CAR 19 virus and CRISPR/Cas9 virus 24 hours later. CD3/CD28 magnetic bead removal was performed on Day +6 and GM-CSFk/o CART19 cells or control CART19 cells were cryopreserved on Day 8.

Generation of GM-CSF$^{k/o}$ CART Cells:

A guide RNA (gRNA) targeting exon 3 of human GM-CSF was selected via screening gRNAs previously reported to have high efficiency for human GM-CSF.25 This gRNA was ordered in a CAS9 third generation lentivirus construct (lentiCRISPRv2), controlled under a U6 promotor (GenScript, Township, NJ, USA). Lentiviral particles encoding this construct were produced as described above. T cells were dual transduced with CAR19 and GM-CSFgRNA-lentiCRISPRv2 lentiviruses, 24 hours after stimulation with CD3/CD28 beads. CAR-T cell expansion was then continued as described above. To analyze efficiency of targeting GM-CSF, genomic DNA was extracted from the GM-CSFk/o CART19 cells using a genomic DNA extraction kit (PureLink™ Genomic DNA Mini Kit, Invitrogen, Carlsbad, CA, USA). The DNA of interest was PCR amplified using Choice Taq Blue Mastermix (Thomas Scientific, Minneapolis, MN, USA) and gel extracted using QIAquick Gel Extraction Kit (Qiagen, Germantown, MD, USA) to determine editing. PCR amplicons were sent for Eurofins sequencing (Louisville, KY, USA) and allele modification frequency was calculated using TIDE (Tracking of Indels by Decomposition) software available at tide.nki.nl. FIG. 15 describes the gRNA sequence, primer sequences, and the schema for generation of GM-CSFk/o CART 19 schema.

GM-CSF Neutralizing Antibodies and Isotype Controls

Lenzilumab (Humanigen, Brisbane, CA) is a humanized antibody that neutralizes human GM-CSF, as described in U.S. Pat. Nos. 8,168,183 and 9,017,674, each of which is incorporated herein by reference in its entirety. For in vitro experiments, lenzilumab or isotype control 10 ug/mL was used. For in vivo experiments, 10 mg/kg of lenzilumab or isotype control was injected, and the schedule, route and frequency are indicated in the individual experimental schema. In some experiments, anti-mouse GM-CSF neutralizing antibody (10 mg/kg) was also used, as indicated in the experimental schema.

T Cell Functional Experiments

Cytokine assays were performed 24 or 72 hours after a co-culture of CART cells with their targets at 1:1 ratio as indicated. Human GM-CSF singleplex (Millipore), 30-plex human multiplex (Millipore), or 30-plex mouse multiplex (Millipore) was performed on supernatant collected from these experiments, as indicated. This was analyzed using flow cytometry bead assay or Luminex, Intracellular cytokine analysis and T cell degranulation assays were performed following incubation of CART cells with targets at 1:5 ratio for 4 hours at 37° C., in the presence of monensin, hCD49d, and hCD28. After 4 hours, cells were harvested and intracellular staining was performed after surface staining, followed by fixation and permealization (FIX & PERM Cell Fixation & Cell Permeabilization Kit, Life Technologies). For proliferation assays, CFSE (Life Technologies) labeled effector cells (CART19), and irradiated target cells were co cultured at 1:1. In some experiments with CD14+ monocytes was added to the co-culture at 1:1:1 ratio as indicated. Cells were co-cultured for 3-5 days, as indicated in the specific experiment and then cells were harvested and surface staining with anti-hCD3 and live/dead aqua was performed. PMA/ionomycin was used as a positive non-specific stimulant of T cells, at different concentrations as indicated in the specific experiments. For killing assays, the CD19+Luciferase+ ALL cell line NALM6 or the CD19$^-$ Luciferase$^+$ control MOLM13 cells were incubated at the indicated ratios with effector T cells for 24 or 48 hours as listed in the specific experiment. Killing was calculated by bioluminescence imaging on a Xenogen IVIS-200 Spectrum camera (PerkinElmer, Hopkinton, MA, USA) as a measure of residual live cells. Samples were treated with 1 µl D-luciferin (30 ug/mL) per 100 µl sample volume, 10 minutes prior to imaging.

Multi-Parametric Flow Cytometry

Anti-human antibodies were purchased from Biolegend, eBioscience, or BD Biosciences. Cells were isolated from in vitro culture or from peripheral blood of animals (after ACK lysis), washed twice in phosphate-buffered saline supplemented with 2% fetal calf serum and stained at 4° C. For cell number quantitation, absolute counting beads (CountBright™ Invitrogen) were used according to the manufacturer's instructions (Invitrogen). In all analyses, the population of interest was gated based on forward vs side scatter characteristics, followed by singlet gating, and live cells were gated using aqua-fluorescent reactive dye (LIVE/DEAD™ Fixable Aqua Stain, Invitrogen). Surface expression of CAR was detected by staining with a goat anti-mouse F(ab')2 antibody. Flow cytometry was performed on a four-laser BD FACSCanto™ II cell analyzer (BD Biosciences). All analyses were performed using FlowJo X10.0.7r2.

Xenogeneic Mouse Models

Male and female 8-12-week old NOD-SCID-IL2ry−/− (NSG) mice were bred and cared for within the Department of Comparative Medicine at the Mayo Clinic under a breeding protocol approved by the Institutional Animal Care and Use Committee (IACUC). Mice were maintained in an animal barrier spaces that is approved by the institutional Biosafety Committee for BSL2+ level experiments.

NALM6 Cell Line Xenografts

The CD19+, luciferase+ ALL NALM6 cell line was used to establish ALL xenografts. These xenograft experiments were approved by a different IACUC protocol. Here, $1 \times 10^6$ cells were injected intravenously via a tail vein injection. After injection, mice underwent bioluminescent imaging using a Xenogen IVIS-200 Spectrum camera six days later, to confirm engraftment. Imaging was performed after the intraperitoneal injection of 10 µl/g D luciferin (15 mg/ml). Mice were then randomized based on their bioluminescent imaging to receive different treatments as outlined in the specific experiments. Typically, $1 \text{-} 2 \times 10^6$ CART cells or UTD cells are injected and exact doses are listed in the specific experimental details. Weekly imaging was performed to assess and follow disease burden. Tail vein bleeding was done 7-10 days after injection of CART cells to assess T cell expansion and as needed following that. Mouse peripheral blood was lysed using ACK lysing buffer (Thermofisher) and then used for flow cytometry studies. Bioluminescent images were acquired using a Xenogen IVIS-200 Spectrum camera (PerkinElmer, Hopkinton, MA, USA) and analyzed using Living Image version 4.4 (Caliper LifeSciences, PerkinElmer). For antibody treated mice, antibody therapy (10 mg/kg lenzilumab or isotype control) was commenced IP, for a total of 10 days.

Primary Patient Derived ALL Xenografts

To establish primary ALL xenografts, NSG mice first received 30 mg/kg busulfan IP. The following day, mice were injected with $2 \times 10^6$ primary blasts derived from the peripheral blood of patients with relapsed refractory ALL. Mice were monitored for engraftment for 4-6 weeks and when CD19+ cells were consistently observed in the blood (>1 cell/µl), they were randomized to receive different treatments of CART19 or UTD ($1 \times 10^6$ cells) with or without antibody therapy (10 mg/kg lenzilumab or isotype control IP for a total of 10 days, starting on the day they received CART cell therapy). Mice were periodically monitored for leukemic burden via tail vein bleeding.

Primary Patient Derived ALL Xenografts for CRS/NT

Similar to the experiments above, mice were IP injected with 30 mg/kg busulfan. The following day, they received $1 \text{-} 2 \times 10^6$ primary blasts derived from the peripheral blood of patients with relapsed refractory ALL. Mice were monitored for engraftment for 4-6 weeks and when CD19+ cell level was high (≥10 cells/µl), they received CART19 ($2 \text{-} 5 \times 10^6$ cells) and commenced antibody therapy for a total of 10 days, as indicated in the details of the specific experiment. Mice were weighed on daily basis as a measure of their well-being. Brian MRI of the mice was performed 5-6 days post CART injection and tail vein bleeding was performed 4-11 days post CART injection. Brain MRI images were analyzed using Azalyze.

MRI Acquisition

A Bruker Avance II 7 Tesla vertical bore small animal MRI system (Bruker Biospin) was used for image acquisition to evaluate central nervous system (CNS) vascular permeability. Inhalation anesthesia was induced and maintained via 3 to 4% isoflurane. Respiratory rate was monitored during the acquisition sessions using an MRI compatible vital sign monitoring system (Model 1030; SA Instruments, Stony Brook, NY). Mice were given an IP injection of gadolinium using weight-based dosing of 100 mg/kg, and after a standard delay of 15 min, a volume acquisition T1-weighted spin echo sequence was used (repetition time=150 ms, echo time=8 ms, field of view: 32 mm×19.2 mm×19.2 mm, matrix: 160×96×96; number of averages=1) to obtain T1-weighted images. Gadolinium-enhanced MRI changes were indicative of blood-brain-barrier disruption. Volumetric analysis was performed using Analyze Software package developed by the Biomedical Imaging Resource at Mayo Clinic.

RNA-Seq on Mouse Brain Tissue

Figure 16:
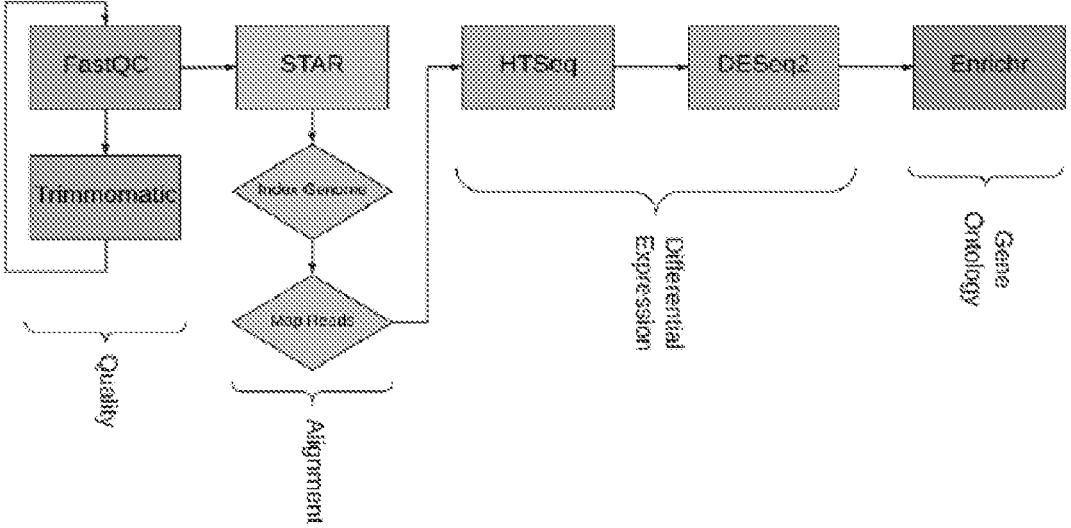
FIG. 16 shows a flow chart for procedures used in RNA sequencing. The binary base call data was converted to fastq using Illumina bcl2fastq software. The adapter sequences were removed using Trimmomatic, and FastQC was used to check for quality. The latest human (GRCh38) and mouse (GRCm38) reference genomes were downloaded from NCBI. Genome index files were generated using STAR30, and the paired end reads were mapped to the genome for each condition. HTSeq was used to generate expression counts for each gene, and DeSeq2 was used to calculate differential expression. Gene ontology was assessed using Enrichr.

RNA was isolated using a micro RNA purification kit (miRNeasy™ Micro Kit, Qiagen, Gaithersburg, MD, USA) and treated with RNase-Free DNase Set (Qiagen, Gaithersburg, MD, USA). RNA-seq was performed on an Illumina HTSeq 4000 (Illumina, San Diego, CA, USA) by the Genome Analysis Core at Mayo Clinic. The binary base call data was converted to fastq using Illumina bcl2fastq software. The adapter sequences were removed using Trimmomatic, and FastQC was used to check for quality. The latest human (GRCh38) and mouse (GRCm38) reference genomes were downloaded from NCBI. Genome index files were generated using STAR, and the paired end reads were mapped to the genome for each condition. HTSeq3 1 was used to generate expression counts for each gene, and DeSeq2 was used to calculate differential expression. Gene ontology was assessed using Enrichr. FIG. 16 summarizes the steps detailed above. RNA sequencing data are available at the Gene Expression Omnibus under accession number GSE121591.

Statistics

Prism Graph Pad and Microsoft Excel used to analyze data. The high cytokine concentrations in the heat map were normalized to "1" and low concentrations normalized to "0" via Prism. Statistical tests described in figure legends.

Results

GM-CSF Neutralization In Vitro Enhances CAR-T Cell Proliferation in the Presence of Monocytes and does not Impair CAR-T Cell Effector Function.

Figure 6A:
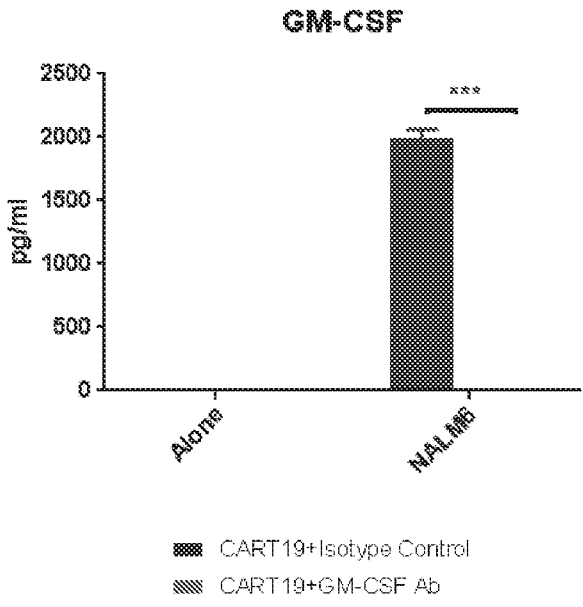
FIGS. 6A-6D show that GM-CSF neutralization in vitro enhances CAR-T cell proliferation in the presence of monocytes and does not impair CAR-T cell effector function.
Figure 6B:
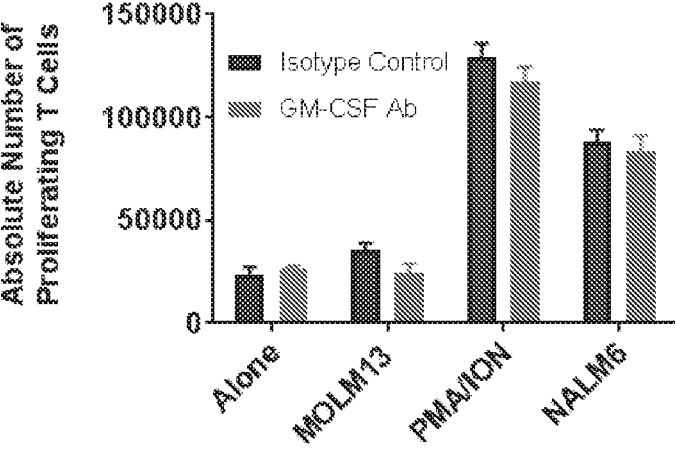
Figure 6C:
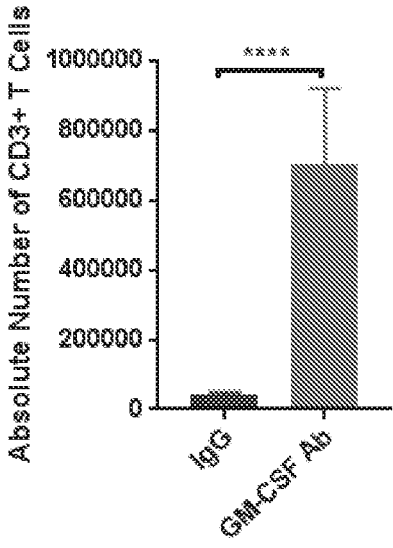
Figure 6D:
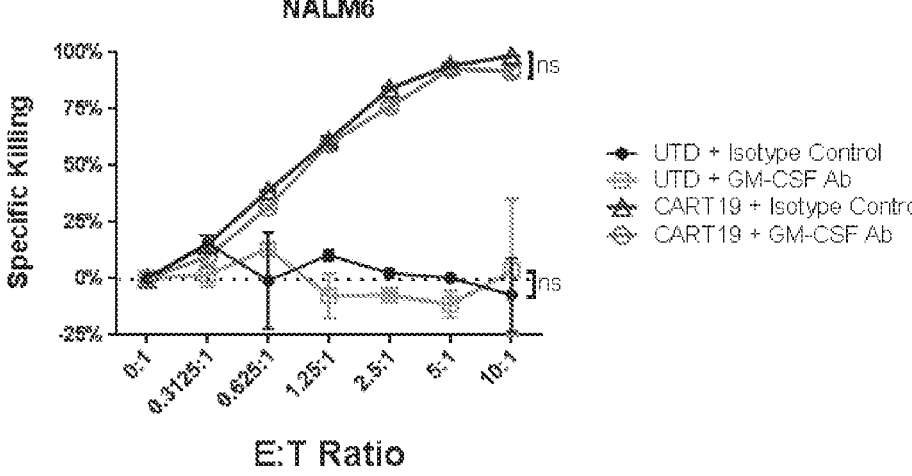

If GM-CSF neutralization after CAR-T cell therapy is to be utilized as a strategy to prevent CRS and NT, it must not inhibit CAR-T cell efficacy. Therefore, our initial experiments aimed to investigate the impact of GM-CSF neutralization on CAR-T cell effector functions. Here, CART19 cells were co-cultured with or without the CD19+ALL cell line NALM6 in the presence of lenzilumab (GM-CSF neutralizing antibody) or an isotype control (IgG). We established that lenzilumab, but not IgG control antibody, was indeed able to completely neutralize GM-CSF (FIG. 6A) but did not inhibit CAR-T cell antigen specific proliferation (FIG. 6B). When CART19 cells were co-cultured with the CD19+ cell line NALM6 in the presence of monocytes, lenzilumab in combination with CART19 demonstrated an exponential increase in antigen specific CART19 proliferation compared to CART19 plus isotype control IgG (P<0.0001, FIG. 6C). To investigate CAR-T specific cytotoxicity, either CART19 or control UTD T cells were cultured with the luciferase+CD19+ NALM6 cell line and treated with either isotype control antibody or GM-CSF neutralizing antibody (FIG. 1D). GM-CSF neutralizing antibody treatment did not inhibit the ability of CAR-T cells to kill NALM6 target cells (FIG. 6D). Overall, these results indicate that lenzilumab does not inhibit CAR-T cell function in vitro and enhances CART19 cell proliferation in the presence of monocytes, suggesting that GM-CSF neutralization may improve CAR-T cell mediated efficacy.

GM-CSF Neutralization In Vivo Enhances CAR-T Cell Anti-Tumor Activity in Xenograft Models.

Figure 7A:
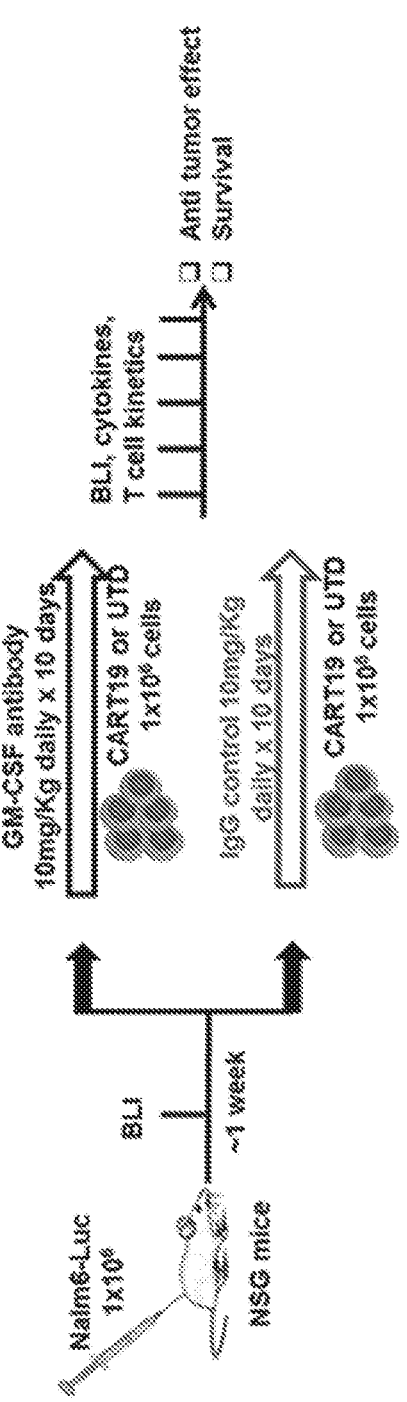
FIGS. 7A-7E show that GM-CSF neutralization in vivo enhances CAR-T cell anti-tumor activity in xenograft models.
Figure 7B:
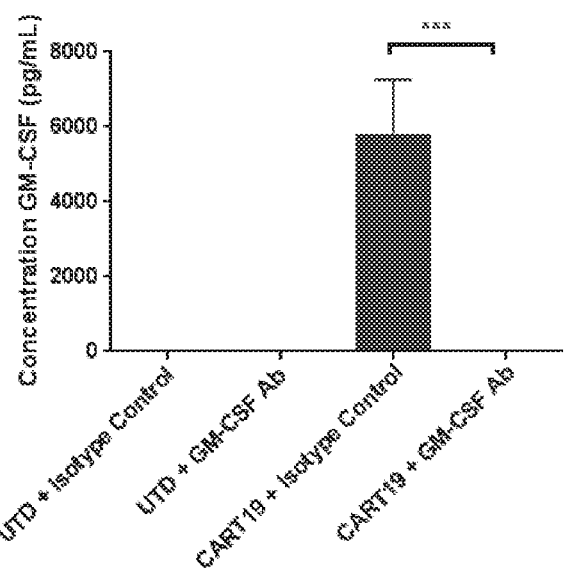
Figure 7C:
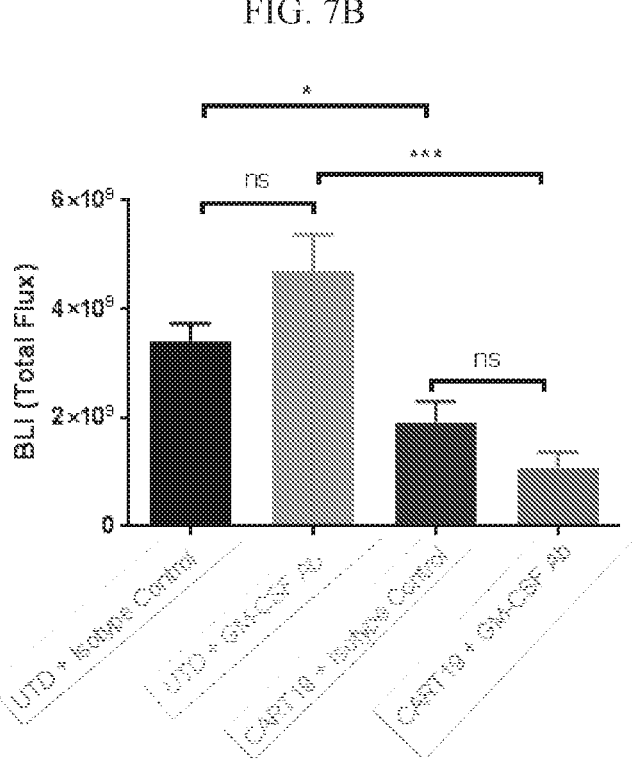
Figure 7D:
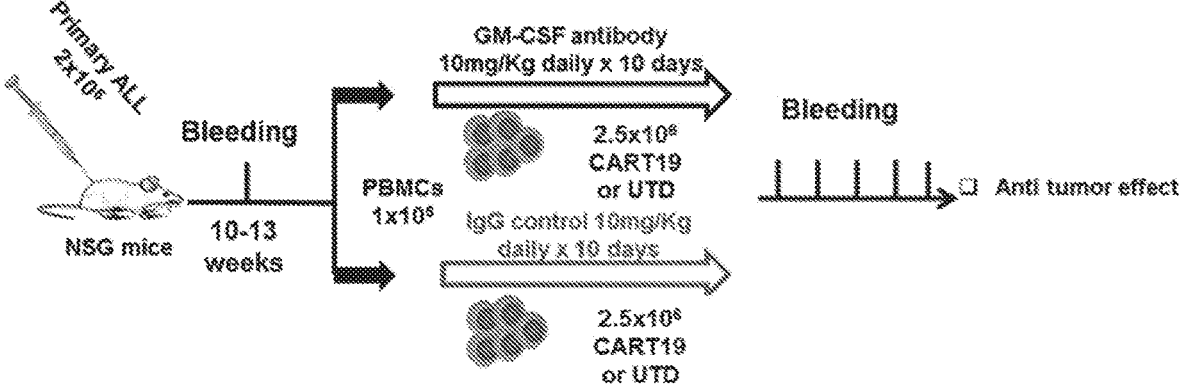
Figure 7E:
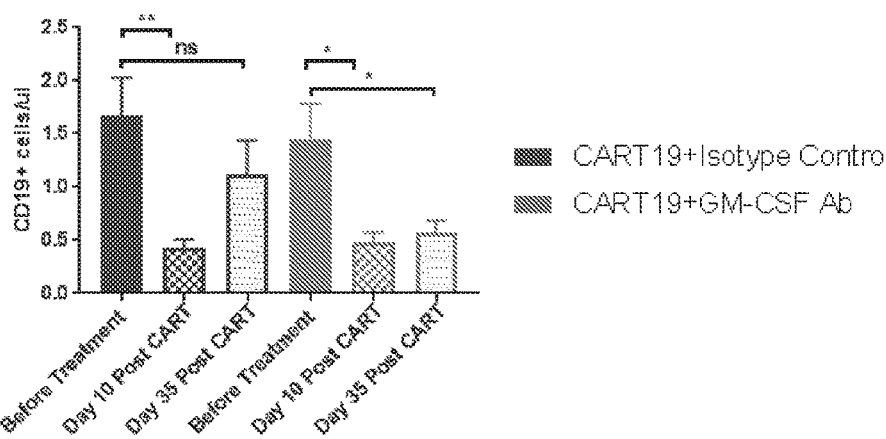
Figure 8:
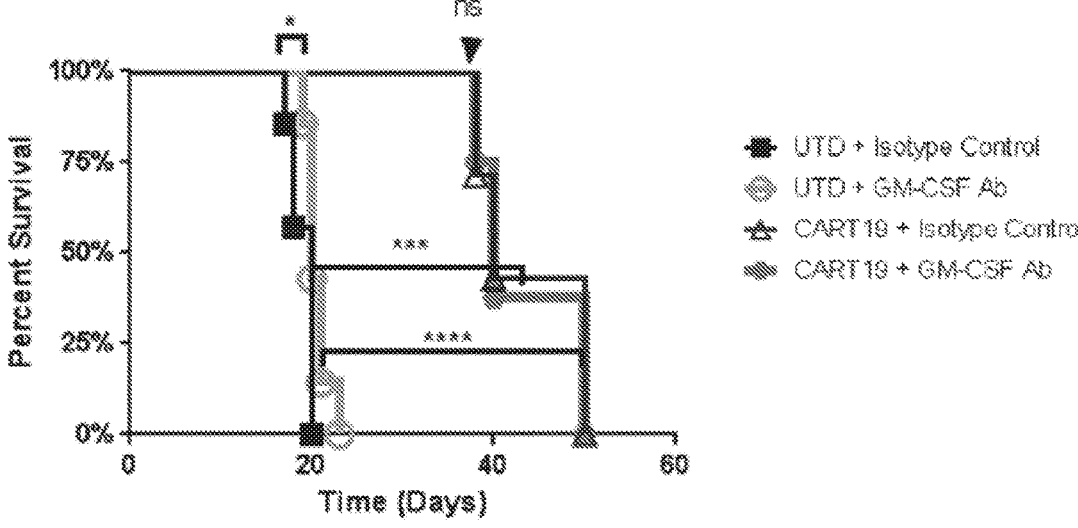
FIG. 8 contains a graph showing that lenzilumab+CAR-T cell treated mice have comparable survival compared to isotype control+CAR-T cell treated mice in a high tumor burden relapse xenograft model of ALL. n=2 experiments, 7-8 mice per group, representative experiment depicted, **p<0.0001, *p<0.001, *p<0.05, log-rank.

To confirm that GM-CSF depletion does not inhibit CART19 effector functions, we investigated the role of GM-CSF neutralization with lenzilumab on CART19 antitumor activity in xenograft models. First, a relapse model intended to vigorously investigate whether the antitumor activity of CART19 cells was impacted by GM-CSF neutralization was used. NSG mice were injected with $1\times10^6$ luciferase+NALM6 cells and then imaged 6 days later, allowing sufficient time for mice to achieve very high tumor burdens. Mice were randomized to receive a single injection of either CART19 or UTD cells and 10 days of either isotype control antibody or lenzilumab (FIG. 7A). GM-CSF assay on serum collected 8 days after CART19 injection revealed that lenzilumab successfully neutralizes GM-CSF in the context of CART19 therapy (FIG. 7B). Bioluminescence imaging one week after CART19 injection showed that CART19 in combination with lenzilumab effectively controlled leukemia in this high tumor burden relapse model and significantly better than control UTD cells (FIG. 7C). Treatment with CART19 in combination with lenzilumab resulted in potent anti-tumor activity and improved overall survival, similar to CART19 with control antibody despite neutralization of GM-CSF levels, indicating that GM-CSF does not impair CAR-T cell activity in vivo (FIG. 8). Second, these experiments were performed in a primary ALL patient derived xenograft model, in the presence of human PBMCs as this represents a more relevant heterogeneous model. After conditioning chemotherapy with busulfan, mice were injected with blasts derived from patients with relapsed ALL. Mice were monitored for engraftment for several weeks through serial tail vein bleedings and when the CD19+ blasts in the blood were ≥1 μL, mice were randomized to receive CART19 or UTD treatment in combination with PBMCs with either lenzilumab plus an anti-mouse GM-CSF neutralization antibody or isotype control IgG antibodies starting on the day of CART19 injection for 10 days (FIG. 7D). In this primary ALL xenograft model, GM-CSF neutralization in combination with CART19 therapy resulted in a significant improvement in leukemic disease control sustained over time for more than 35 days post CART19 administration as compared to CART19 plus isotype control (FIG. 7E). This suggests that GM-CSF neutralization may play a role in reducing relapses and increasing durable complete responses after CART19 cell therapy.

GM-CSF CRISPR Knockout CAR-T Cells Exhibit Reduced Expression of GM-CSF, Similar Levels of Key Cytokines, and Enhanced Anti-Tumor Activity.

Figure 9:
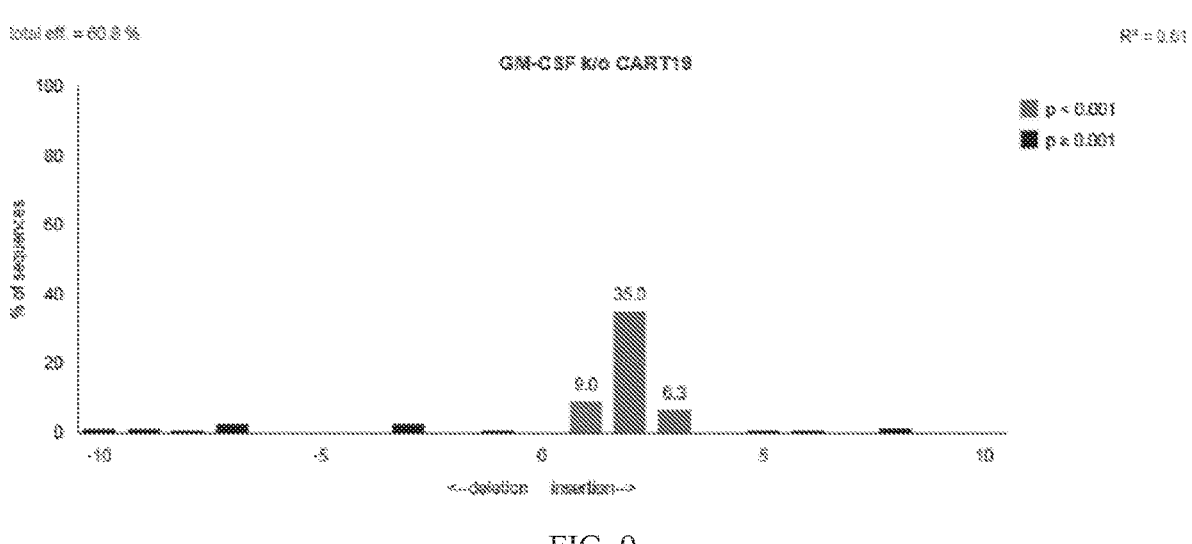
FIG. 9 contains a graph showing a representative TIDE sequence to verify genome alteration in the GM-CSF CRISPR Cas9 knockout CAR-T cells. n=2 experiments, representative experiment depicted.
Figure 10A:
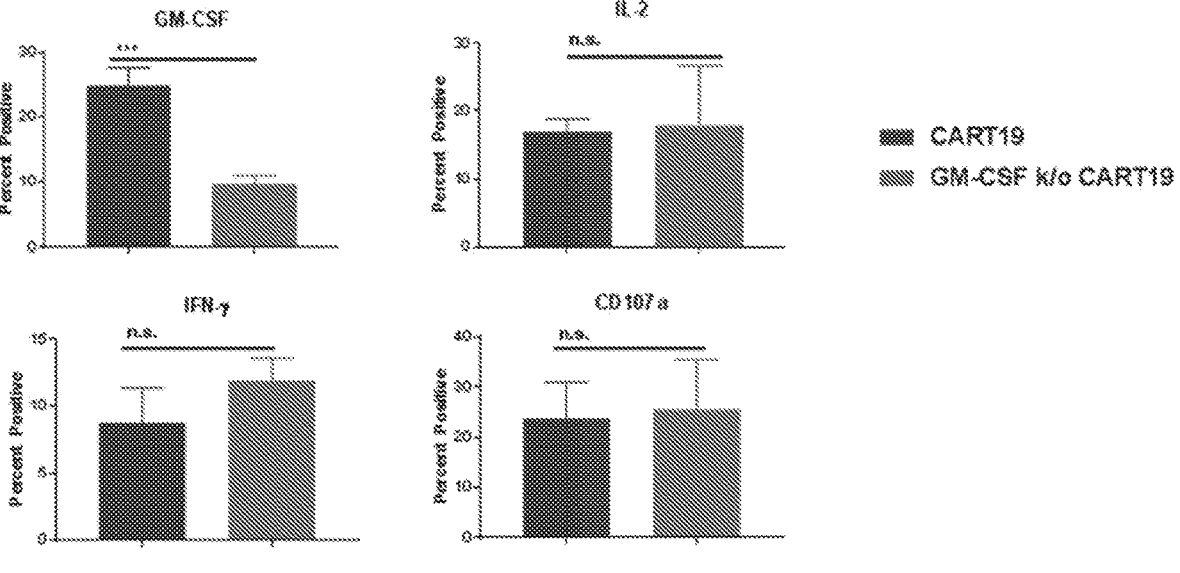
FIGS. 10A-10E show that GM-CSF CRISPR knockout CAR-T cells exhibit reduced expression of GM-CSF, similar levels of key cytokines, and enhanced anti-tumor activity.
Figure 10B:
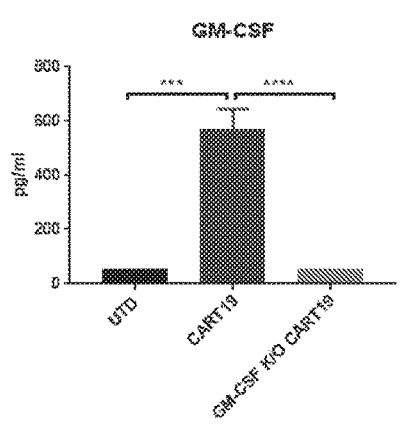
Figure 10C:
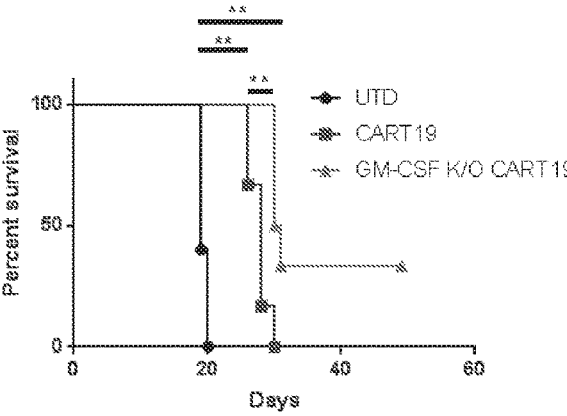
Figure 10D:
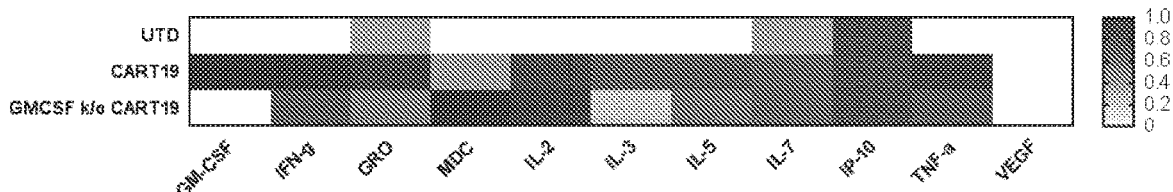
Figure 10E:
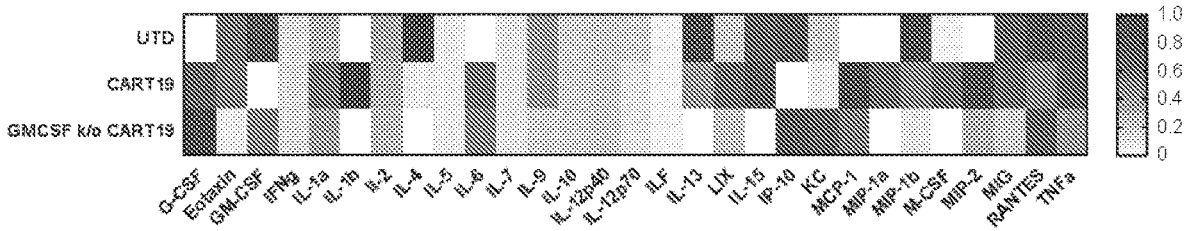
Figure 11:
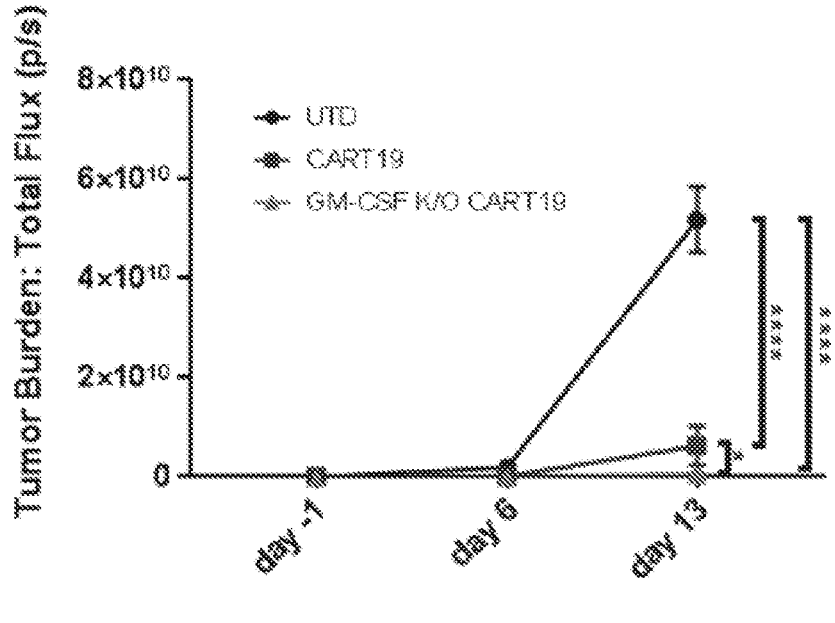
FIG. 11 contains a graph showing that GM-CSF knockout CAR-T cells in vivo shows slightly enhanced control of tumor burden compared to CAR-Tin a high tumor burden relapse xenograft model of ALL. Days post CAR-T injection listed on x-axis, 5-6 mice per group (2 remained in UTD group at day 13), representative experiment depicted, ****p<0.0001, *p<0.05, 2 way ANOVA, mean+SEM.

To confidently exclude any role for GM-CSF critical in CAR-T cell function, we disrupted the GM-CSF gene during CAR-T cell manufacturing using a gRNA that has been reported to yield high efficiency, cloned into a CRISPR lentivirus backbone. Using this gRNA, we achieved around 60% knockout efficiency in CART19 cells (FIG. 9). When CAR-T cells were stimulated with the CD19+ cell line NALM6, GM-CSF$^{k/o}$ CAR-T cells produced statistically significantly less GM-CSF compared to CART19 with a wild-type GM-CSF locus ("wild type CART19 cells"). GM-CSF knockout in CAR-T cells did not impair the production of other key T cell cytokines, including IFN-γ, IL-2, or CAR-T cell antigen specific degranulation (CD107a) (FIG. 10A) but did exhibit reduced expression of GM-CSF (FIG. 10B). To confirm that GM-CSF$^{k/o}$ CAR-T cells continue to exhibit normal functions, we tested their in vivo efficacy in the high tumor burden relapsing xenograft model of ALL (as described in FIG. 7A). In this xenograft model, utilization of GM-CSF$^{k/o}$ CART19 instead of wild type CART19 markedly reduced serum levels of human GM-CSF at 7 days after CART19 treatment (FIG. 10B). Bioluminescence imaging data implied that GM-CSF$^{k/o}$ CART19 cells show enhanced leukemic control compared to CART19 in this model (FIG. 11). Importantly, GM-CSF$^{k/o}$ CART19 cells demonstrated significant improvement in overall survival compared to wild type CART19 cells (FIG. 10C). Other than GM-CSF, no statistically significantly alterations in either human (FIG. 10D) or mouse (FIG. 10E) cytokines were detected. Together, these results confirm FIGS. 6 and 7, indicating that GM-CSF depletion does not impair cytokines that are critical to CAR-T efficacy functions. In addition, the results in FIG. 10 indicate that GM-CSF$^{k/o}$ CART may represent a therapeutic option for "built in" GM-CSF control as a modification during CAR-T cell manufacturing.

Patient Derived Xenograft Model for Neurotoxicity and Cytokine Release Syndrome

Figure 12A:
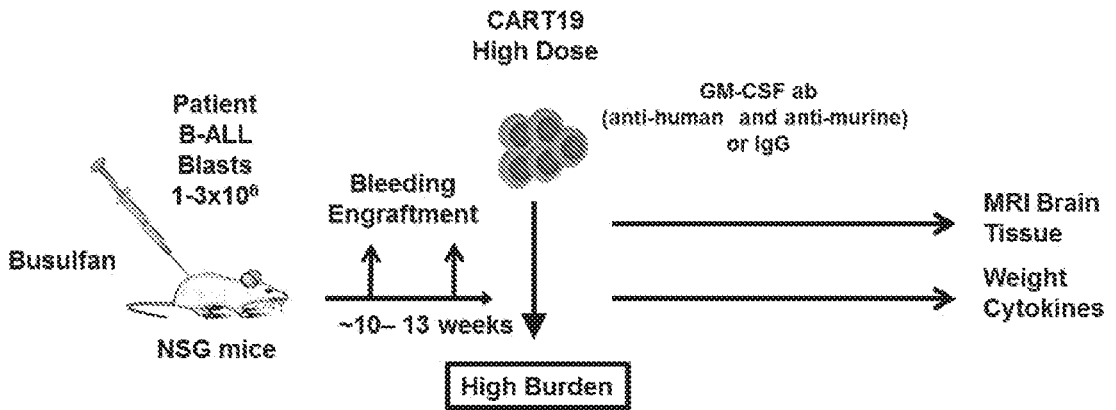
FIGS. 12A-12D show that patient derived xenograft model for neurotoxicity and cytokine release syndrome.
Figure 12B:
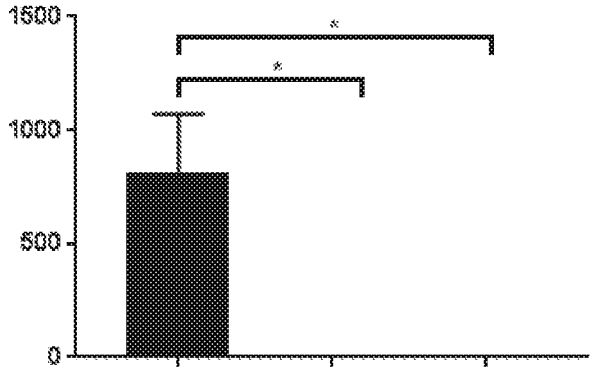
Figure 12C:
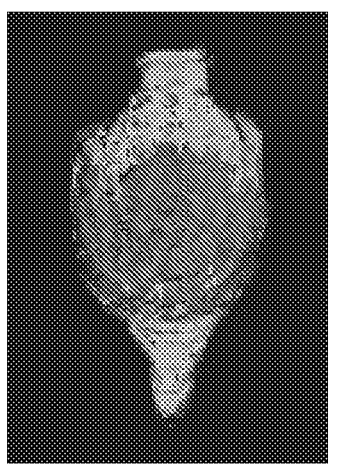
Figure 12D:
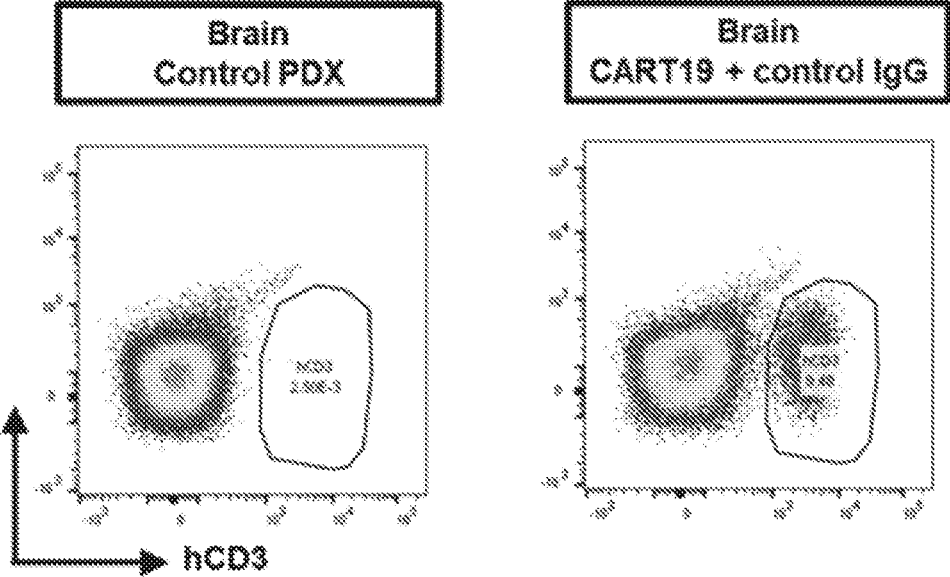

In this model, conditioned NSG mice were engrafted with primary ALL blasts and monitored for engraftment for several weeks until they developed high disease burden (FIG. 12A). When the level of CD19+ blasts in the peripheral blood was ≥10/μL, mice were randomized to receive different treatments as indicated (FIG. 12A). Treatment with CART19 (with control IgG antibodies or with GM-CSF neutralizing antibodies) successfully eradicated the disease (FIG. 12B). Within 4-6 days after treatment with CART19, mice began to develop motor weakness, hunched bodies, and progressive weight loss; symptoms consistent with CRS and NT. This was associated with elevation of key serum cytokines 4-11 days post CART19 injection similar to what is seen in human CRS after CAR-T cell therapy (including human GM-CSF, TNF-a, IFN-γ, IL-10, IL-12, IL-13, IL-2, IL-3, IP-10, MDC, MCP-1, MIP-1a, MIP-1, and mouse IL-6, GM-CSF, IL-4, IL-9, IP-10, MCP-1, and MIG). These mice treated with CART19 also developed NT as indicated by brain MRI analyses revealing abnormal T1 enhancement, suggestive of blood-brain barrier disruption and possibly brain edema (FIG. 12D), together with flow cytometric analysis of the harvested brains revealing infiltration of human CART19 cells (FIG. 12E). In addition, RNA-seq analyses of brain sections harvested from mice that developed these signs of NT showed significant upregulation of genes regulating the T cell receptor, cytokine receptors, T cell immune activation, T cell trafficking, and T cell and myeloid cell differentiation (Table 1).

TABLE 1

| Table of canonical pathways altered in brains from patient derived xenografts after treatment with CART19 cells. | | |
| --- | --- | --- |
| Conical Pathway | Adj P-Value | Genes |
| regulation of immune response (G0:0050776) | 9.45E−14 | IFITM1, ITGB2, TRAC, ICAM3, CD3G, PTPN22, CD3E, ITGAL, SAMHD1, SLA2, CD3D, ITGB7, SLAMF6, B2M, NPDC1, CD96, BTN3A1, ITGA4, SH2D1A, HLA-B, HLA-C, BTN3A2, HLA-A, CD8B, SELL, CD8A, CD226, CD247, CLEC2D, HCST, B1RC3 |

TABLE 1-continued

Table of canonical pathways altered in brains from patient
derived xenografts after treatment with CART19 cells.

| Conical Pathway | Adj P-Value | Genes |
|---|---|---|
| cytokine-mediated signaling pathway (GO:0019221) | 1.36E−12 | IFITM1, SP100, TRADD, ITGB2, IL2RG, SAMHD1, IL27RA, OASL, CNN2, IL18RAP, RIPK1, CCR5, IL12RB1, B2M, GBP1, IL6R, JAK3, CCR2, IL32, ANXA1, IL4R, TGFB1, IL10RB, IL10RA, STAT2, PRKCD, HLA-B, HLA-C, IL16, HLA-A, TNFRSF1B, CD4, IRF3, OAS2, IL2RB, FAS, TNFRSF25, LCP1, P4HB, IL7R, MAP3K14, CD44, IL18R1, IRF9, MYD88, B1RC3 |
| T cell receptor complex (GO:0042101) | 1.30E−11 | ZAP70, CD4, CD6, CD8B, CD8A, CD3G, CD247, CD3E, CD3D, CARD11 |
| T cell activation (GO:0042110) | 2.07E−11 | ITK, RHOH, CD3G, NLRC3, PTPN22, CD3E, SLA2, CD3D, CO2, ZAP70, CD4, PTPRC, CD8B, CD8A, LCK, CD28, LCP1, LAT |
| regulation of T cell activation (GO:0050863) | 2.46E−10 | PTPN22, LAX1, CCDC88B, CD2, CD4, LCK, SIT1, TBX21, TIGIT, JAK3, LAT, PAG1, CCR2 |
| T cell receptor signaling pathway (GO:0050852) | 4.35E−08 | ITK, BTN3A1, TRAC, WAS, CD3G, PTPN22, BTN3A2, CD3E, CD3D, ZAP70, CD4, PTPRC, LCK, GRAP2, LCP2, CD247, CARD11, LAT, PAG1 |
| positive regulation of cytokine production (GO:0001819) | 1.57502E−07 | GBP5, ANXA1, TGFB1, CYBA, PTPN22, PARK7, TMEM173, CCDC88B, MAVS, CD6, IRF3, CD28, RIPK1, SLAMF6, CD46, IL12RB1, TIGIT, IL6R, CARD11, MYD88, CCR2 |
| T cell differentiation (GO:0030217) | 2.36E−07 | ZAP70, CD4, ANXA1, PTPRC, CD8A, LCK, CD28, RHOH, PTPN22, CD3D |
| cytokine receptor activity (GO:0004896) | 2.43E−07 | IL4R, IL10RB, IL10RA, IL2RG, CD4, CXCR3, IL2RB, CCR5, IL12RB1, IL7R, IL6R, CD44, CCR2 |
| type I interferon signaling pathway (GO:0060337) | 3.27E−07 | IFITM1, SP100, IRF3, OAS2, STAT2, HLA-B, HLA-C, HLA-A, SAMHD1, IRF9, MYD88, OASL |
| response to cytokine (GO:0034097) | 0.0004679 | SIGIRR, IFITM1, SP100, HCLS1, RIPK1, PTPN7, IKBKE, IL6R, JAK3, IL18R1, MYD88, AES |
| regulation of innate immune response (GO:0045088) | 0.001452 | GBP5, GFI1, STAT2, ADAM8, NLRC3, PTPN22, SAMHD1, B1RC3 |
| regulation of tumor necrosis factor production (GO:0032680) | 0.003843 | CD2, MAVS, CYBA, NLRC3, PTPN22, RIPK1, SLAMF1 |
| T cell receptor binding (GO:0042608) | 0.0102397 | LCK, CD3G, CD3E |
| regulation of tumor necrosis factor-mediated signaling pathway (GO:0010803) | 0.0124059 | SHARPIN, TRADD, CASP4, RIPK1, TRAF1, B1RC3 |
| positive regulation of myeloid leukocyte differentiation (GO:0002763) | 0.0376647 | CD4, HCLS1, RIPK1, EV12B |

GM-CSF Neutralization In Vivo Ameliorates Cytokine Release Syndrome and Neurotoxicity after CART19 Therapy in a Xenograft Model.

Figure 13A:
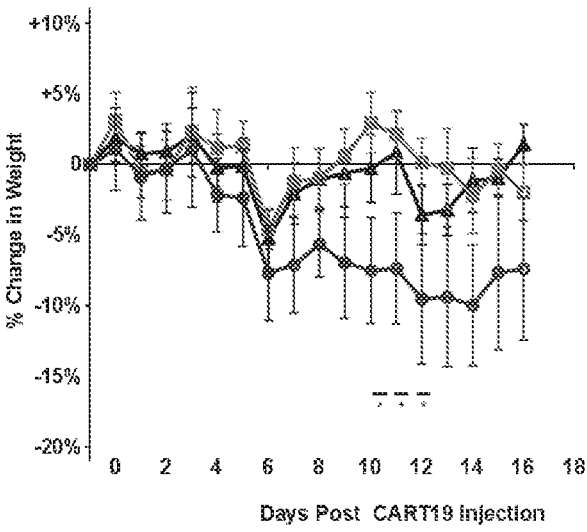
FIGS. 13A-13D show that GM-CSF neutralization in vivo ameliorates cytokine release syndrome after CART19 therapy in a xenograft model.
Figure 13B:
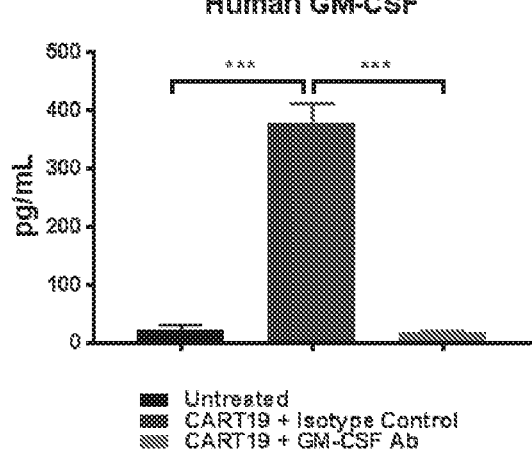
Figure 13C:
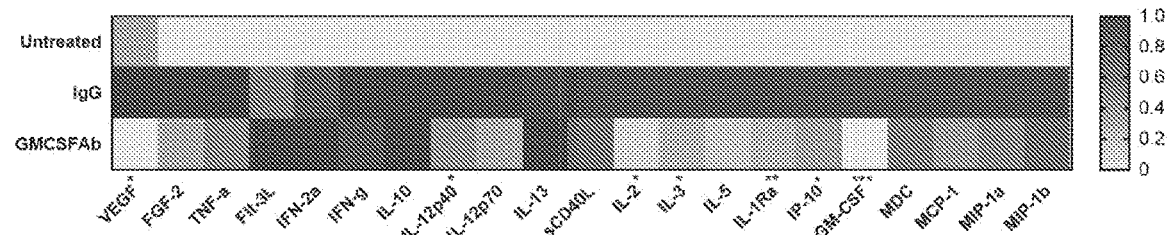
Figure 13D:
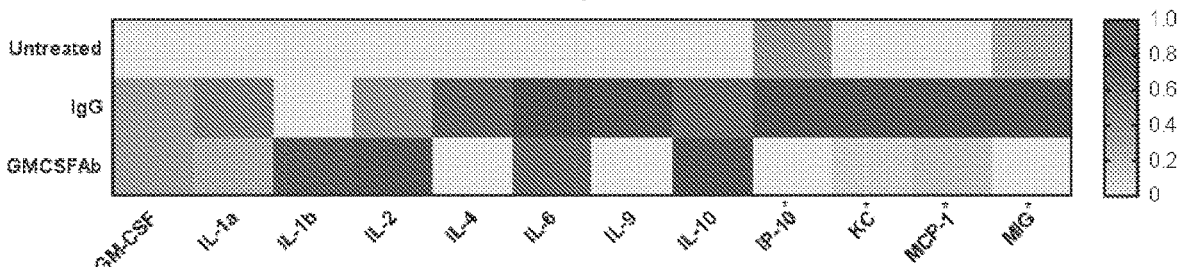

Using the xenograft patient derived model for NT and CRS shown in FIG. 4A, we investigated the effect of GM-CSF neutralization on CART19 toxicities. To rule out the cofounding effect of mouse GM-CSF, mice received CART19 cells in combination with 10 days of GM-CSF antibody therapy (10 mg/kg lenzilumab and 10 mg/kg anti-mouse GM-CSF neutralizing antibody) or isotype control antibodies. GM-CSF neutralizing antibody therapy prevented CRS induced weight loss after CART19 therapy (FIG. 13A). Cytokine analysis 11 days after CART19 cell therapy showed that human GM-CSF was neutralized by the antibody (FIG. 13B). In addition, GM-CSF neutralization resulted in significant reduction of several human (IP-10, IL-3, IL-2, IL-1Ra, IL-12p40, VEGF, GM-CSF) (FIG. 5C) and mouse (MIG, MCP-1, KC, IP-10) (FIG. 13D) cytokines. Interferon gamma-induced protein (IP-10, CXCL1O) is produced by monocytes among other cell types and serves as a chemoattractant for numerous cell types including monocytes, macrophages, and T cells. IL-3 plays a role in myeloid progenitor differentiation. IL-2 is a key T cell cytokine. Interleukin-1 receptor antagonist (IL-1Ra) inhibits IL-1. (IL-1 is produced by macrophages and is a family of critical inflammatory cytokines.) IL-12p40 is a subunit of IL-12, which is produced by macrophages among other cell types and can encourage Th1 differentiation. Vascular endothelial growth factor (VEGF) encourages blood vessel formation. Monokine induced by gamma interferon (MIG, CXCL9) is a T cell chemo attractant. Monocyte chemoattractant protein 1 (MCP-1, CCL2) attracts monocytes, T cells, and dendritic cells. KC (CXCL1) is produced by macrophages among other cell types and attracts myeloid cells such as neutrophils. There was also a trend in reduction of several other human and mouse cytokines after GM-CSF neutralization. This suggests that GM-CSF plays a role in the downstream activity of several cytokines that are instrumental in the cascade that results in CRS and NT.

Figure 14A:
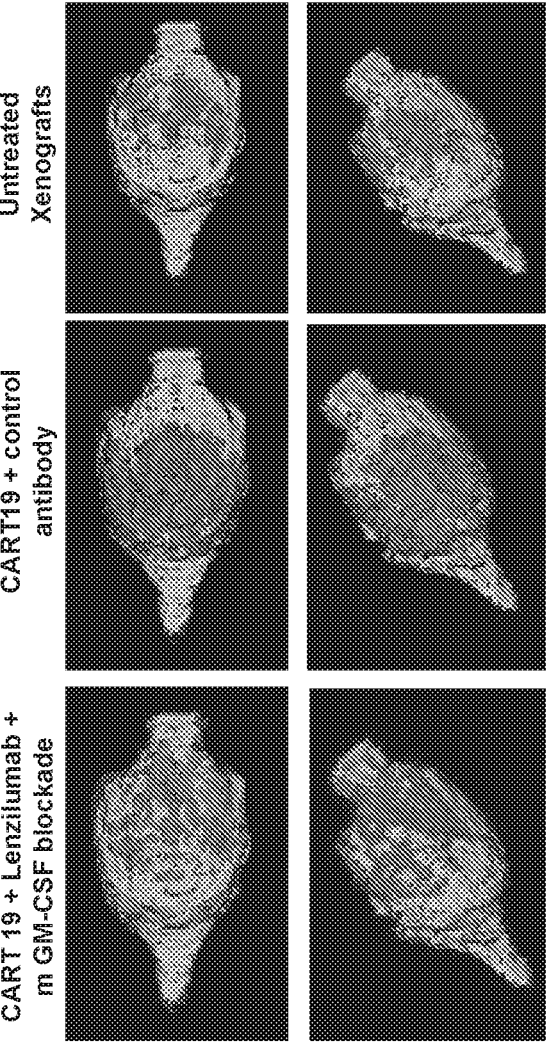
FIGS. 14A-14D show that GM-CSF neutralization in vivo ameliorates neurotoxicity after CART19 therapy in a xenograft model.
Figure 14B:
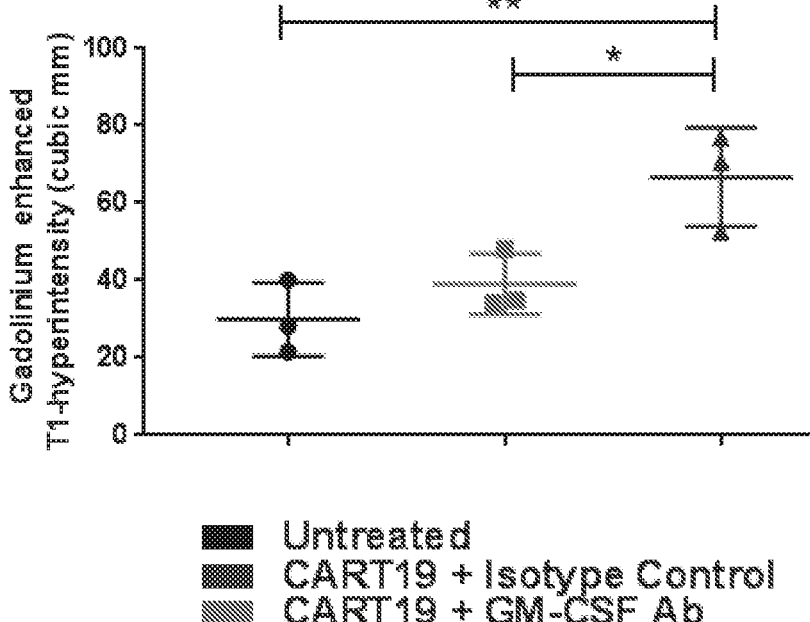
Figure 14C:
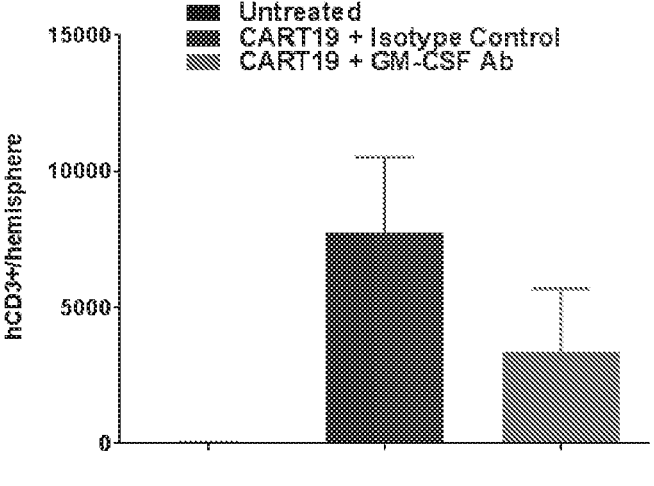
Figure 14D:
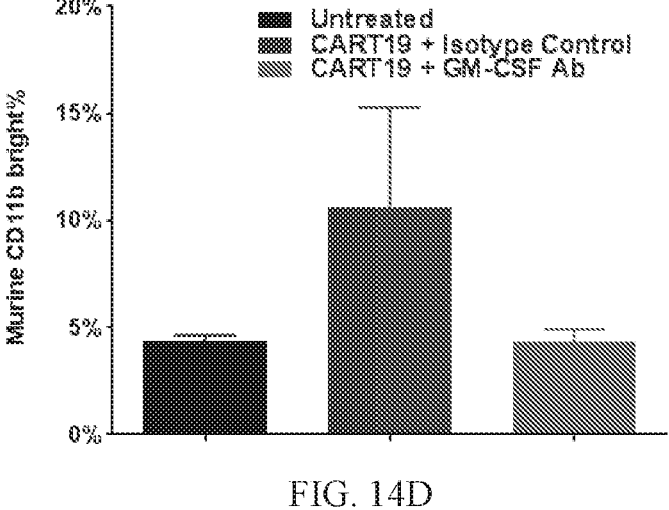

Brain MRIs 5 days after CAR19 treatment showed that GM-CSF neutralization reduced T1 enhancement as a measure of brain inflammation, blood-brain barrier disruption, and possibly edema, compared to CART19 plus control antibodies. The MRI images after GM-CSF neutralization (with lenzilumab and anti-mouse GM-CSF antibody) were similar to baseline pre-treatment scans, suggesting that GM-CSF neutralization effectively helped abrogated the NT associated with CART19 therapy (FIGS. 14A, 14B). Using human ALL blasts and human CART19 in this patient-derived xenograft model, GM-CSF neutralization after CART19 reduced neuro-inflammation by 59% compared to CART19 plus isotype controls (FIG. 14B). This is a significant finding, and the first time it has been demonstrated in vivo that the NT caused by CART19 can be effectively abrogated. Human CD3 T cells were present in the brain after CART19 therapy as assayed by flow cytometry, and with GM-CSF neutralization, there was a trend toward reduction in brain CD3 T cells (FIG. 14C). Finally, a trend in reduction of CD11b+ bright macrophages was observed in the brains of mice receiving GM-CSF neutralization during CAR-T cell therapy compared to isotype control during CAR-T therapy (FIG. 14D), implicating that GM-CSF neutralization helps reduce macrophages within the brain.

Example 3-A

Combination Therapy with GM-CSF Gene KO in CART19 Cells (GM-CSF$^{k/o}$ CART19) and hGM-CSF Neutralizing Antibody (Lenzilumab) for CAR19 T Derived GM-CSF Lenzilumab (e.g., 10 mg/kg or up to 30 mg/kg or 1,800 mg flat dosing) is administered to a subject in combination with GM-CSF$^{k/o}$ CART19 cells. GM-CSF$^{k/o}$ CAR-T cells help control GM-CSF release upon contact/binding of CAR-T cells with tumor cells. The reduction of GM-CSF secretion at the tumor site results in less activation and trafficking of inflammatory myeloid cells and reduced levels of MCP-1, IL-6, IP10, KC, MIP-1a, MIP-1b, MIG, VEGF, IL-1RA, and IL-12p40 in measured systemically. The reduced cytokine levels prevents or reduces the incidence or severity of CRS and NT. The addition of lenzilumab ensures that GM-CSF is neutralized from all sources and helps deplete MDSCs from the tumor microenvironment. Lenzilumab dosing can be repeated at intervals of every two weeks to insure continued depletion of MDSCs. The combination of GM-CSF$^{k/o}$ CAR-T cells with lenzilumab results in improved response rates, improved progression free survival, and improved overall survival in patients treated with the combination therapy vs. control. The combination therapy also results in lower levels (or elimination) of the toxicities associated with CAR-T cell therapy, including CRS and NT.

Example 3-B

Combination Therapy with GM-CSF Gene KO in CART19 Cells (GM-CSF$^{k/o}$ CART19) and hGM-CSF Neutralizing Antibody (Lenzilumab) for CAR19 T Derived GM-CSF Lenzilumab (/600-1800 mg) is administered to a subject in combination with GM-CSF$^{k/o}$ CART19 cells.

Non-Hodgkins Lymphoma cancer patients are pre-conditioned prior to therapy. They are dosed I.V. with anti-hGM-CSF antibody (600-1800 mg) followed by 2×10$^6$ transduced autologous CD19CART cells)(GM-CSF$^{KO}$). At specific times after treatment effects are assessed e.g. safety, blood chemistry, neurologic assessments, disease status. The treatment may be repeated on a monthly basis until there is no further detectable cancer or there is a significant reduction in cancer load.

Example 4

Figure 17B:
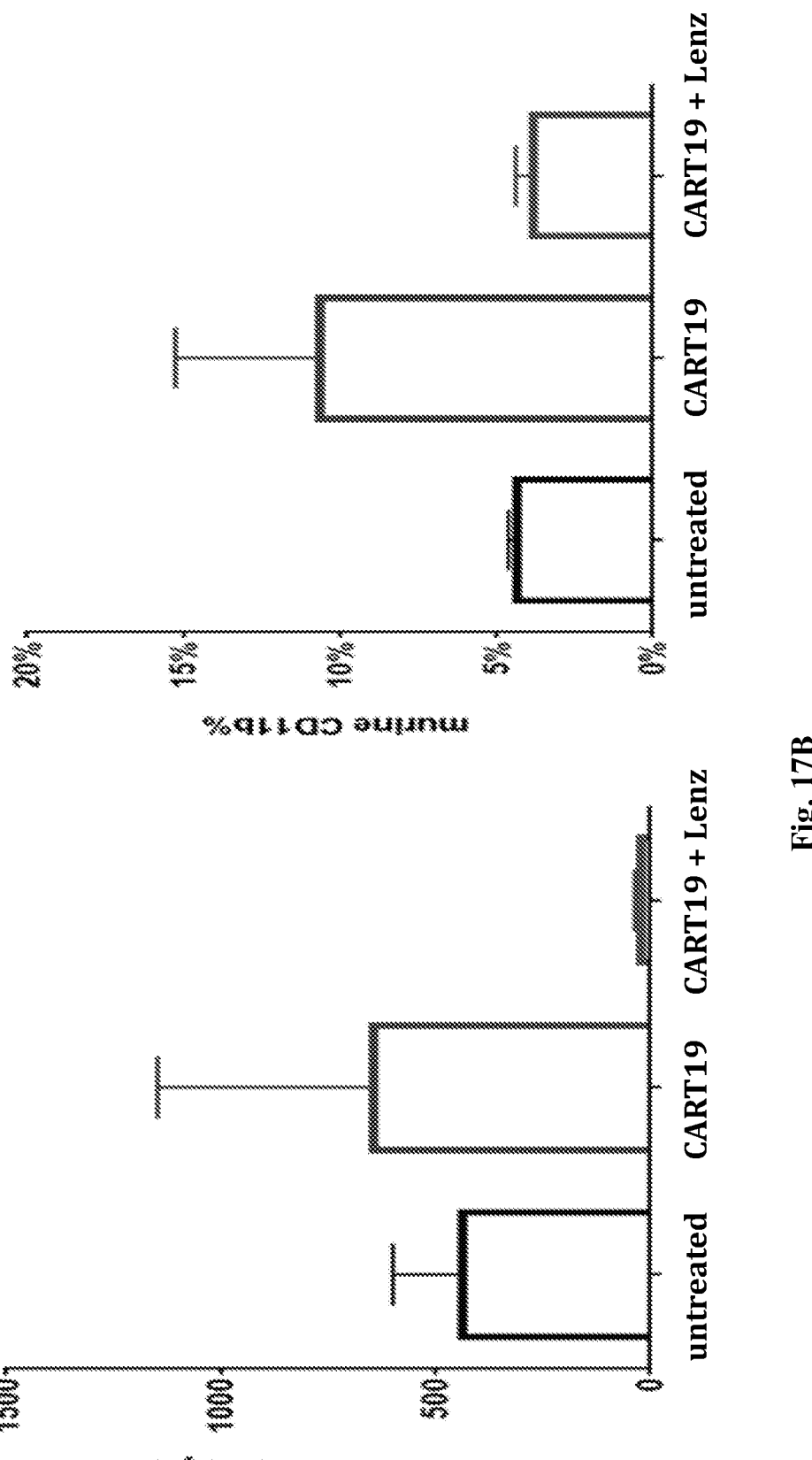

Recombinant Anti-hGM-CSF Antibody, Lenzilumab, Reduces Myeloid Cell Infiltration in the CNS CD14+ cells comprise a greater proportion of the CNS cell population in human patients with grade 3 or above neurotoxicity, as shown in FIG. 17A. Administration of recombinant anti-hGM-CSF antibody (lenzilumab) that binds to and neutralizes human GM-CSF to mice treated with CART19 therapy demonstrated a reduction in CNS infiltration by CD14+ cells and by CD11b+ cells, as shown in FIG. 17B in comparison to untreated mice and mice treated only with CART19 therapy. A primary ALL mouse model was used, as detailed below for the NT experiments.
Primary Patient Derived ALL Xenografts for CRS/NT Similar to the experiments above, mice were IP injected with 30 mg/kg busulfan. The following day, they received 1-2×10$^6$ primary blasts derived from the peripheral blood of patients with relapsed refractory ALL. Mice were monitored for engraftment for 4-6 weeks and when CD19+ cell level was high (≥10 cells/0), they received CART19 (2-5×10$^6$ cells) and commenced antibody therapy for a total of 10 days, as indicated in the details of the specific experiment. (as described in Example 2). Mice were weighed on daily basis as a measure of their well-being. Brian MRI of the mice was performed 5-6 days post CART injection and tail vein bleeding was performed 4-11 days post CART injection. Brain MRI images were analyzed using Azalyze.

Example 5

Gene Editing Technologies to Knockout GM-CSF Genes in T Cells

Several strategies are being pursued by various groups to incorporate gene editing into the development of next-generation chimeric antigen receptor (CAR) T cells for the treatment of various cancers. Severe toxicity (cytokine release syndrome and neurotoxicity) is associated with CAR T cell therapy and can result in poor patient outcomes. A key initiator in the toxicity process seems to be CART cell derived GM-CSF.

Gene-editing (with e.g. engineered nucleases) may be used to KO GM-CSF genes in T cells and/or gene/s encoding proteins essential for GM-CSF gene expression. Nucleases useful for such genome editing include, without limitation, CRISPR-associated (Cas) nucleases, zinc-finger nucleases (ZFNs), transcription activator-like effector (TALE) nucleases, and homing endonucleases (HEs) also known as meganucleases
Zinc-Finger Nuclease use for GM-CSF A GM-CSF gene in CART cells can be inactivated using Zinc Finger Nuclease (ZFN) technology. DNA sequence specific nucleases cleave the GM-CSF gene/s and DNA double strand break repair results in inactivation of the gene/s. The sequence specific nucleases are created by combining sequence specific DNA binding domains (Zinc fingers) with a Fok1 endonuclease domain. The targeted nuclease acts as a dimer and two different DNA recognition domains are employed to provide site specific cleavage. Engineering of the Fok1 endonuclease ensures that heterodimers form rather than homodimers. Thus, the obligate heterodimer Fok1-EL variant provides a higher level of specificity.

Clinical experience to date with gene KO approaches using ZFN technology is limited. However, in a small safety study in which the CCR5 receptor was knocked-out using ZFN technology and the T-cells re-introduced into HIV patients, there was a notable survival advantage of the modified T cells vs unmodified when anti-retroviral drug therapy was stopped.

The best effect was observed when biallelic gene disruption was achieved. This suggests that the KO technology that achieves greatest % gene disruption is likely to be the most effective (Singh 2017, Tebas 2014). In some human cell types biallelic targeting efficiency is increased by RAD51 over expression and valproic acid treatment (Takayama 2017).

Exons 1-4 of the human GM-CSF gene can be targeted with ZFNs that form pairs within the chosen target region. A potential advantage to targeting close to the translational initiation codon within the DNA sequence is that it ensures that the gene knockout does not result in a large fragment of protein that is still synthesized. Such protein fragments could have unwanted biological activities.

A variety of tools are available for the identification of potential zinc finger nuclease (ZFN) sites in specific target sequences. An example of such tools can be found at ZiFiT (Zinc Finger Targeter), web-based tool at Iowa State University. Vectors for the expression of pairs of ZFNs identified in this way (for use in GM-CSF gene KO) are tested in human cells expressing GM-CSF and the effectiveness of gene disruption for each pair is measured by changes in GM-CSF production within a pool of cells. Pairs of ZFNs demonstrating the highest reduction in GM-CSF levels are chosen for testing in human CART cells.

For example, autologous T-cells can be transduced ex vivo with a replication deficient recombinant Ad5 viral vector encoding pairs of the GM-CSF specific ZFNs, resulting in modification of the GM-CSF gene. The vector supports only transient expression of genes encoded by the vector. The two ZFNs bind to a composite bp sequence found specifically in the region chosen for mutagenesis (within exons 1, 2, 3 or 4) of the GM-CSF gene. Expression of the GM-CSF-specific ZFNs induces a double stranded break in the cellular DNA which is repaired by cellular machinery leading to random sequence insertions or deletions in the transduced cells. These insertions and deletions disrupt the GM-CSF coding sequence leading to frameshift mutation and termination of protein expression.

The T Cell Manufacture/Patient-Specific Sample

Study subjects undergo a 10 liter leukapheresis to collect >$10^9$ white blood cells. The leukapheresis product is enriched for CD4+ cells by depleting monocytes via counterflow centrifugal elutriation, and by magnetically depleting CD8+ T-cells, both employing a single-use closed-system disposable set. The resulting enriched CD4+ T-cells are activated with anti-CD3/anti-CD28 mAb coated paramagnetic beads and transduced with vector encoding CAR T and vector encoding ZFNs. Cells are then expanded and cultured in a closed system. T-cell expansion continues after transfer to a WAVE Bioreactor for additional expansion under perfusion conditions. At the end of the culture period, cells are depleted of magnetic beads, washed, concentrated, and cryopreserved.

Primary T cells may also be treated with treated with other agents, e.g. valproic acid in order to increase bi-allelic targeting efficiency of the ZFNs.

Putative Targeting Sequences
Exon 1

(SEQ ID NO: 14)
ATG TGG CTG CAG *AGC CTG* CTG CTC TCG GGC

(SEQ ID NO: 15)
TAC ACC GAC GTC *TCG GAC* GAC GAG AGC CCG (SEQ ID NO: 14 continued)
CTC GCC CAG *CCC CAG* CAC GCA GCC

(SEQ ID NO: 15 continued)
GAG CGG GTC *GGG GTC* GTG CGT CGG

Exon 2

(SEQ ID NO: 16)
AAT GAA ACA GTA *GAA GTC* ATC TCA GAA ATG

(SEQ ID NO: 17)
TTA CTT TGT CAT *CTT CAG* TAG AGT CTT TAC (SEQ ID NO: 16 continued)
GAA GTC ATC *TCA GAA* ATG TTT GAC

(SEQ ID NO: 17 continued)
CTT CAG TAG *AGT CTT* TAC AAA CTG

Design Exon 3

(SEQ ID NO: 18)
GAG CCG A CC TGC *CTA CAG* ACC CGC CTG GAG

(SEQ ID NO: 19)
CTC GGC TGG ACG *GAT GTC* TGG GCG GAC CTC (SEQ ID NO: 18 continued)
GCC TAC AGA *CCCGCCT* GGA GCT GTA

(SEQ ID NO: 19 continued)
CGG ATG TCT *GGGCGGA* CCT CGA CAT

Exon 4

(SEQ ID NO: 20)
GAA ACT TCC TGT *GCA ACC* CAG ATT ATC ACC

(SEQ ID NO: 21)
CTT TGA AGG ACA *CGT TGG* GTC TAA TAG TGG (SEQ ID NO: 20 continued)
TGC AAC CCA *GAT TATC* ACC TTT GAA

(SEQ ID NO: 21 continued)
ACG TTG GGT *CTA ATAG* TGG AAA CTT

TALENS

GM-CSF gene/s in T cells can also be inactivated using activator-like effector nucleases (TALENS). TALENS are similar to ZFNs in that they comprise a Fok1 nuclease domain fused to a sequence specific DNA-binding domain. The targeted nuclease then makes a double-strand break in the DNA and error-prone repair creates a mutated target gene. TALENS can be easily designed using a simple protein-DNA code that uses DNA binding TALE (transcriptional-activator-like effectors) repeat domains to individual bases in a binding site. The robustness of TALEN means that genome editing is a reliable and facile process (Reyon D., et al., 2012 *Nat Biotechnol.* 2012 May; 30(5):460-5. doi: 10.1038/nbt.2170, which is incorporated herein by reference its entirety.)

By way of examples, some TALE target sequences within Exon 1 of human GM-CSF gene are:

1.

(SEQ ID NO:22)
<u>TGGCTGCAGAGCCTGCTG</u>CTCTTGGGCACTGTGG<u>CCTGCAGCATCTCTG</u>
<u>CA</u>

-continued

2.

(SEQ ID NO: 23)

<u>TTGGGCACTGTGGCCTGC</u>AGCATCTCTGCACCCG<u>CCCGCTCGCCCAGCC</u>
<u>CCA</u>

Examples of TALE target sequences in Exon 4 of human GM-CSF gene:

(SEQ ID NO: 24)

<u>TGTGCAACCCAGATTATC</u>ACCTTTGAAAGTTTCA<u>AAGAGAACCTGAAGG</u>
<u>A</u>

(SEQ ID NO: 25)

<u>TCCTGTGCAACCCAGATT</u>ATCACCTTTGAAAGTTT<u>CAAAGAGAACCTGA</u>
<u>A</u>

3.

(SEQ ID NO: 26)

<u>TTATCACCTTTGAAAG</u>TTTCAAAGAGAACCTGA<u>AGGACTTTCTGCTTGT</u>
<u>CA</u>

CRISPR Cas-9 Mediated GM-CSF Gene KO in Primary T-Cells.

The CRISPR (clustered regularly interspaced short palindromic repeats), Cas-9 system is composed of Cas9, a RNA-guided nuclease and a short guide RNA (gRNA) that facilitates the generation of site-specific DNA breaks, which are repaired by cell-endogenous mechanisms. Cas9/gRNA RNP delivery to primary human T-cells results in highly efficient target gene modification. CRISPR/Cas9 mediated methods to knockout the GM-CSF gene are described by Detailed protocols see Oh, S. A., Seki, A., & Rutz, S. (2018) *Current Protocols in Immunology*, 124, e69. doi: 10.1002/cpim.69, and Seki and Rutz, *J Exp. Med.* 2018 Vol. 215 No. 3 985-997, each of which is incorporated herein by reference its entirety.

GM-CSF inactivation by gene KO has been reported to reduce cytokine release syndrome and neurotoxicity and improve anti-tumor activity in CAR T treated mice with tumor xenografts (as described by Sterner R M et al., 2018 Blood 2018:blood-2018-10-881722, which is incorporated herein by reference its entirety.

Inactivation of GM-CSF Gene by CRISPR Approach Targeting Exon 1 or 2 or 3 or 4.

Multiple, e.g. 3 Cas9 constructs targeting 3 different sequences within the GM-CSF gene may be used so as to ensure efficient gene inactivation in all samples. (This is easily done with CRISPR compared to other gene editing methods.)

High frequency of bi-allelic KO reported using Cas9 (as described by Zhang, Y., et al. *Methods*. 2014 September; 69(2): 171-178. doi:10.1016/j.ymeth.2014.05.003, which is incorporated herein by reference its entirety. This high frequency of bi-allelic KO provides a possible advantage. Other Gene Silencing Technologies for GM-CSF KO in CAR T Cells Other methods that can be used for gene silencing are well known to those ordinary skilled in the art and may include, without limitation, homing endonucleases (HEs) also known as meganucleases, RNA interference (RNAi), short interfering RNS (siRNA), DNA-directed RNA interference (ddR-NAi).

Combination of GM-CSF Gene KO in CAR T Cells and Neutralizing Antibody for Non-CAR T Derived GM-CSF.

Removal/neutralization of all GM-CSF in patients requires anti-GM-CSF antibody, anti-receptor antibody, or soluble receptor-Fc fusion used in combination with GM-CSF gene KO in CART cells. The CART cells administered, include but are not limited to, GM-CSF$^{k/o}$ CART cells. In one embodiment, the administered GM-CSF$^{k/o}$ CART cells are GM-CSF$^{k/o}$ CART19.

An anti-GM-CSF neutralizing antibody is administered in this combination therapy, including but not limited to Lenzilumab. Lenzilumab is a novel, high affinity, recombinant human, neutralizing anti-hGM-CSF antibody. Studies in non-human primates have shown that this antibody is safe when repeat-dosed, even at doses as high as >100 mg/kg/wk. for 6 weeks. This antibody is also safe in humans when repeat-dosed (7 doses of 400 mg/dose, over 24 weeks to severe asthmatics). This antibody can be used in combination with GM-CSF KO CART cell therapy in cancer patients providing complete neutralization of human GM-CSF. Cancer patients are dosed I.V. with anti-hGM-CSF antibody (600-1800 mg) followed by 2×10$^6$ CAR T cells (GM-CSF$^{KO}$). At specific times after treatment effects are assessed, e.g. safety, blood chemistry, neurologic assessments, disease status. The treatment may be repeated on a monthly or 3 monthly basis and may result in disease remission and improved progression free survival.

GM-CSF can also be neutralized using an anti-human GM-CSF receptor alpha (R$\alpha$) antibody (as described in Minter, R R, et al. 2012 DOI:10.1111/j.1476-5381.2012.02173.x). Cancer patients are dosed I.V. with anti-hGM-CSF receptor antibody (70-700 mg) followed by 2×10$^6$ CAR T cells)(GM-CSF$^{KO}$). At specific times after treatment effects are assessed, e.g. safety, blood chemistry, neurologic assessments, disease status. Treatment results in disease remission and improved progression free survival. The treatment may be repeated on a monthly basis until there is no further detectable cancer or there is a significant reduction in cancer load.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for enhancing anti-tumor efficacy of chimeric antigen receptor-expressing T19-cell (CAR T19-cell) therapy in a subject having cancer, the method comprising administering to the subject CAR-T19 cells having a granulocyte-macrophage colony-stimulating factor (GM-CSF) gene knockout (GM-CSF$^{k/o}$ CAR-T19 cells), wherein administration of the GM-CSF$^{k/o}$ CAR-T19 cells reduces tumor burden compared to tumor burden reduction by administration of CAR-T19 cells lacking said GM-CSF gene knockout.

2. The method of claim 1, further comprising administering to the subject an anti-hGM-CSF antibody, wherein the anti-hGM-CSF antibody is a recombinant anti-hGM-CSF antibody that binds to and neutralizes human GM-CSF.

3. The method of claim 2, wherein the administration of (i) the GM-CSF$^{k/o}$ CAR-T19 cells or (ii) the GM-CSF$^{k/o}$ CAR-T19 cells and the anti-hGM-CSF antibody decreases or prevents CD14$^+$ myeloid cell trafficking to a central nervous system (CNS) of the subject, wherein a high level of CD14$^+$ myeloid cells in the CNS of the subject is indicative of neurotoxicity.

4. The method of claim 2, wherein an objective response rate of the subject administered the anti-hGM-CSF antibody is improved compared to a subject that is not administered the anti-hGM-CSF antibody.

5. The method of claim 4, wherein the objective response rate is a complete response rate or a partial response rate.

6. The method of claim 2, wherein a progression free response and/or survival of the subject is improved compared to a subject that is not administered the anti-hGM-CSF antibody.

7. The method of claim 6, wherein the survival is overall survival of the subject.

8. The method of claim 2, wherein the anti-hGM-CSF antibody is administered to the subject after administration of the GM-CSF$^{k/o}$ CAR-T19 cells.

9. The method of claim 1, wherein the cancer is lymphoma or a leukemia.

10. The method of claim 9, wherein the lymphoma is a diffuse large B cell lymphoma (DLBCL).

11. The method of claim 9, wherein the leukemia is acute lymphoblastic leukemia (ALL).

* * * * *